(12) United States Patent
Kwok et al.

(10) Patent No.: US 8,344,210 B2
(45) Date of Patent: Jan. 1, 2013

(54) INCREASING LOW LIGHT TOLERANCE IN PLANTS

(75) Inventors: Shing Kwok, Woodland Hills, CA (US); Sam Harris, Malibu, CA (US); James Burns, Valley Village, CA (US)

(73) Assignee: Ceres, Inc., Thousand Oaks, CA (US)

( * ) Notice: Subject to any disclaimer, the term of this patent is extended or adjusted under 35 U.S.C. 154(b) by 509 days.

(21) Appl. No.: 12/307,561

(22) PCT Filed: Jul. 5, 2007

(86) PCT No.: PCT/US2007/072877
§ 371 (c)(1),
(2), (4) Date: Nov. 23, 2009

(87) PCT Pub. No.: WO2008/006033
PCT Pub. Date: Jan. 10, 2008

(65) Prior Publication Data
US 2010/0119688 A1    May 13, 2010

Related U.S. Application Data

(60) Provisional application No. 60/818,569, filed on Jul. 5, 2006.

(51) Int. Cl.
*A01H 5/00* (2006.01)
*A01H 5/10* (2006.01)

(52) U.S. Cl. ..... 800/298; 800/290; 800/306; 800/320.1; 426/531

(58) Field of Classification Search .......... None
See application file for complete search history.

(56) References Cited

U.S. PATENT DOCUMENTS

| | | | |
|---|---|---|---|
| 5,204,253 A | 4/1993 | Sanford et al. | |
| 5,538,880 A | 7/1996 | Lundquist et al. | |
| 6,013,863 A | 1/2000 | Lundquist et al. | |
| 6,329,571 B1 | 12/2001 | Hiei | |
| 7,173,121 B2 | 2/2007 | Fang | |
| 7,214,789 B2 | 5/2007 | Pennell | |
| 7,378,571 B2 | 5/2008 | Apuya | |
| 7,402,667 B2 | 7/2008 | Cook et al. | |
| 7,429,692 B2 | 9/2008 | Dang | |
| 7,598,367 B2 | 10/2009 | Cook et al. | |
| 2002/0023281 A1* | 2/2002 | Gorlach et al. | 800/288 |
| 2006/0021083 A1 | 1/2006 | Cook | |
| 2006/0041952 A1 | 2/2006 | Cook | |
| 2006/0260004 A1 | 11/2006 | Fang et al. | |
| 2007/0006335 A1 | 1/2007 | Cook | |

FOREIGN PATENT DOCUMENTS

| | | |
|---|---|---|
| WO | 2005/098007 | 10/2005 |
| WO | 2006/005023 | 1/2006 |
| WO | 2006/034479 | 3/2006 |

OTHER PUBLICATIONS

Zhao et al (2004, The Plant Journal 37:694-706).*
Kim et al (2003, NCBI Accession No. BT010401).*
Takeda et al (2011, The Plant Journal 66:1066-1077).*
Bowie et al, Science 247:1306-1310, 1990.*
McConnell et al, Nature 411 (6838):709-713, 2001.*
U.S. Appl. No. 60/505,689, filed Sep. 23, 2003, Cook.
U.S. Appl. No. 60/518,075, filed Nov. 6, 2003, Pennell.
U.S. Appl. No. 60/544,771, filed Feb. 13, 2004, Cook.
U.S. Appl. No. 60/558,869, filed Apr. 1, 2004, Cook.
U.S. Appl. No. 60/583,691, filed Jun. 30, 2004, Alexandrov.
U.S. Appl. No. 60/637,140, filed Dec. 16, 2004, Feldman.
U.S. Appl. No. 60/757,544, filed Jan. 9, 2006, Dang.
U.S. Appl. No. 60/776,307, filed Feb. 24, 2006, Kwok.
Bateman et al., "Pfam 3.1: 1313 multiple alignments and profile HMMs match the majority of proteins" *Nucl. Acids Res.*, 27(1):260-262 (1999).
Bechtold and Pelletier, "*In Planta Agrobacterium*-mediated transformation of adult *Arabidopsis thaliana* plants by vacuum infiltration," *Methods Mol. Biol.*, 1998, 82: 259-266.
Boylan et al., "Phytochrome a overexpression inhibits hypocotyl elongation in transgenic *Arabidopsis*," *Proc. Natl. Acad. Sci.*, 1991, 88(23): 10806-10810.
Bustos et al., "Regulation of b-glucuronidase expression in transgenic tobacco plants by an A/T-rich, *cis*-acting sequences found upstream of a French bean b-phaseolin gene" *Plant Cell*, 1(9):839-854 (1989).
Cerdan et al., "A 146 by fragment of the tobacco *Lhcb*1 *2 promoter confers very-low-fluence, low-fluence and high-irradiance responses of phytochrom to a minimal CaMV 35S promoter" *Plant Mol. Biol.*, 33:245-255 (1997).
Cerdan and Chory, "Regulation of flowering time by light quality," *Nature*, 2003, 423: 881-885.
Chen et al., "RF12, a RING-domain zinc finger protein, negatively regulates CONSTANS expression and photoperiodic flowering," *Plant J.*, 2006, 46(5): 823-833.
Chenna et al., "Multiple sequence alignment with the Clustal series of programs" *Nucleic Acids Res.*, 31(13):3497-3500 (2003).
Dai et al., "RF2b, a rice bZIP transcription activator, interacts with RF2a and is involved in symptom development of rice tungro disease" *Proc. Natl. Acad. Sci.* USA, 101(2):687-692 (2004).
Do et al., "ProbCons: Probabilistic consistency-based multiple sequence alignment," *Genome Res.*, 2005, 15(2): 330-340.
Durbin et al., "3-Markov chains and hidden Markov models; 4-Pairwise alignment using HMMS; 5-Profile HMMs for sequence families" In Biological Sequence Analysis: Probabilistic Models of Proteins and Nucleic Acids, (Cambridge University Press, Cambridge, UK, 1998), pp. 47-134.
Fejes et al., "A 268 bp upstream sequence mediates the circadian clock-regulated transcription of the wheat Cab-1 gene in transgenic plants" *Plant Mol. Biol.*, 15:921-932 (1990).

(Continued)

*Primary Examiner* — Stuart F. Baum
(74) *Attorney, Agent, or Firm* — Fish & Richardson P.C.

(57) ABSTRACT

Methods and materials for modulating (e.g., increasing or decreasing) low light tolerance in plants are disclosed. For example, nucleic acids encoding polypeptides that confer plants with tolerance to low light are disclosed as well as methods for using such nucleic acids to transform plant cells. Also disclosed are plants having increased low light tolerance and plant products produced from plants having increased low light tolerance.

15 Claims, 5 Drawing Sheets

OTHER PUBLICATIONS

Fromm et al., "An octopine synthase enhancer element directs tissue-specific expression and binds ASF-1, a factor from tobacco nuclear extracts" *The Plant Cell*, 1:977-984 (1989).

Green et al., "Binding site requirements for pea nuclear protein factor GT-1 correlate with sequences required for light-dependent transcriptional activation of the rbcS-3A gene" *EMBO J.*, 7:4035-4044 (1988).

Hu et al., "Characterization of a novel putative zinc finger gene MIF1: involvement in multiple hormonal regulation of *Arabidopsis* development", *Plant J.*, 2006, 45: 399-422.

Jordano et al., "A sunflower helianthinin gene upstream sequence ensemble contains an enhancer and sites of nuclear protein interaction" *Plant Cell*, 1:855-866 (1989).

Keller and Baumgartner, "Vascular-specific expression of the bean GRP 1.8 gene is negatively regulated" *Plant Cell*, 3(10):1051-1061 (1991).

Luan et al., "A rice *cab* gene promoter contains separate *cis*-acting elements that regulate expression in dicot and monocot plants" *The Plant Cell*, 4:971-981 (1992).

Lubberstedt et al., "Promoters from genes for plastid proteins possess regions with different sensitivities toward red and blue light" *Plant Physiol.*, 104:997-1006 (1994).

Medberry et al., "The *Commelina* yellow mottle virus promoter is a strong promoter in vascular and reproductive tissues" *Plant Cell*, 4(2):185-192 (1992).

Meier et al., "Elicitor-inducible and constitutive in vivo DNA footprints indicate novel *cis*-acting elements in the promoter of a parsley gene encoding pathogenesis-related protein 1" *Plant Cell*, 3:309-316 (1991).

Pfam web cite (describing concensus sequences for a variety of protein motifs and domains at sanger.ac.uk/Pham and genome.wustl.edu.Pfan, 2006.

Rivera et al, "Genomic evidence for two functionally distinct gene classes" *Proc. Natl. Acad. Sci.* USA, 95:6239-6244 (1998).

Sonnhammer et al., "Pfam: A comprehensive database of protein domain families based on seed alignments" *Proteins*, 28:405-420 (1997).

Sonnhammer et al., "Pfam: multiple sequence alignments and HMM-profiles of protein domains" *Nucl. Acids Res.*, 26:320-322 (1998).

Truernit et al., "The promoter of the *Arabidopsis thaliana* SUC2 sucrose-H$^+$ symporter gene directs expression of β-glucuronidase to the phloem: Evidence for phloem loading and unloading by SUC2" *Planta*, 1995, 196:564-570.

Tseng et al., "SPINDLY and GIGANTEA interact and act in *Arabidopsis thaliana* pathways involved in light responses, flowering, and rhythms in cotyledon movement," *Plant Cell*, 2004, 16(6): 1550-1563.

Yamamoto et al., "The promoter of a pine photosynthetic gene allows expression of a β-glucuronidase reporter gene in transgenic rice plants in a light-independent but tissue-specific manner" *Plant Cell Physiol.*, 1994, 35:773-778.

Zhang et al., "DNA sequences that activate isocitrate lyase gene expression during late embryogenesis and during postgerminative growth," *Plant Physiology*, 110:1069-1079 (1996).

Zhao et al., "Overexpression of *LSH1*, a member of an uncharacterised gene family, causes enhanced light regulation of seedling development," *Plant J.*, 2004, 37(5): 694-706.

\* cited by examiner

INCREASING LOW LIGHT TOLERANCE IN PLANTS

CROSS-REFERENCE TO RELATED APPLICATION

This application is a National Stage application under 35 U.S.C. §371 of International Application No. PCT/US2007/072877, having an International Filing Date of Jul. 5, 2007, which claims the benefit of priority of U.S. Provisional Application Ser. No. 60/818,569, having a filing date of Jul. 5, 2006, all of which are incorporated herein in their entirety.

TECHNICAL FIELD

This document relates to methods and materials involved in tolerance of plants to low light conditions. For example, this document provides transgenic plants and seeds comprising nucleic acids encoding polypeptides that confer tolerance to conditions of low light irradiance.

BACKGROUND

Light is the source of energy that fuels plant growth through photosynthesis. Light is also a developmental signal that modulates morphogenesis, such as de-etiolation and the transition to reproductive development. Since plants cannot choose their surroundings, they are forced to adapt their growth to ambient light conditions and have evolved complex mechanisms for monitoring the quantity and quality of the surrounding light. For example, many kinds of plants respond to growth under dense canopies or at high densities by growing faster and taller (Cerdan and Chory (2003) Nature, 423: 881). Densely planted crops tend to place energy into stem and petiole elongation to lift the leaves into the sunlight rather than putting energy into storage or reproductive structures. The response to low light conditions negatively affects crop yields by reducing the amount of harvestable products such as seeds, fruits and tubers. In addition, tall spindly plants tend to be less wind resistant and lodge more easily, further reducing crop yield.

There is a continuing need for plants that can thrive under less than optimal environmental conditions. One strategy to improve a plant's ability to withstand suboptimal environmental conditions relies upon traditional plant breeding methods. Another approach involves genetic manipulation of plant characteristics through the introduction of exogenous nucleic acids conferring a desirable trait.

SUMMARY

This document provides methods and materials related to low light tolerance in plants, plant cells, and seeds. For example, this document provides transgenic plants having increased tolerance to conditions of low light irradiance, nucleic acids used to generate transgenic plants having increased tolerance to low light conditions, and methods for making transgenic plants having increased tolerance to low light conditions. Transgenic plants having increased tolerance to low light conditions can exhibit a reduction in one or more responses typically elicited by low light stress. For example, a low light-tolerant transgenic plant have a hypocotyl length, when exposed to low light conditions, e.g., an irradiance of 0.01 to 20 µmol/m$^2$/s of light, that is shorter than the typical hypocotyl length of corresponding wild-type plants grown under similar conditions. Increasing the tolerance of plants to low light conditions can produce healthier plants and a higher crop yield under conditions of low light irradiance, such as those occurring during high-density cultivation of plants.

In one aspect, a method of modulating the low light tolerance of a plant is provided. The method comprises introducing into a plant cell an exogenous nucleic acid comprising a nucleotide sequence encoding a polypeptide having 80% or greater sequence identity to an amino acid sequence selected from the group consisting of SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, and SEQ ID NO:146, where a plant produced from the plant cell exhibits a phenotypic difference relative to a corresponding control plant under low light conditions. The nucleotide sequence can encode a polypeptide comprising an amino acid sequence corresponding to SEQ ID NO:88.

In another aspect, a method of modulating the low light tolerance of a plant is provided. The method comprises introducing into a plant cell an exogenous nucleic acid comprising a nucleotide sequence having 80 percent or greater sequence identity to a nucleotide sequence selected from the group consisting of SEQ ID NO:87, SEQ ID NO:91, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NOs:129-130, SEQ ID NO:132, SEQ ID NO:134, SEQ ID NO:136, SEQ ID NO:138, SEQ ID NO:140, and SEQ ID NOs:143-145, where a plant produced from the plant cell exhibits a phenotypic difference relative to a corresponding control plant under low light conditions. The nucleotide sequence can comprise the nucleotide sequence set forth in SEQ ID NO:87.

The low light conditions can comprise an irradiance of about 0.01 to about 20 µmol/m$^2$/s of light. The phenotypic difference can comprise a decreased hypocotyl length. The exogenous nucleic acid can be operably linked to a regulatory region. The regulatory region can be a tissue-preferential, broadly expressing, or inducible promoter. The plant can be a dicot. The plant can be a member of the genus Brassica, Glycine, Gossypium, Helianthus, Lactuca, or Medicago. The plant can be a monocot. The plant can be a member of the genus Cocos, Elaeis, Oryza, Panicum, or Zea. The method can further comprises the step of producing a plant from the plant cell. The introducing step can comprise introducing the nucleic acid into a plurality of plant cells. The method can further comprise the step of producing a plurality of plants from the plant cells. The method can further comprise the step of selecting one or more plants from the plurality of plants that have the phenotypic difference.

In another aspect, a method of producing a plant is provided. The method comprises growing a plant cell comprising an exogenous nucleic acid comprising a nucleotide sequence encoding a polypeptide having 80% or greater sequence identity to an amino acid sequence selected from the group consisting of SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, and SEQ ID NO:146, where the plant exhibits a phenotypic difference relative to a corresponding control plant under low light conditions. The nucleotide sequence can encode a polypeptide comprising an amino acid sequence corresponding to SEQ ID NO:88.

In another aspect, a method of producing a plant is provided. The method comprises growing a plant cell comprising an exogenous nucleic acid comprising a nucleotide sequence having 80 percent or greater sequence identity to a nucleotide sequence selected from the group consisting of SEQ ID NO:87, SEQ ID NO:91, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NOs:129-130, SEQ ID NO:132, SEQ ID NO:134, SEQ ID NO:136, SEQ ID NO:138, SEQ ID NO:140, and SEQ ID NOs:143-145, where the plant exhibits a phenotypic difference relative to a corresponding control plant under low light conditions. The nucleotide sequence can comprise the nucleotide sequence set forth in SEQ ID NO:87.

The low light conditions can comprise an irradiance of about 0.01 to about 20 µmol/m$^2$/s of light. The phenotypic difference can comprise a decreased hypocotyl length. The exogenous nucleic acid can be operably linked to a regulatory region. The regulatory region can be a tissue-preferential, broadly expressing, or inducible promoter. The plant can be a dicotyledonous plant. The plant can be a member of the genus *Brassica, Glycine, Gossypium, Helianthus, Lactuca,* or *Medicago*. The plant can be a monocotyledonous plant. The plant can be a member of the genus *Cocos, Elaeis, Oryza, Panicum,* or *Zea*.

In another aspect, a plant comprising an exogenous nucleic acid is provided. The exogenous nucleic acid comprises a nucleotide sequence encoding a polypeptide having 80% or greater sequence identity to an amino acid sequence selected from the group consisting of SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, and SEQ ID NO:146, where the plant exhibits a phenotypic difference relative to a corresponding control plant under low light conditions. The nucleotide sequence can encode a polypeptide comprising an amino acid sequence corresponding to SEQ ID NO:88.

In another aspect, a plant comprising an exogenous nucleic acid is provided. The exogenous nucleic acid comprises a nucleotide sequence having 80 percent or greater sequence identity to a nucleotide sequence selected from the group consisting of SEQ ID NO:87, SEQ ID NO:91, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NOs:129-130, SEQ ID NO:132, SEQ ID NO:134, SEQ ID NO:136, SEQ ID NO:138, SEQ ID NO:140, and SEQ ID NOs:143-145, where the plant exhibits a phenotypic difference relative to a corresponding control plant under low light conditions. The nucleotide sequence can comprise the nucleotide sequence set forth in SEQ ID NO:87.

The low light conditions can comprise an irradiance of about 0.01 to about 20 µmol/m$^2$/s of light. The phenotypic difference can comprise a decreased hypocotyl length. The exogenous nucleic acid can be operably linked to a regulatory region. The regulatory region can be a tissue-preferential, broadly expressing, or inducible promoter. The plant can be a dicot. The plant can be a member of the genus *Brassica, Glycine, Gossypium, Helianthus, Lactuca,* or *Medicago*. The plant can be a monocot. The plant can be a member of the genus *Cocos, Elaeis, Oryza, Panicum,* or *Zea*.

Progeny of any of the plants described above also are provided. The progeny exhibits a phenotypic difference relative to a corresponding control plant under low light conditions. Seed, vegetative tissue, and fruit from any of the plants described above also are provided, as are food products and feed products comprising seed or vegetative tissue from any of the plants described above.

In another aspect, an isolated nucleic acid molecule is provided. The isolated nucleic acid molecule comprises a nucleotide sequence having 95% or greater sequence identity to a nucleotide sequence selected from the group consisting of SEQ ID NO:87, SEQ ID NO:91, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NOs:129-130, SEQ ID NO:132, SEQ ID NO:134, SEQ ID NO:136, SEQ ID NO:138, SEQ ID NO:140, and SEQ ID NOs:143-145.

In another aspect, an isolated nucleic acid is provided. The isolated nucleic acid molecule comprises a nucleotide sequence encoding a polypeptide having 80% or greater sequence identity to an amino acid sequence selected from the group consisting of SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, and SEQ ID NO:146.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Figure 1:
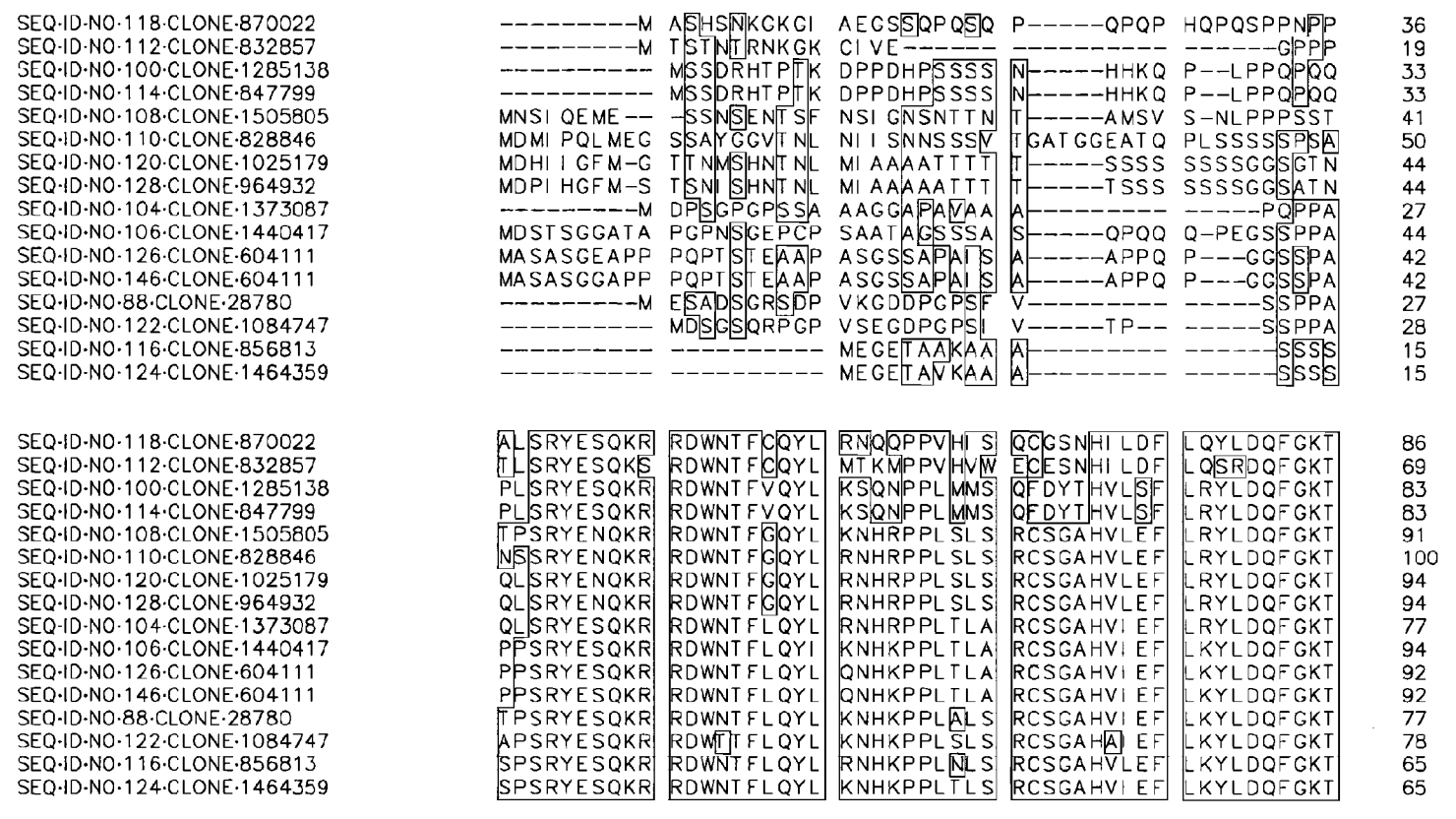
Figure 1:
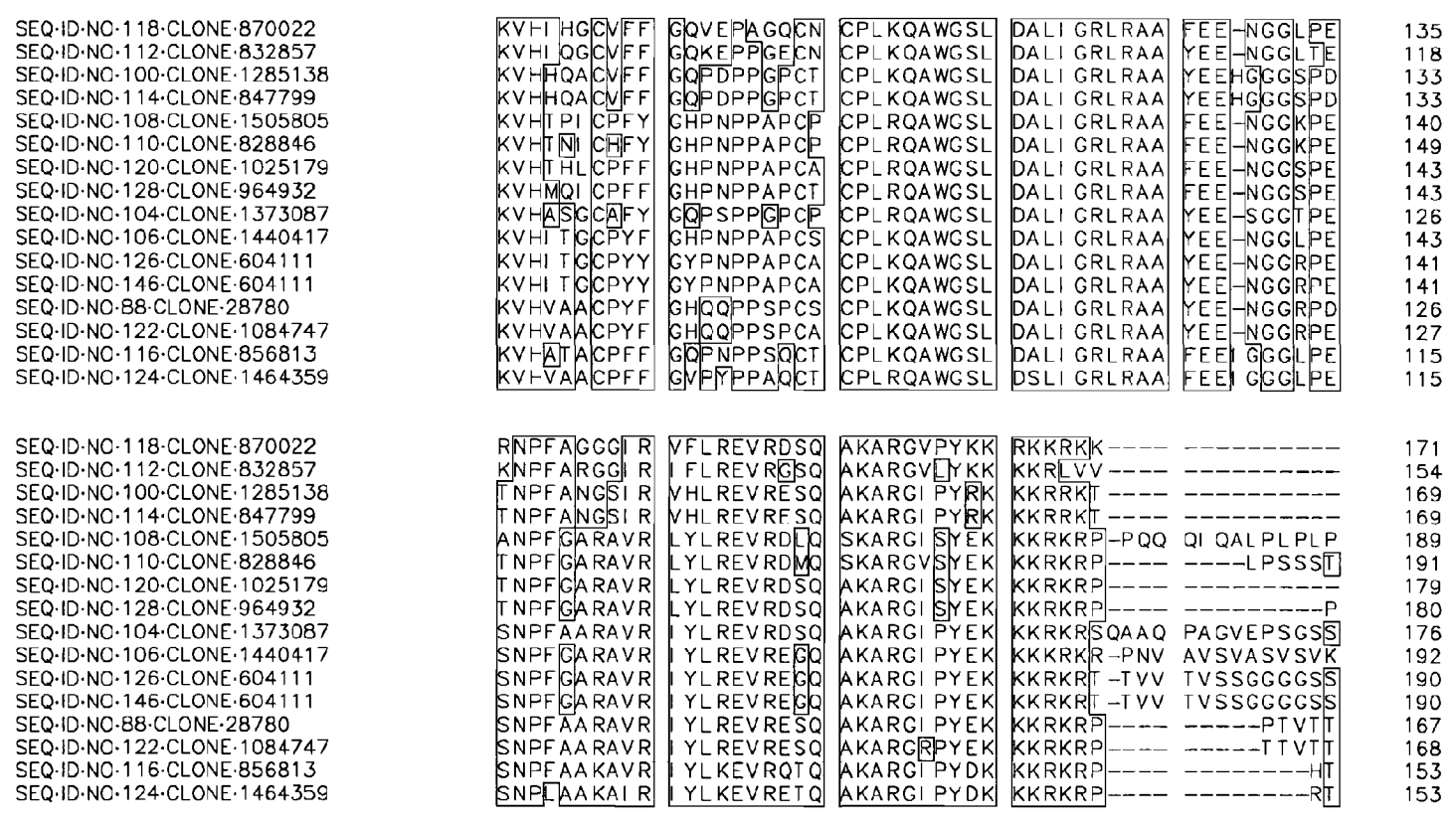
Figure 1:
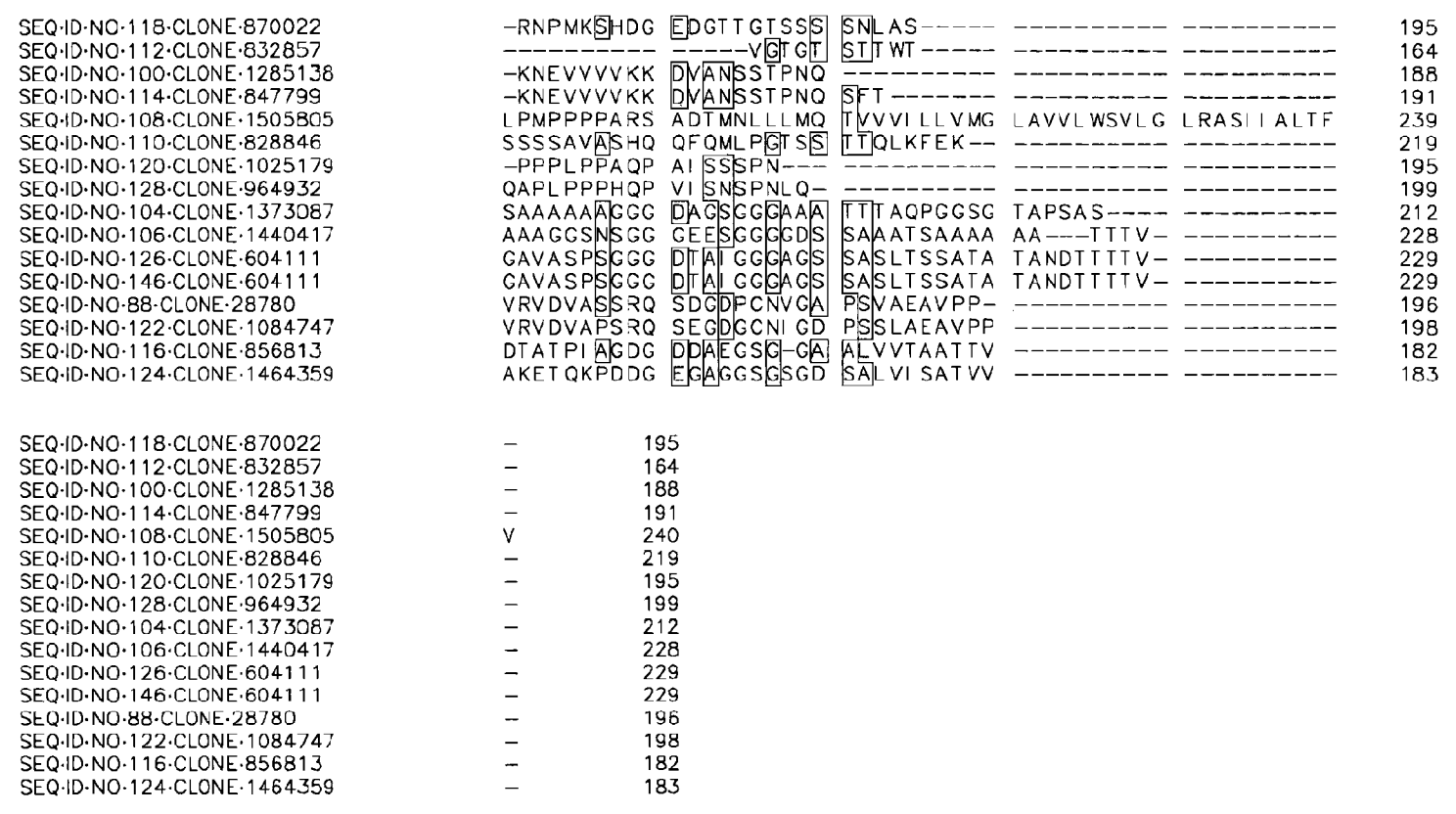

FIG. 1 is an alignment of Clone 28780 (SEQ ID NO:88) with homologous and/or orthologous amino acid sequences Clone 1285138 (SEQ ID NO:100), Clone 1373087 (SEQ ID NO:104), Clone 1440417 (SEQ ID NO:106), Clone 1505805 (SEQ ID NO:108), Clone 828846 (SEQ ID NO:110), Clone 832857 (SEQ ID NO:112), Clone 847799 (SEQ ID NO:114), Clone 856813 (SEQ ID NO:116), Clone 870022 (SEQ ID NO:118), Clone 1025179 (SEQ ID NO:120), Clone 1084747 (SEQ ID NO:122), Clone 1464359 (SEQ ID NO:124), Clone 604111(a) (SEQ ID NO:126), Clone 964932 (SEQ ID NO:128), and Clone 604111(b) (SEQ ID NO:146).

DETAILED DESCRIPTION

Figure 2:
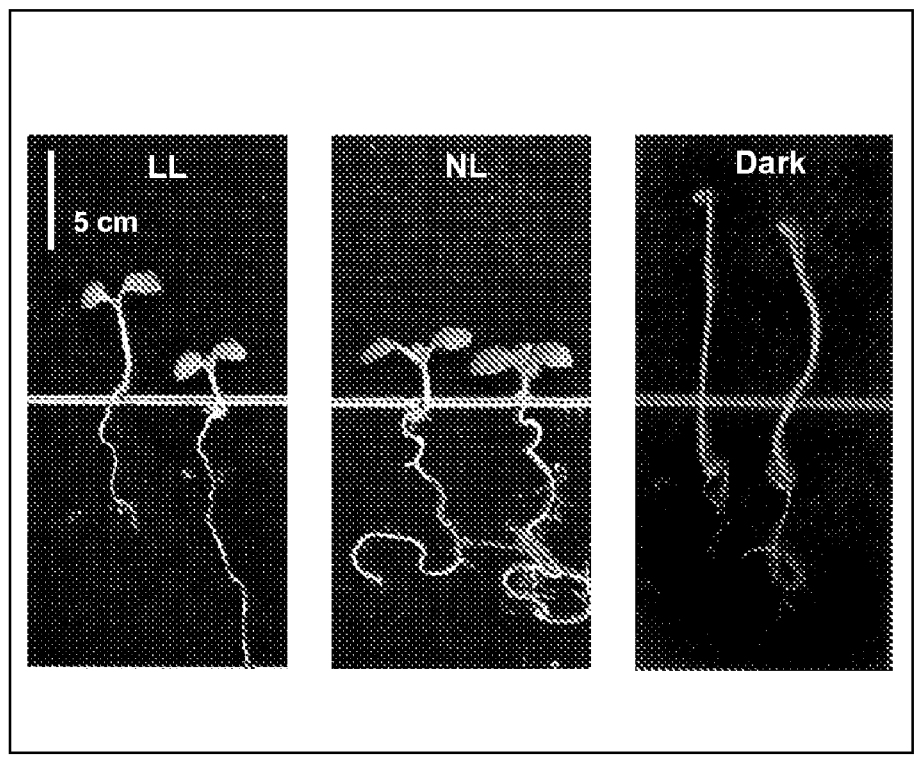
FIG. 2 is an image of $T_3$ seedlings from a single insertion event of transgenic line ME05917 (right) and corresponding non-transgenic segregants (left) that were grown in the dark or under conditions of irradiation with 10 or 100 µmol/m²/s of white light (LL or NL, respectively).

The invention features methods and materials related to modulating the tolerance of plants to conditions of low light irradiation. The methods can include transforming a plant with a nucleic acid encoding a polypeptide, the expression of which results in increased tolerance to low light conditions. Plants produced using such methods can be grown to produce seeds that, in turn, can be used to grow plants having an increased tolerance to conditions of low light irradiance.

Low light conditions can include conditions under which a plant is irradiated with about 0.01 to 20 µmol/m²/s of white light. Plants grown under low light conditions typically exhibit one or more phenotypic changes, or responses, such as an increase in extension growth. Low light tolerance refers to the ability of a plant to grow under low light irradiance levels while exhibiting a low light response that is less than the corresponding low light response exhibited by a control plant. For example, a plant that is tolerant to low light conditions can exhibit less hypocotyl elongation when exposed to low light conditions than a corresponding control plant grown under similar conditions.

Polypeptides

The term "polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. The term "amino acid" refers to natural and/or unnatural or synthetic amino acids, including D/L optical isomers. Full-length proteins, analogs, mutants, and fragments thereof are encompassed by this definition.

Polypeptides described herein include low light-tolerance polypeptides that, when expressed in a plant, can modulate the tolerance of the plant to conditions of low light irradiation. Modulation of the level of low light tolerance can be either an increase or a decrease in the level of low light tolerance relative to the corresponding level in a control plant.

A low light-tolerance polypeptide can contain a DUF640 domain, which is a conserved region found in a family of plant polypeptides including the resistance protein-like polypeptide. SEQ ID NO:88 sets forth the amino acid sequence of an *Arabidopsis* clone, identified herein as Ceres Clone 28780 (SEQ ID NO:87), that is predicted to encode a polypeptide containing a DUF640 domain. A low light-tolerance polypeptide can comprise the amino acid sequence set forth in SEQ ID NO:88. Alternatively, a low light-tolerance polypeptide can be a homolog, ortholog, or variant of the polypeptide having the amino acid sequence set forth in SEQ ID NO:88. For example, a low light-tolerance polypeptide can have an amino acid sequence with greater than 63% sequence identity, e.g., 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity, to the amino acid sequence set forth in SEQ ID NO:88.

Amino acid sequences of homologs and/or orthologs of the polypeptide having the amino acid sequence set forth in SEQ ID NO:88 are provided in FIG. 1. For example, the alignment in FIG. 1 provides the amino acid sequences of Ceres Clone 28780 (SEQ ID NO:88), Clone 1285138 (SEQ ID NO:100), Clone 1373087 (SEQ ID NO:104), Clone 1440417 (SEQ ID NO:106), Clone 1505805 (SEQ ID NO:108), Clone 828846 (SEQ ID NO:110), Clone 832857 (SEQ ID NO:112), Clone 847799 (SEQ ID NO:114), Clone 856813 (SEQ ID NO:116), Clone 870022 (SEQ ID NO:118), Clone 1025179 (SEQ ID NO:120), Clone 1084747 (SEQ ID NO:122), Clone 1464359 (SEQ ID NO:124), Clone 604111(a) (SEQ ID NO:126), Clone 964932 (SEQ ID NO:128), and Clone 604111(b) (SEQ ID NO:146). Other homologs and/or orthologs include SEQ ID NOs:89-90, SEQ ID NOs:92-94, SEQ ID NO:131, SEQ ID NO:133, SEQ ID NO:135, SEQ ID NO:137, SEQ ID NO:139, and SEQ ID NOs:141-142. In some cases, a low light-tolerance polypeptide includes a polypeptide having at least 80% sequence identity, e.g., 80%, 85%, 90%, 95%, 97%, 98%, or 99% sequence identity, to an amino acid sequence corresponding to any one of SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, or SEQ ID NO:146.

A low light-tolerance polypeptide encoded by a recombinant nucleic acid can be a native low light-tolerance polypeptide, i.e., one or more additional copies of the coding sequence for a low light-tolerance polypeptide that is naturally present in the cell. Alternatively, a low light-tolerance polypeptide can be heterologous to the cell, e.g., a transgenic *Lycopersicon* plant can contain the coding sequence for a low light-tolerance polypeptide from a *Glycine* plant.

A low light-tolerance polypeptide can include additional amino acids that are not involved in modulation of low light tolerance, and thus can be longer than would otherwise be the case. For example, a low light-tolerance polypeptide can include an amino acid sequence that functions as a reporter. Such a low light-tolerance polypeptide can be a fusion protein in which a green fluorescent protein (GFP) polypeptide is fused to, e.g., SEQ ID NO:88, or in which a yellow fluorescent protein (YFP) polypeptide is fused to, e.g., SEQ ID NO:88. In some embodiments, a low light-tolerance polypeptide includes a purification tag, a chloroplast transit peptide, a mitochondrial transit peptide, or a leader sequence added to the amino or carboxy terminus.

Low light-tolerance polypeptide candidates suitable for use in the invention can be identified by analysis of nucleotide and polypeptide sequence alignments. For example, performing a query on a database of nucleotide or polypeptide sequences can identify homologs and/or orthologs of low light-tolerance polypeptides. Sequence analysis can involve BLAST, Reciprocal BLAST, or PSI-BLAST analysis of nonredundant databases using known low light-tolerance polypeptide amino acid sequences. Those polypeptides in the database that have greater than 40% sequence identity can be identified as candidates for further evaluation for suitability as a low light-tolerance polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains suspected of being present in low light-tolerance polypeptides, e.g., conserved functional domains.

The identification of conserved regions in a template or subject polypeptide can facilitate production of variants of wild type low light-tolerance polypeptides. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains at sanger.ac.uk/Pfam and genome.wustl.edu/Pfam. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Amino acid residues corresponding to Pfam domains included in low light-tolerance polypeptides provided herein are set forth in the sequence listing. For example, amino acid residues 13 to 145 of the amino acid sequence set forth in SEQ ID NO:88 correspond to a DUF640 domain, as indicated in fields <222> and <223> for SEQ ID NO:88 in the sequence listing.

Conserved regions also can be determined by aligning sequences of the same or related polypeptides from closely related species. Closely related species preferably are from the same family. In some embodiments, alignment of sequences from two different species is adequate. For example, sequences from *Arabidopsis* and *Zea mays* can be used to identify one or more conserved regions.

Typically, polypeptides that exhibit at least about 40% amino acid sequence identity are useful to identify conserved regions. Conserved regions of related polypeptides can exhibit at least 45% amino acid sequence identity (e.g., at least 50%, at least 60%, at least 70%, at least 80%, or at least 90% amino acid sequence identity). In some embodiments, a conserved region of target and template polypeptides exhibit at least 92%, 94%, 96%, 98%, or 99% amino acid sequence identity. Amino acid sequence identity can be deduced from amino acid or nucleotide sequences. In certain cases, highly conserved domains have been identified within low light-tolerance polypeptides. These conserved regions can be useful in identifying functionally similar (orthologous) low light-tolerance polypeptides.

In some instances, suitable low light-tolerance polypeptides can be synthesized on the basis of consensus functional domains and/or conserved regions in polypeptides that are homologous low light-tolerance polypeptides. Domains are groups of substantially contiguous amino acids in a polypeptide that can be used to characterize protein families and/or parts of proteins. Such domains have a "fingerprint" or "signature" that can comprise conserved (1) primary sequence, (2) secondary structure, and/or (3) three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Representative homologs and/or orthologs of the low light-tolerance polypeptide set forth in SEQ ID NO:88 are shown in FIG. 1. FIG. 1 represents an alignment of the amino acid sequence of the low light-tolerance polypeptide set forth in SEQ ID NO:88 with the amino acid sequences of corresponding homologs and/or orthologs. The amino acid sequences of the low light-tolerance polypeptide set forth in SEQ ID NO:88 and its corresponding homologs and/or orthologs have been aligned to identify conserved amino acids, as shown in FIG. 1. A dash in an aligned sequence represents a gap, i.e., a lack of an amino acid at that position. Identical amino acids or conserved amino acid substitutions among aligned sequences are identified by boxes. Each conserved region contains a sequence of contiguous amino acid residues.

Useful polypeptides can be constructed based on the conserved regions in FIG. 1. Such a polypeptide includes the conserved regions arranged in the order depicted in the Figure from amino-terminal end to carboxy-terminal end, and has at least 80% sequence identity to an amino acid sequence corresponding to any one of SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, or SEQ ID NO:146. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

Conserved regions can be identified by homologous polypeptide sequence analysis as described above. The suitability of polypeptides for use as low light-tolerance polypeptides can be evaluated by functional complementation studies.

Useful polypeptides can also be identified based on the polypeptides set forth in FIG. 1 using algorithms designated as Hidden Markov Models. A "Hidden Markov Model (HMM)" is a statistical model of a consensus sequence for a group of homologous and/or orthologous polypeptides. See, Durbin et al., *Biological Sequence Analysis: Probabilistic Models of Proteins and Nucleic Acids*, Cambridge University Press, Cambridge, UK (1998). An HMM is generated by the program HMMER 2.3.2 using the multiple sequence alignment of the group of homologous and/or orthologous sequences as input and the default program parameters. The multiple sequence alignment is generated by ProbCons (Do et al., *Genome Res.*, 15(2):330-40 (2005)) version 1.11 using a set of default parameters: -c, —consistency REPS of 2; -ir, —iterative-refinement REPS of 100; -pre, —pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. The HMMER 2.3.2 package was released Oct. 3, 2003 under a GNU general public license, and is available from various sources on the World Wide Web such as hmmer.janelia.org, hmmer.wustl.edu, and fr.com/hmmer232/. Hmmbuild outputs the model as a text file.

The HMM for a group of homologous and/or orthologous polypeptides can be used to determine the likelihood that a subject polypeptide sequence is a better fit to that particular HMM than to a null HMM generated using a group of sequences that are not homologous and/or orthologous. The likelihood that a subject polypeptide sequence is a better fit to an HMM than to a null HMM is indicated by the HMM bit score, a number generated when the subject sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 400, and often is higher.

A low light-tolerance polypeptide can fit an HMM provided herein with an HMM bit score greater than 400 (e.g., greater than 401, 405, 410, 415, 420, 425, 430, 435, 440, 445, 450, 460, 470, 480, 490, or 500). In some cases, a low light-tolerance polypeptide can fit an HMM provided herein with an HMM bit score that is about 80%, 81%, 82%, 83%, 84%, 85%, 86%, 87%, 88%, 89%, 90%, 91%, 92%, 93%, 94%, 95%, 96%, 97%, 98%, or 99% of the HMM bit score of any homologous and/or orthologous polypeptide provided in Table 34, so long as the low-light tolerance polypeptide is not SEQ ID NO:102.

Nucleic Acids

The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

An "isolated" nucleic acid can be, for example, a naturally-occurring DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

As used herein, the term "percent sequence identity" refers to the degree of identity between any given query sequence and a subject sequence. A subject sequence typically has a length that is more than 80 percent, e.g., more than 82, 85, 87, 89, 90, 93, 95, 97, 99, 100, 105, 110, 115, or 120 percent, of the length of the query sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). Chenna et al., *Nucleic Acids Res.*, 31(13):3497-500 (2003).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The term "exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Recombinant constructs are also provided herein and can be used to transform plants or plant cells in order to modulate low light tolerance. A recombinant nucleic acid construct comprises a nucleic acid encoding a low light-tolerance polypeptide as described herein, operably linked to a regulatory region suitable for expressing the low light-tolerance polypeptide in the plant or cell. Thus, a nucleic acid can comprise a coding sequence that encodes any of the low light-tolerance polypeptides as set forth in SEQ ID NO:88, SEQ ID NO:89, SEQ ID NO:90, SEQ ID NO:92, SEQ ID NO:93, SEQ ID NO:94, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:131, SEQ ID NO:133, SEQ ID NO:135, SEQ ID NO:137, SEQ ID NO:139, SEQ ID NO:141, SEQ ID NO:142, or SEQ ID NO:146. Examples of nucleic acids encoding low light-tolerance polypeptides are set forth in SEQ ID NO:87, SEQ ID NO:91, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NOs:129-130, SEQ ID NO:132, SEQ ID NO:134, SEQ ID NO:136, SEQ ID NO:138, SEQ ID NO:140, and SEQ ID NOs:143-145. In some cases, a recombinant nucleic acid construct can include a nucleic acid comprising less than the full-length coding sequence of a low light-tolerance polypeptide. In some cases, a recombinant nucleic acid construct can include a nucleic acid comprising a coding sequence, a gene, or a fragment of a coding sequence or gene in an antisense orientation so that the antisense strand of RNA is transcribed.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given low light-tolerance polypeptide can be modified such that optimal expression in a particular plant species is obtained, using appropriate codon bias tables for that species.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Mountain View, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus Regulatory Regions The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucleus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110: 1069-1079 (1996).

Examples of various classes of promoters are described below. Some of the promoters indicated below as well as additional promoters are described in more detail in U.S. patent application Ser. Nos. 60/505,689; 60/518,075; 60/544, 771; 60/558,869; 60/583,691; 60/619,181; 60/637,140; 60/757,544; 60/776,307; 10/957,569; 11/058,689; 11/172, 703; 11/208,308; 11/274,890; 60/583,609; 60/612,891; 11/097,589; 11/233,726; 11/408,791; 11/414,142; 10/950, 321; PCT/US05/011105; PCT/US05/034308; and PCT/US05/23639. Nucleotide sequences of promoters are set forth in SEQ ID NOs:1-86. It will be appreciated that a promoter may meet criteria for one classification based on its activity in one plant species, and yet meet criteria for a different classification based on its activity in another plant species.

Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO:75), YP0144 (SEQ ID NO:54), YP0190 (SEQ ID NO:58), p13879 (SEQ ID NO:74), YP0050 (SEQ ID NO:34), p32449 (SEQ ID NO:76), 21876 (SEQ ID NO:1), YP0158 (SEQ ID NO:56), YP0214 (SEQ ID NO:60), YP0380 (SEQ ID NO:69), PT0848 (SEQ ID NO:26), and PT0633 (SEQ ID NO:7) promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104: 997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include PT0535 (SEQ ID NO:3), PT0668 (SEQ ID NO:2), PT0886 (SEQ ID NO:29), YP0144 (SEQ ID NO:54), YP0380 (SEQ ID NO:69), and PT0585 (SEQ ID NO:4).

Vascular Tissue Promoters

Examples of promoters that have high or preferential activity in vascular bundles include YP0087 (SEQ ID NO:82), YP0093 (SEQ ID NO:83), YP0108 (SEQ ID NO:84), YP0022 (SEQ ID NO:80), and YP0080 (SEQ ID NO:81). Other vascular tissue-preferential promoters include the glycine-rich cell wall protein GRP 1.8 promoter (Keller and Baumgartner, *Plant Cell*, 3(10):1051-1061 (1991)), the Commelina yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380 (SEQ ID NO:69), PT0848 (SEQ ID NO:26), YP0381 (SEQ ID NO:70), YP0337 (SEQ ID NO:65), PT0633 (SEQ ID NO:7), YP0374 (SEQ ID NO:67), PT0710 (SEQ ID NO:18), YP0356 (SEQ ID NO:66), YP0385 (SEQ ID NO:72), YP0396 (SEQ ID NO:73), YP0388 (SEQ ID NO:85), YP0384 (SEQ ID NO:71), PT0688 (SEQ ID NO:15), YP0286 (SEQ ID NO:64), YP0377 (SEQ ID NO:68), PD1367 (SEQ ID NO:77), PD0901 (SEQ ID NO:79), and PD0898 (SEQ ID NO:78). Examples of nitrogen-inducible promoters include PT0863 (SEQ ID NO:27), PT0829 (SEQ ID NO:23), PT0665 (SEQ ID NO:10), and PT0886 (SEQ ID NO:29). Examples of shade-inducible promoters include PR0924 (SEQ ID NO:86), and PT0678 (SEQ ID NO:13).

Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Other Promoters

Other classes of promoters include, but are not limited to, leaf-preferential, stem/shoot-preferential, callus-preferential, guard cell-preferential, such as PT0678 (SEQ ID NO:13), and senescence-preferential promoters. Promoters designated YP0086 (SEQ ID NO:35), YP0188 (SEQ ID NO:57), YP0263 (SEQ ID NO:61), PT0758 (SEQ ID NO:22), PT0743 (SEQ ID NO:21), PT0829 (SEQ ID NO:23), YP0119 (SEQ ID NO:48), and YP0096 (SEQ ID NO:38), as described in the above-referenced patent applications, may also be useful.

Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, more than one regulatory region can be operably linked to the sequence of a polynucleotide encoding a low light-tolerance polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Transgenic Plants and Plant Cells

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant. Progeny includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous low light-tolerance polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

Plant Species

The polynucleotides and vectors described herein can be used to transform a number of monocotyledonous and dicotyledonous plants and plant cell systems, including dicots such as alfalfa, almond, amaranth, apple, apricot, avocado, beans (including kidney beans, lima beans, dry beans, green beans), brazil nut, broccoli, cabbage, canola, carrot, cashew, castor bean, cherry, chick peas, chicory, chocolate, clover, cocoa, coffee, cotton, cottonseed, crambe, eucalyptus, flax, foxglove, grape, grapefruit, hazelnut, hemp, jatropha, jojoba, lemon, lentils, lettuce, linseed, macadamia nut, mango, melon (e.g., watermelon, cantaloupe), mustard, neem, olive, orange, peach, peanut, pear, peas, pecan, pepper, pistachio, plum, poplar, poppy, potato, pumpkin, oilseed rape, quinoa, rapeseed (high erucic acid and canola), safflower, sesame, soaptree bark, soybean, spinach, strawberry, sugar beet, sunflower, sweet potatoes, tea, tomato, walnut, and yams, as well as monocots such as banana, barley, bluegrass, coconut, corn, date palm, fescue, field corn, garlic, millet, oat, oil palm, onion, palm kernel oil, pineapple, popcorn, rice, rye, ryegrass, sorghum, sudangrass, sugarcane, sweet corn, switchgrass, turf grasses, timothy, and wheat. Gymnosperms such as fir, pine, and spruce can also be suitable.

Thus, the methods and compositions described herein can be used with dicotyledonous plants belonging, for example, to the orders Apiales, Arecales, Aristolochiales, Asterales, Batales, Campanulales, Capparales, Caryophyllales, Casuarinales, Celastrales, Cornales, Cucurbitales, Diapensales, Dilleniales, Dipsacales, Ebenales, Ericales, Eucomiales, Euphorbiales, Fabales, Fagales, Gentianales, Geraniales, Haloragales, Hamamelidales, Illiciales, Juglandales, Lamiales, Laurales, Lecythidales, Leitneriales, Linales, Magniolales, Malpighiales, Malvales, Myricales, Myrtales, Nymphaeales, Papaverales, Piperales, Plantaginales, Plumbaginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Solanales, Trochodendrales, Theales, Umbellales, Urticales, and Violates. The methods and compositions described herein also can be utilized with monocotyledonous plants such as those belonging to the orders Alismatales, Arales, Arecales, Asparagales, Bromeliales, Commelinales, Cyclanthales, Cyperales, Eriocaulales, Hydrocharitales, Juncales, Liliales, Najadales, Orchidales, Pandanales, Poales, Restionales, Triuridales, Typhales, Zingiberales, and with plants belonging to Gymnospermae, e.g., Cycadales, Ephedrales, Ginkgoales, Gnetales, Taxales, and Pinales.

The methods and compositions can be used over a broad range of plant species, including species from the dicot genera *Abelmoschus, Acer, Acokanthera, Aconitum, Aesculus, Alangium, Alchornea, Alexa, Alseodaphne, Amaranthus, Ammodendron, Anabasis, Anacardium, Andrographis, Angophora, Anisodus, Apium, Apocynum, Arabidopsis, Arachis, Argemone, Artemisia, Asclepias, Atropa, Azadirachta, Beilschmiedia, Berberis, Bertholletia, Beta, Betula, Bixa, Bleekeria, Borago, Brassica, Calendula, Camellia, Camptotheca, Canarium, Cannabis, Capsicum, Carthamus, Carya, Catharanthus, Centella, Cephaelis, Chelidonium, Chenopodium, Chrysanthemum, Cicer, Cichorium, Cinchona, Cinnamomum, Cissampelos, Citrus, Citrullus, Cocculus, Cocos, Coffea, Cola, Coleus, Convolvulus, Coptis, Corylus, Corymbia, Crambe, Crotalaria, Croton, Cucumis, Cucurbita, Cuphea, Cytisus, Datura, Daucus, Dendromecon, Dianthus, Dichroa, Digitalis, Dioscorea, Duguetia, Erythroxylum, Eschscholzia, Eucalyptus, Euphorbia, Euphoria, Ficus, Fragaria, Galega, Gelsemium, Glaucium, Glycine, Glycyrrhiza, Gossypium, Helianthus, Heliotropium, Hemsleya, Hevea, Hydrastis, Hyoscyamus, Jatropha, Juglans, Lactuca, Landolphia, Lavandula, Lens, Linum, Litsea, Lobelia, Luffa, Lupinus, Lycopersicon, Macadamia, Mahonia, Majorana, Malus, Mangifera, Manihot, Meconopsis, Medicago, Menispermum, Mentha, Micropus, Nicotiana, Ocimum, Olea, Origanum, Papaver, Parthenium, Persea, Petunia, Phaseolus, Physostigma, Pilocarpus, Pistacia, Pisum, Poinsettia, Populus, Prunus, Psychotria, Pyrus, Quillaja, Rabdosia, Raphanus, Rauwolfia, Rhizocarya, Ricinus, Rosa, Rosmarinus, Rubus, Rubia, Salix, Salvia, Sanguinaria, Scopolia, Senecio, Sesamum, Simmondsia, Sinapis, Sinomenium, Solanum, Sophora, Spinacia, Stephania, Strophanthus, Strychnos, Tagetes, Tanacetum, Theobroma, Thymus, Trifolium, Trigonella, Vaccinium, Vicia, Vigna, Vinca,* and *Vitis*; and the monocot genera *Agrostis, Allium, Alstroemeria, Ananas, Andropogon, Areca, Arundo, Asparagus, Avena, Cocos, Colchicum, Convallaria, Curcuma, Cynodon, Elaeis, Eragrostis, Erianthus, Festuca, Festulolium, Galanthus, Hemerocallis, Hordeum, Lemna, Lolium, Miscanthus, Musa, Oryza, Panicum, Pennisetum, Phalaris, Phleum, Phoenix, Poa, Ruscus, Saccharum, Secale, Sorghum, Spartina, Triticosecale, Triticum, Uniola, Veratrum, Zea,* and *Zoysia*; and the gymnosperm genera *Abies, Cephalotaxus, Cunninghamia, Ephedra, Picea, Pinus, Pseudotsuga,* and *Taxus.*

In some embodiments, a plant can be a species selected from *Abelmoschus esculentus* (okra), *Abies* spp. (fir), *Acer* spp. (maple), *Allium cepa* (onion), *Alstroemeria* spp., *Ananas comosus* (pineapple), *Andrographis paniculata, Andropogon gerardii* (big bluestem), *Artemisia annua, Arundo donax* (giant reed), *Atropa belladonna, Avena sativa,* bamboo, bentgrass (*Agrostis* spp.), *Berberis* spp., *Beta vulgaris* (sugarbeet), *Bixa orellana, Brassica juncea, Brassica napus* (canola), *Brassica rapa, Brassica oleracea* (broccoli, cauliflower, brusselsprouts), *Calendula officinalis, Camellia sinensis* (tea), *Camptotheca acuminate, Cannabis sativa, Capsicum annum* (hot & sweet pepper), *Carthamus tinctorius* (safflower), *Catharanthus roseus, Cephalotaxus* spp., *Chrysanthemum parthenium, Cinchona officinalis, Citrullus lanatus* (watermelon), *Coffea arabica* (coffee), *Colchicum autumnale, Coleus forskohlii, Cucumis melo* (melon), *Cucumis sativus* (cucumber), *Cucurbita maxima* (squash), *Cucurbita moschata* (squash), *Cynodon dactylon* (bermudagrass), *Datura stomonium, Dianthus caryophyllus* (carnation), *Digitalis lanata, Digitalis purpurea, Dioscorea* spp., *Elaeis guineensis* (palm), *Ephedra sinica, Ephedra* spp., *Erianthus* spp., *Erythroxylum coca, Eucalyptus* spp. (eucalyptus), *Festuca arundinacea* (tall fescue), *Fragaria ananassa* (strawberry), *Galanthus wornorii, Glycine max* (soybean), *Gossypium hirsutum* (cotton), *Gossypium herbaceum, Helianthus annuus* (sunflower), *Hevea* spp. (rubber), *Hordeum vulgare, Hyoscyamus* spp., *Jatropha curcas* (jatropha), *Lactuca sativa* (lettuce), *Linum usitatissimum* (flax), *Lupinus albus* (lupin), *Lycopersicon esculentum* (tomato), *Lycopodium serratum* (=*Huperzia serrata*), *Lycopodium* spp., *Manihot esculenta* (cassava), *Medicago sativa* (alfalfa), *Mentha piperita* (mint), *Mentha spicata* (mint), *Miscanthus* spp., *Miscanthus giganteus* (miscanthus), *Musa paradisiaca* (banana), *Nicotiana tabacum* (tobacco), *Oryza sativa* (rice), *Panicum* spp., *Panicum virgatum* (switchgrass), *Papaver somniferum* (opium poppy), *Papaver orientale, Parthenium argentatum* (guayule), *Pennisetum glaucum* (pearl millet), *Pennisetum purpureum* (elephant grass), *Petunia* spp. (petunia), *Phalaris arundinacea* (reed canarygrass), *Pinus* spp. (pine), *Poinsettia pulcherrima* (poinsettia), *Populus* spp., *Populus balsamifera* (poplar), *Populus tremuloides* (aspen), *Rauwolfia serpentina, Rauwolfia* spp., *Ricinus communis* (castor), *Rosa* spp. (rose), *Saccharum* spp. (energycane), *Salix* spp. (willow), *Sanguinaria canadensis, Scopolia* spp., *Secale cereale* (rye), *Solanum melongena* (eggplant), *Solanum tuberosum* (potato), *Sorghum* spp., *Sorghum almum, Sorghum bicolor* (sorghum), *Sorghum halapense, Sorghum vulgare, Spartina pectinata* (prairie cordgrass), *Spinacea oleracea* (spinach), *Tanacetum parthenium, Taxus baccata, Taxus brevifolia, Theobroma cacao* (cocoa), *Triticale* (wheat×rye), *Triticum aestivum* (wheat), *Uniola paniculata* (oats), *Veratrum californica, Vinca rosea, Vitis vinifera* (grape), and *Zea mays* (corn).

Transgenic Plant Phenotypes

A transformed cell, callus, tissue, or plant can be identified and isolated by selecting or screening the engineered plant material for particular traits or activities, e.g., expression of a selectable marker gene or modulation of low-light tolerance. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known.

A population of transgenic plants can be screened and/or selected for those members of the population that have a desired trait or phenotype conferred by expression of the transgene. For example, a population of progeny of a single transformation event can be screened for those plants having a desired level of expression of a low light tolerance polypeptide or nucleic acid. As an alternative, a population of plants comprising independent transformation events can be screened for those plants having increased tolerance to conditions of low light irradiation. Selection and/or screening can be carried out over one or more generations, which can be useful to identify those plants that have a desired trait, such as an increased tolerance to conditions of low light irradiation. Selection and/or screening can also be carried out in more than one geographic location. In some cases, transgenic plants can be grown and selected under conditions which induce a desired phenotype or are otherwise necessary to produce a desired phenotype in a transgenic plant. In addition, selection and/or screening can be carried out during a particular developmental stage in which the phenotype is exhibited by the plant.

The phenotype of a transgenic plant can be evaluated relative to a control plant that does not express the exogenous polynucleotide of interest, such as a corresponding wild type plant, a corresponding plant that is not transgenic for the exogenous polynucleotide of interest but otherwise is of the same genetic background as the transgenic plant of interest, or a corresponding plant of the same genetic background in which expression of the polypeptide is suppressed, inhibited, or not induced (e.g., where expression is under the control of an inducible promoter). A plant can be said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

The phenotype of a transgenic plant and a corresponding control plant that either lacks the transgene or does not express the transgene can be evaluated under particular environmental conditions. For example, the phenotype of a transgenic plant and a corresponding control plant can be evaluated under conditions of low light irradiance. Low light conditions are conditions under which a plant is exposed to an irradiance of about 0.01 µmol/m$^2$/s of light to about 20 µmol/m$^2$/s of light at room temperature and about 70% relative humidity. For example, conditions under which a plant is exposed to 0.01, 1, 5, 10, 15, or 20 µmol/m$^2$/s of light are low light conditions. Sources of lighting and other equipment appropriate for controlling light conditions are known to those in art.

Low light conditions typically have light of a combination of wavelengths, such as white light. White light can be supplied, e.g., by 32 watt fluorescent bulbs (Sylvania, F032/841/ECO, Danvers, Mass.), providing a red:far-red ratio of 13:1. Red wavelengths typically range from a photon irradiance of about 630 to about 700 nm. Far-red wavelengths typically range from a photon irradiance of about 700 to about 750 nm.

In some embodiments, the phenotype of a transgenic plant is assayed under low light conditions in which there is continuous low light during the light period of a light/dark cycle. Continuous low light conditions can be, for example, 16 hours of irradiance with 0.01 to 20 µmol/m$^2$/s of light alternating with 8 hours of darkness. The phenotype of a transgenic plant is assayed once the plant has been exposed to continuous low light conditions during the light period of the light/dark cycle for seven days.

A transgenic plant comprising an exogenous nucleic acid encoding a low light-tolerance polypeptide can exhibit one or more of the following phenotypic differences relative to a corresponding control plant under low light conditions: decreased extension growth, e.g., decreased petiole length, decreased hypocotyl length, decreased internode spacing, and decreased leaf elongation in cereals; increased leaf development, e.g., increased leaf thickness and reduced leaf area growth; decreased apical dominance, e.g., increased branching and tillering; increased chloroplast development, e.g., increased chlorophyll synthesis and a change in the balance of the chlorophyll a:b ratio; alterations in flowering and seed/fruit production, e.g., an increased rate of flowering, an increase in seed set, and increased fruit development; and an increase in storage organ deposition.

Typically, a difference (e.g., an increase) in a morphological feature in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the dimensions of any individual morphological feature is statistically significant at $p<0.01$, $p<0.005$, or $p<0.001$. A statistically significant difference in, for example, a morphological feature in a transgenic plant compared to the corresponding morphological feature a control plant indicates that (1) expression of the recombinant nucleic acid present in the transgenic plant confers the alteration in the morphological feature and/or (2) the recombinant nucleic acid warrants further study as a candidate for altering the morphological feature in a plant.

One suitable phenotype to measure is hypocotyl length. When wild-type seedlings are grown under low light conditions, the hypocotyl length is typically significantly increased relative to the hypocotyl length found in wild-type seedlings grown under conditions of irradiance with about 100 µmol/m$^2$/s of white light.

Seedlings of a transgenic plant and seedlings of a corresponding control plant that either lacks the transgene or does not express the transgene can be grown under low light conditions and, at the appropriate time, hypocotyl lengths from seedlings of each group can be measured. Under low light conditions, a seedling in which the expression of a low light-tolerance polypeptide is increased can have a significantly shorter hypocotyl length than a seedling of a corresponding control plant. The hypocotyl length can be shorter by at least 10 percent, e.g., 10, 15, 20, 25, 30, 35, 40, 45, 50, 55, 60, 65, 70, 75, or more than 75 percent, as compared to the hypocotyl length of a corresponding control plant.

Transgenic plants provided herein have particular uses in agricultural industries. For example, transgenic plants expressing a low light-tolerance polypeptide provided herein can be superior to corresponding control plants in maintaining development and maturation under low light conditions. Such a trait can increase plant survival and seedling establishment at high plant densities, even in crops when plants are near mature growth stages. Transgenic plants expressing a low light-tolerance polypeptide can be more densely planted than those that are not tolerant to low light conditions. Expression of a low light-tolerant polypeptide in plants can provide increased yields compared to plants that are not low light tolerant and that are grown under similar conditions. In addition, expression of polypeptide conferring low light-tolerance in a plant, such as corn, can ensure reasonable seed set in the event that low light conditions prevail during critical stages of plant development, e.g., pollination.

The materials and methods described herein are useful for modifying biomass characteristics, such as characteristics of biomass renewable energy source plants. A biomass renewable energy source plant is a plant having or producing material (either raw or processed) that comprises stored solar energy that can be converted to fuel. In general terms, such plants comprise dedicated energy crops as well as agricultural and woody plants. Examples of biomass renewable energy source plants include: switchgrass, elephant grass, giant chinese silver grass, energycane, giant reed (also known as wild cane), tall fescue, bermuda grass, sorghum, napier grass (also known as uganda grass), triticale, rye, winter wheat, shrub poplar, shrub willow, big bluestem, reed canary grass, and corn.

Information that the polypeptides disclosed herein can modulate low light tolerance can be useful in breeding of plants. Based on the effect of disclosed polypeptides on low light tolerance, one can search for and identify polymorphisms linked to genetic loci for such polypeptides. Polymorphisms that can be identified include simple sequence repeats (SSRs), rapid amplification of polymorphic DNA (RAPDs), amplified fragment length polymorphisms (AFLPs) and restriction fragment length polymorphisms (RFLPs).

If a polymorphism is identified, its presence and frequency in populations is analyzed to determine if it is statistically significantly correlated to an alteration in low light tolerance. Those polymorphisms that are correlated with an alteration in low light tolerance can be incorporated into a marker assisted breeding program to facilitate the development of lines that have a desired alteration in low light tolerance. Typically, a polymorphism identified in such a manner is used with polymorphisms at other loci that are also correlated with a desired alteration in low light tolerance.

Articles of Manufacture

Seeds of transgenic plants described herein can be conditioned and bagged in packaging material by means known in the art to form an article of manufacture. Packaging material such as paper and cloth are well known in the art. A package of seed can have a label e.g., a tag or label secured to the packaging material, a label printed on the packaging material, or a label inserted within the package.

Plants, plant tissues, and/or seeds from plants grown from seeds having an exogenous nucleic acid encoding a low light-tolerance polypeptide can be used for making products including, without limitation, human and animal foods, textiles, oils, and/or ethanol.

The invention will be further described in the following examples, which do not limit the scope of the invention described in the claims.

EXAMPLES

Example 1

Transgenic Plants

The following symbols are used in the Examples: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

Ceres Clone 28780 (genomic locus At1g07090; SEQ ID NO:87) is a cDNA clone that was isolated from *Arabidopsis* and is predicted to encode a 196 amino acid polypeptide (SEQ ID NO:88) designated LSH6. Ceres Clone 28780 was cloned into a Ti plasmid vector, CRS 338, containing a phosphinothricin acetyltransferase gene, which confers transformed plants with Finale® resistance. The construct made using the CRS 338 vector contained Ceres Clone 28780 operably linked to a CaMV 35S promoter. Wild-type *Arabidopsis thaliana* ecotype Wassilewskija (Ws) plants were transformed with the construct containing Ceres Clone 28780. The transformation was performed essentially as described in Bechtold and Pelletier, *Methods Mol Biol.*, 82:259-66 (1998).

A transgenic *Arabidopsis* line containing Ceres Clone 28780 was designated ME05917. The presence of the vector containing Ceres Clone 28780 in the transgenic *Arabidopsis* line transformed with the vector was confirmed by Finale® resistance, polymerase chain reaction (PCR) amplification from green leaf tissue extract, and/or sequencing of PCR products.

The segregation of Finale® resistance for $T_2$ plants from events -01 and -08 of ME05917 was 3:1 (resistant:sensitive).

Example 2

Identification of Transgenic Plants Tolerant to Low Light Conditions

Wild-type and transgenic seeds were sterilized, plated on solid 0.5×MS medium containing 5 g/L sucrose, and stratified at 4° C. in the dark for three days. After stratification, plates containing the seeds were allowed to reach room temperature. The plates were then transferred to a Conviron walk-in growth chamber (Controlled Environments Inc., Pambina, N. Dak.) at 22° C. and 70% humidity with a 16:8 hour light:dark cycle. Lighting was supplied by 32 watt fluorescent bulbs (Sylvania, F032/841/ECO, Danvers, Mass.), providing a red: far-red ratio of 13:1. The plates were covered with three layers of shade cloth (New York wire, charcoal fiberglass screen, 857650; Home Depot, Atlanta, Ga.) such that the irradiance was about 10 μmol/m²/s. The plates were rotated daily and monitored for changes in hypocotyl elongation. After 48 hours, the plates were scored for late germinators, which were eliminated from consideration as candidate plants having reduced hypocotyl elongation under low light conditions. Each seedling was transplanted to an 8×8 cm well of a flat containing a total of 18 wells (three wells by six wells) and measuring 24 cm by 48 cm in size.

Seedlings maintained under conditions of irradiance with about 10 µmol/m$^2$/s of light for seven days at 22° C. were analyzed for hypocotyl length. Transgenic seedlings having a shorter hypocotyl length than the hypocotyl length of corresponding wild-type seedlings were selected and analyzed using PCR and DNA sequencing to identify the transgenes. The transgenic *Arabidopsis* line ME05917, described in Example 1, was identified as having reduced hypocotyl elongation under the low light conditions as compared to wild-type control plants.

Example 3

Characterization of the Low Light Tolerance of Seedlings from ME05917 Events $T_2$ and $T_3$ seedlings from events -01 and -08 of ME05917 were grown under low light conditions and evaluated for hypocotyl length as described in Example 2. A Chi-square test was performed to compare transgenic seedlings and corresponding non-transgenic segregants having a short or a long hypocotyl. A hypocotyl having a length similar to the hypocotyl length typically exhibited by wild-type *Arabidopsis* seedlings grown under normal light conditions (e.g., about 100 µmol/m$^2$/s of white light) was considered a short hypocotyl, whereas a hypocotyl having a length similar to that typically exhibited by wild-type *Arabidopsis* seedlings grown under low light conditions (e.g., about 10 µmol/m$^2$/s of white light) was considered a long hypocotyl. Wild-type *Arabidopsis* seeds grown for seven days at 22° C. under conditions of irradiance with about 100 µmol/m$^2$/s of white light and a 16:8 hour light:dark cycle typically form hypocotyls that are about 1-3 mm in length. Under conditions of irradiance with about 10 µmol/m$^2$/s of white light, the hypocotyls typically are about 5-7 mm in length.

Seedlings from events -01 and -08 of ME05917 displayed a short hypocotyl under low light conditions in both the $T_2$ and $T_3$ generations, and the transgene was linked to the short hypocotyl phenotype with a confidence level of p<0.05 (Table 1).

TABLE 1

Chi-square comparison of the hypocotyl length of transgenic seedlings and non-transgenic segregants grown under low light irradiance (10 µmol/m$^2$/s) for seven days

| Plants | Short Hypocotyl | Long Hypocotyl | Chi-Square | p-value |
| --- | --- | --- | --- | --- |
| T$_2$ seedlings from event-01 of ME05917 | 42 | 0 | 39.71 | 2.95E-10 |
| T$_2$ non-transgenic segregants of event-01 of ME05917 | 2 | 8 | | |
| T$_3$ seedlings from event-01 of ME05917 | 38 | 2 | 46.93 | 7.37E-12 |
| T$_3$ non-transgenic segregants of event-01 of ME05917 | 2 | 21 | | |
| T$_2$ seedlings from event-08 of ME05917 | 15 | 7 | 10.91 | 9.57E-04 |
| T$_2$ non-transgenic segregants of event-08 of ME05917 | 0 | 8 | | |
| T$_3$ seedlings from event-08 of ME05917 | 37 | 8 | 43.8 | 3.63E-11 |
| T$_3$ non-transgenic segregants of event-08 of ME05917 | 1 | 28 | | |

The expression level of genomic locus At1g07090 in two week old $T_3$ plants from single insertion events -01-09 and -08-28 of the transgenic line ME05917 was determined using RT-PCR and quantitative RT-PCR. The plants were grown under conditions of irradiance with about 100 µmol/m$^2$/s of white light. Aerial tissue was collected from five plants from each of events -01-09 and -08-28 of ME05917 and from five corresponding non-transgenic segregant plants. The tissues were flash frozen in liquid nitrogen, and total RNA was extracted from the tissues using a plant RNeasy kit (Qiagen, Valencia, Calif.). First strand cDNA was synthesized using 1000 ng of total RNA and Superscript II (Invitrogen, Carlsbad, Calif.). PCR was performed using one µL of the first strand cDNA reaction. The PCR conditions were as follows: 94° C. for five minutes; 25 cycles of 94° C. for 30 seconds, 58° C. for one minute, and 72° C. for 40 seconds; and 72° C. for seven minutes. Expression of tubulin was measured as an internal standard. The primers used to detect expression of tubulin were: TUB-F1, 5'-GTTGAGCCGTACAATGCAAC-3' (SEQ ID NO:95) and TUB-R1, 5'-CTGTTCGTCCACT-TCCTTG-3' (SEQ ID NO:96). The primers used to detect expression of At1g07090 were: 05917-F, 5'-AGCAGGTAT-GAGTCACAGAAGCGA-3' (SEQ ID NO:97) and 05917-R, 5'-ACAGATGGAGCACCGACGTTACAA-3' (SEQ ID NO:98). Equal volumes of the PCR reactions were analyzed using 1% agarose gel electrophoresis. Quantitative PCR was performed using an iCycler system (BioRad, Hercules, Calif.) and standard protocols.

The expression level of At1g07090, as analyzed using RT-PCR, was elevated in $T_3$ plants from both events of ME05917 analyzed, -01-09 and -08-28, as compared to the expression level of At1g07090 in corresponding wild-type or non-transgenic segregant plants. Analysis of At1g07090 expression using quantitative PCR indicated that the expression level of At1g07090 was increased by 312-fold and 233-fold in ME05917 plants from events -01-09 and -08-28, respectively, compared to the expression level of At1g07090 in non-transgenic segregant plants of event -01-28 of ME05917. These results indicated that the expression level of At1g07090 in plants from event -01-09 was about 34% higher than the expression level in plants from event -08-28.

The low light tolerance, as measured by reduced hypocotyl elongation, of seedlings from ME05917 events was characterized further. $T_2$ seedlings from events -01 and -08 of ME05917, $T_3$ seedlings from single insertion events -01-09 and -08-28 of the homozygous ME05917 line, $T_3$ non-transgenic segregants of ME05917-01-28, and wild-type *Arabidopsis thaliana* ecotype Wassilewskija (Ws) seedlings were grown under conditions of irradiance with about 10 µmol/m$^2$/s of white light as described in Example 2. The hypocotyl lengths of about ten seedlings from each event were measured after seven days using digital calipers.

The average hypocotyl length of $T_2$ and $T_3$ seedlings from each event of ME05917 analyzed was significantly shorter than the average hypocotyl length of corresponding non-transgenic segregants or wild-type seedlings (Table 2).

TABLE 2

Hypocotyl length of seedlings from ME05917 events grown under conditions of irradiance with about 10 μmol/m² /s of white light

|  | $T_2$ seedlings from event -01 | $T_2$ seedlings from event -08 | $T_3$ seedlings from event -01-09 | $T_3$ seedlings from event -08-28 | Non-transgenic segregants of event -01-28 | Wild-type seedlings |
|---|---|---|---|---|---|---|
| Average hypocotyl length (mm) ± standard deviation | 2.098 ± 0.451 | 2.503 ± 0.893 | 1.868 ± 0.169 | 2.071 ± 0.289 | 4.358 ± 0.443 | 4.931 ± 0.312 |
| p-value versus non-transgenic segregants | 4.54E−09 | 2.54E−03 | 2.00E−09 | 4.67E−10 | N/A | N/A |
| p-value versus wild-type seedlings | 2.66E−10 | 7.68E−04 | 5.43E−12 | 3.43E−13 | N/A | N/A |

$T_3$ seedlings from single insertion events -01-09 and -08-28 of the homozygous ME05917 line, $T_3$ non-transgenic segregants of ME05917-01-28, and wild-type *Arabidopsis thaliana* ecotype Wassilewskija (Ws) seedlings were also grown under conditions of irradiance with about 100 μmol/m²/s of white light as described in Example 2. The hypocotyl lengths of about ten seedlings from each event were measured after seven days using digital calipers.

The average hypocotyl length of $T_3$ seedlings from each event of ME05917 analyzed was significantly shorter than the average hypocotyl length of corresponding non-transgenic segregants or wild-type seedlings (Table 3).

regants of ME05917-01-28, and wild-type *Arabidopsis thaliana* ecotype Wassilewskija (Ws) seedlings were also grown in the dark. The seeds were prepared as described in Example 2 and exposed to about 100 μmol/m²/s of white light for two hours to promote uniform germination prior to covering the plates with aluminum foil. The seeds were grown in the dark at 22° C. and 70% humidity for five days, after which the hypocotyl lengths of about ten seedlings from each event were measured using digital calipers.

The average hypocotyl length of $T_3$ seedlings from each event of ME05917 analyzed was significantly shorter than the

TABLE 3

Hypocotyl length of $T_3$ seedlings from ME05917 events grown under conditions of irradiance with about 100 μmol/m2/s of white light

|  | Event-01-09 | Event-08-28 | Non-transgenic segregants of event-01-28 | Wild-type seedlings |
|---|---|---|---|---|
| Average hypocotyl length (mm) ± standard deviation | 1.535 ± 0.232 | 1.754 ± 0.183 | 2.187 ± 0.356 | 2.077 ± 0.224 |
| p-value versus non-transgenic segregants | 1.95E−04 | 4.39E−03 | N/A | N/A |
| p-value versus wild-type seedlings | 4.70E−05 | 2.50E−03 | N/A | N/A |

$T_3$ seedlings from single insertion events -01-09 and -08-28 of the homozygous ME05917 line, $T_3$ non-transgenic segaverage hypocotyl length of corresponding non-transgenic segregants or wild-type seedlings (Table 4).

TABLE 4

Hypocotyl length of $T_3$ seedlings from ME05917 events grown in the dark

|  | Event-01-09 | Event-08-28 | Non-transgenic segregants of event-01-28 | Wild-type seedlings |
|---|---|---|---|---|
| Average hypocotyl length (mm) ± standard deviation | 9.496 ± 1.526 | 10.850 ± 0.887 | 13.008 ± 1.317 | 12.494 ± 1.420 |
| p-value versus non-transgenic segregants | 1.28E−05 | 3.32E−04 | N/A | N/A |

TABLE 4-continued

Hypocotyl length of $T_3$ seedlings from ME05917 events grown in the dark

| | Event-01-09 | Event-08-28 | Non-transgenic segregants of event-01-28 | Wild-type seedlings |
|---|---|---|---|---|
| p-value versus wild-type seedlings | 1.70E−04 | 7.18E−03 | N/A | N/A |

No cotyledon phenotypes were observed in transgenic seedlings as compared to non-transgenic segregating controls (FIG. 2). Interestingly, $T_3$ seedlings from event -01-09 of ME05917 had a shorter average hypocotyl length than $T_3$ seedlings from event -08-28 of ME05917 when grown in the dark or under conditions of irradiance with about 100 μmol/m²/s of white light (p<0.05). As presented above, the expression level of At1g07090 in plants from event -01-09 was higher than the expression level in plants from event -08-28. Taken together, these results suggest that reduction in hypocotyl elongation is proportional to the expression level of At1g07090 in ME05917 plants.

Example 4

Characterization of the Low Light Tolerance of Adult Plants from ME05917 Events

Seeds from transgenic ME05917 plants and corresponding control plants were sown in a checkerboard pattern in no-hole utility flats. Wild-type *Arabidopsis thaliana* ecotype Wassilewskija (Ws) plants and non-transgenic segregating plants were used as control plants. The flats were covered with propagation domes and maintained at 4° C. in the dark for three days. The flats were then transferred to a Conviron walk-in growth chamber (Controlled Environments Inc.) with a 16:8 hour light:dark cycle, a relative humidity of 70%, a temperature of 22° C., and an irradiance of about 150 μmol/m²/s of light having a red to far-red ratio greater than one. The propagation domes were removed after four days. After three weeks, the flats were divided into two groups of plants. One group, referred to as the normal light treatment (NLT) group, remained under the same conditions, with a 16:8 hour light:dark cycle, a relative humidity of 70%, a temperature of 22° C., and an irradiance of about 150 μmol/m²/s of light having a red to far-red ratio greater than one, for the duration of the experiment. The other group, referred to as the low light stress treatment (LLT) group, was placed under three layers of shade screen to reduce the irradiance to about 15 μmol/m²/s without altering the spectral quality. After one week, the shade screens were removed, and the low light stress treatment group was once again grown under an irradiance of about 150 μmol/m²/s.

Figure 3:
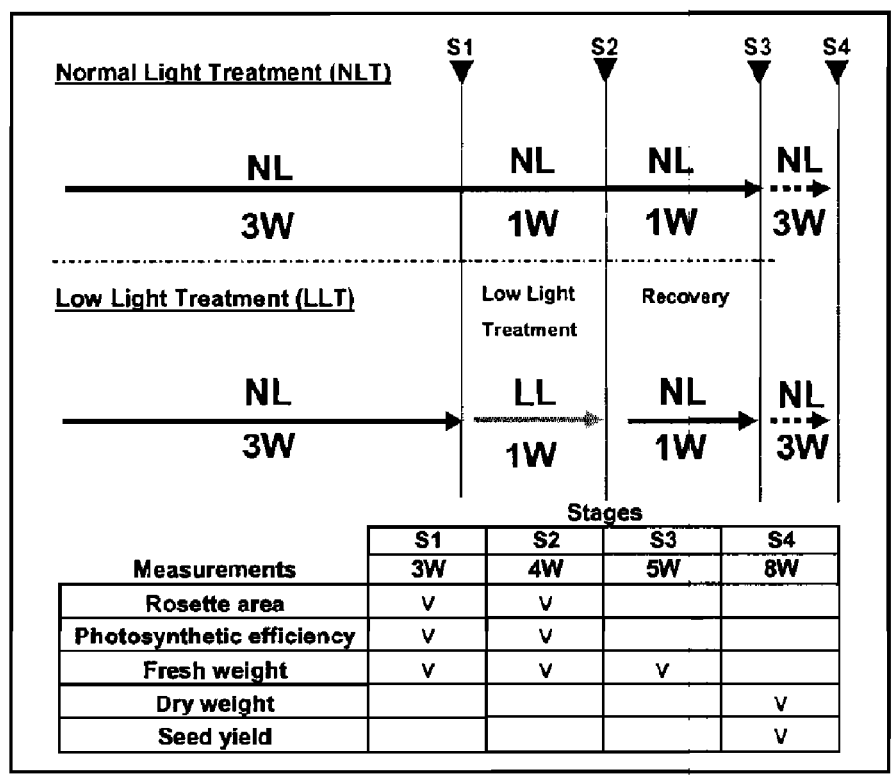
FIG. 3 is a schematic diagram depicting the time course for measuring parameters of adult plants grown under normal light (NL) or low light (LL) conditions. NL and LL refer to conditions of irradiance with about 150 and 15 µmol/m²/s of light, respectively.

Measurements were taken at four different stages (FIG. 3). Stage one occurred after three weeks of growth under normal light conditions (irradiance of about 150 μmol/m²/s) and before transfer of the LLT group to low light conditions (irradiance of about 15 μmol/m²/s). Stage two occurred after three weeks of growth under normal light conditions and one week of growth under low light conditions for the LLT group, and before transfer of the LLT group back to normal light conditions. Stage three occurred one week after transfer of the LLT back to normal light conditions, when the plants were five weeks old. Stage four occurred after senescence, when the plants were eight weeks old. Photosynthetic efficiency was measured at stage two, and rosette areas were measured at stages one and two. Fresh weight was measured at stages one, two, and three. Dry weight and seed yield were determined at stage four. Six to nine replicate plant samples were measured at each stage for each treatment group, and the average values and standard deviations were calculated.

To measure photosynthetic efficiency, plants were first placed in the dark for at least 20 minutes. Rosettes were removed from the plants by cutting at the rosette-root junction. Detached rosettes were placed in the middle of the stage of a CF Imager (Technologica Ltd., Essex, UK). Chlorophyll fluorescence was measured with a pulse intensity of 4400 μmol/m²/s and a pulse length of 800 ms. The area of each rosette was also measured using the CF imager.

After measuring photosynthetic efficiency and rosette area, the rosette was removed from the CF imager and weighed along with the stem from which it was removed. The weight was recorded as the fresh weight measurement.

Seed and dry weight measurements were obtained when plants were eight weeks old. Plants were harvested individually and allowed to dry completely at 28° C. for three days. The seed was separated from the dried plant material using a sieve (300 μM mesh size) and weighed. The dried plant material was added to the seed and the combined weight was recorded as the dry weight.

Results $T_3$ plants from single insertion events -01-09 and -08-28 of the homozygous ME05917 line, $T_3$ non-transgenic segregants of ME05917-01-28, and wild-type *Arabidopsis thaliana* ecotype Wassilewskija (Ws) plants were grown under conditions of irradiance with about 150 μmol/m²/s of light and analyzed to determine the number of days that elapsed between seed sowing (after stratification) and primary bolt emergence of about one cm, or days to bolt. $T_3$ plants from event -01-09 were not observed to differ significantly in days to bolt from corresponding non-transgenic segregant or wild-type control plants (Table 5). $T_3$ plants from event -08-28 also were observed to not differ significantly from non-transgenic segregants in days to bolt, whereas the average number of days to bolt for plants from event -08-28 was significantly lower than the average number of days to bolt for wild-type plants (Table 5). On average, transgenic and control plants bolted about 15 to 17 days post-germination (Table 5).

TABLE 5

Days to bolt for $T_3$ plants from ME05917 events

|  | Event -01-09 | Event -08-28 | Non-transgenic segregants of event -01-28 | Wild-type Arabidopsis Ws plants |
|---|---|---|---|---|
| Average days to bolt ± standard deviation | 17.267 ± 1.163 | 15.278 ± 1.274 | 16.529 ± 0.943 | 17.056 ± 0.791 |
| p-value versus non-transgenic segregants | 6.12E−02 | 5.40E−02 | N/A | N/A |
| p-value versus wild-type plants | 5.27E−01 | 1.49E−05 | N/A | N/A |

Rosette areas of $T_3$ plants from single insertion events -01-09 and -08-28 of the homozygous ME05917 line, $T_3$ non-transgenic segregants of ME05917-01-28, and wild-type *Arabidopsis thaliana* ecotype Wassilewskija (Ws) plants in the NLT or LLT group were analyzed at stage one (three weeks old) and stage two (four weeks old), as described above. The average rosette area of $T_3$ plants from events -01-09 and -08-28 of ME05917 was significantly smaller than the average rosette area of corresponding non-transgenic segregants and wild-type plants after three weeks of growth under conditions of irradiance of about 150 mol/m$^2$/s of light, in the absence of any low light treatment (Table 6). As presented in Table 6, the average rosette area of plants from events -01-09 and -08-28 was about 50% smaller than the average rosette area of non-transgenic segregants, and more than 60% smaller than the average rosette area of wild-type plants under conditions of irradiance with about 150 mol/m$^2$/s of light.

TABLE 6

Rosette area of $T_3$ plants from ME05917 events

|  | Average rosette area ± standard deviation | p-value versus non-transgenic segregants | p-value versus wild-type plants |
|---|---|---|---|
| Event -01-09 3 weeks under 150 μmol/m$^2$/s of light | 210.286 ± 25.736 | 1.34E−07 | 3.01E−07 |
| Event -01-09 3 weeks under 150 μmol/m$^2$/s of light and 1 week under 15 μmol/m$^2$/s of light | 508.171 ± 88.517 | 5.66E−03 | 4.63E−03 |
| Event -01-09 4 weeks under 150 μmol/m$^2$/s of light | 455.942 ± 93.474 | 7.59E−04 | 1.42E−07 |
| Event -08-28 3 weeks under 150 μmol/m$^2$/s of light | 208.410 ± 44.842 | 8.91E−08 | 3.32E−08 |
| Event -08-28 3 weeks under 150 μmol/m$^2$/s of light and 1 week under 15 μmol/m$^2$/s of light | 332.390 ± 75.840 | 7.57E−06 | 3.08E−06 |
| Event -08-28 4 weeks under 150 μmol/m$^2$/s of light | 465.543 ± 100.938 | 1.55E−03 | 4.10E−07 |
| Non-transgenic segregants of event -01-28 3 weeks under 150 μmol/m$^2$/s of light | 414.811 ± 49.785 | N/A | N/A |
| Non-transgenic segregants of event -01-28 3 weeks under 150 μmol/m$^2$/s of light and 1 week under 15 μmol/m$^2$/s of light | 663.623 ± 114.433 | N/A | N/A |
| Non-transgenic segregants of event -01-28 4 weeks under 150 μmol/m$^2$/s of light | 721.074 ± 164.671 | N/A | N/A |
| Wild-type Arabidopsis Ws plants 3 weeks under 150 μmol/m$^2$/s of light | 558.520 ± 67.430 | N/A | N/A |
| Wild-type Arabidopsis Ws plants 3 weeks under 150 μmol/m$^2$/s of light and 1 week under 15 μmol/m$^2$/s of light | 632.495 ± 63-954 | N/A | N/A |
| Wild-type Arabidopsis Ws plants 4 weeks under 150 μmol/m$^2$/s of light | 1003.666 ± 122.442 | N/A | N/A |

At stage two, the average rosette area of plants from events -01-09 and -08-28 of ME05917 was significantly smaller than the average rosette area of control plants, regardless of whether the plants were in the LLT or the NLT group. As presented in Table 6, the average rosette area of plants from events -01-09 and -08-28 in the LLT group was about 23% and 50% smaller, respectively, than the average rosette area of non-transgenic segregants in the LLT group. The average rosette area of plants from events -01-09 and -08-28 in the NLT group was about 37% and 35% smaller, respectively, than the average rosette area of non-transgenic segregants in the NLT group (Table 6).

Although the rosette areas of plants from events -01-09 and -08-28 of ME05917 were reduced (Table 6), the photosynthetic efficiency was similar to that of non-transgenic segregating and wild-type controls. As presented in Table 7, there were no significant differences in photosynthetic efficiency between plants from events -01-09 and -08-28 of ME05917 and non-transgenic segregrants or wild-type plants in the LLT or NLT group at stage two.

TABLE 7

Photosynthetic efficiency of four week old $T_3$ plants from ME05917 events

| | Average photosynthetic efficiency ± standard deviation | p-value versus non-transgenic segregants | p-value versus wild-type plants |
|---|---|---|---|
| Event -01-09 4 weeks under 150 µmol/m²/s of light | 0.784 ± 0.011 | 6.70E−01 | 2.12E−01 |
| Event -01-09 3 weeks under 150 µmol/m²/s of light and 1 week under 15 µmol/m²/s of light | 0.769 ± 0.009 | 4.07E−01 | 6.95E−01 |
| Event -08-28 4 weeks under 150 µmol/m²/s of light | 0.780 ± 0.011 | 2.12E−01 | 5.12E−02 |
| Event -08-28 3 weeks under 150 µmol/m²/s of light and 1 week under 15 µmol/m²/s of light | 0.768 ± 0.010 | 4.19E−01 | 8.32E−01 |
| Non-transgenic segregants of event -01-28 4 weeks under 150 µmol/m²/s of light | 0.787 ± 0.010 | N/A | N/A |
| Non-transgenic segregants of event -01-28 3 weeks under 150 µmol/m²/s of light and 1 week under 15 µmol/m²/s of light | 0.772 ± 0.007 | N/A | N/A |
| Wild-type *Arabidopsis* Ws plants 4 weeks under 150 µmol/m²/s of light | 0.790 ± 0.003 | N/A | N/A |
| Wild-type *Arabidopsis* Ws plants 3 weeks under 150 µmol/m²/s of light and 1 week under 15 µmol/m²/s of light | 0.767 ± 0.007 | N/A | N/A |

Biomass accumulation was assessed based on measurement of the fresh weight of aerial tissues from ME05917 plants and non-transgenic segregants, as described above. The fresh weights of $T_3$ plants from events -01-09 and -08-28 of ME05917 were significantly less than the fresh weights of non-transgenic segregating controls in the LLT group at stages one (3 weeks old), two (four weeks old), and three (five weeks old; Table 8). In the NLT group, the fresh weights of $T_3$ plants from events -01-09 and -08-28 were also significantly less than the fresh weights of non-transgenic segregating controls at stages one and two (Table 8). At stage three, plants from events -01-09 and -08-28 also had fresh weights that were less than the fresh weights of non-transgenic segregating controls, but the difference was less statistically significant (Table 8).

TABLE 8

Fresh weights of three, four, and five week old $T_3$ plants from ME05917 events

| | Average fresh weight ± standard deviation | p-value versus non-transgenic segregants |
|---|---|---|
| Event -01-09 3 weeks under 150 µmol/m²/s of light | 0.155 ± 0.031 | 4.27E−06 |

TABLE 8-continued

Fresh weights of three, four, and five week old $T_3$ plants from ME05917 events

| | Average fresh weight ± standard deviation | p-value versus non-transgenic segregants |
|---|---|---|
| Event -08-28 3 weeks under 150 µmol/m²/s of light | 0.127 ± 0.030 | 4.23E−07 |
| Non-transgenic segregants of event -01-28 3 weeks under 150 µmol/m²/s of light | 0.283 ± 0.044 | N/A |
| Event -01-09 3 weeks under 150 µmol/m²/s of light and 1 week under 15 µmol/m²/s of light | 0.583 ± 0.090 | 4.92E−04 |

TABLE 8-continued

Fresh weights of three, four, and five week old
$T_3$ plants from ME05917 events

| | Average fresh weight ± standard deviation | p-value versus non-transgenic segregants |
|---|---|---|
| Event -08-28<br>3 weeks under 150 µmol/m²/s of light and<br>1 week under 15 µmol/m²/s of light | 0.443 ± 0.149 | 1.33E−04 |
| Non-transgenic segregants of event -01-28<br>3 weeks under 150 µmol/m²/s of light and<br>1 week under 15 µmol/m²/s of light | 0.841 ± 0.144 | N/A |
| Event -01-09<br>3 weeks under 150 µmol/m²/s of light,<br>1 week under 15 µmol/m²/s of light and<br>1 week under 150 µmol/m²/s of light | 1.786 ± 0.534 | 1.25E−03 |
| Event -08-28<br>3 weeks under 150 µmol/m²/s of light,<br>1 week under 15 µmol/m²/s of light and<br>1 week under 150 µmol/m²/s of light | 1.199 ± 0.416 | 3.19E−05 |
| Non-transgenic segregants of event -01-28<br>3 weeks under 150 µmol/m²/s of light,<br>1 week under 15 µmol/m²/s of light and<br>1 week under 150 µmol/m²/s of light | 2.686 ± 0.429 | N/A |
| Event -01-09<br>4 weeks under 150 µmol/m²/s of light | 1.001 ± 0.177 | 1.56E−03 |
| Event -08-28<br>4 weeks under 150 µmol/m²/s of light | 1.136 ± 0.213 | 1.91E−02 |
| Non-transgenic segregants of event -01-28<br>4 weeks under 150 µmol/m²/s of light | 1.498 ± 0.324 | N/A |
| Event -01-09<br>5 weeks under 150 µmol/m²/s of light | 2.002 ± 0.500 | 5.31E−02 |
| Event -08-28<br>5 weeks under 150 µmol/m²/s of light | 2.005 ± 0.486 | 5.61E−02 |
| Non-transgenic segregants of event -01-28<br>5 weeks under 150 µmol/m²/s of light | 3.050 ± 1.347 | N/A |

Although differences in biomass were observed between plants in the LLT and NLT group (Table 8), all of the plants appeared developmentally similar at all stages of growth through bolting, flowering, and senescence. All of the plants flowered prior to low light treatment (Table 5), but growth of reproductive tissue seemed to slow down during low light treatment and the stems appeared weak and spindly. Most of the biomass increases during this time appeared to be due to growth of the rosette. After one week of low light treatment, plants in the LLT group were returned to conditions of irradiance with 150 µmol/m²/s of light for one week. During this period, the stems of $T_3$ plants from events -01-09 and -08-28 of ME05917 and non-transgenic segregating control plants increased in strength, and growth of reproductive tissues seemed to accelerate. After one week of irradiance with 150 µmol/m²/s of light, at stage three, both transgenic ME05917 plants and control plants had segments on most stems where siliques failed to form. No visible differences were observed between transgenic ME05917 plants and non-transgenic segregating control plants in the ability to form siliques under low light stress. All plants continued to develop normally through the termination of flowering and senescence.

After senescence, plants were collected and average dry weight, seed weight, and harvest index (total seed weight divided by total dry weight) were calculated. At harvest, $T_3$ plants from events -01-09 and -08-28 of ME05917 in the LLT group had average dry weights that were 31% and 42% lower, respectively, than the average dry weight of non-transgenic segregating controls in the LLT group (Table 9).

TABLE 9

Dry weight of eight week old $T_3$ plants
from ME05917 events after senescence

| | Average dry weight ± standard deviation | p-value versus non-transgenic segregants | p-value versus wild-type plants |
|---|---|---|---|
| Event -01-09<br>3 weeks under 150 µmol/m²/s of light,<br>1 week under 15 µmol/m²/s of light,<br>and<br>4 weeks under 150 µmol/m²/s of light | 0.480 ± 0.113 | 2.18E−02 | 2.79E−03 |
| Event -08-28<br>3 weeks under 150 µmol/m²/s of light,<br>1 week under 15 µmol/m²/s of light,<br>and<br>4 weeks under 150 µmol/m²/s of light | 0.407 ± 0.125 | 4.54E−03 | 2.68E−04 |
| Non-transgenic segregants of event -08-27<br>3 weeks under 150 µmol/m²/s of light,<br>1 week under 15 µmol/m²/s of light,<br>and<br>4 weeks under 150 µmol/m²/s of light | 0.695 ± 0.218 | N/A | N/A |
| Wild-type *Arabidopsis* Ws plants<br>3 weeks under 150 µmol/m²/s of light,<br>1 week under 15 µmol/m²/s of light,<br>and<br>4 weeks under 150 µmol/m²/s of light | 0.683 ± 0.166 | N/A | N/A |
| Event -01-09<br>8 weeks under 150 µmol/m²/s of light | 0.535 ± 0.188 | 1.15E−05 | 5.80E−06 |
| Event -08-28<br>8 weeks under 150 µmol/m²/s of light | 0.833 ± 0.161 | 3.27E−04 | 1.12E−02 |
| Non-transgenic segregants of event -08-27<br>8 weeks under 150 µmol/m²/s of light | 1.463 ± 0.267 | N/A | N/A |

TABLE 9-continued

Dry weight of eight week old $T_3$ plants from ME05917 events after senescence

| | Average dry weight ± standard deviation | p-value versus non-transgenic segregants | p-value versus wild-type plants |
|---|---|---|---|
| Wild-type *Arabidopsis* Ws plants 8 weeks under 150 μmol/m²/s of light | 1.082 ± 0.295 | N/A | N/A |

$T_3$ plants from events -01-09 and -08-28 of ME05917 in the NLT group had average dry weights that were 63% and 43% lower, respectively, than the average dry weight of non-transgenic segregating controls in the NLT group (Table 9).

The average seed weight of $T_3$ plants from events -01-09 and -08-28 of ME05917 in the LLT group was 25% and 37% lower, respectively, than the average seed weight of non-transgenic segregating controls in the LLT group (Table 10).

TABLE 10

Seed weight of eight week old $T_3$ plants from ME05917 events after senescence

| | Average seed weight ± standard deviation | p-value versus non-transgenic segregants | p-value versus wild-type plants |
|---|---|---|---|
| Event -01-09 3 weeks under 150 μmol/m²/s of light, 1 week under 15 μmol/m²/s of light, and 4 weeks under 150 μmol/m²/s of light | 0.162 ± 0.045 | 3.58E−02 | 7.01E−04 |
| Event -08-28 3 weeks under 150 μmol/m²/s of light, 1 week under 15 μmol/m²/s of light, and 4 weeks under 150 μmol/m²/s of light | 0.136 ± 0.043 | 2.98E−03 | 2.57E−05 |
| Non-transgenic segregants of event -08-27 3 weeks under 150 μmol/m²/s of light, 1 week under 15 μmol/m²/s of light, and 4 weeks under 150 μmol/m²/s of light | 0.215 ± 0.052 | N/A | N/A |
| Wild-type *Arabidopsis* Ws plants 3 weeks under 150 μmol/m²/s of light, 1 week under 15 μmol/m²/s of light, and 4 weeks under 150 μmol/m²/s of light | 0.245 ± 0.051 | N/A | N/A |
| Event -01-09 8 weeks under 150 μmol/m²/s of light | 0.181 ± 0.044 | 3.00E−06 | 1.56E−07 |
| Event -08-28 8 weeks under 150 μmol/m²/s of light | 0.265 ± 0.042 | 3.24E−05 | 1.84E−04 |
| Non-transgenic segregants of event -08-27 8 weeks under 150 μmol/m²/s of light | 0.515 ± 0.077 | N/A | N/A |
| Wild-type *Arabidopsis* Ws plants 8 weeks under 150 μmol/m²/s of light | 0.397 ± 0.110 | N/A | N/A |

The average seed weight of $T_3$ plants from events -01-09 and -08-28 of ME05917 in the NLT group was 65% and 49% lower, respectively, than the average seed weight of non-transgenic segregating controls in the NLT group (Table 10).

The average harvest index of $T_3$ plants from events -01-09 and -08-28 of ME05917 was not observed to differ significantly from the average harvest index of non-transgenic segregating controls in the LLT or NLT group (Table 11).

TABLE 11

Harvest index of eight week old T₃ plants from ME05917 events after senescence

|  | Average harvest index ± standard deviation | p-value versus non-transgenic segregants | p-value versus wild-type plants |
|---|---|---|---|
| Event -01-09<br>3 weeks under 150 μmol/m²/s of light,<br>1 week under 15 μmol/m²/s of light,<br>and<br>4 weeks under 150 μmol/m²/s of light | 0.337 ± 0.035 | 2.40E−01 | 8.18E−02 |
| Event -08-28<br>3 weeks under 150 μmol/m²/s of light,<br>1 week under 15 μmol/m²/s of light,<br>and<br>4 weeks under 150 μmol/m²/s of light | 0.332 ± 0.031 | 3.25E−01 | 3.22E−02 |
| Non-transgenic segregants of event -08-27<br>3 weeks under 150 μmol/m²/s of light,<br>1 week under 15 μmol/m²/s of light,<br>and<br>4 weeks under 150 μmol/m²/s of light | 0.316 ± 0.038 | N/A | N/A |
| Wild-type *Arabidopsis* Ws plants<br>3 weeks under 150 μmol/m²/s of light,<br>1 week under 15 μmol/m²/s of light,<br>and<br>4 weeks under 150 μmol/m²/s of light | 0.364 ± 0.014 | N/A | N/A |
| Event -01-09<br>8 weeks under 150 μmol/m²/s of light | 0.348 ± 0.034 | 6.86E−01 | 1.56E−01 |
| Event -08-28<br>8 weeks under 150 μmol/m²/s of light | 0.324 ± 0.051 | 1.53E−01 | 4.84E−02 |
| Non-transgenic segregants of event -08-27<br>8 weeks under 150 μmol/m²/s of light | 0.354 ± 0.020 | N/A | N/A |
| Wild-type *Arabidopsis* Ws plants<br>8 weeks under 150 μmol/m²/s of light | 0.367 ± 0.014 | N/A | N/A |

Overall, T₃ plants from events -01-09 and -08-28 of ME05917 were observed to have a shorter plant height at harvest than non-transgenic segregating controls or wild type plants.

Example 5

Transgenic Plants

The following DNA clones were isolated from *Arabidopsis thaliana* plants. Each of the DNA clones encodes a polypeptide that is the same as or similar to members of a family designated as the light-dependent short hypocotyls (LSH) polypeptide family (Zhao et al., *Plant J.,* 37(5):694-706 (2004)). Ceres ANNOT ID no. 832857 (genomic locus At1g16910; SEQ ID NO:111) is a DNA clone that is predicted to encode a 164 amino acid polypeptide (SEQ ID NO:112) designated LSH8. Ceres ANNOT ID no. 1290753 (genomic locus At5g28490; SEQ ID NO:101) is a DNA clone that is predicted to encode a 190 amino acid polypeptide (SEQ ID NO:102) designated LSH1. Ceres ANNOT ID no. 856813 (genomic locus At5g58500; SEQ ID NO:115) is a DNA clone that is predicted to encode a 182 amino acid polypeptide (SEQ ID NO:116) designated LSH5. Ceres ANNOT ID no. 828846 (SEQ ID NO:109) is a DNA clone that is predicted to encode a 219 amino acid polypeptide (SEQ ID NO:110) designated LSH3. Ceres CLONE ID no. 1025179 (SEQ ID NO:119) is a DNA clone that is predicted to encode a 195 amino acid polypeptide (SEQ ID NO:120) designated LSH4. Ceres ANNOT ID no. 870022 (SEQ ID NO:117) is a DNA clone that is predicted to encode a 195 amino acid polypeptide (SEQ ID NO:118) designated LSH7. Ceres ANNOT ID no. 1285138 (SEQ ID NO:99) is a DNA clone that is predicted to encode a 188 amino acid polypeptide (SEQ ID NO:100) designated LSH9. Ceres ANNOT ID no. 847799 (SEQ ID NO:113) is a DNA clone that is predicted to encode a 191 amino acid polypeptide (SEQ ID NO:114) designated LSH9.

Ceres CLONE ID no. 604111(a) (SEQ ID NO:125) and Ceres CLONE ID no. 604111(b) (SEQ ID NO:129) are DNA clones that were isolated from a *Glycine max* plant. Ceres CLONE ID no. 604111(a) (SEQ ID NO:125) is predicted to encode a 229 amino acid polypeptide (SEQ ID NO:126) designated as an orthologous LSH6 polypeptide. Ceres CLONE ID no. 604111(b) (SEQ ID NO:129) is predicted to encode a 229 amino acid polypeptide (SEQ ID NO:146) designated as an orthologous LSH6 polypeptide.

Ceres CLONE ID no. 1464359 (SEQ ID NO:123) is a DNA clone that was isolated from a *Zea mays* plant. Ceres CLONE ID no. 1464359 (SEQ ID NO:123) is predicted to encode a 183 amino acid polypeptide (SEQ ID NO:124) designated as an orthologous LSH6 polypeptide.

The following DNA clones were isolated from *Brassica napus* plants. Ceres CLONE ID no. 964932 (SEQ ID NO:127) is a DNA clone that is predicted to encode a 199 amino acid polypeptide (SEQ ID NO:128) designated as an orthologous LSH6 polypeptide. Ceres CLONE ID no. 1084747 (SEQ ID NO:121) is a DNA clone that is predicted to encode a 198 amino acid polypeptide (SEQ ID NO:122) designated as an orthologous LSH6 polypeptide.

Ceres ANNOT ID no. 1373087 (SEQ ID NO:103) is a DNA clone that was isolated from an *Oryza sativa* plant. Ceres ANNOT ID no. 1373087 (SEQ ID NO:103) is predicted to encode a 212 amino acid polypeptide (SEQ ID NO:104) designated as an orthologous LSH6 polypeptide.

The following DNA clones were isolated from *Populus balsamifera* subsp. *Trichocarpa* plants. Ceres ANNOT ID no. 1440417 (SEQ ID NO:105) is a DNA clone that is predicted to encode a 228 amino acid polypeptide (SEQ ID NO:106) designated as an orthologous LSH6 polypeptide. Ceres ANNOT ID no. 1505805 (SEQ ID NO:107) is a DNA clone that is predicted to encode a 240 amino acid polypeptide (SEQ ID NO:108) designated as an orthologous LSH6 polypeptide.

Each of Ceres ANNOT ID no. 832857, Ceres ANNOT ID no. 1290753, Ceres ANNOT ID no. 856813, Ceres ANNOT ID no. 828846, Ceres ANNOT ID no. 870022, Ceres ANNOT ID no. 1285138, Ceres ANNOT ID no. 847799, Ceres CLONE ID no. 604111(a), Ceres CLONE ID no. 1464359, Ceres CLONE ID no. 964932, Ceres CLONE ID no. 1084747, Ceres ANNOT ID no. 1373087, Ceres ANNOT ID no. 1440417, and Ceres ANNOT ID no. 1505805 was cloned into a Ti plasmid vector, CRS 338, containing a phosphinothricin acetyltransferase gene, which confers transformed plants with Finale® resistance. The constructs made using the CRS 338 vector contained Ceres ANNOT ID no. 832857, Ceres ANNOT ID no. 1290753, Ceres ANNOT ID no. 856813, Ceres ANNOT ID no. 828846, Ceres ANNOT ID no. 870022, Ceres ANNOT ID no. 1285138, Ceres ANNOT ID no. 847799, Ceres CLONE ID no. 604111(a), Ceres CLONE ID no. 1464359, Ceres CLONE ID no. 964932, Ceres CLONE ID no. 1084747, Ceres ANNOT ID no. 1373087, Ceres ANNOT ID no. 1440417, or Ceres ANNOT ID no. 1505805, each operably linked to a CaMV 35S promoter. Constructs also were made using CRS 338 that contained Ceres CLONE ID no. 1025179, Ceres CLONE ID no. 604111(a), or Ceres CLONE ID no. 604111(b), each operably linked to a p326 promoter. Wild-type *Arabidopsis thaliana* ecotype Wassilewskija (Ws) plants were transformed separately with each construct containing Ceres ANNOT ID no. 832857, Ceres ANNOT ID no. 1290753, Ceres ANNOT ID no. 856813, Ceres ANNOT ID no. 828846, Ceres CLONE ID no. 1025179, Ceres ANNOT ID no. 870022, Ceres ANNOT ID no. 1285138, Ceres ANNOT ID no. 847799, Ceres CLONE ID no. 604111(a), Ceres CLONE ID no. 604111(b), Ceres CLONE ID no. 1464359, Ceres CLONE ID no. 964932, Ceres CLONE ID no. 1084747, Ceres ANNOT ID no. 1373087, Ceres ANNOT ID no. 1440417, or Ceres ANNOT ID no. 1505805. The transformations were performed essentially as described in Bechtold and Pelletier, *Methods Mol Biol.*, 82:259-66 (1998). The following information about each transgenic *Arabidopsis* line is presented in Table 12: DNA clone, sequence identifier of the nucleotide sequence of the DNA clone, sequence identifier of the amino acid sequence of the polypeptide encoded by the DNA clone, the promoter operably linked to the DNA clone, and the designation of the transgenic line.

TABLE 12

Transgenic *Arabidopsis* lines

| DNA clone | DNA SEQ ID NO: | Amino acid SEQ ID NO: | Promoter | Transgenic line designation |
|---|---|---|---|---|
| Ceres ANNOT ID no. 832857 | 111 | 112 | CaMV 35S | ME23423 |
| Ceres ANNOT ID no. 856813 | 115 | 116 | CaMV 35S | ME23517 |
| Ceres ANNOT ID no. 1290753 | 101 | 102 | CaMV 35S | ME23453 ME16623 |
| Ceres ANNOT ID no. 828846 | 109 | 110 | CaMV 35S | ME25288 |

TABLE 12-continued

Transgenic *Arabidopsis* lines

| DNA clone | DNA SEQ ID NO: | Amino acid SEQ ID NO: | Promoter | Transgenic line designation |
|---|---|---|---|---|
| Ceres CLONE ID no. 1025179 | 119 | 120 | p326 | ME24513 ME24480 ME24762 |
| Ceres ANNOT ID no. 870022 | 117 | 118 | CaMV 35S | ME16579 |
| Ceres ANNOT ID no. 1285138 | 99 | 100 | CaMV 35S | ME16572 |
| Ceres ANNOT ID no. 847799 | 113 | 114 | CaMV 35S | ME23459 |
| Ceres CLONE ID no. 604111(a) | 125 | 126 | CaMV 35S | ME25680 ME24978 |
| Ceres CLONE ID no. 604111(a) | 125 | 126 | p326 | ME24758 |
| Ceres CLONE ID no. 604111(b) | 129 | 146 | p326 | ME24507 |
| Ceres CLONE ID no. 1464359 | 123 | 124 | CaMV 35S | ME25661 |
| Ceres CLONE ID no. 964932 | 127 | 128 | CaMV 35S | ME25647 |
| Ceres CLONE ID no. 1084747 | 121 | 122 | CaMV 35S | ME25665 |
| Ceres ANNOT ID no. 1373087 | 103 | 104 | CaMV 35S | ME25698 |
| Ceres ANNOT ID no. 1440417 | 105 | 106 | CaMV 35S | ME25953 |
| Ceres ANNOT ID no. 1505805 | 107 | 108 | CaMV 35S | ME25957 |

The presence of the vector containing Ceres ANNOT ID no. 832857, Ceres ANNOT ID no. 1290753, Ceres ANNOT ID no. 856813, Ceres CLONE ID no. 1025179, Ceres ANNOT ID no. 870022, Ceres ANNOT ID no. 1285138, Ceres ANNOT ID no. 847799, Ceres CLONE ID no. 1464359, Ceres CLONE ID no. 964932, or Ceres CLONE ID no. 1084747 in each transgenic *Arabidopsis* line transformed with the vector was confirmed by Finale® resistance, polymerase chain reaction (PCR) amplification from green leaf tissue extract, and/or sequencing of PCR products. The presence of the vector containing Ceres ANNOT ID no. 828846, Ceres ANNOT ID no. 1373087, Ceres ANNOT ID no. 1440417, or Ceres ANNOT ID no. 1505805 in each transgenic *Arabidopsis* line transformed with the vector was confirmed by Finale® resistance, polymerase chain reaction (PCR) amplification from green leaf tissue extract, and/or partial sequencing of PCR products. The presence of the vector containing Ceres CLONE ID no. 604111(a) in transgenic *Arabidopsis* lines ME25680 and ME24978 was confirmed by Finale® resistance, polymerase chain reaction (PCR) amplification from green leaf tissue extract, and/or sequencing of PCR products. The presence of the vector containing Ceres CLONE ID no. 604111(a) in transgenic *Arabidopsis* line ME24758 was confirmed by Finale® resistance, polymerase chain reaction (PCR) amplification from green leaf tissue extract, and/or partial sequencing of PCR products. The presence of the vector containing Ceres CLONE ID no. 604111(b) in transgenic *Arabidopsis* line ME24507 was confirmed by Finale® resistance, polymerase chain reaction (PCR) amplification from green leaf tissue extract, and/or sequencing of PCR products.

The segregation of Finale® resistance for $T_2$ plants from events -02, -03, and -04 of ME23423 was 3:1 (resistant: sensitive), and the segregation for $T_2$ plants from event -01 of ME23423 was 15:1. The segregation of Finale® resistance for $T_2$ plants from events -01, -02, and -03 of ME23517 was 15:1, 3:1, and 2:1, respectively. The segregation of Finale® resistance for $T_2$ plants from events -02, -04, and -05 of ME23453 was 3:1.

Wild-type seeds and seeds from transgenic lines ME23423, ME23517, ME25288, ME16579, ME16572, ME23459, ME25661, ME25647, ME25665, ME25698, ME25953, ME25957, ME16623, ME23453, ME24513, ME24480, ME24762, ME25680, ME24978, ME24758, and ME24507 were plated as described in Example 2. Seedlings maintained under conditions of irradiance with about 10 $\mu mol/m^2/s$ of light for seven days at 22° C. were analyzed for hypocotyl length. The transgenic *Arabidopsis* lines ME23423, ME23517, ME25288, ME16579, ME16572, ME23459, ME25661, ME25647, ME25665, ME25698, ME25953, ME25957, ME16623, ME23453, ME24513, ME24480, ME24762, ME25680, ME24978, ME24758, and ME24507 were identified as having reduced hypocotyl elongation under the low light conditions as compared to wild-type control plants.

Example 6

Characterization of the Low Light Tolerance of Seedlings from ME23423 Events $T_2$ and $T_3$ seedlings from events -01, -02, -03, -04, and -08, and $T_2$ seedlings from events -07 and -09, of ME23423 containing Ceres ANNOT ID no. 832857 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, -03, -04, and -08 of ME23423 displayed a short hypocotyl under low light conditions in both the $T_2$ and $T_3$ generations, and seedlings from events -07 and -09 displayed a short hypocotyl under low light conditions in the $T_2$ generation. The transgene was linked to the short hypocotyl phenotype with a confidence level of $p \leq 0.05$ (Table 13).

TABLE 13

Chi-square comparison of the hypocotyl length of ME23423 transgenic seedlings and non-transgenic segregants grown under low light irradiance (10 $\mu mol/m^2/s$) for seven days

| Plants | Short Hypocotyl | Long Hypocotyl | Chi-Square | p-value |
|---|---|---|---|---|
| $T_2$ seedlings from event -01 | 29 | 6 | 12.93 | 3.24E−04 |
| $T_2$ non-transgenic segregants of event -01 | 0 | 4 | | |
| $T_3$ seedlings from event -01-99 | 42 | 2 | 34.72 | 3.80E−09 |
| $T_3$ non-transgenic segregants of event -01-99 | 1 | 8 | | |
| $T_2$ seedlings from event -02 | 19 | 10 | 9.17 | 2.46E−03 |
| $T_2$ non-transgenic segregants of event -02 | 1 | 9 | | |
| $T_3$ seedlings from event -02-99 | 59 | 4 | 38.63 | 5.13E−10 |
| $T_3$ non-transgenic segregants of event -02-99 | 1 | 8 | | |
| $T_2$ seedlings from event -03 | 20 | 13 | 3.94 | 4.70E−02 |
| $T_2$ non-transgenic segregants of event -03 | 1 | 5 | | |
| $T_3$ seedlings from event -03-99 | 38 | 3 | 23.44 | 1.29E−06 |
| $T_3$ non-transgenic segregants of event -03-99 | 5 | 11 | | |
| $T_2$ seedlings from event -04 | 26 | 2 | 25.28 | 4.96E−07 |
| $T_2$ non-transgenic segregants of event -04 | 0 | 7 | | |
| $T_3$ seedlings from event -04-99 | 55 | 5 | 38.36 | 5.89E−10 |
| $T_3$ non-transgenic segregants of event -04-99 | 0 | 8 | | |
| $T_2$ seedlings from event -07 | 56 | 4 | 10.96 | 9.29E−04 |
| $T_2$ non-transgenic segregants of event -07 | 12 | 7 | | |
| $T_2$ seedlings from event -08 | 65 | 7 | 26.8 | 2.26E−07 |
| $T_2$ non-transgenic segregants of event -08 | 1 | 6 | | |
| $T_3$ seedlings from event -08-99 | 43 | 9 | 4.32 | 3.77E−02 |
| $T_3$ non-transgenic segregants of event -08-99 | 1 | 2 | | |
| $T_2$ seedlings from event -09 | 52 | 6 | 38.26 | 6.18E−10 |
| $T_2$ non-transgenic segregants of event -09 | 3 | 16 | | |

The physical appearances of $T_1$ ME23423 plants were similar to those of corresponding control plants. There were no observable or statistically significant differences between $T_2$ ME23423 and control plants in germination, onset of flowering, rosette area, fertility, and general morphology/architecture.

Example 7

Characterization of the Low Light Tolerance of Seedlings from ME23517 Events $T_2$ and $T_3$ seedlings from events -01, -02, and -03 of ME23517 containing Ceres ANNOT ID no. 856813 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, and -03 of ME23517 displayed a short hypocotyl under low light conditions in both the $T_2$ and $T_3$ generations, and the transgene was linked to the short hypocotyl phenotype with a confidence level of $p \leq 0.05$ (Table 14).

TABLE 14

Chi-square comparison of the hypocotyl length of ME23517 transgenic seedlings and non-transgenic segregants grown under low light irradiance (10 $\mu mol/m^2/s$) for seven days

| Plants | Short Hypocotyl | Long Hypocotyl | Chi-Square | p-value |
|---|---|---|---|---|
| $T_2$ seedlings from event -01 | 77 | 0 | 79 | 6.21E−19 |
| $T_2$ non-transgenic segregants of event -01 | 0 | 2 | | |
| $T_3$ seedlings from event -01-99 | 13 | 1 | 12.57 | 3.92E−04 |
| $T_3$ non-transgenic segregants of event -01-99 | 3 | 9 | | |
| $T_2$ seedlings from event -02 | 57 | 2 | 64.23 | 1.11E−15 |
| $T_2$ non-transgenic segregants of event -02 | 1 | 19 | | |

TABLE 14-continued

Chi-square comparison of the hypocotyl length of ME23517 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| T₃ seedlings from event -02-99 | 14 | 1 | 12.8 | 3.74E−04 |
| T₃ non-transgenic segregants of event -02-99 | 2 | 7 | | |
| T₂ seedlings from event -03 | 42 | 2 | 53.36 | 2.78E−13 |
| T₂ non-transgenic segregants of event -03 | 4 | 28 | | |
| T₃ seedlings from event -03-99 | 16 | 3 | 18.84 | 1.42E−05 |
| T₃ non-transgenic segregants of event -03-99 | 2 | 15 | | |

The physical appearances of $T_1$ ME23517 plants were similar to those of corresponding control plants. There were no observable or statistically significant differences between $T_2$ ME23517 and control plants in germination, onset of flowering, rosette area, fertility, and general morphology/architecture.

Example 8

Characterization of the Low Light Tolerance of Seedlings from ME23453 and ME16623 Events $T_2$ and $T_3$ seedlings from events -02, -04, and -05, and $T_3$ seedlings from event -03, of ME23453 containing Ceres ANNOT ID no. 1290753 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -02, -04, and -05 of ME23453 displayed a short hypocotyl under low light conditions in both the $T_2$ and $T_3$ generations, and seedlings from event -03 displayed a short hypocotyl under low light conditions in the $T_3$ generation. The transgene was linked to the short hypocotyl phenotype with a confidence level of $p \leq 0.05$ (Table 15).

TABLE 15

Chi-square comparison of the hypocotyl length of ME23453 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| T₂ seedlings from event -02 | 52 | 0 | 62.49 | 2.68E−15 |
| T₂ non-transgenic segregants of event -02 | 4 | 23 | | |
| T₃ seedlings from event -02-99 | 33 | 0 | 27.79 | 1.35E−07 |
| T₃ non-transgenic segregants of event -02-99 | 5 | 10 | | |
| T₃ seedlings from event -03-99 | 27 | 1 | 19.28 | 1.13E−05 |
| T₃ non-transgenic segregants of event -03-99 | 1 | 4 | | |
| T₂ seedlings from event -04 | 63 | 0 | 68.42 | 1.32E−16 |
| T₂ non-transgenic segregants of event -04 | 2 | 15 | | |
| T₃ seedlings from event -04-99 | 30 | 0 | 43 | 5.47E−11 |
| T₃ non-transgenic segregants of event -04-99 | 0 | 13 | | |
| T₂ seedlings from event -05 | 50 | 2 | 54.45 | 1.59E−13 |
| T₂ non-transgenic segregants of event -05 | 3 | 21 | | |
| T₃ seedlings from event -05-99 | 13 | 0 | 9.45 | 2.11E−03 |
| T₃ non-transgenic segregants of event -05-99 | 5 | 6 | | |

$T_1$ ME23453 plants exhibited a late flowering phenotype as compared to corresponding control plants. There were no observable or statistically significant differences between $T_2$ ME23453 and control plants in germination, onset of flowering, rosette area, fertility, and general morphology/architecture.

$T_2$ and $T_3$ seedlings from events -03 and -04, and $T_2$ seedlings from event -02, of ME16623 containing Ceres ANNOT ID no. 1290753 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -03 and -04 of ME16623 displayed a short hypocotyl under low light conditions in both the $T_2$ and $T_3$ generations, and seedlings from event -02 displayed a short hypocotyl under low light conditions in the $T_2$ generation. The transgene was linked to the short hypocotyl phenotype with a confidence level of $p \leq 0.05$ (Table 16).

TABLE 16

Chi-square comparison of the hypocotyl length of ME16623 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| T₂ seedlings from event -02 | 56 | 3 | 53.68 | 2.63E−13 |
| T₂ non-transgenic segregants of event -02 | 2 | 17 | | |
| T₂ seedlings from event -03 | 48 | 4 | 24.62 | 7.00E−07 |
| T₂ non-transgenic segregants of event -03 | 4 | 9 | | |
| T₃ seedlings from event -03-99 | 39 | 6 | 9.53 | 2.02E−03 |
| T₃ non-transgenic segregants of event -03-99 | 9 | 9 | | |
| T₂ seedlings from event -04 | 56 | 3 | 61.32 | 4.86E−15 |
| T₂ non-transgenic segregants of event -04 | 0 | 17 | | |
| T₃ seedlings from event -04-99 | 13 | 3 | 7.72 | 5.47E−03 |
| T₃ non-transgenic segregants of event -04-99 | 0 | 3 | | |

Example 9

Characterization of the Low Light Tolerance of Seedlings from ME25288 Events $T_2$ and $T_3$ seedlings from event -02 of ME25288 containing Ceres ANNOT ID no. 828846 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from event -02 of ME25288 displayed a short hypocotyl under low light conditions in both the $T_2$ and $T_3$ generations, and the transgene was linked to the short hypocotyl phenotype with a confidence level of $p \leq 0.05$ (Table 17).

TABLE 17

Chi-square comparison of the hypocotyl length of ME25288 transgenic seedlings and non-transgenic segregants grown under low light irradiance (10 μmol/m²/s) for seven days

| Plants | Short Hypocotyl | Long Hypocotyl | Chi-Square | p-value |
| --- | --- | --- | --- | --- |
| $T_2$ seedlings from event -02 | 35 | 5 | 10.11 | 1.48E−03 |
| $T_2$ non-transgenic segregants of event -02 | 3 | 5 | | |
| $T_3$ seedlings from event -02-99 | 39 | 6 | 24.73 | 6.58E−07 |
| $T_3$ non-transgenic segregants of event -02-99 | 2 | 11 | | |

Example 10

Characterization of the Low Light Tolerance of Seedlings from ME24513, ME24480, and ME24762 Events $T_2$ and $T_3$ seedlings from events -01, -02, -03, and -08 of ME24513 containing Ceres CLONE ID no. 1025179 operably linked to a p326 promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, -03, and -08 of ME24513 displayed a short hypocotyl under low light conditions in both the $T_2$ and $T_3$ generations, and the transgene was linked to the short hypocotyl phenotype with a confidence level of $p \leq 0.05$ (Table 18).

TABLE 18

Chi-square comparison of the hypocotyl length of ME24513 transgenic seedlings and non-transgenic segregants grown under low light irradiance (10 μmol/m²/s) for seven days

| Plants | Short Hypocotyl | Long Hypocotyl | Chi-Square | p-value |
| --- | --- | --- | --- | --- |
| $T_2$ seedlings from event -01 | 53 | 2 | 59.52 | 1.21E−14 |
| $T_2$ non-transgenic segregants of event -01 | 0 | 15 | | |
| $T_3$ seedlings from event -01-99 | 17 | 0 | 19 | 1.31E−05 |
| $T_3$ non-transgenic segregants of event -01-99 | 0 | 2 | | |
| $T_2$ seedlings from event -02 | 43 | 17 | 14.13 | 1.70E−04 |
| $T_2$ non-transgenic segregants of event -02 | 4 | 14 | | |
| $T_3$ seedlings from event -02-99 | 50 | 0 | 34.64 | 3.97E−09 |
| $T_3$ non-transgenic segregants of event -02-99 | 1 | 2 | | |
| $T_2$ seedlings from event -03 | 55 | 2 | 33.69 | 6.46E−09 |
| $T_2$ non-transgenic segregants of event -03 | 8 | 13 | | |
| $T_3$ seedlings from event -03-99 | 15 | 0 | 18 | 2.21E−05 |
| $T_3$ non-transgenic segregants of event -03-99 | 0 | 3 | | |
| $T_2$ seedlings from event -08 | 50 | 14 | 21.07 | 4.44E−06 |
| $T_2$ non-transgenic segregants of event -08 | 2 | 12 | | |
| $T_3$ seedlings from event -08-99 | 34 | 4 | 8.1 | 4.43E−03 |
| $T_3$ non-transgenic segregants of event -08-99 | 5 | 5 | | |

$T_2$ and $T_3$ seedlings from events -02, -04, and -05, and $T_2$ seedlings from events -01 and -07, of ME24480 containing Ceres CLONE ID no. 1025179 operably linked to a p326 promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -02, -04, and -05 of ME24480 displayed a short hypocotyl under low light conditions in both the $T_2$ and $T_3$ generations, and seedlings from events -01 and -07 displayed a short hypocotyl under low light conditions in the $T_2$ generation. The transgene was linked to the short hypocotyl phenotype with a confidence level of $p \leq 0.05$ (Table 19).

TABLE 19

Chi-square comparison of the hypocotyl length of ME24480 transgenic seedlings and non-transgenic segregants grown under low light irradiance (10 μmol/m²/s) for seven days

| Plants | Short Hypocotyl | Long Hypocotyl | Chi-Square | p-value |
| --- | --- | --- | --- | --- |
| $T_2$ seedlings from event -01 | 39 | 2 | 23.46 | 1.28E−06 |
| $T_2$ non-transgenic segregants of event -01 | 3 | 7 | | |
| $T_2$ seedlings from event -02 | 36 | 1 | 5.26 | 2.19E−02 |
| $T_2$ non-transgenic segregants of event -02 | 6 | 2 | | |
| $T_3$ seedlings from event -02-99 | 16 | 0 | 19 | 1.31E−05 |
| $T_3$ non-transgenic segregants of event -02-99 | 0 | 3 | | |
| $T_2$ seedlings from event -04 | 24 | 3 | 11.19 | 8.21E−04 |
| $T_2$ non-transgenic segregants of event -04 | 5 | 8 | | |
| $T_3$ seedlings from event -04-99 | 23 | 0 | 24.22 | 8.61E−07 |
| $T_3$ non-transgenic segregants of event -04-99 | 8 | 17 | | |

TABLE 19-continued

Chi-square comparison of the hypocotyl length of ME24480 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedings from event -05 | 38 | 0 | 23.62 | 1.17E−06 |
| $T_2$ non-transgenic segregants of event -05 | 4 | 5 | | |
| $T_3$ seedings from event -05-99 | 26 | 0 | 18.72 | 1.51E−05 |
| $T_3$ non-transgenic segregants of event -05-99 | 4 | 6 | | |
| $T_2$ seedings from event -07 | 41 | 0 | 15.58 | 7.89E−05 |
| $T_2$ non-transgenic segregants of event -07 | 16 | 8 | | |

$T_2$ and $T_3$ seedlings from events -01, -02, -03, -04, -05, and -06 of ME24762 containing Ceres CLONE ID no. 1025179 operably linked to a p326 promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, -03, -04, -05, and -06 of ME24762 displayed a short hypocotyl under low light conditions in both the $T_2$ and $T_3$ generations, and the transgene was linked to the short hypocotyl phenotype with a confidence level of $p \leqq 0.05$ (Table 20).

TABLE 20

Chi-square comparison of the hypocotyl length of ME24762 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedings from event -01 | 53 | 2 | 46.93 | 7.34E−12 |
| $T_2$ non-transgenic segregants of event -01 | 1 | 10 | | |
| $T_3$ seedings from event -01-99 | 41 | 0 | 38.81 | 4.67E−10 |
| $T_3$ non-transgenic segregants of event -01-99 | 8 | 18 | | |
| $T_2$ seedings from event -02 | 44 | 0 | 57.25 | 3.83E−14 |
| $T_2$ non-transgenic segregants of event -02 | 1 | 17 | | |
| $T_3$ seedings from event -02-99 | 31 | 1 | 40.57 | 1.90E−10 |
| $T_3$ non-transgenic segregants of event -02-99 | 1 | 16 | | |
| $T_2$ seedings from event -03 | 39 | 1 | 43 | 5.48E−11 |
| $T_2$ non-transgenic segregants of event -03 | 0 | 9 | | |
| $T_3$ seedings from event -03-99 | 45 | 0 | 45.37 | 1.63E−11 |
| $T_3$ non-transgenic segregants of event -03-99 | 1 | 7 | | |
| $T_2$ seedings from event -04 | 46 | 5 | 8.63 | 3.30E−03 |
| $T_2$ non-transgenic segregants of event -04 | 10 | 7 | | |
| $T_3$ seedings from event -04-99 | 45 | 7 | 14.28 | 1.58E−04 |
| $T_3$ non-transgenic segregants of event -04-99 | 0 | 3 | | |
| $T_2$ seedings from event -05 | 42 | 0 | 54.41 | 1.63E−13 |
| $T_2$ non-transgenic segregants of event -05 | 2 | 19 | | |
| $T_3$ seedings from event -05-99 | 51 | 2 | 47.24 | 6.27E−12 |
| $T_3$ non-transgenic segregants of event -05-99 | 1 | 11 | | |
| $T_2$ seedings from event -06 | 23 | 0 | 9.55 | 2.00E−03 |
| $T_2$ non-transgenic segregants of event -06 | 11 | 6 | | |
| $T_3$ seedings from event -06-99 | 37 | 1 | 13.38 | 2.54E−04 |
| $T_3$ non-transgenic segregants of event -06-99 | 5 | 4 | | |

Example 11

Characterization of the Low Light Tolerance of Seedlings from ME16579 Events $T_2$ and $T_3$ seedlings from event -07, $T_3$ seedlings from event -02, and $T_3$ and $T_4$ seedlings from event -05 of ME16579 containing Ceres ANNOT ID no. 870022 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from event -07 of ME16579 displayed a short hypocotyl under low light conditions in both the $T_2$ and $T_3$ generations, seedlings from event -02 displayed a short hypocotyl under low light conditions in the $T_3$ generation, and seedlings from event -05 displayed a short hypocotyl under low light conditions in the $T_3$ and $T_4$ generations. The transgene was linked to the short hypocotyl phenotype with a confidence level of $p \leqq 0.05$ (Table 21).

TABLE 21

Chi-square comparison of the hypocotyl length of ME16579 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_3$ seedings from event -02-99 | 6 | 11 | 3.85 | 4.97E−02 |
| $T_3$ non-transgenic segregants of event -02-99 | 39 | 24 | | |
| $T_3$ seedings from event -05-99 | 42 | 0 | 57 | 4.36E−14 |
| $T_3$ non-transgenic segregants of event -05-99 | 0 | 15 | | |
| $T_4$ seedings from event -05-99-99 | 60 | 1 | 58.52 | 2.01E−14 |
| $T_4$ non-transgenic segregants of event -05-99-99 | 0 | 7 | | |
| $T_2$ seedings from event -07 | 26 | 1 | 24.58 | 7.14E−07 |
| $T_2$ non-transgenic segregants of event -07 | 1 | 7 | | |
| $T_3$ seedings from event -07-99 | 59 | 0 | 73.8 | 8.65E−18 |
| $T_3$ non-transgenic segregants of event -07-99 | 1 | 19 | | |

Example 12

Characterization of the Low Light Tolerance of Seedlings from ME16572 Events $T_2$ and $T_3$ seedlings from events -01, -04, and -05, and $T_2$ seedlings from events -02 and -03, of ME16572 containing Ceres ANNOT ID no. 1285138 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -04, and -05 of ME16572 displayed a short hypocotyl under low light conditions in both the $T_2$ and $T_3$ generations, and seedlings from events -02 and -03 displayed a short hypocotyl under low light conditions in the $T_2$ generation. The transgene was linked to the short hypocotyl phenotype with a confidence level of $p \leqq 0.05$ (Table 22).

TABLE 22

Chi-square comparison of the hypocotyl length of ME16572 transgenic seedlings and non-transgenic segregants grown under low light irradiance (10 μmol/m²/s) for seven days

| Plants | Short Hypocotyl | Long Hypocotyl | Chi-Square | p-value |
| --- | --- | --- | --- | --- |
| $T_2$ seedlings from event -01 | 46 | 9 | 6.23 | 1.25E−02 |
| $T_2$ non-transgenic segregants of event -01 | 3 | 4 | | |
| $T_3$ seedlings from event -01-99 | 27 | 3 | 6.98 | 8.27E−03 |
| $T_3$ non-transgenic segregants of event -01-99 | 0 | 1 | | |
| $T_2$ seedlings from event -02 | 21 | 0 | 45.8 | 1.31E−11 |
| $T_2$ non-transgenic segregants of event -02 | 7 | 43 | | |
| $T_2$ seedlings from event -03 | 57 | 5 | 37.53 | 9.02E−10 |
| $T_2$ non-transgenic segregants of event -03 | 2 | 11 | | |
| $T_2$ seedlings from event -04 | 37 | 3 | 16.49 | 4.90E−05 |
| $T_2$ non-transgenic segregants of event -04 | 8 | 10 | | |
| $T_3$ seedlings from event -04-99 | 20 | 2 | 6.97 | 8.29E−03 |
| $T_3$ non-transgenic segregants of event -04-99 | 0 | 1 | | |
| $T_2$ seedlings from event -05 | 64 | 0 | 24.58 | 7.11E−07 |
| $T_2$ non-transgenic segregants of event -05 | 7 | 4 | | |
| $T_3$ seedlings from event -05-99 | 39 | 3 | 6.49 | 1.08E−02 |
| $T_3$ non-transgenic segregants of event -05-99 | 7 | 4 | | |

Example 13

Characterization of the Low Light Tolerance of Seedlings from ME23459 Events $T_2$ and $T_3$ seedlings from events -02, -05, and -08, and $T_2$ seedlings from event -04, of ME23459 containing Ceres ANNOT ID no. 847799 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -02, -05, and -08 of ME23459 displayed a short hypocotyl under low light conditions in both the $T_2$ and $T_3$ generations, and seedlings from event -04 displayed a short hypocotyl under low light conditions in the $T_2$ generation. The transgene was linked to the short hypocotyl phenotype with a confidence level of $p \leqq 0.05$ (Table 23).

TABLE 23

Chi-square comparison of the hypocotyl length of ME23459 transgenic seedlings and non-transgenic segregants grown under low light irradiance (10 μmol/m²/s) for seven days

| Plants | Short Hypocotyl | Long Hypocotyl | Chi-Square | p-value |
| --- | --- | --- | --- | --- |
| $T_2$ seedlings from event -02 | 52 | 3 | 32.79 | 1.03E−08 |
| $T_2$ non-transgenic segregants of event -02 | 7 | 14 | | |
| $T_3$ seedlings from event -02-99 | 53 | 1 | 64.66 | 8.89E−16 |
| $T_3$ non-transgenic segregants of event -02-99 | 0 | 16 | | |
| $T_2$ seedlings from event -04 | 62 | 3 | 18.73 | 1.50E−05 |
| $T_2$ non-transgenic segregants of event -04 | 5 | 5 | | |
| $T_2$ seedlings from event -05 | 64 | 0 | 52.44 | 4.44E−13 |
| $T_2$ non-transgenic segregants of event -05 | 4 | 10 | | |
| $T_3$ seedlings from event -05-99 | 44 | 1 | 36.81 | 1.30E−09 |
| $T_3$ non-transgenic segregants of event -05-99 | 7 | 16 | | |
| $T_2$ seedlings from event -08 | 63 | 0 | 74.12 | 7.36E−18 |
| $T_2$ non-transgenic segregants of event -08 | 1 | 16 | | |
| $T_3$ seedlings from event -08-99 | 54 | 1 | 54.61 | 1.47E−13 |
| $T_3$ non-transgenic segregants of event -08-99 | 2 | 14 | | |

Example 14

Characterization of the Low Light Tolerance of Seedlings from ME25680, ME24978, ME24758, and ME24507 Events $T_2$ and $T_3$ seedlings from events -01, -04, -06, -07, -08, -09, and -10 of ME25680 containing Ceres CLONE ID no. 604111(a) operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -04, -06, -07, -08, -09, and -10 of ME25680 displayed a short hypocotyl under low light conditions in both the $T_2$ and $T_3$ generations, and the transgene was linked to the short hypocotyl phenotype with a confidence level of $p \leqq 0.05$ (Table 24).

TABLE 24

Chi-square comparison of the hypocotyl length of ME25680 transgenic seedlings and non-transgenic segregants grown under low light irradiance (10 µmol/m²/s) for seven days

| Plants | Short Hypo-cotyl | Long Hypocotyl | Chi-Square | p-value |
|---|---|---|---|---|
| $T_2$ seedlings from event -01 | 54 | 1 | 34.65 | 3.95E−09 |
| $T_2$ non-transgenic segregants of event -01 | 9 | 13 | | |
| $T_3$ seedlings from event -01-99 | 58 | 7 | 20.43 | 6.20E−06 |
| $T_3$ non-transgenic segregants of event -01-99 | 5 | 9 | | |
| $T_2$ seedlings from event -04 | 43 | 14 | 22.24 | 2.40E−06 |
| $T_2$ non-transgenic segregants of event -04 | 1 | 13 | | |
| $T_3$ seedlings from event -04-99 | 46 | 5 | 7.61 | 5.81E−03 |
| $T_3$ non-transgenic segregants of event -04-99 | 9 | 6 | | |
| $T_2$ seedlings from event -06 | 60 | 2 | 29.96 | 4.41E−08 |
| $T_2$ non-transgenic segregants of event -06 | 8 | 10 | | |
| $T_3$ seedlings from event -06-99 | 62 | 7 | 34.14 | 5.12E−09 |
| $T_3$ non-transgenic segregants of event -06-99 | 0 | 7 | | |
| $T_2$ seedlings from event -07 | 49 | 7 | 30.22 | 3.86E−08 |
| $T_2$ non-transgenic segregants of event -07 | 4 | 15 | | |
| $T_3$ seedlings from event -07-99 | 57 | 4 | 17.17 | 3.42E−05 |
| $T_3$ non-transgenic segregants of event -07-99 | 7 | 7 | | |
| $T_2$ seedlings from event -08 | 57 | 5 | 20.05 | 7.54E−06 |
| $T_2$ non-transgenic segregants of event -08 | 7 | 9 | | |
| $T_3$ seedlings from event -08-99 | 13 | 1 | 14.7 | 1.26E−04 |
| $T_3$ non-transgenic segregants of event -08-99 | 0 | 5 | | |
| $T_2$ seedlings from event -09 | 50 | 8 | 41.69 | 1.07E−10 |
| $T_2$ non-transgenic segregants of event -09 | 2 | 20 | | |
| $T_3$ seedlings from event -09-99 | 57 | 0 | 46.98 | 7.16E−12 |
| $T_3$ non-transgenic segregants of event -09-99 | 3 | 8 | | |
| $T_2$ seedlings from event -10 | 49 | 20 | 11.46 | 7.11E−04 |
| $T_2$ non-transgenic segregants of event -10 | 2 | 9 | | |
| $T_3$ seedlings from event -10-99 | 49 | 12 | 14.71 | 1.25E−04 |
| $T_3$ non-transgenic segregants of event -10-99 | 4 | 10 | | |

$T_2$ and $T_3$ seedlings from event -01, and $T_3$ seedlings from events -02 and -03, of ME24978 containing Ceres CLONE ID no. 604111(a) operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from event -01 of ME24978 displayed a short hypocotyl under low light conditions in both the $T_2$ and $T_3$ generations, and seedlings from events -02 and -03 displayed a short hypocotyl under low light conditions in the $T_3$ generation. The transgene was linked to the short hypocotyl phenotype with a confidence level of $p \leq 0.05$ (Table 25).

TABLE 25

Chi-square comparison of the hypocotyl length of ME24978 transgenic seedlings and non-transgenic segregants grown under low light irradiance (10 µmol/m²/s) for seven days

| Plants | Short Hypo-cotyl | Long Hypocotyl | Chi-Square | p-value |
|---|---|---|---|---|
| $T_2$ seedlings from event -01 | 47 | 1 | 44.01 | 3.27E−11 |
| $T_2$ non-transgenic segregants of event -01 | 3 | 13 | | |
| $T_3$ seedlings from event -01-99 | 51 | 5 | 30.81 | 2.85E−08 |
| $T_3$ non-transgenic segregants of event -01-99 | 3 | 11 | | |
| $T_3$ seedlings from event -02-99 | 50 | 11 | 15.34 | 8.97E−05 |
| $T_3$ non-transgenic segregants of event -02-99 | 1 | 6 | | |
| $T_3$ seedlings from event -03-99 | 54 | 2 | 15.53 | 8.12E−05 |
| $T_3$ non-transgenic segregants of event -03-99 | 7 | 5 | | |

$T_2$ and $T_3$ seedlings from event -03, and $T_2$ seedlings from event -01, of ME24758 containing Ceres CLONE ID no. 604111(a) operably linked to a p326 promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from event -03 of ME24758 displayed a short hypocotyl under low light conditions in both the $T_2$ and $T_3$ generations, and seedlings from event -01 displayed a short hypocotyl under low light conditions in the $T_2$ generation. The transgene was linked to the short hypocotyl phenotype with a confidence level of $p \leq 0.05$ (Table 26).

TABLE 26

Chi-square comparison of the hypocotyl length of ME24758 transgenic seedlings and non-transgenic segregants grown under low light irradiance (10 µmol/m²/s) for seven days

| Plants | Short Hypo-cotyl | Long Hypocotyl | Chi-Square | p-value |
|---|---|---|---|---|
| $T_2$ seedlings from event -01 | 55 | 4 | 15.04 | 1.06E−04 |
| $T_2$ non-transgenic segregants of event -01 | 8 | 7 | | |
| $T_2$ seedlings from event -03 | 54 | 2 | 39.72 | 2.93E−10 |
| $T_2$ non-transgenic segregants of event -03 | 5 | 13 | | |
| $T_3$ seedlings from event -03-99 | 13 | 1 | 20.26 | 6.76E−06 |
| $T_3$ non-transgenic segregants of event -03-99 | 0 | 10 | | |

$T_2$ and $T_3$ seedlings from events -01, -03, -05, and -09, $T_2$ seedlings from event -02, and $T_3$ seedlings from event -10 of ME24507 containing Ceres CLONE ID no. 604111(b) operably linked to a p326 promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -03, -05, and -09 of ME24507 displayed a short hypocotyl under low light conditions in both the $T_2$ and $T_3$ generations, seedlings from event -02 displayed a short hypocotyl under low light conditions in the $T_2$ generation, and seedlings from event -10 displayed a short hypocotyl under low light conditions in the $T_3$ generation. The transgene was linked to the short hypocotyl phenotype with a confidence level of $p \leq 0.05$ (Table 27).

TABLE 27

Chi-square comparison of the hypocotyl length of ME24507 transgenic seedlings and non-transgenic segregants grown under low light irradiance (10 μmol/m$^2$/s) for seven days

| Plants | Short Hypocotyl | Long Hypocotyl | Chi-Square | p-value |
|---|---|---|---|---|
| T$_2$ seedlings from event -01 | 21 | 4 | 8.73 | 3.13E−03 |
| T$_2$ non-transgenic segregants of event -01 | 1 | 4 | | |
| T$_3$ seedlings from event -01-99 | 28 | 0 | 22.65 | 1.95E−06 |
| T$_3$ non-transgenic segregants of event -01-99 | 6 | 10 | | |
| T$_2$ seedlings from event -02 | 42 | 8 | 4.67 | 3.08E−02 |
| T$_2$ non-transgenic segregants of event -02 | 12 | 8 | | |
| T$_2$ seedlings from event -03 | 46 | 13 | 38.52 | 5.41E−10 |
| T$_2$ non-transgenic segregants of event -03 | 0 | 21 | | |
| T$_3$ seedlings from event -03-99 | 35 | 2 | 13.19 | 2.81E−04 |
| T$_3$ non-transgenic segregants of event -03-99 | 6 | 6 | | |
| T$_2$ seedlings from event -05 | 42 | 11 | 30.39 | 3.54E−08 |
| T$_2$ non-transgenic segregants of event -05 | 4 | 23 | | |
| T$_3$ seedlings from event -05-99 | 42 | 4 | 28.69 | 8.51E−08 |
| T$_3$ non-transgenic segregants of event -05-99 | 8 | 18 | | |
| T$_2$ seedlings from event -09 | 70 | 6 | 24.25 | 8.44E−07 |
| T$_2$ non-transgenic segregants of event -09 | 0 | 3 | | |
| T$_3$ seedlings from event -09-99 | 47 | 2 | 39.57 | 3.71E−10 |
| T$_3$ non-transgenic segregants of event -09-99 | 0 | 6 | | |
| T$_3$ seedlings from event -10-99 | 54 | 6 | 8.28 | 4.02E−03 |
| T$_3$ non-transgenic segregants of event -10-99 | 1 | 2 | | |

Example 15

Characterization of the Low Light Tolerance of Seedlings from ME25661 Events

T$_2$ and T$_3$ seedlings from events -01, -02, -03, -04, -05, and -09 of ME25661 containing Ceres CLONE ID no. 1464359 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, -03, -04, -05, and -09 of ME25661 displayed a short hypocotyl under low light conditions in both the T$_2$ and T$_3$ generations, and the transgene was linked to the short hypocotyl phenotype with a confidence level of p≦0.05 (Table 28).

TABLE 28

Chi-square comparison of the hypocotyl length of ME25661 transgenic seedlings and non-transgenic segregants grown under low light irradiance (10 μmol/m$^2$/s) for seven days

| Plants | Short Hypocotyl | Long Hypocotyl | Chi-Square | p-value |
|---|---|---|---|---|
| T$_2$ seedlings from event -01 | 61 | 0 | 52.73 | 3.82E−13 |
| T$_2$ non-transgenic segregants of event -01 | 5 | 13 | | |
| T$_3$ seedlings from event -01-99 | 37 | 0 | 29.82 | 4.75E−08 |
| T$_3$ non-transgenic segregants of event -01-99 | 2 | 5 | | |
| T$_2$ seedlings from event -02 | 61 | 1 | 58.23 | 2.34E−14 |
| T$_2$ non-transgenic segregants of event -02 | 3 | 15 | | |
| T$_3$ seedlings from event -02-99 | 55 | 0 | 40.66 | 1.81E−10 |
| T$_3$ non-transgenic segregants of event -02-99 | 5 | 9 | | |
| T$_2$ seedlings from event -03 | 61 | 2 | 37.24 | 1.04E−09 |
| T$_2$ non-transgenic segregants of event -03 | 6 | 11 | | |
| T$_3$ seedlings from event -03-99 | 48 | 9 | 17.56 | 2.78E−05 |
| T$_3$ non-transgenic segregants of event -03-99 | 6 | 12 | | |
| T$_2$ seedlings from event -04 | 57 | 0 | 79 | 6.21E−19 |
| T$_2$ non-transgenic segregants of event -04 | 0 | 22 | | |
| T$_3$ seedlings from event -04-99 | 53 | 3 | 35.12 | 3.10E−09 |
| T$_3$ non-transgenic segregants of event -04-99 | 7 | 15 | | |
| T$_2$ seedlings from event -05 | 53 | 3 | 58.9 | 1.66E−14 |
| T$_2$ non-transgenic segregants of event -05 | 1 | 20 | | |
| T$_3$ seedlings from event -05-99 | 61 | 1 | 66.22 | 4.04E−16 |
| T$_3$ non-transgenic segregants of event -05-99 | 1 | 15 | | |
| T$_2$ seedlings from event -09 | 53 | 1 | 71.35 | 2.99E−17 |
| T$_2$ non-transgenic segregants of event -09 | 0 | 22 | | |

TABLE 28-continued

Chi-square comparison of the hypocotyl length of ME25661 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| of event -09 | | | | |
| T₃ seedlings from event -09-99 | 65 | 0 | 72.25 | 1.90E−17 |
| T₃ non-transgenic segregants of event -09-99 | 1 | 13 | | |

Example 16

Characterization of the Low Light Tolerance of Seedlings from ME25647 Events $T_2$ and $T_3$ seedlings from events -01, -03, -04, -05, -06, -08, -09, and -10 of ME25647 containing Ceres CLONE ID no. 964932 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -03, -04, -05, -06, -08, -09, and -10 of ME25647 displayed a short hypocotyl under low light conditions in both the $T_2$ and $T_3$ generations, and the transgene was linked to the short hypocotyl phenotype with a confidence level of $p \leq 0.05$ (Table 29).

TABLE 29

Chi-square comparison of the hypocotyl length of ME25647 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| T₂ seedlings from event -01 | 39 | 1 | 68.19 | 1.49E−16 |
| T₂ non-transgenic segregants of event -01 | 1 | 35 | | |
| T₃ seedlings from event -01-99 | 19 | 0 | 22.19 | 2.47E−06 |
| T₃ non-transgenic segregants of event -01-99 | 10 | 21 | | |
| T₂ seedlings from event -03 | 45 | 17 | 16.89 | 3.97E−05 |
| T₂ non-transgenic segregants of event -03 | 3 | 14 | | |
| T₃ seedlings from event -03-99 | 39 | 12 | 29.83 | 4.71E−08 |
| T₃ non-transgenic segregants of event -03-99 | 1 | 19 | | |
| T₂ seedlings from event -04 | 62 | 0 | 60.45 | 7.55E−15 |
| T₂ non-transgenic segregants of event -04 | 3 | 13 | | |
| T₃ seedlings from event -04-99 | 38 | 0 | 40.71 | 1.77E−10 |
| T₃ non-transgenic segregants of event -04-99 | 1 | 8 | | |
| T₂ seedlings from event -05 | 55 | 1 | 68.85 | 1.06E−16 |
| T₂ non-transgenic segregants of event -05 | 0 | 18 | | |
| T₃ seedlings from event -05-99 | 48 | 0 | 42.35 | 7.62E−11 |
| T₃ non-transgenic segregants of event -05-99 | 3 | 9 | | |
| T₂ seedlings from event -06 | 55 | 2 | 46.05 | 1.15E−11 |

TABLE 29-continued

Chi-square comparison of the hypocotyl length of ME25647 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| T₂ non-transgenic segregants of event -06 | 2 | 11 | | |
| T₃ seedlings from event -06-99 | 51 | 7 | 19.89 | 8.22E−06 |
| T₃ non-transgenic segregants of event -06-99 | 5 | 10 | | |
| T₂ seedlings from event -08 | 54 | 0 | 73 | 1.30E−17 |
| T₂ non-transgenic segregants of event -08 | 0 | 19 | | |
| T₃ seedlings from event -08-99 | 68 | 1 | 37.19 | 1.07E−09 |
| T₃ non-transgenic segregants of event -08-99 | 3 | 5 | | |
| T₂ seedlings from event -09 | 51 | 6 | 53 | 3.34E−13 |
| T₂ non-transgenic segregants of event -09 | 0 | 20 | | |
| T₃ seedlings from event -09-99 | 44 | 5 | 38.67 | 5.03E−10 |
| T₃ non-transgenic segregants of event -09-99 | 0 | 12 | | |
| T₂ seedlings from event -10 | 62 | 8 | 21.85 | 2.95E−06 |
| T₂ non-transgenic segregants of event -10 | 0 | 4 | | |
| T₃ seedlings from event -10-99 | 61 | 6 | 36.28 | 1.71E−09 |
| T₃ non-transgenic segregants of event -10-99 | 0 | 7 | | |

Example 17

Characterization of the Low Light Tolerance of Seedlings from ME25665 Events $T_2$ and $T_3$ seedlings from events -03, -06, and -08, and $T_2$ seedlings from event -04, of ME25665 containing Ceres CLONE ID no. 1084747 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -03, -06, and -08 of ME25665 displayed a short hypocotyl under low light conditions in both the $T_2$ and $T_3$ generations, and seedlings from event -04 displayed a short hypocotyl under low light conditions in the $T_2$ generation. The transgene was linked to the short hypocotyl phenotype with a confidence level of $p \leq 0.05$ (Table 30).

TABLE 30

Chi-square comparison of the hypocotyl length of ME25665 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| T₂ seedlings from event -03 | 58 | 18 | 11.1 | 8.63E−04 |
| T₂ non-transgenic segregants of event -03 | 0 | 4 | | |
| T₃ seedlings from event -03-99 | 57 | 4 | 11.59 | 6.64E−04 |
| T₃ non-transgenic segregants of event -03-99 | 0 | 1 | | |

TABLE 30-continued

Chi-square comparison of the hypocotyl length of ME25665 transgenic seedlings and non-transgenic segregants grown under low light irradiance (10 μmol/m²/s) for seven days

| Plants | Short Hypo-cotyl | Long Hypocotyl | Chi-Square | p-value |
|---|---|---|---|---|
| $T_2$ seedlings from event -04 | 20 | 11 | 8.43 | 3.70E−03 |
| $T_2$ non-transgenic segregants of event -04 | 0 | 6 | | |
| $T_2$ seedlings from event -06 | 46 | 11 | 39.42 | 3.41E−10 |
| $T_2$ non-transgenic segregants of event -06 | 1 | 22 | | |
| $T_3$ seedlings from event -06-99 | 46 | 7 | 24.91 | 6.00E−07 |
| $T_3$ non-transgenic segregants of event -06-99 | 2 | 10 | | |
| $T_2$ seedlings from event -08 | 53 | 11 | 34.2 | 4.97E−09 |
| $T_2$ non-transgenic segregants of event -08 | 1 | 15 | | |
| $T_3$ seedlings from event -08-99 | 67 | 3 | 48.5 | 3.31E−12 |
| $T_3$ non-transgenic segregants of event -08-99 | 0 | 6 | | |

Example 18

Characterization of the Low Light Tolerance of Seedlings from ME25698 Events $T_2$ seedlings from events -01, -02, -04, -05, and -07 of ME25698 containing Ceres ANNOT ID no. 1373087 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01, -02, -04, -05, and -07 of ME25698 displayed a short hypocotyl under low light conditions in the $T_2$ generation, and the transgene was linked to the short hypocotyl phenotype with a confidence level of $p \leq 0.05$ (Table 31).

TABLE 31

Chi-square comparison of the hypocotyl length of ME25698 transgenic seedlings and non-transgenic segregants grown under low light irradiance (10 μmol/m²/s) for seven days

| Plants | Short Hypo-cotyl | Long Hypocotyl | Chi-Square | p-value |
|---|---|---|---|---|
| $T_2$ seedlings from event -01 | 47 | 15 | 11.25 | 7.94E−04 |
| $T_2$ non-transgenic segregants of event -01 | 6 | 12 | | |
| $T_2$ seedlings from event -02 | 38 | 23 | 16.92 | 3.89E−05 |
| $T_2$ non-transgenic segregants of event -02 | 1 | 16 | | |
| $T_2$ seedlings from event -04 | 42 | 13 | 30.2 | 3.90E−08 |
| $T_2$ non-transgenic segregants of event -04 | 2 | 21 | | |
| $T_2$ seedlings from event -05 | 51 | 11 | 24.08 | 9.24E−07 |
| $T_2$ non-transgenic segregants of event -05 | 3 | 13 | | |
| $T_2$ seedlings from event -07 | 43 | 6 | 11.88 | 5.66E−04 |
| $T_2$ non-transgenic segregants of event -07 | 11 | 11 | | |

Example 19

Characterization of the Low Light Tolerance of Seedlings from ME25953 Events $T_2$ seedlings from events -01 and -02 of ME25953 containing Ceres ANNOT ID no. 1440417 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01 and -02 of ME25953 displayed a short hypocotyl under low light conditions in the $T_2$ generation, and the transgene was linked to the short hypocotyl phenotype with a confidence level of $p \leq 0.05$ (Table 32).

TABLE 32

Chi-square comparison of the hypocotyl length of ME25953 transgenic seedlings and non-transgenic segregants grown under low light irradiance (10 μmol/m²/s) for seven days

| Plants | Short Hypo-cotyl | Long Hypocotyl | Chi-Square | p-value |
|---|---|---|---|---|
| $T_2$ seedlings from event -01 | 77 | 0 | 78 | 1.03E−18 |
| $T_2$ non-transgenic segregants of event -01 | 0 | 1 | | |
| $T_2$ seedlings from event -02 | 46 | 4 | 57.48 | 3.42E−14 |
| $T_2$ non-transgenic segregants of event -02 | 1 | 26 | | |

Example 20

Characterization of the Low Light Tolerance of Seedlings from ME25957 Events $T_2$ seedlings from events -01 and -06 of ME25957 containing Ceres ANNOT ID no. 1505805 operably linked to a CaMV 35S promoter were grown under low light conditions and evaluated for hypocotyl length as described in Example 2. A Chi-square test was performed to compare transgenic seedlings and corresponding non-transgenic segregants having a short or a long hypocotyl, as described in Example 3.

Seedlings from events -01 and -06 of ME25957 displayed a short hypocotyl under low light conditions in the $T_2$ generation, and the transgene was linked to the short hypocotyl phenotype with a confidence level of $p \leq 0.05$ (Table 33).

TABLE 33

Chi-square comparison of the hypocotyl length of ME25957 transgenic seedlings and non-transgenic segregants grown under low light irradiance (10 μmol/m²/s) for seven days

| Plants | Short Hypocotyl | Long Hypocotyl | Chi-Square | p-value |
|---|---|---|---|---|
| $T_2$ seedlings from event -01 | 48 | 4 | 56.6 | 5.33E−14 |
| $T_2$ non-transgenic segregants of event -01 | 0 | 21 | | |
| $T_2$ seedlings from event -06 | 46 | 0 | 16.59 | 4.64E−05 |
| $T_2$ non-transgenic segregants of event -06 | 17 | 8 | | |

Example 21

Determination of Functional Homolog and/or Ortholog Sequences

A subject sequence was considered a functional homolog or ortholog of a query sequence if the subject and query sequences encoded proteins having a similar function and/or activity. A process known as Reciprocal BLAST (Rivera et al., *Proc. Natl. Acad. Sci. USA*, 95:6239-6244 (1998)) was used to identify potential functional homolog and/or ortholog sequences from databases consisting of all available public and proprietary peptide sequences, including NR from NCBI and peptide translations from Ceres clones.

Before starting a Reciprocal BLAST process, a specific query polypeptide was searched against all peptides from its source species using BLAST in order to identify polypeptides having BLAST sequence identity of 80% or greater to the query polypeptide and an alignment length of 85% or greater along the shorter sequence in the alignment. The query polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog and/or ortholog sequence with a specific query polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a query polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original query polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog or ortholog.

Functional homologs and/or orthologs were identified by manual inspection of potential functional homolog and/or ortholog sequences. Representative functional homologs and/or orthologs for SEQ ID NO:88 are shown in FIG. 1.

Example 22

Generation of Hidden Markov Models

Hidden Markov Models (HMMs) were generated by the program HMMER 2.3.2 using groups of sequences as input that are homologous and/or orthologous to SEQ ID NO:88. To generate each HMM, the default HMMER 2.3.2 program parameters configured for glocal alignments were used. An HMM was generated using the sequences aligned in FIG. 1 as input. When fitted to the HMM, the sequences had the HMM bit scores listed in Table 34. Other homologous and/or orthologous sequences also were fitted to the HMM, and these sequences are listed in Table 34 along with their corresponding HMM bit scores.

TABLE 34

HMM bit scores of polypeptides that are homologous and/or orthologous to Ceres Clone 28780 (SEQ ID NO: 88)

| Designation | Species | SEQ ID NO: | HMM bit score |
|---|---|---|---|
| Ceres CLONE ID no. 28780 | *Arabidopsis thaliana* | 88 | 428.7 |
| Ceres Clone 1073674 | *Glycine max* | 89 | 419 |
| Ceres Clone 1118987 | *Brassica napus* | 90 | 418.4 |
| Ceres ANNOT 1461298 | *Populus balsamifera* subsp. *trichocarpa* | 92 | 435 |
| Public GI 34907938 | *Oryza sativa* subsp. *japonica* | 93 | 419.6 |
| Ceres Clone 1603237 | *Parthenium argentatum* | 94 | 345.8 |
| Ceres ANNOT ID no. 1285138 | *Arabidopsis thaliana* | 100 | 391.8 |
| Ceres ANNOT ID no. 1373087 | *Oryza sativa* | 104 | 419.6 |
| Ceres ANNOT ID no. 1440417 | *Populus balsamifera* subsp. *trichocarpa* | 106 | 431.3 |
| Ceres ANNOT ID no. 1505805 | *Populus balsamifera* subsp. *trichocarpa* | 108 | 414.8 |
| Ceres ANNOT ID no. 828846 | *Arabidopsis thaliana* | 110 | 422.5 |
| Ceres ANNOT ID no. 832857 | *Arabidopsis thaliana* | 112 | 372.2 |
| Ceres ANNOT ID no. 847799 | *Arabidopsis thaliana* | 114 | 391.8 |
| Ceres ANNOT ID no. 856813 | *Arabidopsis thaliana* | 116 | 414.2 |
| Ceres ANNOT ID no. 870022 | *Arabidopsis thaliana* | 118 | 390.3 |
| Ceres CLONE ID no. 1025179 | *Arabidopsis thaliana* | 120 | 421.5 |
| Ceres CLONE ID no. 1084747 | *Brassica napus* | 122 | 418.2 |
| Ceres CLONE ID no. 1464359 | *Zea mays* | 124 | 408.4 |
| Ceres CLONE ID no. 604111(a) | *Glycine max* | 126 | 429.7 |
| Ceres CLONE ID no. 964932 | *Brassica napus* | 128 | 427 |
| Ceres CLONE ID no. 1855399 | *Gossypium hirsutum* | 131 | 424 |
| Ceres CLONE ID no. 1858527 | *Panicum virgatum* | 133 | 380.7 |
| Ceres CLONE ID no. 1896482 | Unknown | 135 | 416.3 |
| Ceres CLONE ID no. 1934537 | *Gossypium hirsutum* | 137 | 424.2 |
| Ceres CLONE ID no. 1942084 | *Gossypium hirsutum* | 139 | 416.4 |
| Ceres CLONE ID no. 1988960 | *Panicum virgatum* | 141 | 380.9 |
| Public GI ID no. 92891522 | *Medicago truncatula* | 142 | 418.1 |
| Ceres CLONE ID no. 604111(b) | *Glycine max* | 146 | 429.9 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A plant comprising an exogenous nucleic acid, said exogenous nucleic acid comprising a nucleotide sequence encoding a polypeptide having 90 percent or greater sequence identity to the amino acid sequence set forth in SEQ ID NO:116, wherein said plant exhibits a short hypocotyl relative to a corresponding control plant when grown under low light conditions.

2. A plant comprising an exogenous nucleic acid, said exogenous nucleic acid comprising a nucleotide sequence having 95 percent or greater sequence identity to the nucleotide sequence set forth in SEQ ID NO:115, wherein said plant exhibits a short hypocotyl relative to a corresponding control plant when grown under low light conditions.

3. The plant of claim 1 or claim 2, wherein said low light conditions comprise an irradiance of about 0.01 to about 20 μmol/m$^2$/s of light.

4. The plant of claim 1 or claim 2, wherein said exogenous nucleic acid is operably linked to a regulatory region.

5. The plant of claim 4, wherein said regulatory region is a tissue-preferential, broadly expressing, or inducible promoter.

6. The plant of claim 1 or claim 2, wherein said plant is a dicot.

7. The plant of claim 6, wherein said plant is a member of the genus *Brassica, Glycine, Gossypium, Helianthus, Lactuca,* or *Medicago*.

8. The plant of claim 1 or claim 2, wherein said plant is a monocot.

9. The plant of claim 8, wherein said plant is a member of the genus *Cocos, Elaeis, Oryza, Panicum,* or *Zea*.

10. Progeny of the plant of claim 1 or claim 2, wherein said progeny comprises said exogenous nucleic acid and exhibits a short hypocotyl relative to a corresponding control plant when grown under low light conditions.

11. Seed from the plant of claim 1 or claim 2, wherein said seed comprises said exogenous nucleic acid.

12. Vegetative tissue from the plant of claim 1 or claim 2.

13. Fruit from the plant of claim 1 or claim 2.

14. A food product comprising seed or vegetative tissue from the plant of claim 1 or claim 2.

15. A feed product comprising seed or vegetative tissue from the plant of claim 1 or claim 2, said seed or vegetative tissue comprising said exogenous nucleic acid.

* * * * *

SEQUENCE LISTING

<160> NUMBER OF SEQ ID NOS: 146

<210> SEQ ID NO 1
<211> LENGTH: 1823
<212> TYPE: DNA
<213> ORGANISM: Arabidopsis thaliana
<220> FEATURE:
<221> NAME/KEY: misc_feature
<223> OTHER INFORMATION: Ceres Promoter 21876

<400> SEQUENCE: 1

```
gtctcttaaa aaggatgaac aaacacgaaa ctggtggatt atacaaatgt cgccttatac      60
atatatcggt tattggccaa aagagctatt ttaccttatg gataatggtg ctactatggt     120
tggagttgga ggtgtagttc aggcttcacc ttctggttta agccctccaa tgggtaatgg     180
taaatttccg gcaaaaggtc ctttgagatc agccatgttt tccaatgttg aggtcttata     240
ttccaagtat gagaaaggta aaataaatgc gtttcctata gtggagttgc tagatagtag     300
tagatgttat gggctacgaa ttggtaagag agttcgattt tggactagtc cactcggata     360
cttttttcaat tatggtggtc ctggaggaat ctcttgtgga gtttgatatt tgcgagtata     420
atctttgaac ttgtgtagat tgtacccaaa accgaaaaca tatcctatat aaatttcatt     480
atgagagtaa aattgtttgt tttatgtatc atttctcaac tgtgattgag ttgactattg     540
aaaacatatc ttagataagt ttcgttatga gagttaatga tgattgatga catacacact     600
cctttatgat ggtgattcaa cgttttggag aaaatttatt tataatctct cataaattct     660
ccgttattag ttgaataaaa tcttaaatgt ctcctttaac catagcaaac caacttaaaa     720
atttagattt taaagttaag atggatattg tgattcaacg attaattatc gtaatgcata     780
ttgattatgt aaaataaaat ctaactaccg gaatttattc aataactcca ttgtgtgact     840
gcatttaaat atatgtttta tgtcccatta attaggctgt aatttcgatt tatcaattta     900
tatactagta ttaatttaat tccatagatt tatcaaagcc aactcatgac ggctagggtt     960
ttccgtcacc ttttcgatca tcaagagagt tttttttataa aaaaatttat acaattatac    1020
aatttcttaa ccaaacaaca cataattata agctatttaa catttcaaat tgaaaaaaaa    1080
aatgtatgag aattttgtgg atccattttt gtaattcttt gttgggtaaa ttcacaacca    1140
aaaaaataga aaggcccaaa acgcgtaagg gcaaattagt aaaagtagaa ccacaaagag    1200
aaagcgaaaa ccctagacac ctcgtagcta taagtaccct cgagtcgacc aggattaggg    1260
tgcgctctca tatttctcac attttcgtag ccgcaagact cctttcagat tcttacttgc    1320
aggttagata ttttctctct ttagtgtctc cgatcttcat cttcttatga ttattgtagc    1380
tgtttagggt ttagattctt agttttagct ctatattgac tgtgattatc gcttattctt    1440
tgctgttgtt atactgcttt tgattctcta gctttagatc cgtttactcg tcgatcaata    1500
ttgttcctat tgagtctgat gtataatcct ctgattaatt gatagcgttt agttttgata    1560
tcgtcttcgc atgttttta tcatgtcgat ctgtatctgc tctggttata gttgattctg    1620
atgtatttgg ttggtgatgt tccttagatt tgatatacct gttgtctcgt ggtttgatat    1680
gatagctcaa ctggtgatat gtggttttgt ttcagtggat ctgtgtttga ttatattgtt    1740
gacgttttgg ttgttgtatg gttgatggtt gatgtatttt tgttgattct gatgtttcga    1800
ttttttgtttt tgtttttgaca gct                                          1823
```

<210> SEQ ID NO 2
<211> LENGTH: 1000

```
<212> TYPE: DNA
<213> ORGANISM: Arabidopsis thaliana
<220> FEATURE:
<221> NAME/KEY: misc_feature
<223> OTHER INFORMATION: Ceres Promoter PT0668

<400> SEQUENCE: 2
atagagtttt actatgcttt tggaatcttt cttctaatgt gccaactaca gagaaataca      60
tgtattacca ctaggaatcg gaccatatca tagatatcag gattagataa ctagttctcg     120
tcgctatcac ttcgcattaa gttctagtaa ttgttaaaga ttctaatttt ttactaaaca     180
aaaactaaat caacatcaaa tatgcaaagt gtgtgttgtc cacacaagtg actcaaagta     240
tacgcaggtg ggattggacc atattattgc aaatcgtttc cgaaccactc atatttcttt     300
tttctctcc ttttttatc cggagaatta tggaaccact tcatttcaac ttcaaaacta      360
attttttggt tcagtgatca aatacaaaaa aaaaaaaaa gttatagata ttaaatagaa     420
aactattcca atcttaaaaa tacaaatgaa accataattt taatttatac aaaactattt     480
aattagctaa gggttgtctt aacgtttaga aaataaaaaa ttatgattgt ctgtttaaaa     540
ttacaatgaa tgaataaaaa aaatatgcaa tgaatgaaag aataaatttt gtacatccga     600
tagaatgaga aaatgaattt tgtacaaacc actcaagaat tcaaaacaat tgtcaaagtt     660
ttcttctcag ccgtgtgtcc tcctctccta gccgccacat ctcacacact aatgctaacc     720
acgcgatgta accgtaagcg ctgagttttt gcatttcaga tttcacttcc accaaacaaa     780
actcgccacg tcatcaatac gaatcattcc gtataaacgt ctagattctt tacagcctac     840
aatgttctct tctttggtcg gccattattt aacgctttga acctaaatct agcccagcca     900
acgaagaaga cgaagcaaat ccaaaccaaa gttctccatt tcgtagcttt ctttaagctt     960
tttcagtatc atagagacac tttttttttt ttgattagaa                          1000

<210> SEQ ID NO 3
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0535

<400> SEQUENCE: 3
ttagtgaaat tatgacatta agtaaggttt tcttagttag ctaatgtatg gctattcaat      60
tgttatgtta ggctatttta gttagtatat gaatttaggc agtctatgca aatgatttcg     120
ttttcatttt ttcatatgta aacatcaaga tcaagtaacg ccattcgagt tgatattttt     180
tttttaaatt agtgtgtgta aattttggac cgcttatttg agtttgctaa tgaagttgca     240
tatatattac gttaaaccat aggcaaacta atttgaaaca tccgattcga tttcctgtaa     300
ttttttcttgg ttaattgacc aaaatcaaga tcttcagaaa taaaataaaa gacgaaagaa     360
agctgtcgca aagcagattg tgttaaaaaa aagtggattg ggctcaaacg caacttgtcc     420
agcccgtgac aattaccctat tacgcaagta agagtaacgt atcactggca aaagttggta     480
ttagttacga tatctttgtc atgggggcat gcatgggcat ggcttaagag ttaagcctta     540
agaagagtcc cacactcgtg actctcatga tcacttgttg tttcttacgg gcaaatacat     600
ttaacttttat tcttcattta ttcacctata ttcttttgga taataacttt tctctatata     660
aaataacaaa catcgtacgt ttcatttatt tacaacaagc gatgagaatt aaaaggagac     720
cttaattgat gatactcttc ttttctctcg gttacaacgg gattattaca gataatgata     780
atctatatgg atgctgacgt ggaaaaacaa aatttggtga aacacgtcaa ttaagcacga     840
```

| | |
|---|---|
| cttttccatg gctagtggct aagatcgttt catcacatgg ctatatcata taatacttgg | 900 |
| atgaattcaa aataaacgac tgagaaaatg tccacgtcac ggcgcaccgc tttggactta | 960 |
| agtctcctat aataaataca acaccaaaca ttgcattcca | 1000 |

<210> SEQ ID NO 4
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0585

<400> SEQUENCE: 4

| | |
|---|---|
| tgaagtcatt taatatgagt ttgacattag gtaaacctaa tctatgagat tatagaatgt | 60 |
| agcaaaacta tcaatgtttc ttttccaaaa tattttgtgg ttttttcttt tggttcatta | 120 |
| tgttttgtta tttgtgaatt attttaatat gaagtaatta tattgatttt atatgatata | 180 |
| catattattt tgatataaaa tttaacactt atccattaaa atagcatggg cataatcaaa | 240 |
| atcgggacta ttacgatgaa aaagatagtt aaattgtatg ataaaataaa atgtgtaaga | 300 |
| ttaaaatttt gggttttaga aaattactaa acaaaatata gacaaagtat gttgactatt | 360 |
| atttaaaatt taaatatcat caataagata tagttaaagt cattaagtgt atagcaaaat | 420 |
| gaaaattcta agattaaaat tcgattaaaa ttttttttac taaattaaat atttaaaaat | 480 |
| agggattatc atttactatt tacaattcta atatcatggg taaaaattga aactttttt | 540 |
| taaacccgcc tatctaggtg ggcctaacct agtttactaa ttactatatg attaacttat | 600 |
| taccactttt acttcttctt ttttggtcaa attactttat tgttttttat aaagtcaaat | 660 |
| tactctttgc attgtaaata atagtagtaa ctaaaatctt aaaacaaaat attcaacctt | 720 |
| tcccattatt ggaatggtaa tgtcttcaac accattgacc aacgttaagg aatgtctttt | 780 |
| aatattttg gaacctaaat gctaatactg tataccacaa tcacttatga gtattgaagt | 840 |
| tgagatagag gaggtacaag gagacccttat ctgcagaaga caaaaagcca ttttagcaa | 900 |
| aactaaagaa agaaaaaaga ttgaaacaca aatatgcgcc actcgtagtc caccccctatc | 960 |
| tctttggcaa aagccacttc actctttttc ccttttttat | 999 |

<210> SEQ ID NO 5
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0613

<400> SEQUENCE: 5

| | |
|---|---|
| ttaatactaa cattgtagaa agccacaaaa aagaaattga aatgtgagta gatgctgagt | 60 |
| cagaggtttg gtcaatacac aacagctaat tgagataata ttatacacgt cacgatgact | 120 |
| tgttttttct cctcccaact tgttaatttc tttattctta aaattaaacc atcgcaaaaa | 180 |
| cagaagaaca cagctgtttt tctcgactcc caatttctat tttgctgcta aggacatttc | 240 |
| atttcattat ttcccaattc aggactcctt agattttcct aaatttgttt tcctaacttg | 300 |
| ctctctctca ttctaacatt ttctcatttt tttagattat cttgtacttt ttagtagatt | 360 |
| attttatcag gttttacaaa catacattga cattctaaaa agggcttcta aaaattcagt | 420 |
| gtggaatgct gatatactaa aaaaaggtca tgcaaaatta tctacgattt atctaaaatt | 480 |
| agataaattg ccatatataa ctattaacta ataatcgatc ctttgatttt ttgtttagat | 540 |

```
aaaacgaaac agctatatct tttttttttg ttatcggatt ttaatcgaat aaaagctgaa    600
aaataacagt tatatcttct tctttttttaa ctaatgaaac agttatatct taaacaaaca   660
acagaaacag taaatatta atgcaaatcc gcgtcaagag ataaattta acaaactaat     720 aacaattgag ataagattag cgcaaaagaa actctaattt tagagcgtgt aaacacaaac   780
acgtcttgaa agtaaacgtg aattacacgc ttctaaaacg agcgtgagtt ttggttataa   840
cgaagatacg gtgaagtgtg acacctttct acgttaattt cagtttgagg acacaactca   900
agttatgttt gatatctaag gacttgcact gtctccaaat ctgcaggaag gacttttga    960 ttggatcaat ataaatacca tctccattct cgtctccttc                         1000
```

<210> SEQ ID NO 6
<211> LENGTH: 351
<212> TYPE: DNA
<213> ORGANISM: Arabidopsis thaliana
<220> FEATURE:
<221> NAME/KEY: misc_feature
<223> OTHER INFORMATION: Ceres Promoter PT0625

<400> SEQUENCE: 6

```
gatcatgatc agtttcaact cgctgtgccc acgtgtcgag agatcggcac gtgcctgagc     60
tctcagccgc tcataaatac acttgtttag tagcaacagt atactatagt agtcctctcc   120
tgtttggctt ttagcttgca tcgatggatg gatggatgga tcgcatgaga gggcttcgcg   180
aaggtacgga accttacaca acgcgtgtcc tttctacgtg gccatcgtgt aggcgtctcg   240
ccatgctacg tgtcccggag gatgtctcga tgccaacccct tataaatact gttccattcc   300
aatcccatcg ccacagccag tgcaaatctg atcgatcaag ataatcgagc a            351
```

<210> SEQ ID NO 7
<211> LENGTH: 1022
<212> TYPE: DNA
<213> ORGANISM: Arabidopsis thaliana
<220> FEATURE:
<221> NAME/KEY: misc_feature
<223> OTHER INFORMATION: Ceres Promoter PT0633

<400> SEQUENCE: 7

```
cccgatcggc cttaatctga gtcctaaaaa ctgttatact taacagttaa cgcatgattt     60
gatggaggag ccatagatgc aattcaatca aactgaaatt tctgcaagaa tctcaaacac   120
ggagatctca agtttgaaa gaaaatttat ttccttcgact caaaacaaac ttacgaaatt   180
taggtagaac ttatatacat tatattgtaa ttttttgtaa caaaatgttt ttattattat   240
tatagaattt tactggttaa attaaaaatg aatagaaaag gtgaattaag aggagagagg   300
aggtaaacat tttcttctat tttttcatat tttcaggata aattattgta aaagtttaca   360 agattccat ttgactagtg taaatgagga atattctcta gtaagatcat tatttcatct   420
acttctttta tcttctacca gtagaggaat aaacaatatt tagctccttt gtaaatacaa   480 attaatttc gttcttgaca tcattcaatt ttaattttac gtataaaata aaagatcata   540
cctattagaa cgattaagga gaaatacaat tcgaatgaga aggatgtgcc gtttgttata   600
ataaacagcc acacgacgta aacgtaaaat gaccacatga tgggcaaata gacatggacc   660
gactactaat aatagtaagt tacatttag gatggaataa atatcatacc gacatcagtt    720
tgaaagaaaa gggaaaaaaa gaaaaaataa ataaagata tactaccgac atgagttcca   780
aaaagcaaaa aaaagatca agccgacaca gacacgcgta gagagcaaaa tgactttgac   840
gtcacaccac gaaaacagac gcttcatacg tgtcccttta tctctctcag tctctctata   900
```

```
aacttagtga gaccctcctc tgttttactc acaaatatgc aaactagaaa acaatcatca    960
ggaataaagg gtttgattac ttctattgga aagaaaaaaa tctttggaaa aggcctgcag   1020
gg                                                                  1022
```

<210> SEQ ID NO 8
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0650

<400> SEQUENCE: 8

```
catacttaat tctaaaaaaa caacacttat agtttataag cagctcttat gataaaaatc     60
tttctgagtt atagctctgt taaacttgta ttcaccccaa aaacggatgt ttcatttctt    120
attttttact tggagtattt tattgtaatt tgtaaaaaaa aatgtaaagt gggggatatc    180
atgaaaaaca acgtcacttt gtttggtcac aatatacatt tgataaaata atggtcgtcg    240
cgtgatttag ttgattttg ttttatcaac cacgtgtttc acttgatgag tagtttatat    300
agttaacatg attcggccac ttcagatttg ggtttgccca catgacat accgacatag     360 aaggttaaat ccacgtggga aatgccaata ttcaatgttt ggttttcaaa agagaatcat    420
ttctttatat gatctcaaaa gtatggaatt gaaatgacta atgagcacat gcaattggtg    480
ctatcttaaa aaccgaacgt ctttgaattt aattgttttt tcaccaaagg tacctaatga    540 aacccttca ttaaaaaata aaggtaacaa acaaaatttt gtattggaaa aaacatttt     600 tggaatatat aatttggtaa tagaattatg agcaaaaaag aaaagaaaa gaagaataa     660 tgagcataat aaagccttta cagtattact aattgggccg agcagttttg ggctcttgat   720
catgtctagt aatcttaaac agacgataaa gttaactgca atttagttgg ttcaggtgag    780
ctaccaaatc caaaaatacg cagattaggt tcaccgtacc ggaacaaacc ggattatca    840 aaatccttaa gttatacgaa atcacgcttt tccttcgatt tctccgctct tctccactct    900
tcttctctgt tctatcgcag acattttgt ttatatgcat acataataat aatacactct    960
tgtcaggatt tttgattctc tctttggttt tctcggaaaa                         1000
```

<210> SEQ ID NO 9
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0660

<400> SEQUENCE: 9

```
caagtcaagt tccaatattc taaggagaaa taatagtata ctaaacatac attagagagg     60
ttaaacttct ttttggattt aagtgtgtat gcataggcta tttattctta agtataacta    120
ttaactgtag ctagatttat acaagaaata cataaaactt tatgcatgtg aggtagccat    180
gaatatacgt acatgttgca atcgattata catgttgtat ttggatttct ctatacatgt    240
tttaacttgt cattctctaa gtatatacat accattaata ctgtgggcat gagtttatga    300
taagactttt cttttggaga ccagtttgt tttccttcc acctatattt gtctataggc      360
ttcacggtac actagtttac aagtgttttt atatgttcta aataaattg agattttccg    420 gaacggtatg atctgtttgc aaataaggac gtatatataa cagtatcaaa tatatttgtt    480
gttataaggc aataatatat tttctgagat attgcgtgtt acaaaaaaga aatatttgtt    540
```

```
aagaaaaaaa aagatggtcg aaaaagggga gtaggtgggg gcggtcggct tttgattagt      600
aataaaagaa accacacgag tgacctaccg attcgactca acgagtctac cgagctaaca      660
cagattcaac tcgctcgagc ttcgttttat gacaagttgg ttttttttt tttttttaat      720 tttttcatct tcttgggttt ggttgggtca ctcttcaggt caggtgtgta aaaagaaag      780 aaagaaaaga gagattgttg tgttgtaacc cctttgacta aaatctaatg aactttttta     840
acacaacaaa actccttcag atctgaaagg gttcttcttc tctcttagtc tcttcgtcct     900
tttattctcc gtcgtcgttt catgatctga ctctctggtc ttctcttctt cttcttcttc     960
ttctattttt tcttacttcg tcactgttgt gtctgaac                            998

<210> SEQ ID NO 10
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0665

<400> SEQUENCE: 10
aaaaaggatg ggtaatggga cctattttcc ccaacatccc acatgcacac ttccctctcc      60
attctctcac atttatttct ttcattctaa tttatccatt ccgtgtgtaa catattcact     120
aataatctca tctcactaac tcattcattg attgtgatat gtttatctag aattagtgtt    180
ttaacactgt gtctacatat gatttccttt tcattgtatg tgaacatgtt aactcactaa    240
tcattttgta ttttcgagtt aacatgagtc tccacttcgg tagactaaag taaagatagg    300
tttgagtata ataaagttta aaatttgctt taaaatcaat atttataaat aagtttttat   360
cataagtgat ttttgtatgt tatattggac cttgtataaa cagactacag aagaaaatta   420
tttatgagaa cttgtaatgt tagagtggac ctcgtataaa ctaattatgt gggcttttac   480
cataaactat ttatgaaaat tattatggcc cacaccacta taactaaagc ccacatattt   540
agcagcccag tttcattgta agagacatgt tcgctctgga actagaattt tctggttttt   600
gggtatttgt tttcttatgt gtagagaaat gatggtaacg attaaatgtt gtgtattaca   660
atttacaatg gtaagacgat taatatattt acacacaatt tgttgttgc tgtaacacgt    720 tagtgtgtgt gatgatagaa tttcataaag ctttaactac gaggggcaaa atgttaattc   780
taaatagttg acagcagaaa aagatatgta tacataatat aaggattaaa acgtaaataa   840
taataaataa ggcgagttaa attaaaaccc tgttaaaacc ctagcttgaa acacatgtat    900
aaaaacactt gcgagcgcag cttcatcgcc atcgccattc tctctctcat caaaagcttt   960
tctccttgat tttcgcattc tttagagtct taacgcaaag                         1000

<210> SEQ ID NO 11
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0672

<400> SEQUENCE: 11
cagccgtaaa tcctccataa atttattttg caagttttgc tcattatata atgagcggaa      60
tttatgatat aatcgtttgt aataatgtta tgttttgatc aaaatttgaa attaaaagta    120
ggtgagaact tgttatacag tgtagataag gtggatcttg aatataaaaa taaaatttat   180
aagatgtatt taaagcagaa aagcataaaa ctttagataa aataatgtaa aaatgtgtta   240
```

```
gcatcaatgt tgggatattg gccgacccga acttaatcaa tgtcggaagc cattacttct    300
ctcccaaaag accttttcc ttcggagaac taggaacttc ctcactacct ttcgcttaac    360
gtgaaagcca taaatttcat atattcataa aaatcagaaa atctaaaact gtttagtatc    420 acctgtttt ggtatagact attggttttg tgttacttcc taaactatat gatttcgtac    480
ttcattggat cttatagaga tgaatattcg taaaaagata agttatctgg tgaaacgtta    540
cttcagtcat gttgggtcta gatttacata ctactatgaa acattttaag ataataatta    600
tcctagccaa ctatatgttc tatattatgg gccaagaaga tatagaacta aaagttcaga    660
atttaacgat ataaattact agtatattct aatacttgaa tgattactgt tttagttgtt    720
tagaataaat agtagcgtgt tggttaagat accatctatc cacatctata tttgtgtggg    780
ttacataaaa tgtacataat attatataca tatatatgta tatttttgat aaagccatat    840
attactcctt gacctctgcc cccatttcct tttactataa ataggaatac tcatgatcct    900
ctaattcagc aatcaacacc aacgaacaca accttttcca aagccaataa taaaagaaca    960 aaagcttta gtttcatcaa agacgaagct gccttagaa                           999

<210> SEQ ID NO 12
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0676

<400> SEQUENCE: 12
aagatagtac agtttcagtg ttttgagaaa aaaagctgaa ctaaaactaa aatgtttaag     60
gacacaatat ttagtttcaa ttagataatt caacagtttg aacaatttt tttttttttt    120 tttgaagtca tttatttata caatgtttta aaacgcatta agcatttagg cagccgacaa    180
acgcctattg tctaactgta aataggcgct tccacttagg ttcatattgc atatttacta    240
tatgtgtata gtgacaaaaa ccaatatttc tcttattttg gatgaaggta tagtagttgt    300
taaatgttca atataattaa gcattaatga caaataaaat aaaattaatt tagttgataa    360
aaagataatc ttataaaaag atcgatgaat agatataatg gtttactgaa ttctatagct    420
cttaccttgc acgactatgt cccaaggaga ggaagtacct taactataat tctgaacata    480
attttgtcta tcttggtgag tattatatga cctaaaccct ttaataagaa aagtataat    540 actggcgtaa cgtaataaat taacacaatc ataagttgtt gacaagcaaa aaacataca    600 taatttgttt aatgagatat attagttata gttcttatgt caaagtacaa ttatgcctac    660
caaaattaat taatgatttc aacaggaagt ctgagatgat gggccgacgt gtagttacgt    720
ttcttgaatt gtgagagatg gtatttatta tactgaagaa aacattattt actaaataaa    780
ttttcatttc acatcttctg taatcaatgc gggtagatga agaagttgtt aatacgatgg    840
ccaaccatat ggatctcttt tttggcgttt ctatatatag taacctcgac tccaaaggca    900
ttacgtgact caataaaatc aagtcttttg tttccttta tccaaaaaaa aaaaaagtc     960 ttgtgtttct cttaggttgg ttgagaatca tttcatttca                        1000

<210> SEQ ID NO 13
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0678
```

<400> SEQUENCE: 13

```
aattaaatga aaccgcccct aaattaggag ggatttgggt aagtggtaac acattcactg      60
gaaacatgtg aagaaggag gatgtcaagt agctgaaaac tcagtatagt aaccaacggc     120
ttctcaccaa cctttcatta ataatttggt catccctata tttttattca acattttgtt    180
tttcaatagc ttagagcacc ttaatacctt tcagtgtttt tttataaaaa aaacaaaaat    240
tgggattaat catcaatccc caaatgtaac gtttacttag attatgttca tttttctata    300
cacacaaatc atattctttt gttttaatct tcgaaaaacg agaggacatt aaataccct     360
aaaaaggag gggacattac taccaacgta cattaacatg tttgatagca aacgattat      420
tttgttcgtt ttgaaaaggg gaaagtaatg tgtaaattat gtaaagatta ataaactttt    480
atggtatagt aacattttcg aataataaga gagggaaaac actcgccatt gtcggcaatt    540
tagaaccaat attagaaggg ttttttttaga gaaaaaggac ttaaaagttt agagaccta    600
acaacaactt atttagaaat agacatgctt aagttgacaa cagcgagttt attttctata    660
tcgaagaaaa atacgaactt tttcttaatt agatttcgaa tgcatgcact atcgagaatc    720
gaccgtcaca agaaaaaact aatatacata ctgtacatat ctatattcaa tattggtggg    780
gatgggttta atgtgtattt ataattcatg gataaattca cacaataagg tccatgaaac    840
tagaaggtac caaaataag cattaatgac tctttgccac ttatatatat gattctctca     900
tagtaccatt ttattctccc aaacctatct tcttcttcct ctcttgtctc tctcgctctc    960
tctcttctac attgtttctt gaggtcaatc tattaaaa                            998
```

<210> SEQ ID NO 14
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0683

<400> SEQUENCE: 14

```
gattgaatga tgagtgtgca cccttgtatt actaataaaa aatttagcaa cagttataag      60
ctaacgtcat ccatgagtca ttcattagat tcactatttg cgttctcaaa aatcgaattg    120
ttaaaatttg agaagctcta atatacgagt caatgagatg tggcaaaagc atgtccttga    180
ccataaaatt tcgaggggtc aactcattag ataaggacaa gaatcaacca attgaaggcg    240
tcttctataa caagtttctt tattactaat attaaagtcc aatggggtga gggggagaag    300
aacttaaata aaaggaaata attggtaagt gaataaaatc taaatacgat actagatgat    360
tgatttgtgc tagtgcatgg tattagatca gatatgtgtt actattcgaa ttcaaattgg    420
catattccat gttgttgata agaaaattgt agaagtgtaa aagctgagtt actatattca    480
aactagtggt ttcataaag tgagacaaca actgtttcac aaaaatgact ataaaatagt     540
aagtagtatt aggtcaattg attttaaaat tttaatcaaa ttcaaatttg tgatataatc    600
aaatttgttt atagaaaatg ttaagaaatc aattttggca gaactaattc agtgagaaac    660
aatcatttac aaaaacaatt ttaacattat ttaacagtaa gatttgacat ttaacccgtt    720
cgtgtgaacc catcatatct aacatggctc tacccatgac gcctccatgc catggacaat    780
tttgacagat cagaagttct gaacgtggac gaggtaagaa caccatgatg atacgattgg    840
agttagttat gtcgccaccg acatcactgc caatctcatt aataaaagtg gtactaaatc    900
tctaatctct attaactata aatataacaa agaaccaaaa gaaagtttct tatctctctt    960
```

| atctttcata atttccaaga aacacaaacc ttttctacta | 1000 |

```
<210> SEQ ID NO 15
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0688

<400> SEQUENCE: 15
```

| | |
|---|---|
| acgttcagag gcatcgcttt tgtacaaatt gaagcgggtt tgttcaatat ttaaaataac | 60 |
| acaggaaaca ttcaaatgta ttattgatgt tgcttaggtt tgtgaaatga tatgaaccat | 120 |
| atcgtatata ttactagatt tttcttatat gttttaaggg tagtggggct gacctatcat | 180 |
| tctgtttggc attaccaatc agactatcag agtattcacc attcaggatt ccataactag | 240 |
| aaaaagaagg ggtttacatt ttctcatact gtataatttt ctactatcag agattttatc | 300 |
| gattacatta atctcatagt gattattctg atttataaaa aagttgacaa ataattaaa | 360 |
| accagtattt tataacaaga ttgtctctct cccatggcca ttattttgac ctctgactta | 420 |
| tttaaatctt aattaacagc ataatactgt attaagcgta tttaaatgaa acaaaataaa | 480 |
| agaaaaaaag aacaaaacga aagagtggac cacatgcgtg tcaagaaagg ccggtcgtta | 540 |
| ccgttaaggt gtgtcgaact gtgattgggc cacgttaacg gcgtatccaa aagaaagaaa | 600 |
| gggcacgtgt atagatctag gaaaaagaa agaatggacg gtttagattg tatctaggta | 660 |
| ccaggaaatg gaacgtcaca ccaaacggta cgtgtcggat cctgcccgtt gatgctgacg | 720 |
| gtcagcaact tcccttatt catgccccc tgcccgttaa ttacgtgtaa cccttccatg | 780 |
| cgaaaatcaa accctttttt ttttttgcgt tcttcttcaa ctttctttt taaatcaaac | 840 |
| cttttctttt taaatcaca ttgcatttcc taacgctcaa caaaatctct ctctactaat | 900 |
| atctctctct ctctctctct attgttgaag aagactcata atcggagatt gtttgttttt | 960 |
| ggtttgctct gtaaattgga gaagttttgt tagagatcaa | 1000 |

```
<210> SEQ ID NO 16
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0695

<400> SEQUENCE: 16
```

| | |
|---|---|
| aacattttct ttaacttact cttaaatttt aatagtaagt tgatgcatgt tatgttgatc | 60 |
| cgtcttgatc acaaatattg ttttatggac gaattctttg acagtaaatg gctatagtga | 120 |
| ctcagcttgg agcatcccga tatgaaaaca aagtgcagta ttgtgtcgtg gtcatcacta | 180 |
| acgcactttc ctagaactat cgcgcgtgtt tgacctatgc aacacaccag atgtcatgaa | 240 |
| cgtatactta aatagaaaca atgatataga caattggcta tattctgtca tggaacgcaa | 300 |
| accggataac atgtctatta gattcatcgg acttgatcat ggttatgtct taatagacga | 360 |
| attctttgtt aacgattggt taaaacggct cacgttagag catcctacta tgacttcaaa | 420 |
| attgataaat attacatgga aatcacttta atttagtta gaaggtagtt aatttagata | 480 |
| ttcttatttta ataaattaaa aaatagaaga aaaaagatg agaagagttt tgttttataa | 540 |
| aataagaaat atcttttatt gtaatttttaa aattaaacaa atttaattta tattaaaatt | 600 |
| atctttgttt tattgttaag gcaataatta ttttttttggt gggaattgtt aaaacaataa | 660 |

| | |
|---|---|
| ttagtatact gttaagtggt cctttaataa taagataacg tgatttaaaa aagaacgaga | 720 |
| caggctaata tagtagagag gaaaaaatac aatttaggcc caataaagcc caatatagag | 780 |
| ttgtgctcaa acacaggtct tcgccagatt tcctatgacg ccgtgtgtca atcatgacgc | 840 |
| caagtgtcat tcaagaccgt cacgtggcgt tgtttctaca cataggcgat ccatacaaat | 900 |
| cagtaacaaa cacgaaaaga gcattcatat gtacgaaagt agaaagaag agactctttg | 960 |
| tgataaaact aagtaagaaa tagcataaaa gtaaaaggga | 1000 |

```
<210> SEQ ID NO 17
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0708

<400> SEQUENCE: 17
```

| | |
|---|---|
| gtttccaaaa ctagtattct ttatttgctc tattcattat atttttatat ttgtaacgtc | 60 |
| ccgaccgtct ttattaggtt tcgacaatca cttctcggaa ggtcgtccat cctgaaatta | 120 |
| ctctatccta aacatgttta actataaaat tctctcgaaa cttttgtaac gtatataacc | 180 |
| acataaattc tcttaaactt atttgcatac accattatat ttctgaaatc gatatgttac | 240 |
| aatattattt aatatttaga ttacttttac tgaatcgaat taaatatcaa atcgaaacaa | 300 |
| atctaatcta ccaaaaataa ttttgttata acatttctt gcctagttct acctcatata | 360 |
| cattttagtt aaagaaagaa atcacaacaa ttcccataat tcaataatta aatccacaaa | 420 |
| atcttggagt aagtaagaga aataaaaaga tagtatctta acataaacaa ttcaaagatg | 480 |
| ctctctcaca caattcacac acacttacaa aacaaaagac agaaacaatg ttttcattca | 540 |
| aatcaaaaga agttataaca ctagtacaaa aaaagctcaa attctaatag taactctttt | 600 |
| tatttcccaa ttacccaaag attctctctc acttcacaaa actagctttg agagtcgtgt | 660 |
| tccacaaaat ccattaaagc tgaaacggtt ttgctcacca ttcaaacaaa tacaaaattg | 720 |
| caaaaccccca aattataaca aaataatata aaaattaaac cgctaaaaag agtgaaccaa | 780 |
| caaaaatcgc cgaatgtgtg tgtaatgaga aaaccgaccc atcatcccaa tcatctcttc | 840 |
| ccgtgtcact ctcttcctct cccacgtttc ttctctcttc cctttatggg ttttaacttc | 900 |
| tccttcttct tcttcttcaa tcttcagtttt tcaaattcaa caacaattca cattttgatt | 960 |
| tcttcatcat ctctctctct ctcgcttctc tctcaaatcg | 1000 |

```
<210> SEQ ID NO 18
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0710

<400> SEQUENCE: 18
```

| | |
|---|---|
| tagtgcgcgt ggggagaggg aatggtgaaa ccttagtggt taagttatga ggaaaatgat | 60 |
| aaaaggataa aacaatcaaa tgcagcttga aacggccata acataaagta ccttatggtg | 120 |
| gtgcgaatat ttttgtgttt ctttcactct tttattgctg aaagctacga cacttgtctt | 180 |
| aatatattgt ttccgcaagt cacatgatct acttttttatt taacgtctag aaacgccgag | 240 |
| atatatgatg attagtatat cacgtctatg caaattgtta gttcgtgttt ggccaaaaga | 300 |
| tatcgagaca tgtctgaaga accgagtctg gttttgagat atttcttcaa gcattactat | 360 |

-continued

| | |
|---|---|
| acaatagaaa aaggagacac gcgaatatga taatagcaaa aggcataaaa aggcgaaaat | 420 |
| taaagaaaaa cgtaaagtga tttggcctca atcaacggga acgtatctta atttagagg | 480 |
| ttcttcttt actttgaga cgagagagtt tgcgtctttg cgagctgctt tggttgacta | 540 |
| aacattatca tattgaaaac caaaatacaa cggaggaata tttgtcacag tttcactttc | 600 |
| acattgttc cttaacgttt aatcaacctt gttcaaaatt tctatagttg taatcatcat | 660 |
| tgtttacaaa atttcgttc aaagatgatt ttaaataaaa ttgtgaaaga aaacctttc | 720 |
| tgaaataagg attggatgat agtgttaaaa gaaaatatg aactgaggca aaagaggag | 780 |
| tggtccccgg aagattgtga aatgtgtcat ctaaaccagc cagacgtagt cacgtgttct | 840 |
| ctctagcttt atgaacttcc ttagccagca ccatcattgt gattgtagta tatatgtaac | 900 |
| cctaccttca tctctcccat tttccattct ccatatagac tcctttacaa tatacaaaac | 960 |
| ctatccaaaa gcgaagaagc caagcaaaca tattataaaa | 1000 |

<210> SEQ ID NO 19
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter PT0723

<400> SEQUENCE: 19

| | |
|---|---|
| gtcatatctt atcaacacgt caacgatcaa aaccttagc ctattaaatt caacggctta | 60 |
| gatcaaaacg aaactaggtg ggtcccactt ttaatatcgt ggctgcataa catttcctcg | 120 |
| ataactgaag ccgttgtggt ctttctcaga atctggtgct taaacactct ggtgagttct | 180 |
| agtacttctg ctatgatcga tctcattacc atttcttaaa tttctctccc taaatattcc | 240 |
| gagttcttga tttttgataa cttcaggttt tctcttttg ataaatctgg tctttccatt | 300 |
| tttttttt tgtggttaat ttagtttcct atgttcttcg attgtattat gcatgatctg | 360 |
| tgtttggatt ctgttagatt atgttattgg tgaatatgta tgtgttttg catgtctggt | 420 |
| tttggtctta aaaatgttca aatctgatga tttgattgaa gctttttag tgttggtttg | 480 |
| attcttctca aaactactgt taatttacta tcatgttttc caactttgat tcatgatgac | 540 |
| acttttgttc tgctttgtta taaaattttg gttggtttga ttttgtaatt atagtgtaat | 600 |
| tttgttagga atgaacatgt tttaatactc tgtttcga tttgtcacac attcgaatta | 660 |
| ttaatcgata atttaactga aaattcatgg ttctagatct tgttgtcatc agattatttg | 720 |
| tttcgataat tcatcaaata tgtagtcctt ttgctgattt gcgactgttt cattttttct | 780 |
| caaaattgtt ttttgttaag tttatctaac agttatcgtt gtcaaaagtc tctttcattt | 840 |
| tgcaaaatct tcttttttt tttgtttgta actttgtttt ttaagctaca catttagtct | 900 |
| gtaaaatagc atcgaggaac agttgtctta gtagacttgc atgttcttgt aacttctatt | 960 |
| tgtttcagtt tgttgatgac tgctttgatt ttgtaggtca aa | 1002 |

<210> SEQ ID NO 20
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter PT0740

<400> SEQUENCE: 20

| | |
|---|---|
| tgtggccact aaagatttac ccttaaccgg gcccatataa gcccacgtca agtggcgctt | 60 |

```
atacgctctc cgtaagagag ccaacatttg gtatgtaatg ttgcaaatta ttcttcaaga      120
caataaattc aaatataatt caatattgtc caaatatagt gatgtacttc agttgtgcac      180
atagaaactc cactaaacca acttttagat agatgcattc acaaattttc aacaatgtcg      240
cgaaagtcta atccatcacc agattctaac attttaatta ttatatttaa ctatacatac      300
tctaatcagc atgagtcaaa cgtgtacaat agcccaagca tataataaga ccaaagtcaa      360
actcaaataa atgtctccaa actcaaaact tgaaaaagac ctaattatta catggtagat      420
atgactttgt cgacaagtaa accaactaat cctcgaagct accttctctt cccagttatt      480
atgtgtgatc gatttataaa tctcttcttc taataacacc tatattttc ttatgatgtg       540 aataaatata aaacttttaa ctttaaaaca tatttatccg aaatattgca cttagatttc      600
aaatagataa ataatagtac tatctaactg atattgaaaa gacctaacac ggaaaacagt      660
tttataaaaa atcccaaatg tgggtaatta tcttgatttc ttgggggaaa cagaaaatgg      720
attaagatta atcggagtcg tgtcaagcag ctcgttaata actgtagcaa gttgactgag      780
taagcatcaa cgtgtcatct ccgtaaagcc cattatttct agtctcgccg cgtcttctct      840
tccacgtagc acttcacttt ttctctcctt ttgtttcctt tggaacacaa acgtttctat      900
ttataggaat aattacgtcg tccgtatctg tgtcggaaca tagatccaaa ttaaaagcga      960
cttacttaat tacatatcgt tcgtgttttt ttcttcaaaa a                        1001

<210> SEQ ID NO 21
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter PT0743

<400> SEQUENCE: 21
tcgattggcc cgatcggccc caaaatcaag ctgagccgct tcaaacttca gcttttgaaa       60 tcaccccccaa actcatgtcc tcttatcatt ataactaaag gatctttcat tttatttaac    120
tcatcgtctt gcactaccca acccaaaggt tccaactata cccgaagctt tctaaaggtc     180
caaagacttt tttttttcgag ccagactatt caagccaaga aaagccaaac cccacaagcc   240
agtacttttc aattccatat tataaactta tctgtcttgt tttagtccca ctaaaaacaa    300
cagaatttaa tttaggttga gctaaaaccc ttgacaaaag tgtatagtcg tcgattcagt    360
agcacactca tcactcatca gatttgatag ttgacctaaa gtatgactac tccatttcaa    420
ctaacaaatg aaaataaaag agacctaagg gttagaggat tgaaactata ctctcaagtc    480
ttttatcact aggctactac cagctagtta acttgatgga tttaagcaag aaaacgtaga    540
atttatattc gagcagattg tttagctaaa aaagcttggg tttgaaattg ccttttctcc    600
catataagca cgtcggttcc taaataactc tttctagcgg agagtgtctt tccaataatt    660
taataaaaat ggtgtttgta tatcaaaaaa aaaagaaaaa agaaactgat cgagatagaa    720
cgtttgcagt tttataaaca atttaaaaaa caaaaaaaat taaactcaat gtattttta    780 ttaattcaca aacaataata aatcatagga tcgaatattt acacggtatc aaaacctact    840
cgccgctact atataaaaat tgaagtcaaa tatcaaccgc aattattaaa ccagcaagac    900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                                1024
```

```
<210> SEQ ID NO 22
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0758

<400> SEQUENCE: 22
agctagccac atcagtgacc aaaaaagata attaacaaac caaataaaat aacaaatttt      60
gatcatttgg aataaaattt ataaaaggaa cgaaagcgcc ttctcacggg tcccatccat     120
tgaaatatat tctctctttt tgctctatat aataataacg cgtactaatt tgtagtatat     180
attattacaa agtcgatatt tgattgtttt gtgaacgttg atatattaat tttcttggat     240
gatgacaaaa aaagtcatag aaagtaacgt gtgaacatag cattaacaaa atacaaacat     300
aatatataac caaatatatg aaaataggat aaaatctcat tgaatagatc ttcttctatt     360
caaatatata aatatttgtt tgtctataaa attaacagag cattcacatt atctaaaata     420
atagtaaaat caaaataaaa ctaaataaaa ataactctgg ttttataacg attgatttta     480
aatattagtt tttgttgtaa agagatcatt atatatgtct gtaatatttt tatactgagt     540
tacatgatat ttagttatta tagcgtaatt aactaagata agaaattaac taaagtgata     600
ttctgattat tattattttt gttaggacac gtacgtggaa aaactaaaca ctataggtta     660
caaaacggta taataaactc accattactg gaaaatgttt gcatttgact caataagtaa     720
cttattataa gttactgata taatgcatag ttttgaaatt cttaaataaa ttattttggt     780
ttcgcatgaa aatatgaaag gagagaaatt tattattgtc acttatatat atatacatcg     840
taatcatttt ttcgtgaata attctctctc ccattccatt atttctcagt atctctcttt     900 cttttcccтта ctttattgtt gcttttaaac cttcaatttg ctcataaacc aaatatataa     960
tatcaaaaca aacaaacaaa aaatcagaat tcccctaata                          1000

<210> SEQ ID NO 23
<211> LENGTH: 921
<212> TYPE: DNA
<213> ORGANISM: Arabidopsis thaliana
<220> FEATURE:
<221> NAME/KEY: misc_feature
<223> OTHER INFORMATION: Ceres Promoter PT0829

<400> SEQUENCE: 23
aaagttttga attattggga atcaatttcg aagttttgta attctttggg ggctaatagg      60
atattttatt ttcttggttt cgtctattgt tgttttttcta tttatggttg ggcttttaga    120
actctggaca ggcccatgtc atatgttttc ccttctcctt atattttttca tttttcattt    180 tgttaaatta atgcataata tccaaaaaca atttaaattt ttgaaggaac cctttagtta    240
cggctccgaa gctttcacaa gtgagaatgt gagatcaaag aaggcaaatg gaggattta    300 aaagttaaaa tcatctttta tctgcaaaag ttgacaattt ttttgtatca aatctaaatc    360
atcaaactct cttaaactac aagagcataa caacctctat gtaatccatg aaataatctg    420
cttgaaggac ataacataaa tcattatggc tagagtgact aacttcaatc aaatcctctt    480
aactctagct cccttacaat ggtatcgtaa acattatgc attagggatt gttgtcctag     540
gaaaataaaa taaaaatccc cacagaccaa ctaccatttt aacttaaaaa taagcttcgt    600
ccgcgacgaa ttgttttcca tcctaaaaat agaatggtgt aatctgctaa tggtttagtt    660
ccattaactt gcaagttcta ttgaaagcct aaatgtcaat aaagatatta aaattcggag    720
tcaaaagaca aatgaatcaa aagcaacaag acaagtcagc tccattcttc actacccatc    780
```

```
ttttacaata aatcatctct cttttcacaa atttcaaact actctcattg ccctttagct    840
ttgttataga gccaacacta cagagagact cacacacttg tttcaataat taaatctgaa    900
tttggctctt cttataaact a                                              921

<210> SEQ ID NO 24
<211> LENGTH: 763
<212> TYPE: DNA
<213> ORGANISM: Arabidopsis thaliana
<220> FEATURE:
<221> NAME/KEY: misc_feature
<223> OTHER INFORMATION: Ceres Promoter PT0837

<400> SEQUENCE: 24
aactacaagg gagacataat atccaccatct ggttcctgtt atcatctgaa gatttcttgt    60
tttaccttcc agtgataaaa tgatccttat aatacatata gatatattaa attgctgtat   120
tttaagatta tagatatata aggtacatga gagtgtttat ttaaaaaaat tcacttggaa   180
ttcatgtttt gtgatacgtt agattggaat ccatttggga aaagaagaat catctgttct   240
tatgtctcaa atttttgactt cattcacttt tcttcttgtc ttttaagaaa gcttccacaa   300
tctaactgtt cgatgtgaaa actgagattc gagtaagaaa atgtgaactg tgttatactg   360
ttttttaatt agataaattta gattgcactc agataaatta ataacattcc tcgaatactt   420
ttatgtgatt ggatatatta ggtatatctg ccaaccaacc aataaactgc tatgtttaaa   480
caaattaaat aaattagtat atgtttactc aagaataaag aagatagaaa agaaaattct   540
atatgagcta aatttgctgg aggaggcatc ggacgtgggt accagacctt tccaagcaca   600
cgagtagtgc ttagccatgt catgctaaca tacaccattt ggttcataca aaatccaaat   660
caaaatctat ttttaaaatc ttttgcacac gtctttgaaa acacctctc atactatagc   720 tacggaagct tcaatttcaa ggtttgtcta aaagctaacg att                     763

<210> SEQ ID NO 25
<211> LENGTH: 751
<212> TYPE: DNA
<213> ORGANISM: Arabidopsis thaliana
<220> FEATURE:
<221> NAME/KEY: misc_feature
<223> OTHER INFORMATION: Ceres Promoter PT0838

<400> SEQUENCE: 25
atactggtat gcttaaggtt gaagccaaga tctctgtctt acccaagtaa ccactttcta    60
ttagaaggga tcaacactaa gaatatggag atttaagcct aagggctaag gcggttctca   120
acaatacatg atgtgaatac aatcacagac gatttactga ggtttgttga taagatcttg   180
atcagtctct gcatcatctg ttcaacaatc tcaatctttg actgtttgct ttcggagcca   240
taaacagagg aatcccttat tccctgttat aggagcaata caccaagtat tatttccatg   300 gctgaaaattc tcttatggaa acctaattgt tccattgaag ctgtaaaatc gaatctggtg   360
aatattctcg agcaaagccg catgctaatt atgtcaattc agaagagttt gattaggaga   420
ctcgaagcga gtttgatgat cttttcttgat gttcaactcc gattgtaagg gtataattga   480
cttttcatgt attacggctc caccacctga cactaaggca ctctttgtcc atctcgttgg   540
tatcatcgga ttcggatggt aaaaataaaa agagcagagg aaacttgtta ctcatgcaag   600
cttctcaggt gccacgtcac tccattacgt gtcatcttca cacaccatct cgctcaaaac   660
cgatctcatt tttcaaacct taaggcaga agcaactgat taagttaaca ctcttgagaa   720
gctctcgatt aagcttgaac ttggaggatc a                                  751
```

<210> SEQ ID NO 26
<211> LENGTH: 669
<212> TYPE: DNA
<213> ORGANISM: Arabidopsis thaliana
<220> FEATURE:
<221> NAME/KEY: misc_feature
<223> OTHER INFORMATION: Ceres Promoter PT0848

<400> SEQUENCE: 26

```
tctctttaaa tcagttaact aaccgtttat atatttacga taaggtttga agagattatt      60
gataaaataa tacatttcat aatcccgcgt tcaaccgttt aaagtaacat ttaagttgac     120
tatatctaat ttttttttcca ttaaatatgg agctggtaaa ctttatcaac ttctaaaaag    180
tgtaacaaca aaaattaggt caatcacaat tctgttttttt ttattatttt ggattgactt    240
ccaattgcaa atagtcttag tgatcaccat tatcatacat atatacatca gtaggtttc     300
atcatgatat accacaaagt atttgacaag ccatatggtt ttggatcaaa aagtcggtcc    360
aaaattaatg ttttatgtgc aagaaccgac ccattgtaca cacgtgttaa catcttcaag    420
actttcatct ctattttttct tttggtcatt aagatacca ttgatccgaa tctgttacat    480
tcccacctac ttttttaatt tttactatcc actccaaatt aaacacaacc gatgatttta    540
ataattggaa gcttttaaaa atatttcaaa acaagcctct ttgtgtttgt ctatatat      600
acacgtaata agaaggtgaa tgaatctcac agcttacttg ttctaaggct tccaataacg    660
aaaacagta                                                            669
```

<210> SEQ ID NO 27
<211> LENGTH: 702
<212> TYPE: DNA
<213> ORGANISM: Arabidopsis thaliana
<220> FEATURE:
<221> NAME/KEY: misc_feature
<223> OTHER INFORMATION: Ceres Promoter PT0863

<400> SEQUENCE: 27

```
cgggaaacga caatctgatc tctagtccag tcgattggcc cgatcggccg attataaact     60
tacatgagac aagtataaat aattattata aacttattaa gtttaagatc aaggcttttg    120
tgcaatgtat caatgaatgt tagatgtgat atgatgaaag caatgttta aacacataca    180
tagtcattga tcggaatgtg tgttattaga aatgcatgcc taagccgata gggttatcta    240
tgtttggtct tggacattat agccaaattt cgaatctaat tcttccaata tatatttttt    300
tttttttgct tagggccact actagtattg cttatcaatt ttaagagctc atgaaaatgc    360
aacaatatag tagttgcaaa tccttgtttc aagagaaatc aaagggccac ttgtgaattg    420
aataataata atatttgcaa ataaccttc actaaaccat accaacaaaa ccacacagat     480
ttggcaaaga cataaccttt gggagacgtg aaaaggctca aaatttgaca attgtcctta    540
caaattcgct cattagtgca attgtgagat ttgtttgcat ccaaatccaa ttcataactc    600
acactcgtct caaattcgaa aaggcctgca gggccagtgc actgggatcc aacaatgtcc    660
tccgactcgt ccaagatcaa gaggaagcgg aaccgcaccg cg                       702
```

<210> SEQ ID NO 28
<211> LENGTH: 435
<212> TYPE: DNA
<213> ORGANISM: Arabidopsis thaliana
<220> FEATURE:
<221> NAME/KEY: misc_feature
<223> OTHER INFORMATION: Ceres Promoter PT0879

<400> SEQUENCE: 28

```
ttctaggaag actggtcaag ctaagctgtt tctgtttttt gtttttgtac tttacttttt      60
gtttgctagt gggaactggg tttattgggc cttgaagttg ataaaagatg aataaaagac     120
atatcgccta aagcccatat gagaagcaga agacaaaaac ctccaacttt gggcataaat     180
tttgattata gttaaaagtc cagacccaat ttggcacctg gcttagttac gattctaagg     240
catgacacct gcctaatatg tttattacag aaaataaaga gaatcagcta ggtgtccctt     300
attgaacaca ttaacaaact ccaacgacac tacgtgtctt cgtgactctt actatatcca     360
aaaacctata gctaaagctg aattttccat gattagtata gtcccaacca aaaaaatact     420
gaagaaggca taagc                                                      435
```

<210> SEQ ID NO 29
<211> LENGTH: 397
<212> TYPE: DNA
<213> ORGANISM: Arabidopsis thaliana
<220> FEATURE:
<221> NAME/KEY: misc_feature
<223> OTHER INFORMATION: Ceres Promoter PT0886

<400> SEQUENCE: 29

```
agtgtatttg aaaacgacat tgaagaatta atatattttt ttttaatttt agtttttat      60
agtacaaata ttaaaacaaa caatcctacc atatcataac atttgtaaat aacattttaa    120
gttttgtttt gagttttaat taattttcta tgacaaaaaa atgaagtcaa tagactaagt    180
gaatcatata gtataaataa acacaattta aatagtttca aataaattta gaaagaataa    240
aacaaataga aatcagaagg tgtctgtttc ctcctcgcaa catacgatca aagagaaaca    300
acttgacccct ttacattgct caagagctca tctcttccct ctacaaaaat ggccgcacgt    360
ctccaacctt ctcccaactc cttcttccgc catcatc                            397
```

<210> SEQ ID NO 30
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0007

<400> SEQUENCE: 30

```
agcagaacaa ctatatttat tgtgtcacat aaatctgaga tcatttataa ccaccaaaga     60
acctatacac agtaaatgac aaatgtatct ccctctatct ctattgccca tatgtagatg    120
ctaaagtaag atttctcttt tttttaatgt acttttttttt gtataaagta tattccataa    180
gaaaaaggaa aagcttgttt atggatcaat tgacccccaaa aaaagttttt agatcaaagc    240
ccaatataaa aaaaaaacac agtagtgaca caaaggaact taaataaacc atgaattgat    300
ctataaacag tagagatcga taaggcgaac attttccatg tgaagtgtct tctttcatct    360
ataatatttt tgacatccaa taatttcctc tataatatca ttcacataat tgatagaaac    420
attatgttag aattgtccac atcatttgag ctgtaatata ttctgttta acaaattata    480
tggtagttgc ttaatcttat gtccatcttc ttctatgcat cgttttcgcg cctagttgtc    540
cagtccattt caactaccta cctctaattc ttatcttaaa acaacatttt ttaatttaag    600
tattatgctc aaagactaac tagatagaaa accgttatta acattaaac gaattaaaag     660
tcttacatgg aaaatgtagg tttataaacc acgagttatg attgacaata aaaaaaatgc    720
aaatcatcaa tcaaaagaga cttgagtgcg actctatatc aaccattgca attaaaatta    780
```

```
tctatcacaa aaattttaga cagattaagt taatttagtc taaattcact aatttatttt      840
ctataattag taattaacta tatttattta tttacacatt ttctgataat ttagaaattt      900
gcatgaataa caaatataag attttggaaa ttagtagcaa atttaattaa taattatttt      960
tgcctaaatg aaccaaacta taaaacctcc acatacacca gtcatcaaat ttacagagac     1020
aaca                                                                  1024
```

<210> SEQ ID NO 31
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0008

<400> SEQUENCE: 31

```
ctcgagagat gaagtcttag taatgtttga acaaacaata atcacgtttt ccatcaaatt       60
cgagcattta aagtttatat tactacatgc cccaagatga taccgtccat ctcatccgaa      120
aatatttctg aaattgcgct aagacaacaa tgtttgctca aattcgatca tttaaagttt      180
acaaatctct catcaatctt acaaacttct cacactaaac agaggtacat attttcttat      240
aaagacaaaa ggttcgaaca gctggcttct caactcgagt tgtttgtcag ggcctctctt      300
cactaactac aagttggtac ttcaaatatt ggtggctagc ttcacgtgat attgtctaca      360
aattaaaccc atgaaaaagc tgcattaatt gttccaagtg aaccctgagg agtgtcaata      420
gtctttgctt tagtgtgatc attaaaccaa atctctaaat tcctaatttg tactaacatt      480
tggaacgtat ttcctactct tctccctgct ccaactccca aaaataagat tagttagatt      540
tctataacta atatacatgt atactcccaa aaacagtaaa accatattaa taaagctaat      600
tttgcataga tttatttcgg taaaccggcg gttcaagttg gggaaaaaaa agacaaacgg      660
tctaaagtca tccaaagaca aaaaaccaaa gacaagttga gagagacgag accaatcaca      720
acattgcttc gtagattgcg tgacatcatc cttgacggct actttcattt gtgtcttatt      780
tggataaaac gcacgtgttt aattcacgaa ccttcatagc aataagaaat ttccattact      840
ttcatatttt caactttttt tattacccat tacatgctta aaatattaat tcacaagtct      900
ttgtcaaaat tcaatatttt ccaggttcat gaacccttt tatctcaatc tactctataa       960
tatctcccta taaattacaa caaaacctct ttatttttca                          1000
```

<210> SEQ ID NO 32
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0028

<400> SEQUENCE: 32

```
gtcagtgaag tcgattggta gtacttgaaa cacttggttg gtttcatgta tttggcctat       60
atataaacaa acatcgtaat tatatacgga ttttttttcgg aattttacgc catatctgta     120
agtatatata acatgcatgt cgttttcaaa ttcatatgat gaacgatcca cgtaagtgct      180
actactccta caatattgca tgagagagat atgtatttat aaattttatt ttgaagaaga      240
aataagaggg aaggttactt gggtggatcg atgtgaaaac aaaagaagaa aaagcgaaac      300
ccactaagcc attacatgat atcgaccttc ttatctttttt cctctttatt ttattttttct    360 catcttcttt ttgtcaggac tttttttctac ttaatgaaac ctccaaacta tctaactaat     420
```

```
acactcccat gtagaataaa gaaaattata taagatattg ttgatatttt gtaactagaa    480
aatatatttg ctctgtaatt tttcgtaagt taaatcaaca ttttaaagta gaaacaaata    540
ttactgcaaa aagtaggatc attattttg tccaaaatct cagttagcta tagggttgta    600
gtaaaaacaa aacacattct tgatttgccc caaaaaataa agagagagaa gaatattgtt    660
caaaagtggt ctcttctctc tctaattatg ttttcactaa acccaattag attcaaacag    720
tctacaaagt ccaaaagata aacatgggac aacaattcga tgcaaaaaat cctcttttca    780
tgctcttttt ttattctcta gtcttttaaa ttactaataa aaactcacaa atccaccaaa    840
cccattctct acaactcacc ttcatctaga tttacccact cccaccgaga aacacaagaa    900
aaaaaatata catatataaa tatacaagac aacacatgat gctgatgcaa tatacacaac    960
aaagtattaa atcttagata ttgtgggtct ccctttcttc tattcatttt cttattcatt   1020
aaaa                                                                1024

<210> SEQ ID NO 33
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0039

<400> SEQUENCE: 33
ccgttcgagt atttgaaaat ttcgggtaca cccgcctaaa taggcggacc ttatctagta     60
tatatataca tttgaactat attgtttact ttttagttga tttaggctat gtcatgacat    120
tgacataaat ctacctgtta tttatcacgt gtaattcgtg taaagtgtaa actagaaagt    180
tcaaatacgt atttgttttt gttctgttat ataggattgt catagttgta aatctacaat    240
ttattacaac atgaataagt acacaagcaa tgtaattgga tttaattgct aaactcttta    300
catggtcaat ctaaatttga taagaaatac gtcacatatt actaagactg atagtttttt    360
tgttgtcacc aattattttt gttaaattga cgaaaacaat tccaaaaact caaatgtaca    420
aaatcataca gtctcacaaa catctcatag agaaagatat aaatctccca tatgggaacg    480
ataacacgag gtcgaaatac tattcgtaaa actaaaacgc cttagttata aatcgttagt    540
tgtaaccgcg gtcgagaata catacagatc cacgaaacta ctactacaca tgctgctgaa    600
ttggaatttg gaaaagacca tcttctttag gaagagctca cccaatgagt gacaaaggtg    660
tcggtggctt gttttctacc catatgtata catcaaatgg tagtttcatt aacgtttggt    720
tttgagaaaa gtaagacttt ggctagtagc taggttcgta tataataaac tcttttgaga    780
aagttcatca ctggtggaaa atgttaaacc ggttttttct catttttttcc gccatgttaa    840 ccaccggttt aaaaagaccg taacacattg aaagattaat aagggtatat ttgtaattac    900
ggtttgctgg caattttaa ttattatttt aattagagaa aatagagaag ccctatcaat    960
gtacatggta tatatataaa aggcaaaacc ctagaaaacg atactattcg actcagccgt   1020
cctt                                                                1024

<210> SEQ ID NO 34
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0050

<400> SEQUENCE: 34
```

```
aatctgatct ctagtccagt cgattggtac ttgagggaaa catcatatttt ttaaaccttg      60 tctcagtaag ctaacacaca ccccttgtga ttacttatcc atgtttatcc acaagaatgc     120
agttggattg agatattttc ttctttgttg aaatcaggcc tcaaggtgtt catgtggtct     180
gcaaaaaaat tcccaaaaat aaagatagtg acatctgaaa tcgataatgg attagacgaa     240
gagtttcgtg ttattccttg gtatgggcgg gtttggggac agatattttg gcacagacga     300
ggactaggcc actgtggtcc tgcagcatta ggtgtcccctt ccatgtcctg cattacattt     360
tattgatgga ttcatcaccc tatctactac aacggctaca caaactatga agagttttgt     420
ttactaataa atgcccaagt gaggggtcga tcgaacccgg gacacgtttt tcagtttacc     480
atatagaatt atccttggaa cccttgatac tccatagaac atcaccacct ctgttgtcat     540
ctcaggaatc caggttcaaa cctagtctct ctctccctag tgggaggtat atggccactg     600
ggccaatgat gacaaaatgc aaaaaaaata aaatacattt gggttcatta tctaaaatat     660
ctcttgtgtt tgtaagtttt ggttgcacac tcgtgtggtt gaagtgtgtg tgagaggtac     720
tatacaatac actctgcttt tgttttgtac ctatctcttt ctcttctcca catatccaag     780
actttgggga taaagctgag atcattggtt gccatttggt tgtgtagaag caatcaccca     840
tttgctttat ccgaggttga taaatttcct cgggttctcc ttctgacacg tatgacaaat     900
tctaatagta tattcctcgt agatattacc tatatattct caatagttgc aggtacttaa     960
ggctttgtct tggcatcctc gtcctcttca gcaaaactcg tctctcttgc actccaaaaa    1020
gcaa                                                                 1024
```

<210> SEQ ID NO 35
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0086

<400> SEQUENCE: 35

```
cttatccttt aacaatgaac aggttttag aggtagcttg atgattcctg cacatgtgat       60
cttggcttca ggcttaattt tccaggtaaa gcattatgag atactcttat atctcttaca     120
tacttttgag ataatgcaca agaacttcat aactatatgc tttagtttct gcatttgaca     180
ctgccaaatt cattaatctc taatatcttt gttgttgatc tttggtagac atgggtacta     240
gaaaaagcaa actacaccaa ggtaaaatac ttttgtacaa acataaactc gttatcacgg     300
aacatcaatg gagtgtatat ctaacggagt gtagaaacat ttgattattg caggaagcta     360
tctcaggata ttatcggttt atatggaatc tcttctacgc agagtatctg ttattcccct     420
tcctctagct ttcaatttca tggtgaggat atgcagtttt ctttgtatat cattcttctt     480
cttctttgta gctggagtc aaaatcggtt ccttcatgta catacatcaa ggatatgtcc     540
ttctgaattt ttatatcttg caataaaaat gcttgtacca attgaaacac cagcttttg     600 agttctatga tcactgactt ggttctaacc aaaaaaaaaa aaatgtttaa tttacatatc     660
taaaagtagg tttagggaaa cctaaacagt aaaatatttg tatattattc gaatttcact     720
catcataaaa acttaaattg caccataaaa ttttgtttta ctattaatga tgtaatttgt     780
gtaacttaag ataaaaataa tattccgtaa gttaaccggc taaaaccacg tataaaccag     840
ggaacctgtt aaaccggttc tttactggat aaagaaatga aagcccatgt agacagctcc     900
attagagccc aaaccctaaa tttctcatct atataaaagg agtgacatta gggttttgt     960 tcgtcctctt aaagcttctc gttttctctg ccgtctctc                           999
```

<210> SEQ ID NO 36
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0088

<400> SEQUENCE: 36

| | | | | | |
|---|---|---|---|---|---|
| tcgattggga | ttactacttc | atctagtaag | gttctgaaaa | cgtttgttgt | tgataaggaa | 60 |
| gattcgtctc | aggttattac | tgttgatctt | caaggtttgt | gattgtgacg | cttatacatg | 120 |
| tgctgaaact | gtggtgttta | tttattgaaa | acaaaaaaaa | agtctctctt | gtagtttcat | 180 |
| tgtactaaat | agaaaacaag | aaacgttttt | ttctttaatc | ttctacattg | ataatattgg | 240 |
| atcaaaggat | tgtttctgca | agacacaaca | caaacatact | tatactagtt | tacttctact | 300 |
| aagtactaac | tacataccca | tacacacact | tgcacctaga | ctttacttct | agacatcatt | 360 |
| accctaaggt | agaaccaagc | ttacaagcaa | gttttaccga | caactcttac | attacaactc | 420 |
| tagtctgtag | tctttaacgt | agacttacta | actagtcatt | agtggtttaa | ttttttaaat | 480 |
| tttcatccat | atgttttttgt | tgtagatata | aactaaagtc | ggtcacattt | aataattgtc | 540 |
| attatgtccg | cgtaaaagtc | aattcagcta | ttggacattt | atgaaatgta | agattttctc | 600 |
| tctcatttcc | ccgtgcgtga | agacatgcat | tggttttttct | gtaataatca | acaaatccaa | 660 |
| acccctttc | gatctttatt | tggacattgt | tagagacaaa | atttctctat | agtctttttc | 720 |
| ctaatttgat | accatgtttt | tgtttctgca | caaatttact | cactggttta | actaactatc | 780 |
| cacttattta | tgattttacc | attaggcgtc | agctagccct | agtcaaattt | gtaaacaagc | 840 |
| caagctatct | acataaatcg | agatgtcatt | aacgttaatc | gtcgttaatt | cgaatttgaa | 900 |
| aacatagata | gctttagcag | tacaatgggc | aatggtaaga | agaatagcaa | aaggcccaat | 960 |
| atttggtttg | cagaaattaa | agccttaaaa | aaaagcccac | agatatttgt | caaagaaccc | 1020 |
| taat | | | | | | 1024 |

<210> SEQ ID NO 37
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0092

<400> SEQUENCE: 37

| | | | | | |
|---|---|---|---|---|---|
| aaagattgag | ttgagagaga | tggtggagac | gcagaacaga | caaagggagt | ttaccatata | 60 |
| gtgctctaaa | gggcaatgag | attgcagtga | tgtggctatc | cggggaatca | tcgcaggtta | 120 |
| ttccttccca | tgagcaacaa | tcaatggatg | ggttccaatt | cagaggagaa | acagaagaag | 180 |
| aaacgttttcc | agagaaccac | agtagggatt | ctcgatcttg | cgagttgcag | agagcctctg | 240 |
| aaactgcaat | agaaaggaca | ctgatgaaaa | gaacacactg | aaggagtatg | ccaatcatgt | 300 |
| gaaaactcag | agcttgtatt | ggtcttgtgg | ttgatgaagt | tctcacaaaa | cctttggctt | 360 |
| tgaatctccc | ctcattagtc | atggtgagaa | caagaacaag | acgagaaaca | gacaagaag | 420 |
| atgaaaaaac | ttgttggcca | gtgttgacta | agggggaata | gccccagaca | taacaaaatt | 480 |
| agacttgtcg | tacatctttta | atattttttt | atctgtttct | ttgtcctgac | gctttcatta | 540 |
| ttcctgtgat | caatttctctc | ataccattgg | tccatcgtta | atcctttctt | aatttcattt | 600 |
| tctacgtaac | atgagaggag | accaagtcct | atgagaacag | ttgacgtaac | agtggttgtt | 660 |

```
aagttaagtt aaaaagagga agctagtgag agtgaccgtt aggtagagaa gtgagatctt     720
taaccactct tctttctctc tctctctgct tttttcgtcg tctttcacat ctactgttcg     780
caaactctct tatgcttcca ataatggtga taccaattga gacttgcagg agaatctcct     840
cttctccaca ctctatcaac tggtcagcca tggaatggtc gtttcagttt caatattcct     900
ggattctttt taaggattcc tgtttctctt ctgttcctgg tatattctta acgacgaaat     960
tagtatcgga tcctggtaat acattttgaa gcttttaagt accattgcac tgggatccaa    1020
caat                                                                 1024

<210> SEQ ID NO 38
<211> LENGTH: 1020
<212> TYPE: DNA
<213> ORGANISM: Arabidopsis thaliana
<220> FEATURE:
<221> NAME/KEY: misc_feature
<223> OTHER INFORMATION: Ceres Promoter YP0096

<400> SEQUENCE: 38
gaggtcagtg agtcgattgg tgcaaaattg aaaaattgaa gggtgaaaca aatttaaaga     60
taatatctat taaatcctct aattttaaaa atttagcaaa aattgtattt tcttatggat    120
ctgttagttc acacgtatct taattagtac caaatcatat ctaatgatta gtgataaaac    180
tagttagata tctatatgtg tctttaccat ttaacttgaa tccttcttct tttttttacg    240
taaacaactt gaatccttcg ttaatacata aatttaaagc attttttctt taattctatt    300
gatcggtata tatttactat aagttttagc tcatatgcaa tttcaaatga tatgcttta     360 aattttgtct aggtgtgata gttgtatctt taacataaat cttatagcaa aatttatactt    420 gatattctaa atttatctat ttgctcttgt gaacctcata ttagtctaga gaaactttga    480
aatcctttca attagttgta tgtccaatac attttacta acattatta gtctttttaa    540 ttaagattat tgttagaaaa aaaaagattt tttaaaaata aataatatgt tttagataca    600
atgtgagtta ggcttcttat atttttaaaaa ataaatttat ttcatactta aaaatagttt    660
ggaatttcaa tttatttggc tgaataccat aaaatatgtc aatttgaacc ttatacccat    720
tgactatttg gtgttagaaa cccttttaaca aaaaaaaact atttggtgtt agatatcaaa    780
ataaaaaaag tttaaccatt ggtttcttat attgaattgg atattgttac atgtattaaa    840 gttttttttgg tttaattttg aaacgttgat agaaactatt aagtttaagt ttggtagtat    900
attattttgt ggaaaattta attgccatta aatataacgt caacttttt tggttttttt    960 tgagaagtta cgttgtgatt ttgatttcct atataaagt tagattacgt cattttttaa    1020

<210> SEQ ID NO 39
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0097

<400> SEQUENCE: 39 ttcatctttta tatttaagag tttaaaaact gcaacttttg ttttttcttc actaagtctt     60
atggccacag ttaattaaaa gcagatgaaa ggtggtccaa tggaaaagga gaatgtgatt    120
gggctagttg ggagagttct gatgtctagt gttgggtaca cgtgtccgtc agttacacat    180
agcattaaat cagacggcat gtcattattc aaatctagtt cacatagtac gactaatagc    240
tgataaatta atgattatac agcatatgaa ttatgaattc aaaaaaaaaa aaaaattgaa    300
```

```
aatgttaagg agatgctata ttttacaaaa ttcatcgcaa tgctttctac taatttgcta    360
agtggtcttc tccagttagt cttgtcgatt ccaagcgata ttattaaatc ttgaagcatc    420
gctcaaagca ttatagctta agataaccaa attgttatta aaacaccta gtgaaatttt     480 taaattaaaa caattttgat atctttgtaa tatctaatac tactctttct gtgtctaaaa    540
ggattaattt tcaaaaattt cacacatatt aaaaaaaaaa aaaattact agctaaacaa     600 ttttcaataa tcataaaaca atagtaactt aataattttt ttttattttc aaaatagtcc    660
ttcaagttta caattcattt tagtattata atcaacaaaa tttgtattaa aaagttggaa    720
aattaatctt tgtggaacaa aaaaatctag aaatcatttt ttagaattag agagaggttt    780
gataaaaaaa aataaaaaaa aatagagaga ggtagtacat actaaacgat gtgatactac    840
tattgacaaa atcttaattc tcagtttagt agaataaact agaaggaatg aatgaagtaa    900
atgcgaatcc aactactaac aaaccctact tagtcatcat attttcccat atgaaatccc    960
tatataaacc catcatcatc tcccacttttt ttcatatcca                         1000

<210> SEQ ID NO 40
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0101

<400> SEQUENCE: 40
ttctcgttct ctagaatatt gctggaccgg attaggtcaa tattattggg ccagattaga    60
tattgaattg tcgacgttgc ttacgttacg ttatatcttg tttaagaatt aaacctatcg    120
acttagtctt aattaagaaa acattgcctt aaattctctg gtctgcgacc gttttttga     180 ccgttaaccc ctaattaaag aaacaaaata attatagaaa gagcactgaa atgtgattat    240
tttaacagta ctcttatgag aaaattcgta cttttttagtt ttttttttgt acaaatctct    300
aagaaaaaca ctactactaa ttaagaaacg tttcaaacaa ttttattttc gttggctcat    360
aatctttctt tctcggtccg ggactaaccg ttggcaaaaa aaaaaaaaaa gttgacaata    420
attattaaag cgtaaatcat acctctcaaa taaaaacttg aatttggaaa caaagacaac    480
taaaaaactc gaatttaaga gaattcctaa aatcaagtga agtatcatca cttggtaaaa    540
tttcataacc gttggcttct atttctatgt gtgccttggt ttgcaggaga taatatttca    600
tttccaacca atgatattcg tacacatagt caaacaaatg tttgtctttg ttattatatt    660
gagaaagaaa caagaaagag agagagagat agataagacg aaggaagtga agcttccaag    720
cgcccaccgt taaaatctc gtgtgcaagt ttcaaataca agtggccggt ggtctccata    780
atttgatcgt catccaatta aaaggaaga aaaagcgtgt tttatacaag aaaactcatt    840
aaaatagcaa gtctagaaat atctcaacac taatctacca cgtctattac acacacacac    900
acacacactt gatcttaatt tattttcaag attcaagaaa atacccattc cattaccaca    960
acttgaccac acgcctatat ataaaacata aagcccttt cccc                     1004

<210> SEQ ID NO 41
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0102

<400> SEQUENCE: 41
```

```
atttggttga taacgttttc actcgactaa ttatatactt cagaaggata gtaatagaat      60
accaaaataa ttaaatgatt ggttagtgcc ttagtggaga cttttttaacc gattctaata    120 gactaatgat gtagctaagc atttatttgg gatcatcact gtttgaaaac gtgaaatgtg    180
ataaaagtta tgaaacgatt aaaatataaa ataaccgtac aaaacattat gtaccgtttt    240
tttctctgtt cttttggcga tttggtttag ttcgttacac tctaaatgtt attgcagata    300
tatatataat gatgcatttg catctgagga acatataatt ccggttaaca cttccaaatc    360
ttatatccgt ctaggtaggg attttataaa tcatttgtgt catcatgcgt tatgcttgtc    420
ggctttgacc ataacgcaga gatatagaac tagcttttac ttaactttta gatttattat    480
ttgatctaga gttaagtgga gatatatagt gttttttgtta gattattggt ggatgtgaga    540
gtttgtcttt agtttcaagt tgagaatata aggcaagagg agactctgag gcaatcagag    600
gttttgattg gcaaaatatc caaaggccc aaaccaagtc gaagcccatc tcgtacaaaa      660
aaagaaagag atctgtaaga aaaatattc tttgatattc ttacaaaaat aagtgtaaaa    720
cttttattag tcaaaatctt caatcttttaa aaactctcat cactcctacg aaagcgcgtg    780
agagttatga gacattcctt aatagcatta ctcacaagtc acaagttcaa aacgtctgac    840
tgaaacagaa acaagccttt gttgaagtct tgaagaagag acattagtac tcgtcgtata    900
gccataaaag gtaatatacg aaatttcttc gctaatctct tcaccttcct ctacgcgttt    960
cactttcact ttataaatcc aaatctccct tcgaaaacat                          1000

<210> SEQ ID NO 42
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0103

<400> SEQUENCE: 42
gttttgaaga acaatctgga tcgaaatcta acataaggtc atcgtattca agttacgcag      60
tcaaggactt gacatcatcc tactctggtc tgaggttacc acttccaaag atgggatttt    120
tcgactcggt atgcttccta agaaattcgt tttattgaac ctagcaaata tcttgtaatg    180
taagattcct gagatgatga agaaaaaaca aacttttgtt acagcaggag aacggagaga    240
aagaaaacag agaaccaaat gctcttgaag caaacagaag aagaagacac aaatccaaac    300
ttgagacttc ttctacacca gaaaaccgca gcattctggg acaacgcaaa acacgaaagt    360
gaaacgggca atgatatata tgtcttgggt gcgttacaag gcatcgtttg caactgttga    420
gttggataag tcaactgtct tcttttcctt tggttgtagt agctgccttt tttttcctttt    480 gttgctttaa gaaatagccc gaaaaaaga atgttctaca tttcggagca gaaaactaac    540
cgaatgagtt tttggtcgga tcatcggatc gatcagatat attttgagtt acgaactgtt    600
ataaaaaaag ccataatttt gtgttgagtt tgcaaaatac cttataactt gttatttgag    660
attgcacctc catatatatt aattcgtaag agtatttatt aagtaagctt tagtatataat    720 cctttttttcc tttaaagtaa gttaatgttc tactaaataa tagtaaagtt gaagaaccgc    780
tccgttttta caccatgcac gtgttatcta acaaagaaaa tatggtacac ctaatgcta      840 atgcaaagga caacacaatg aaactaactt gactctgtgt tatagaaacc catagacatc    900
tgcatacatc ctagtatttg tataaattgg actcaaattc ctgaggacaa tcatagcaaa    960
caatcacatc atcgcaatat acataaacaa aagaggaaga aaaa                    1004
```

<210> SEQ ID NO 43
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0107

<400> SEQUENCE: 43

| | | | | | |
|---|---|---|---|---|---|
| taacaatcct | tgggaacatt | gcatccatag | atatccggtt | aagatcgatc | tttgaactca | 60 |
| taaaaactag | tagattggtt | ggttggtttc | catgtaccag | aaggcttacc | ctattagttg | 120 |
| aaagttgaaa | ctttgttccc | tactcaattc | ctagttgtgt | aaatgtatgt | atatgtaatg | 180 |
| tgtataaaac | gtagtactta | aatgactagg | agtggttctt | gagaccgatg | agagatggga | 240 |
| gcagaactaa | agatgatgac | ataattaaga | acgaatttga | aaggctctta | ggtttgaatc | 300 |
| ctattcgaga | atgttttgt | caaagatagt | ggcgattttg | aaccaaagaa | aacatttaaa | 360 |
| aaatcagtat | ccggttacgt | tcatgcaaat | agaaagtggc | taggatctg | attgtaattt | 420 |
| tagacttaaa | gagtctctta | agattcaatc | ctggctgtgt | acaaaactac | aaataatcta | 480 |
| ttttagacta | tttgggcctt | aactaaactt | ccactccatt | atttactgag | gttagagaat | 540 |
| agacttgcga | ataaacacat | tccccgagaa | atactcatga | tcccataatt | agtcggaggg | 600 |
| tatgccaatc | agatctaaga | acacacattc | cctcaaattt | taatgcacat | gtaatcatag | 660 |
| tttagcacaa | ttcaaaaata | atgtagtatt | aaagacagaa | atttgtagac | ttttttttgg | 720 |
| cgttaaaaga | agactaagtt | tatacgtaca | ttttatttta | agtggaaaac | cgaaattttc | 780 |
| catcgaaata | tatgaattta | gtatatatat | ttctgcaatg | tactattttg | ctattttggc | 840 |
| aactttcagt | ggactactac | tttattacaa | tgtgtatgga | tgcatgagtt | tgagtataca | 900 |
| catgtctaaa | tgcatgcttt | gtaaaacgta | acggaccaca | aaagaggatc | catacaaata | 960 |
| catctcatag | cttcctccat | tattttccga | cacaaacaga | gca | | 1003 |

<210> SEQ ID NO 44
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0110

<400> SEQUENCE: 44

| | | | | | |
|---|---|---|---|---|---|
| gggatgcggt | tccgcttcct | cttgatcttg | gacgagtcgg | aggacattgt | tggatcccag | 60 |
| tgcaatggta | atataaaaca | agaaaacaag | agatttata | ggacaatcac | taaatgacat | 120 |
| ttaattgatt | aaacatttat | tcattaataa | ttgtatgtta | ctaacttcaa | catttaataa | 180 |
| ttttgtttaa | gatacgttta | catcagagac | tattaatatt | tttacaggtt | gtaactttaa | 240 |
| actttgtctt | gaatcgaaca | tgactataga | ttttgggcaa | acttaaagat | aacaacattt | 300 |
| ccgttttttt | tcaaattatt | acaaatcaaa | ctgatatatt | agacacaaca | cgattacacg | 360 |
| taatgaaaaa | agaaaaagat | aaaaagataa | aagaagggat | cgattctgtt | tggtctggtt | 420 |
| tagtgagatt | caaagttaag | ctcttccttt | caagacatgc | cttcttaaac | cgggaatgtg | 480 |
| aacgttgta | atgtagtccg | tccagttaat | gcttccaaca | tcaaatccaa | attctctctt | 540 |
| ctcgtcctct | gacatattct | ccattaatct | ctggggtatt | gctgttatca | aatctgtaaa | 600 |
| agaaaccaaa | aaaaaagat | gaaactttg | cgggtaccgg | ttttgtctgc | tctaagaatt | 660 |
| agaatgttaa | tgagttctgt | cttaccttcc | accatagaaa | gtgtatggct | cataaatagt | 720 |

```
agcaaggtgt ttggcttgtt caacagattt cttgcatata aactttagct tctgcatcat    780
cttactatcc actgaactca taccactcat caacccactc cgttcttgag catctctcca    840
caaatgatcc gagaaatcat caacggaatt gaaaagtttc atcaaacgca ccataatagg    900 atcacccttta gagtccatgc atggagatgt tttgtagtgg ttataaagaa gctccgctaa    960
gtcttcgaaa accagcgggt ttatcgccga agaagcgatc tgatacacgt ttatttcagg   1020
ttcc                                                                1024

<210> SEQ ID NO 45
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0111

<400> SEQUENCE: 45
cgattggatt tagtctatac attatagggc gcaagtttgt ggatttaaga attatataaa     60
aacttgaaat atatagtttt tatgcattct cctcttgtgt aatacataaa ccaaatatga    120
gataggttaa tctgtatttc agataatatt aaattccaaa caatattttt acttgttata    180
agaaggcaat taatatctct ctgttaatgg caagtggtac caagtagtat taaactatta    240
atgcaatgga agagtactgt tggaaattat aatcctctat cacacattca aacagatctc    300
ctgaaatctt ctcttccaaa cttgtacttc tctgatccaa atgtaggctc caaaatatag    360
acatttacca tttactaagt ccacaactcc tttcttgtct ccttcaaaaa tgactcttgt    420
gtaaccacca tatgactccg acagttcggc attgccatga tgagagctta aaaattcacc    480
ttcctgagca tttcaagtct tcactccctt agcttgacct gaaccaagat aaaatgcctt    540
tgtcgtcccg taatatccat cctgctttgg acggcatcat agttacattc gatccatcct    600
atttacaatg ttattttagt attaaaaaca tgacaataaa tttgttgtta acatattca    660 aatacaatat gattggattt ataagtaatt gtaatatgaa atgtccttag taatatgtta    720
aaaaatacat agatacacac acgtactaaa agaggcaacg cgggagatgt cattagagga    780
agaactagga agcagagcgt tcatgcaaaa tgctaccaaa aacgttaatg caatatctca    840
actaatcagc acagtccatt tcatactgag aatgtaaaaa ccaatcagca tcgtccattt    900
tttcatctaa ttatttgtta actcttaatt ggccacaact tccaaccaca tgacgctctt    960
tctattccct ttatatattc ccatctcaaa tgttcttgga gacacaaaat atcataaaca   1020
tata                                                               1024

<210> SEQ ID NO 46
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0115

<400> SEQUENCE: 46
gtcgattgga tgatgaacat tctacatata taattattat gtttaagcac ttagacagca     60
taaattcttt ctaattatat aaatctaacc ttgttacatt gtacatctat aaattacttg    120
aagaaataac gagttctatt tcttttttaaa aattaaaaat actataccat atctcagtga    180
ttaagttgaa ccaaaaggta cggaggagaa acaagcattt gattcttcct tatttttattt    240 tattcatctc tcactaatga tggtggagaa aaaaagaaaa tacctaacaa acaaatatat    300
```

```
attgtcatac aaaaatattt ctatattttt agttaattag tttatattcc tcacttttca      360
gggcttatat aagaaagtga gcaaacacaa atcaaaatgc agcagcaaat actatcatca      420
cccatctcct tagttctatt ttataattcc tcttcttttt gttcatagct ttgtaattat      480
agtcttattt ctctttaagg ctcaataaga ggaggtacta ttactacact tctctctact      540
tttacttgta ttttagcatt aaaatcctaa aatccgtttt aaattcaaaa ataaacttag      600
agatgtttaa tctcgattcg gttttttcggc tttaggagaa taattatatg aaattagtat     660
ggatatcttt actagtttcc attcaaatga ttctgatttc aatctaatac tctcactctt      720
taattaaact atatgtagtg taatttcaca ctgttaaatt tctaccatgt catgtatatt      780
agagttgcat agaaaattgt aaaacatcca tttgaattcg aatgaaacaa aatgttttaa      840
aataaaattt tggttttaa aagaaaaatc taaaactgaa ttatatcgtt taaccaagtt       900
gtaaaagtca taaaacgtag tatcttgtaa atcgctcttc cacggtccaa atagacttct      960
agtaataaac aagtaaaact aattttggtt tcttac                                996
```

```
<210> SEQ ID NO 47
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0117

<400> SEQUENCE: 47
gtcagtgagt cgattggatc acagtccttt atgataaaac aaactcataa ttattccacc       60
gacaacatgc gttttaaatt attttttctt aaattatatt atattatatt gatatcaacc      120
tagctaaaat aattcggatg gcgaaatcgg acaattttta atagaaaaaa tgggtatgaa      180
gatagtctat gattccgttc ttagcgacta gagggacctg ctcaaatctc ccgggtgata     240
cgcgatgtca agctcaatag aaccccacaa ccgacgagac cgagaaatcc ttgatttggg      300
ctagaagatt ttgaaataaa tttaatatat tctaagtaac ttgcttaaat ttttttttcaa    360 actctaaaga cataactaac ataaagtaaa aaaaaaaaag ttaatacatg ggaagaaaaa     420
aattaaacta atgattagct ctctaacgtg tttaatctcg tatcaagttt ttttttaaaa     480
attatattgc tattaaaaca ttgtactatt gtttctattt tgtttagcta ttattcttgt     540
gaaatgaaaa gttgtgttta ttcaattact aaatggcaat atttatcttg gaaaactata     600
cctctaattg gattaggccc tagacatcct ctttagctta ttgacgttaa aattattccc     660
aaaactatta aagtttagta gtttgaaaga tgcatcaaga cctactcaga taggtaaaag     720
tagaaaacta cagttagtgt gattatattt taaaatatat aaaacaatct tattaaacta    780
aatattcaag atatatactc aaatggaaga taaaaacatt tagtctgtta ccactaccag     840
cctagctagt cactaatagt cactttggaa ctgagtagat atttgcatct tgagttacca     900
tggactcaaa agtccaaaaa gagaccccga gtgaaaatgc taccaactta ataacaaaga    960
agcatttaca gcggtcaaaa agtatctata aatgtttaca caacagtagt cataagcacc    1020
attg                                                                 1024
```

```
<210> SEQ ID NO 48
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0119
```

<400> SEQUENCE: 48

```
taccaaaaat aaggagtttc caaaagatgg ttctgatgag aaacagagcc catccctctc      60
cttttcccct tcccatgaaa gaaatcggat ggtcctcctt caatgtcctc cacctactct     120
tctcttcttt ctttttttct ttcttattat taaccattta attaatttcc ccttcaattt     180
cagtttctag ttctgtaaaa agaaaataca catctcactt atagatatcc atatctattt     240
atatgcatgt atagagaata aaaaagtgtg agtttctagg tatgttgagt atgtgctgtt     300
tggacaattg ttagatgatc tgtccatttt tttctttttt cttctgtgta taaatatatt     360
tgagcacaaa gaaaaactaa taaccttctg ttttcagcaa gtagggtctt ataaccttca     420
aagaaatatt ccttcaattg aaaacccata aaccaaaata gatattacaa aaggaaagag     480
agatattttc aagaacaaca taattagaaa agcagaagca gcagttaagt ggtactgaga     540
taaatgatat agtttctctt caagaacagt ttctcattac ccaccttctc cttttttgctg    600
atctatcgta atcttgagaa ctcaggtaag gttgtgaata ttatgcacca ttcattaacc     660
ctaaaaataa gagatttaaa ataaatgttt cttctttctc tgattcttgt gtaaccaatt     720
catgggtttg atatgtttct tggttattgc ttatcaacaa agagatttga tcattataaa     780
gtagattaat aactcttaaa cacacaaagt ttctttatt tttagttaca tccctaattc       840
tagaccagaa catggatttg atctatttct tggttatgta ttcttgatca ggaaaaggga    900
tttgatcatc aagattagcc ttctctctct ctctctagat atctttcttg aatttagaaa    960
tctttattta attatttggt gatgtcatat ataggatcaa                         1000
```

<210> SEQ ID NO 49
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0120

<400> SEQUENCE: 49

```
tagttttga tttaatctac gttttcttaa atcataaatg ggtaattatt agttttgca       60
aaatcaaaat ccaaaaattg ttctaaacac tgcaaccatt taaggcctat atcactcaga    120
aaatttctgg tgggagaact aatcgtttgt cctttctaaa tctcacatat tagaatttag    180
aattagtgtg ctacataaga atattagttc agctcggaac aactattttt tggtaaaaca    240
gagaacttaa acaaatgcat tattttatca acatgcattt tgaattgaat ataaaatttc    300
ataattgtaa agacataaat tacataaaat tttacatgaa aaaatagata tagaaagaaa    360
atgaaactaa ctgatgatat gctctctaaa ttttttaatc tcataacaag aattcaaatt    420
aattagttca tattttggt taatataaca tttacctgtc taagttggaa cttcattt        480
tttctgttt gtttagtcag tattcttaat gtgaaacgga aagttgaatt tattcaaact     540
taaattcaat agcattaatt aaaggcgaaa gctattatct ctacatgtgg ttcaaactag    600
acatccaatt taattagctt attgacgttg aaatgttttc caaaactact atagtttggc    660
aatttgaaag atgcatcaga actactcaga caggtaaaag tagaacctct agctgtgtga    720
attgtatgtt agtccataaa gaacatcttg taaacttcat acttaagata tatattacaa    780
tatatacttg aatggtagat aaaaacgatt agtctgattg ctagcatact cacaactatt    840
tggaaatgag taagatattg gcattctaga gttactacta tggagacaaa agtcgaataa    900
aagagacctc acgtgaaaat gttacgagct agtaaaaaaa gcatttacac taacggtaaa    960
aaaagtatct ataaatgttt acacaaggta gtagtcatt                           999
```

```
<210> SEQ ID NO 50
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0121

<400> SEQUENCE: 50
ttggattttt ttttgttga gtcagcagac catctaatct ctcttttttcc accacagcct      60 gctttctatg aagcatttgg gcttacggtt gtggaatcaa tgacttgtgc actcccaacg     120
tttgctacct gtcatggtgg acccgcagag attatcgaaa acggagtttc tgggttccac     180
attgacccat atcatccaga ccaggttgca gctaccttgg tcagcttctt tgagacctgt     240
aacaccaatc caaatcattg ggttaaaatc tctgaaggag ggctcaagcg aatctatgaa     300
aggttggccc attctccttg acaggcttaa caatacaact tgtatcgctt caacaagatg     360
atggcttaat aaggattttt gcatgtatag gtacacatgg aagaagtact cagagagact     420
gcttaccctg gctggagtct atgcattctg gaaacatgtg tctaagctcg aaggagaga      480 aacacgacgt tacctagaga tgttttactc attgaaattt cgtgatttgg ttagtgtaac     540
ccactgttat tcttttgatg tctacatcta ctttacttac attattcttt tcttcggttt     600
gcaggccaat tcaatcccgc tggcaacaga tgagaactga tcatgacagg gtaggatttt     660
atttcctgca ctttctttag atcttttgtt tgtgttatct tgaataaaaa ttgttgggtt     720
ttgtttcctt cagtggtttg attttggact tatttgtgtt aatgttgttt tggctgttct     780
cttaatatca ataacaaata aatttactgg ttggtatcta agatctaaca atagttacta     840
tttttagagg taaagacacc aaccttgtta tattggtcag agagctaaaa ccttgacttg     900
ttgggaaaac aaaactctaa tgacagaaaa tctgacatga tgccttataa ttcacagcct     960
catgttctac ataaatccta acaatagcac tttgtttct                            999

<210> SEQ ID NO 51
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0128

<400> SEQUENCE: 51
gataaactga taatggaaaa gaacaaagaa accagttttt aactatttgc atatgtaatt      60
tatttgttgc aaattatatt tagttaaaat gtttcctcta tttatatata tatatatcag     120
tcaagcacta tgtataagaa atgtcaattt ataattttt acatgtcctt taacagaaag      180
aaaatgaatt tttacatgtc attcatagag agtcactcgt ttatttctta tatagagaat     240
aacacactca catgcatatg catgcaatat gatacatttt atgacaaaga taatcaacgg     300
aaacggtcaa gacataattt gataaacaac ttgcacgatg cacagatctg atcaaatata     360
taactcttta acatatccaa aatattcaaa aagaaaaact cgatccaaac tagcaacatc     420
acgctcacgc ggtaggctaa aaatttatta atctccaaaa gtctttctta tgaacactgc     480
aaacacaaca acttgaaaag tcatataggt ttagatgatg acgcgtattg gctatcgctt     540
accggagtgg ctcataaata caataaacaa tacgtaaaag tcaaagtcaa atatatttag     600
tcaactataa ccattaatcg ggcaaaacct ttagctgtca aaacaacgtg aaaacgatat     660
ttgtatatat catcaagaat cagtagataa gagaatgatt taatcccctg actattacaa     720
```

```
tttggtgta ataaacagtc tctattggtt tttattcttt gttttaattt ctcatgacct    780
atagagagaa ttaggtagtt tcgaaaattg gctaatcaac ttttgaaaac tactgtctac    840
tttgcttaaa ttctctacac ttagtttcgg ataagataat tgtcggacta atagttaatc    900
ccttgacaat ctttgatatt ataaaaggtt tagttaatct cttctctata taaatattca    960
tacaccagct ttcaaaaata tataatccaa acaccaaaaa caaa                    1004
```

<210> SEQ ID NO 52
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0137

<400> SEQUENCE: 52

```
gtggcacatg ctgaaacccc gagcatctct ccggaagaca cgcgtcgttc gctccaaaga     60
aaacagtcac agctgccgga gaatctccgc cgtcttcttc tgccaccgga aaaactctct    120
ccaccacttt cagtgcccac ctcgtgttat atccactgta tcctcgtagc accatatcag    180
cctaataaaa ttttatgtat caaattttaa gacatagccg aaactacact atactagaca    240
ataataatat gatttgtttc ctgaaaaatt atggtttcat gagaaacatt aatcatctat    300
aaaacaaatt agctatggca tcgaagagtt atcaatcaaa actgatgaat ctttacttaa    360
tatatacaac atatctttac cttgcggcgg agaagatcgg cgagagaagc accccagcca    420
ccgtcactaa aggattcttc agtgatggaa tcaccaaaga gaaaaacctt ccgtctcatc    480
atcttccaca caatcttctt gagaaaatct gagagataag aaaggtgtag tggttttgct    540
gaagtgatcg tgtttgattt agtaaagaaa tgctttattt attgttgggg gaaacataaa    600
taaataaagt aaaagtggat gcactaaatg ctttcacccca ctaatcaccg accttttcatg    660 gtttattgtg aaatacactc atagatagac atacaatacc ttatgtacgt aaataacatt    720
ttatttgtcg acacttatgt aagtaacgca tagattattt tctatgtgat tgccactctc    780
agactctcag tttcaaccaa taataacaat aactacaaca acattaatca taaacatatg    840
ctctggttta caattaaagc ttagattaag aaactgtaac aacgttacag aaaaaaaatg    900
ttatttacgt tttgtaagat tagtctctag aatcatcacc gttttttata tattaatgat    960
tctttcttat atataaaacc tttctcgaaa tacccatgaa a                       1001
```

<210> SEQ ID NO 53
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0143

<400> SEQUENCE: 53

```
atacaacaga tggcagatat cgagttaaat acgtgaatca gccgttacga tattttaaaa     60
ctagaaaatt atttaaaaat attgcaaaat accatttaat ttcattgttc ataaaaaaaa    120
gaaattcaaa aacttaaaaa ctgattcaaa aatttggatt aattctcatt aacagtcttc    180
aacactacaa caacatgttt ctaatttatt ttatatttta ataattaaac aatatatacg    240
tctgcacatt gttgctccga cataatctag tataaaaata gttgcagcat atgtgaaaag    300
caagcagcat ttatcactca atactttaaa ttttatctgt tgtatgtatt aaggttttgt    360
agctttaaga aaacgcttat aatataaaat aacttctaaa agatatttca tgcgtataca    420
```

```
ataaatattt gtgaaaaaac atttcgaaaa cgtgtacaat atataaacta ttgtgttatc        480
ttttgacatt caaacaaatg ttgacaatgt aattttatcc atgatatgat tggccaatta        540
gctgcgaggt aaaaatccgt atacgagtaa agtaagata aaatttcgca agaagatttt         600
tagcaggaaa tctaagacaa gtgtcatgaa cgtgtcaatc aacaaacgaa aaggagaatt        660
atagaatcca gattcgacgt accacattaa taaatatcaa acatttat gttattttat          720 ttttgctctg gcagttacac tcttttttcat tgctccaata aaaaatcac tcgcatgcat        780 gcatatatat acaccatagt aaactccgcc tcttcttcat tttaaaagta tcagtttaca        840
ctgacacaat ccttaactat tttcctttgt tcttcttcat ctttattaca cattttttc        900 aaggtaacaa ataatctttt taagtcactt ttatactctt taaatcttag attgatatat       960
gaatgcatgt taatatttca agatttatag gtctaccaaa c                          1001

<210> SEQ ID NO 54
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0144

<400> SEQUENCE: 54
aaacgttgca agattattga ttgtgagaaa gagtgctcaa ggtagtactg atttctgtaa       60
agctcacggt ggtgggaaac gatgttcttg gggagatggg aaatgtgaga aaatttgcta     120
gaggaaagaa gcggtttatg cgctgcgcat aacactatta tgtctcggga gaacaaagat     180
ggaagcaaga gcggtttgat tggaccggga ctctttagtg gccttgtttt tggctctact     240
tctgatcatt ctcagtctgg agctagcgct gtctctgatt gtactgattc tgttgaacga     300
atacagtttg agaataggca gaagaacaag aagatgatga taccgatgca ggttctagta     360
ccttcatcaa tgaaatctcc aagtaattca catgaaggag aaacaaacat ctatgacttc     420
atggttccgg aggagagagt tcacggcggt gggctagtaa tgtctttact tggtggctcc     480
attgatcgaa actgaaagcc atttatggta aaagtgtcac attctcagca aaaacctgtg     540
taaagctgta aaatgtgtgg gaatctccga atctgtttgt agccggttac gttatgctgg     600
atcaaaaact caagatttgt tggatattgt tatgctggat cggtggtgaa accacttccc     660
ggttgctaaa taaataaacg ttttttgtttt ataatctttt tcactaaacg gcagtatggg     720
cctttagtgg gcttccttta agcgaccaat acaatcgtcg caccggaatc tactaccatt     780
tataggttta ttcatgtaaa acctcggaaa atttgagagc cacaacggtc aagagacaaa     840
aacaacttga agataaaggg ataaggaagg cttcctacat gatggacaac atttcttttcc    900 acacaaattc tcataataaa aatcttataa tacaaatact tacgtcataa tcattcaatc     960
tagtccccat gttttaaggt cctgtttctt gtctgataca aat                        1003

<210> SEQ ID NO 55
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0156

<400> SEQUENCE: 55
ttggtttgca ttgtgaagat ttgtattaac tatagaaacat tgaattgatg gtgttaagtt    60
cttacacaag cgtgcttctc ggtttgaact gtttcttttg tatgttgaat cagagcttag    120
```

```
tttataggaa ccagagtatc tacttagtca ttctctgatg ctaagtgcta aggttctacc        180
tagttgccct ctaggccctt atgttattga aacttatga agctatttga acacttgatt        240
cttaggagac ctaagttggt acagccagat agagtgtatg ttcttgttct ctatgtgaca        300
ggatcaagct gccacacata gttcaagggt atgctctgtg tgggtttgct cagattgagg        360
acaaatctat acaaggaagt agagtctttg acattttgat gttgtatgat aagaagaaga        420 aggagagta ataaagaaag agaaaaggga aacagaaaca cgtgggagaa catcccaaag         480
aggaagcaca cgcggatctt catgcaaagc tccccgattc tcccatgtgg tccctttctc        540
cctttgtccc cctcctcttt cttctttct catttactc ctttttttac cattatacaa         600
cgaatctttt ttatcataat tttttggttt tggtttattt tccaataaca ctttcttggt        660
tacttcccat tctcactttt tcatataaga aactcacttt gggaaactta tgtttgagaa        720
tgacaagtct ttttagagaa agtgatgtaa caaatctaaa gtgattatat aataaccttg        780
cacaatgttt ttgattttt gtaagattcg aatattaggt ttattattcg tagggaataa        840
acttactttc aaaagcgttc ataagttaat actttcatat atgatcataa gtacggacac        900
tattgttttt tgtttgtttg tgtttattct aaaagaaagt agcttttaat tgaaatgtcc        960
tcggaggcac agtttaaagt tcgagtgtaa cagtttctaa ggca                        1004

<210> SEQ ID NO 56
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0158

<400> SEQUENCE: 56
ttattagatt aatagattgc attgcattgc ttgtgctttc aatttacaaa ttgtctccca        60
actccatcga cacatctctt tttgtgtata taagattcag acttgttata tttttttat        120 aaatatgtta ttagcatctt aagttaaatt gatttttat atctgcatta aggattacac        180
gactatattt gcgattgtgt gttggttaaa atataaattta ggattgtctt taactacatt        240
taggattata tgactatatt tggttaaata taaaatctag ctgtgattat tagtattcaa        300
aaataagtag cctaaccaat taaaacaacg gctattgggg caaattagaa catttagtg        360 tgtccaaaat ataatggtca ttaggtcata ttcctcctag cttcatcgca gcataattga        420
atgattgcct tatttagaag agcttttcca ctttcccaaa atctaggtgg gatcttttg        480 ttttgaccttt catttttctt gtttaccatt tttagctaaa ttatttacga ttacaaaaga        540
tatcaaaagt tggatcataa tacaatttat agacttactg tagaaaattc gtatgtacaa        600
gtacaacaaa ttcttcataa taaattttga aaattctatt acaaatgttg taagaaatag        660
aatttgaaat atatataaac taaggagaaa aaaaagaga acatgcattg ctctagtcag        720
agtggaccaa catcaacgag ataagataac ataaaaacca actcaccata actaaaaaca        780
tcccaagaga tccaacgatt catatcaaac acaaaaacat cgaacgatca gatttaaacc        840
atctctggta tctccaaaac acaaacactt tttttttct tttgtctgaa tggaacaaaa        900
gcatgcgaca tctctgtgtc tttatcttct ctctcctctt cttgaaaaac tgaacccttta        960 attctttctt cacatctcct ttagctttct gaagctgcta                            1000

<210> SEQ ID NO 57
<211> LENGTH: 1005
<212> TYPE: DNA
```

```
<213> ORGANISM: Arabidopsis thaliana
<220> FEATURE:
<221> NAME/KEY: misc_feature
<223> OTHER INFORMATION: Ceres Promoter YP0188

<400> SEQUENCE: 57
gattggtatg aaatttcgga gaccaacaaa aaaaacttta ttgagcttgg agtgaagcta      60
tatatatggg gcaagatcat aatatgttta tatcggcctt ttcgttaact gaaaataata     120
gttttgagaa atatatcaaa tggtaaacag acatcatctt tgaaaaatac catcaatgaa     180
gttaatattg ttattggcat atggtttacc catcttaatt ttaatgcaac caaacaaaca     240
agaaacaaaa actgtataag atacaaggtg ttttacgatt ttccgtctta aaaccgaaat     300 attttttgttc ctacgactttt aaacggactt tgcttaagtt gtgtgcatgt aagctcgtcg    360
tccctcgatt gtcatcaaca ttcaccaata tcagcctcta tcacacgagt gaaggtggtg     420
attcggctta atgaaaacag agaaatattt caatatgatt cctattaaat tttaaatctt     480
ttttctcaat ctctagattt tcattaaaag catcatgatt ttttttccact atgttcatat    540 atctctatca cagttttagg tacattgtag aaattggata agatacgtca tacgtctaac    600
atgaatttgg tctagcaagg aaggtttgag ataataagtg aaaagaaaac acaagataat     660
aaattataat ttataaatgc tttatagtat tgaaaaataa gatgattttt tttttttta     720 ataccggatt ggctgatcca cttatgatga ctcaaatgtt attaagtttc aagacaattt     780
atgatgacac aaatcacaat gagtcaatag tagccacgaa gccagaaaaa aaaaatgtac     840
tacaaaaaga taatgatagt acaaaatgat acgtcgtact gccacatgta cgacacaact     900
cgattaccaa aaagcagagc catccaacca taaaactcaa aacacacaga ttccactggc     960
gtgtgctctc ctcacttcac tcgtccttga aacttgaggt actga              1005

<210> SEQ ID NO 58
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter YP0190

<400> SEQUENCE: 58
taaatagtga cattggtaag aagaaaaaaa acactattaa atagtgaaaa aatggtttat      60
aactctctta attaacatta cttattattg ctagcaccta aaatctccca caaaatattt     120
gttgtaaaac acaaatttac aaaatgattt tgttttaaa ttagtaacac atgttcatat      180
atacgttaat aagaacatac cctatatgat tttatataaa aaaatttctt tgagacgtct     240 tattctttt tctttaataa tatgcaattg tgagagtttg gatttgaatg gtagcattag      300
aagcaaactt gaaccaaaca tatttcatga agtcaaactt gaaccaatgt gatcactaat     360
cacagtgttc gcagtgtaag gcatcagaaa atagaagaag ggacatagct atgaatcata     420
taatcttgac acatgtttta taggttttag gtgtgtatgc taacaaaaaa tgagacagct     480
ttcttctaat agacttaata tttgggctaa atgtaccaca gttgtgaatt tcttacaaaa     540
atgggccgag ctacaaaaaa ctacaggccc actctcaact cttatcaaac gacagcgttt     600
tactttttta aaagcacaca cttttgtttt ggtgtcggtg acggtgagtt tcgtccgctc     660
ttcctttaaa ttgaagcaac ggtttgatc cgatcaaatc caacggtgct gattacacaa     720
agcccgagac gaaaacgttg actattaagt taggttttaa tctcagccgt taatctacaa     780
atcaacggtt ccctgtaaaa cgaatcttcc ttccttcttc acttccgcgt cttctctctc     840
```

| aatcacctca aaaaaatcga tttcatcaaa atattcaccc gcccgaattt gactctccga | 900 |
| tcatcgtctc cgaatctaga tcgacgagat caaaacccta gaaatctaaa tcggaatgag | 960 |
| aaattgattt tgatacgaat tagggatctg tgtgttgagg ac | 1002 |

<210> SEQ ID NO 59
<211> LENGTH: 995
<212> TYPE: DNA
<213> ORGANISM: Arabidopsis thaliana
<220> FEATURE:
<221> NAME/KEY: misc_feature
<223> OTHER INFORMATION: Ceres Promoter YP0212

<400> SEQUENCE: 59

| agtcgattgg tacactctta atttaattag agtaagagat caacaaaaat atagaatttt | 60 |
| ctttatatcg aagtgctacg acctatata tatagaaaaa aaagcatagg tgaatctcta | 120 |
| aattgagatt gtgctgtagt aaacatatta agttttagt tttttttaaga aatgaatctt | 180 |
| tttgttgatt aattcaaact agtagtcatt aagattccgg agattccaat ttagaaaagt | 240 |
| caaagattca agaacaagt ccaggtccac atgttgaatc cgattcatca tccactcatc | 300 |
| cttcatatct tcctccaccg tctccgccca aaaaatcaat aacaataaaa aatcctaaaa | 360 |
| aaacatattt gattttgaaa aaactttatc atatattata ttaattaaat agttatccga | 420 |
| tgactcatcc tatggtcagg gccttgctgt ctctgacgtc cttaattatc attatttta | 480 |
| aatttgtctc tctcagaaaa ttacgccaca atcttcctct ttccctttc cgaaaacagc | 540 |
| taatatttgt ggacctaaac taaataacgt agcctctaga ttttatataa ttactaatac | 600 |
| tatatgctac tacttgttat tatttactcc aatcatatat gataccaatc aagaatcact | 660 |
| acataagtag aaaactttgc aatgagtcca ttaattaaaa ttaagaataa acttaaaatt | 720 |
| ttatggtatt ttaagattcc ctttggattg taatgacaag aaatcagcaa attagtcgta | 780 |
| actcgtaaga ataaacaaga tcaatttta ctttctttac aaagattccg ttgtaatttt | 840 |
| agaaatttt ttttgtcact gttttttat agattaattt atctgcatca atccgattaa | 900 |
| gaagtgtaca catgggcatc tatatatc taacaggtaa aacgtgtatg tacatgcata | 960 |
| aggttttacg tgcttctata aatatatgtg gcagt | 995 |

<210> SEQ ID NO 60
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0214

<400> SEQUENCE: 60

| ccagtcgatt ggcgcctcgc atgcctatca tatttaaccg tcaataatgg atttggcggt | 60 |
| tttggtaggc cgggtcaacc ggattaaaag aaaacggttt ggagtccttc cttgcaattg | 120 |
| aattttcaca cattcgggtt ttgtgatttc tctgtcataa tgggcccggc acatatggtt | 180 |
| cataacccat gtgggcctat ggtataattt ttccaattaa aactattgtt aggtcgataa | 240 |
| aacaaaaaac aataaaaacg agtggaatac acataccaaa agaatgtga tgaacattag | 300 |
| taatttattt tgatggtta atgaaaaaca aaataaatgc atcttggcat cttccgttgg | 360 |
| aaagcgcaaa tagggcagat tttcagacag atatcactat gatgggggt gagagaaaga | 420 |
| aaacgaggcg tacctaatgt aacactactt aattagtcgt tagttatagg acttttttt | 480 |
| tgtttgggcc tagttatagg atcataaggt aaaaatgaag aatgaatatt agattagtag | 540 |

-continued

```
gagctaatga tggagttaag tatgcacgtg taagaactgg gaagtgaaac ctcctgtatg      600
gtgaagaaac tatacaacaa agcccttttgt tggtgtatac gtattaattt ttattctttt    660
atcacaagcg atacgtatct taagacataa taaatatata tcttactcat aataaatatc     720
ttaagatata tatacagtat acacctgtat atatataata aataggcata tagtagaaat     780
taatatgagt tgttgttgtt gcaaatatat aaatcaatca aaagatttaa aacccaccat     840
tcaatcttgg taagtaacga aaaaaaggg aagcaagaag aaccacagaa aaggggggcta    900 acaactagac acgtagatct tcatctgccc gtccatctaa cctaccacac tctcatcttc     960
tttttcccgt gtcagtttgt tatataagct ctcactctcc ggtatatttc cccattgcac   1020
tgga                                                                 1024

<210> SEQ ID NO 61
<211> LENGTH: 911
<212> TYPE: DNA
<213> ORGANISM: Arabidopsis thaliana
<220> FEATURE:
<221> NAME/KEY: misc_feature
<223> OTHER INFORMATION: Ceres Promoter YP0263

<400> SEQUENCE: 61
atctagctgt ggattccacc aaaattctgg cagggccatg atctaaaaac tgagactgcg      60
cgtgttgttt tgcagtgatt tgtatttcat atttgcacca tcctacacag tccacttggt    120
atcgtaacca aacataagga gaacctaatt acattattgt tttaatttcg tcaaactggt    180 ttttacccttt tagttacata gttgattctt catttgtttt agtagttatg gagcacaata    240
atgtgcaaca agaaagatc atagtggatt aatatgttga gaggtcagaa attcttggtt     300
aacaaaaaaa agttacaagg actgagattt tgggtgggag aaagccatag ctttttaaaac   360 atgattgaac ttaaaagtga tgttatggtt tgaggggaaa aaggttgatg tcaactaaga    420
tagttgaagt aatgtcttaa actaaagtaa accaccggtc caaccgtggt ccggaagcat    480
ctctggtatg atttatccta aaaatcaaaa tagtagaaac atactttaaa tatatacatt    540
gatcggacga aaattgtaaa ctagtatagt ttcaaaaact agttgaacag gttatgtacc     600
ttaaacattt atttcaaact taaacactaa agaacatata tgaatagaag tttatataaa    660
ttactatata tctaccataa atctcttata attatgatgt cacgatgagg aagtgttgaa    720
acgttaaaat gccaaaatat aagcatgcga cggaattttg gcagaagatt gtagagttgt    780
aatctgtcgc aatcattact cgtgctagca ttttttcattt tcccttcatt tgtggataac    840
gcacgatata acattctaca caccaacaag attctataaa aacgcaaagg ttgtctccat    900
agaatatcgt c                                                         911

<210> SEQ ID NO 62
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0275

<400> SEQUENCE: 62
aaacattaat atgtagtaac tatgggcgta tgctttactt tttaaaatgg gcctatgcta      60
taattgaatg acaaggatta acaactaat aaaattgtag atgggttaag atgacttatt     120
tttttactta ccaatttata aatgggcttc gatgtactga aatatatcgc gcctattaac    180
gaggccattc aacgaatgtt ttaagggccc tatttcgaca ttttaaagaa cacctaggtc    240
```

-continued

```
atcattccag aaatggatat tataggattt agataaattc ccacgtttgg tttatttatc    300
tattttttga cgttgaccaa cataatcgtg cccaaccgtt tcacgcaacg aatttatata    360
cgaaatatat atattttca aattaagata ccacaatcaa aacagctgtt gattaacaaa    420
gagatttttt ttttttggtt ttgagttaca ataacgttag aggataaggt tccttgcaac    480
gattaggaaa tcgtataaaa taaaatatgt tataattaag tgttttattt tataatgagt    540
attaatataa ataaaacctg caaaggata gggatattga ataataaaga gaaacgaaag    600
agcaatttta cttctttata attgaaatta tgtgaatgtt atgtttacaa tgaatgattc    660
atcgttctat atattgaagt aaagaatgag tttattgtgc ttgcataatg acgttaactt    720
cacatataca cttattacat aacatttatc acatgtgcgt cttttttttt ttttactttg    780
taaaatttcc tcacttttaa gactttata acaattacta gtaaaataaa gttgcttggg    840
gctacaccct ttctccctcc aacaactcta tttatagata acattatatc aaaatcaaaa    900
catagtccct ttcttctata aaggttttt cacaaccaaa tttccattat aaatcaaaaa    960
ataaaaactt aattagtttt tacagaagaa aagaaaaca                           999
```

<210> SEQ ID NO 63
<211> LENGTH: 981
<212> TYPE: DNA
<213> ORGANISM: Arabidopsis thaliana
<220> FEATURE:
<221> NAME/KEY: misc_feature
<223> OTHER INFORMATION: Ceres Promoter YP0285

<400> SEQUENCE: 63

```
gggattatat atgatagacg attgtatttg cgggacattg agatgtttcc gaaaatagtc     60
atcaaatatc aaaccagaat ttgatgtgaa aacactaatt aaaacatata attgacaact    120
agactatatc atttgttaag ttgagcgttg aaagaaaatg aaagagtgta gactgtagta    180
cgtatgagtt tcccaaaaga tggtgcttga atattattgg gaagagactt tggttggttc    240
ggttgaatga agatttttac ctgccatgtt gatagagaaa ggcaaataaa tgtaggggtc    300
gatgtctaac gtaaagactg gatcaaccaa gagtcctcct cctcgtcttc accaaaaaaa    360
aagagtcctc ctcgtggaaa cttatttctt ctccagccaa gatctcatct catctcttca    420
ctctatgaaa tataaaggaa tcttatggtt tttctaaaaa ctatagtacg tctatatacc    480
aaaggaaaca atataaaatc agttaatctg ataaattttg agtaaataat aaagttaact    540
ttgtacttac ctatatcaaa ctaattcaca aaataaagta ataataacaa agaatttta    600 gtagatccac aatatacaca cacactatga gaaatcataa tagagaattt taatgatttt    660
gtctaactca tagcaacaag tcgctttggc cgagtggtta aggcgtgtgc ctgctaagta    720
catgggctct gcccgcgaga gttcgaatct ctcaggcgac gtttcttttg ttttcggcca    780
taaaggaaaa agcccaatta acacgtctcg cttataagcc cataaagcaa acaatgggct    840
gtctctgtct cactcacaca cgcgttttcc tacttttga ctattttat aaccggcggg     900 tctgacttaa ttagggtttt ctttaataat cagacactct ctcactcgtt tcgtcaacat    960
tgaacacaga caaaaccgcg t                                             981
```

<210> SEQ ID NO 64
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0286

-continued

```
<400> SEQUENCE: 64
gaaaacaatc ataggttacg ctattatcat cgaaaggtat gtgatgcata ttcccattga        60
accagatttc catatatttt atttgtaaag tgataatgaa tcacaagatg attcaatatt       120
aaaaatgggt aactcacttt gacgtgtagt acgtggaaga atagttagct atcacgcata       180
catatatcta tgaataagtg tgtatgacat aagaaactaa aatatttacc taaagtccag       240
ttactcatac tgatttcatg catatatgta ttatttattt atttttaata aagaagcgat       300
tggtgttttc atagaaatca tgatagattg ataggtattt cagttccaca aatctagatc       360
tgtgtgctat acatgcatgt attaattttt tcccttaaa tcatttcagt tgataatatt       420
gctctttgtt ccaactttag aaaaggtatg aaccaacctg acgattaaca agtaaacatt       480
aattaatctt tatatgagat aaaaccgagg atatatatga ttgtgttgct gtctattgat       540
gatgtgtcga tattatgctt gttgtaccaa tgctcgagcc gagcgtgatc gatgccttga       600
caaactatat atgtttcccg aattaattaa gttttgtatc ttaattagaa taacatttttt      660 atacaatgta atttctcaag cagacaagat atgtatccta tattaattac tatatatgaa       720
ttgccgggca cctaccagga tgtttcaaat acgagagccc attagtttcc acgtaaatca       780
caatgacgcg acaaaatcta gaatcgtgtc aaaactctat caatacaata atatatattt       840
caagggcaat ttcgacttct cctcaactca atgattcaac gccatgaatc tctatataaa       900
ggctacaaca ccacaaagga tcatcagtca tcacaaccac attaactctt caccactatc       960
tctcaatctc tcgtttcatt tcttgacgcg tgaaaa                                 996

<210> SEQ ID NO 65
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0337

<400> SEQUENCE: 65
taattttttt attttggaa ctaacactta ttagtttagg tttccatcac ctatttaatt        60
cgtaattctt atacatgcat ataatagaga tacatatata caaatttatg atcattttg       120 cacaacatgt gatctcattc attagtatgc attatgcgaa aacctcgacg cgcaaaagac       180
acgtaatagc taataatgtt actcatttat aatgattgaa gcaagacgaa aacaacaaca       240
tatatatcaa attgtaaact agatatttct taaaagtgaa aaaaaacaaa gaaatataaa       300
ggacaatttt gagtcagtct cttaatatta aaacatatat acataaataa gcacaaacgt       360
ggttacctgt cttcatgcaa tgtggacttt agtttatcta atcaaaatca aaataaaagg       420
tgtaatagtt ctcgtcattt ttcaaatttt aaaaatcaga accaagtgat ttttgtttga       480
gtattgatcc attgtttaaa caattttaaca cagtatatac gtctcttgag atgttgacat       540
gatgataaaa tacgagatcg tctcttggtt ttcgaatttt gaactttaat agttttcttt       600
tttagggaaa ctttaatagt tgtttatcat aagattagtc acctaatggt tacgttgcag       660
taccgaacca attttttacc cttttttcta aatgtggtcg tggcataatt tccaaaagag       720
atccaaaacc cggtttgctc aactgataag ccggtcggtt ctggtttgaa aaacaagaaa       780
taatctgaaa gtgtgaaaca gcaacgtgtc tcggtgtttc atgagccacc tgccacctca       840
ttcacgtcgg tcattttgtc gtttcacggt tcacgctcta gacacgtgct ctgtccccac       900
catgactttc gctgccgact cgcttcgctt tgcaaactca aacatgtgtg tatatgtaag       960
tttcatccta ataagcatct cttaccacat taattaaaaa                           1000
```

<210> SEQ ID NO 66
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0356

<400> SEQUENCE: 66

| | | | | | |
|---|---|---|---|---|---|
| ttagttcatt | gaaacgtcaa | cttttactt | gcaaccactt | tgtaggacca | ttaactgcaa | 60 |
| aataagaatt | ctctaagctt | cacaagggt | tcgtttggtg | ctataaaaac | attgttttaa | 120 |
| gaactggttt | actggttcta | taaatctata | atccaaata | tgaagtatgg | caataataat | 180 |
| aacatgttag | cacaaaaaat | actcattaaa | ttcctaccca | aaaaaaatct | ttatatgaaa | 240 |
| ctaaaactta | tatacacaat | aatagtgata | caaagtaggt | cttgatattc | aactattcgg | 300 |
| gattttctgg | tttcgagtaa | ttcgtataaa | aggtttaaga | tctattatgt | tcactgaaat | 360 |
| cttaactttg | ttttgtttcc | agttttaact | agtagaaatt | gaaattttta | aaaattgtta | 420 |
| cttacaataa | aatttgaatc | aatatcctta | atcaaaggat | cttaagacta | gcacaattaa | 480 |
| aacatataac | gtagaatatc | tgaaataact | cgaaaatatc | tgaactaagt | tagtagtttt | 540 |
| aaaatatat | cccggttggg | accgggcagt | atgtacttca | atacttgtgg | gttttgacga | 600 |
| ttttggatcg | gattgggcgg | gccagccaga | ttgatctatt | acaaatttca | cctgtcaacg | 660 |
| ctaactccga | acttaatcaa | agattttgag | ctaaggaaaa | ctaatcagtg | atcacccaaa | 720 |
| gaaaacattc | gtgaataatt | gtttgctttc | catggcagca | aaacaaatag | gacccaaata | 780 |
| ggaatgtcaa | aaaaagaaa | gacacgaaac | gaagtagtat | aacgtaacac | acaaaaataa | 840 |
| actagagata | ttaaaaacac | atgtccacac | atggatacaa | gagcatttaa | ggagcagaag | 900 |
| gcacgtagtg | gttagaaggt | atgtgatata | attaatcggc | ccaaatagat | tggtaagtag | 960 |
| tagccgtcta | tatcatccat | actcatcata | acttcaacct | | | 1000 |

<210> SEQ ID NO 67
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0374

<400> SEQUENCE: 67

| | | | | | |
|---|---|---|---|---|---|
| aagacacccg | taaatgttgt | catgtagaag | aaactagaaa | cgttaaacgc | atcaaatcaa | 60 |
| gaaattaaat | tgaaggtaat | ttttaacgcc | gcctttcaaa | tattcttcct | aggagaggct | 120 |
| acaagacgcg | tatttctttc | gaattctcca | aaccattacc | attttgatat | ataataccga | 180 |
| catgccgttg | ataaagtttg | tatgcaaatc | gttcattggg | tatgagcaaa | tgccatccat | 240 |
| tggttcttgt | aattaaatgg | tccaaaaata | gtttgttccc | actactagtt | actaatttgt | 300 |
| atcactctgc | aaaataatca | tgatataaac | gtatgtgcta | tttctaatta | aaactcaaaa | 360 |
| gtaatcaatg | tacaatgcag | agatgaccat | aaaagaacat | taaaacacta | cttccactaa | 420 |
| atctatgggg | tgccttggca | aggcaattga | ataaggagaa | tgcatcaaga | tgatatagaa | 480 |
| aatgctattc | agtttataac | attaatgttt | tggcggaaaa | ttttctatat | attagacctt | 540 |
| tctgtaaaaa | aaaaaaaatg | atgtagaaaa | tgctattatg | tttcaaaaat | ttcgcactag | 600 |
| tataatacgg | aacattgtag | tttacactgc | tcattaccat | gaaaaccaag | gcagtatata | 660 |
| ccaacattaa | taaactaaat | cgcgatttct | agcaccccca | ttaattaatt | ttactattat | 720 |

| | |
|---|---|
| acattctctt tgcttctcga ataataaaac ttctctatat cattctacat aataaataag | 780 |
| aaagaaatcg acaagatcta aatttagatc tattcagctt tttcgcctga gaagccaaaa | 840 |
| ttgtgaatag aagaaagcag tcgtcatctt cccacgtttg gacgaaataa aacataacaa | 900 |
| taataaaata ataaatcaaa tatataaatc cctaatttgt ctttattact ccacaatttt | 960 |
| ctatgtgtat atatataccc acctctctct tgtgtatttg | 1000 |

<210> SEQ ID NO 68
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0377

<400> SEQUENCE: 68

| | |
|---|---|
| tataaaccat tcctataaca ccatatttaa acataacaat gaattgcttg gatttcaaac | 60 |
| tttattaaat ttggatttta aattttaatt tgattgaatt atacccccctt aattggataa | 120 |
| attcaaatat gtcaactttt tttttgtaag attttttttat ggaaaaaaaa attgattatt | 180 |
| cactaaaaag atgacaggtt acttataatt taatatatgt aaaccctaaa aagaagaaaa | 240 |
| tagtttctgt tttcactta ggtcttatta tctaaacttc tttaagaaaa tcgcaataaa | 300 |
| ttggtttgag ttctaacttt aaacacatta atatttgtgt gctatttaaa aataatttta | 360 |
| caaaaaaaaa aacaaattga cagaaaatat caggttttgt aataagatat ttcctgataa | 420 |
| atatttaggg aatataacat atcaaaagat tcaaattctg aaaatcaaga atggtagaca | 480 |
| tgtgaaagtt gtcatcaata tggtccactt tctttgctc tataacccaa aattgaccct | 540 |
| gacagtcaac ttgtacacgc ggccaaacct ttttataatc atgctattta tttccttcat | 600 |
| ttttattcta tttgctatct aactgatttt tcattaacat gataccagaa atgaatttag | 660 |
| atggattaat tcttttccat ccacgacatc tggaaacact tatctcctaa ttaaccttac | 720 |
| tttttttta gtttgtgtgc tccttcataa aatctatatt gtttaaaaca aaggtcaata | 780 |
| aatataaata tggataagta taataaatct ttattggata tttcttttttt taaaaaagaa | 840 |
| ataaatcttt tttggatatt ttcgtggcag catcataatg agagactacg tcgaaaccgc | 900 |
| tggcaaccac ttttgccgcg tttaatttct ttctgaggct tatataaata gatcaaaggg | 960 |
| gaaagtgaga tataatacag acaaaacaag agaaaaga | 998 |

<210> SEQ ID NO 69
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0380

<400> SEQUENCE: 69

| | |
|---|---|
| acaagtacca ttcactttttt tacttttcaa tgtatacaat catcatgtga taaaaaaaaa | 60 |
| aatgtaacca atcaacacac tgagatacgg ccaaaaaatg gtaatacata aatgtttgta | 120 |
| ggttttgtaa tttaaatact ttagttaagt tatgattta ttattttttgc ttatcactta | 180 |
| tacgaaatca tcaatctatt ggtatctctt aatcccgctt tttaatttcc accgcacacg | 240 |
| caaatcagca aatggttcca gccacgtgca tgtgaccaca tattgtggtc acagtactcg | 300 |
| tcctttttttt ttctttttgta atcaataaat ttcaatccta aaacttcaca cattgagcac | 360 |
| gtcggcaacg ttagctccta aatcataacg agcaaaaaag ttcaaattag ggtatatgat | 420 |

```
caattgatca tcactacatg tctacataat taatatgtat tcaaccggtc ggtttgttga    480
tactcatagt taagtatata tgtgctaatt agaattagga tgaatcagtt cttgcaaaca    540
actacggttt catataatat gggagtgtta tgtacaaaat gaaagaggat ggatcattct    600
gagatgttat gggctcccag tcaatcatgt tttgctcgca tatgctatct tttgagtctc    660
ttcctaaact catagaataa gcacgttggt tttttccacc gtcctcctcg tgaacaaaag    720
tacaattaca ttttagcaaa ttgaaaataa ccacgtggat ggaccatatt atatgtgatc    780
atattgcttg tcgtcttcgt tttcttttaa atgtttacac cactacttcc tgacacgtgt    840
ccctattcac atcatccttg ttatatcgtt ttacttataa aggatcacga acaccaaaac    900
atcaatgtgt acgtcttttg cataagaaga aacagagagc attatcaatt attaacaatt    960
acacaagaca gcgagattgt aaaagagtaa gagagagag                          999

<210> SEQ ID NO 70
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0381

<400> SEQUENCE: 70
cacggtcaaa gtattgctaa catggtcatt acattgaaaa agaaaattaa ttgtctttac     60
tcatgtttat tctatacaaa taaaaatatt aaccaaccat cgcactaaca aaatagaaat    120
cttattctaa tcacttaatt gttgacaatt aaatcattga aaaatacact taaatgtcaa    180
atattcgttt tgcatacttt tcaatttaaa tacatttaaa gttcgacaag ttgcgtttac    240
tatcatagaa aactaaatct cctaccaaag cgaaatgaaa ctactaaagc gacaggcagg    300
ttacataacc taacaaatct ccacgtgtca attaccaaga gaaaaaaaga gaagataagc    360
ggaacacgtg gtagcacaaa aaagataatg tgatttaaat taaaaaacaa aaacaaagac    420
acgtgacgac ctgacgctgc aacatcccac cttacaacgt aataaccact gaacataaga    480
cacgtgtacg atcttgtctt tgttttctcg atgaaaacca cgtgggtgct caaagtcctt    540
gggtcagagt cttccatgat tccacgtgtc gttaatgcac caaacaaggg tactttcggt    600
attttggctt ccgcaaatta gacaaaacag cttttttgttt gattgatttt tctcttctct    660
ttttccatct aaattctctt tgggctctta atttcttttt gagtgttcgt tcgagatttg    720
tcggagattt tttcggtaaa tgttgaaatt ttgtgggatt tttttttatt tctttattaa    780
actttttttt attgaattta taaaaaggga aggtcgtcat taatcgaaga aatggaatct    840
tccaaaattt gatattttgc tgttttcttg ggatttgaat tgctctttat catcaagaat    900
ctgttaaaat ttctaatcta aaatctaagt tgagaaaaag agagatctct aatttaaccg    960
gaattaatat tctccgaccg aagttattat gttgcaggct                        1000

<210> SEQ ID NO 71
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0384

<400> SEQUENCE: 71
tttaaaaaat tggataaaac accgataaaa attcacattt gcaaattttta ttcagtcgga    60 atatatattt gaaacaagtt ttgaaatcca ttggacgatt aaaattcatt gttgagagga   120
```

```
taaatatgga tttgttcatc tgaaccatgt cgttgattag tgattgacta ccatgaaaaa    180
tatgttatga aaagtataac aacttttgat aaatcacatt tattaacaat aaatcaagac    240
aaaatatgtc aacaataata gtagtagaag atattaattc aaattcatcc gtaacaacaa    300
aaaatcatac cacaattaag tgtacagaaa aacctttttgg atatatttat tgtcgctttt    360
caatgatttt cgtgaaaagg atatatttgt gtaaaataag aaggatcttg acgggtgtaa    420
aaacatgcac aattcttaat ttagaccaat cagaagacaa cacgaacact tctttattat    480
aagctattaa acaaaatctt gcctatttttg cttagaataa tatgaagagt gactcatcag    540
ggagtggaaa atatctcagg atttgctttt agctctaaca tgtcaaacta tctagatgcc    600
aacaacacaa agtgcaaatt cttttaatat gaaaacaaca ataatatttc taatagaaaa    660
ttaaaagggg aaataaaata ttttttttaaa atatacaaaa gaagaaggaa tccatcatca    720
aagttttata aaattgtaat ataatacaaa cttgtttgct tccttgtctc tccctctgtc    780
tctctcatct ctcctatctt ctccatatat acttcatctt cacacccaaa actccacaca    840
aaatatctct ccctctatct gcaaattttc caaagttgca tcctttcaat ttccactcct    900
ctctaatata attcacattt tcccactatt gctgattcat ttttttttgt gaattatttc    960
aaacccacat aaaaaaatct ttgtttaaat ttaaaacca                           999

<210> SEQ ID NO 72
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0385

<400> SEQUENCE: 72
actcaacaat aggacaagcc aaaaaaattc caattattgt gttactctat tcttctaaat     60
ttgaacacta atagactatg acatatgagt atataatgtg aagtcttaag atattttcat    120
gtgggagatg aataggccaa gttggagtct gcaaacaaga agctcttgag ccacgacata    180
agccaagttg atgaccgtaa ttaatgaaac taaatgtgtg tggttatata ttagggaccc    240
atggccatat acacaatttt tgtttctgtc gatagcatgc gtttatatat atttctaaaa    300
aaactaacat atttactgga tttgagttcg aatattgaca ctaatataaa ctacgtacca    360
aactacatat gtttatctat atttgattga tcgaagaatt ctgaactgtt ttagaaaatt    420
tcaatacact taacttcatc ttacaacggt aaaagaaatc accactagac aaacaatgcc    480
tcataatgtc tcgaaccctc aaactcaaga gtatacattt tactagatta gagaatttga    540
tatcctcaag ttgccaaaga attggaagct tttgttacca aacttagaaa cagaagaagc    600
cacaaaaaaa gacaagggga gttaaagatt gaagtgatgc atttgtctaa gtgtgaaagg    660
tctcaagtct caactttgaa ccataataac attactcaca ctcccttttt ttttcttttt    720
ttttcccaaa gtaccttttt taattccctc tataacccac tcactccatt ccctctttct    780
gtcactgatt caacacgtgg ccacactgat gggatccacc tttcctctta cccacctccc    840
ggtttatata aacccttcac aacacttcat cgctctcaaa ccaactctct cttctctctt    900
ctctcctctc ttctacaaga agaaaaaaaa cagagccttt acacatctca aaatcgaact    960
tactttaacc accaaatact gattgaacac acttgaaa                            998

<210> SEQ ID NO 73
<211> LENGTH: 1000
<212> TYPE: DNA
```

```
<213> ORGANISM: Arabidopsis thaliana
<220> FEATURE:
<221> NAME/KEY: misc_feature
<223> OTHER INFORMATION: Ceres Promoter YP0396

<400> SEQUENCE: 73
catagtaaaa gtgaatttaa tcatactaag taaaataaga taaaacatgt tatttgaatt      60
tgaatatcgt gggatgcgta tttcggtatt tgattaaagg tctggaaacc ggagctccta     120
taacccgaat aaaaatgcat aacatgttct tccccaacga ggcgagcggg tcagggcact     180
agggtcattg caggcagctc ataaagtcat gatcatctag gagatcaaat tgtatgtcgg     240
ccttctcaaa attacctcta agaatctcaa acccaatcat agaacctcta aaagacaaa      300 gtcgtcgctt tagaatgggt tcggtttttg gaaccatatt tcacgtcaat ttaatgttta     360
gtataatttc tgaacaacag aattttggat ttatttgcac gtatacaaat atctaattaa     420
taaggacgac tcgtgactat ccttacatta agtttcactg tcgaaataac atagtacaat     480
acttgtcgtt aatttccacg tctcaagtct ataccgtcat ttacggagaa agaacatctc     540
tgttttccat ccaaactact attctcactt tgtctatata tttaaaatta agtaaaaaag     600
actcaatagt ccaataaaat gatgaccaaa tgagaagatg gttttgtgcc agattttagg     660
aaaagtgagt caaggtttca catctcaaat ttgactgcat aatcttcgcc attaacaacg     720
gcattatata tgtcaagcca attttccatg ttgcgtactt ttctattgag gtgaaaatat     780
gggtttgttg attaatcaaa gagtttgcct aactaatata actcgactt  tttcagtgac     840 cattccatgt aaactctgct tagtgtttca tttgtcaaca atattgtcgt tactcattaa     900
atcaaggaaa aatatacaat tgtataattt tcttatattt taaaattaat tttgatgtat     960
taccccttta taaataggct atcgctacaa caccaataac                          1000

<210> SEQ ID NO 74
<211> LENGTH: 1514
<212> TYPE: DNA
<213> ORGANISM: Arabidopsis thaliana
<220> FEATURE:
<221> NAME/KEY: misc_feature
<223> OTHER INFORMATION: Ceres Promoter p13879

<400> SEQUENCE: 74
tttcgatcct cttctttttt aggtttcttg atttgatgat cgccgccagt agagccgtcg      60
tcggaagttt cagagattaa aaccatcacc gtgtgagttg gtagcgaatt aacggaaagt     120
ctaagtcaag attttttaaa aagaaattta tgtgtgaaaa gaagccgttg tgtatattta     180
tataatttag aaaatgtttc atcatttta  ttaaaaaatt aataatttgt agaagaaaga     240
agcatttttt atacataaat catttacctt ctttactgtg ttttctcca  cttacttcat     300 ttttactttt ttacaaaaaa gtgaaaagta aattacgtaa ttggtaacat aaattcactt     360
taaatttgca tatgttttgt tttcttcgga actatatcg aaaagcaaac ggaaagaact     420
tcacaaaaaa ccctagctaa ctaaagacgc atgtgttctt cttattcttc atatatcctc     480
tgtttcttgt gttctgtttt gagtcttaca ttttcaatat ctgactctga ttactatatc     540
taaaagggaa catgaagaac ttgagaccat gttaaactgt acaatgcctt caaacatggc     600
taactaaaga tacattagat ggctttacag tgtgtaatgc ttattatctt taggtttttt     660
aaatcccttg tattaagtta tttaccaaat tatgttcttg tactgcttat tggcttggtt     720
gttgtgtgct ttgtaaacaa caccctttggc tttatttcat cctttgtaaa cctactggtc     780
tttgttcagc tcctcttgga agtgagtttg tatgcctgga acgggttttta atggagtgtt     840
```

```
tatcgacaaa aaaaaaatgt agcttttgaa atcacagaga gtagttttat attcaaatta      900
catgcatgca actaagtagc aacaaagttg atatggccga gttggtctaa ggcgccagat      960
taaggttctg gtccgaaagg gcgtgggttc aaatcccact gtcaacattc tcttttctc     1020
aaattaatat ttttctgcct caatggttca ggcccaatta tactagacta ctatcgcgac     1080
taaaataggg actagccgaa ttgatccggc ccagtatcag ttgtgtatca ccacgttatt     1140
tcaaatttca aactaaggga taaagatgtc atttgacata tgagatattt ttttgctcca     1200
ctgagatatt tttctttgtc ccaagataaa atatcttttc tcgcatcgtc gtctttccat     1260
ttgcgcatta aaccaaaaag tgtcacgtga tatgtcccca accactacga atttaacta      1320
cagatttaac catggttaaa ccagaattca cgtaaaccga ctctaaacct agaaaatatc     1380
taaaccttgg ttaatatctc agccccctta taaataacga gacttcgtct catcgttct     1440
acacatctca ctgctcacta ctctcactgt aatcccttag atcttctttt caaatttcac     1500
cattgcactg gatg                                                       1514
```

<210> SEQ ID NO 75
<211> LENGTH: 1954
<212> TYPE: DNA
<213> ORGANISM: Arabidopsis thaliana
<220> FEATURE:
<221> NAME/KEY: misc_feature
<223> OTHER INFORMATION: Ceres Promoter p326

<400> SEQUENCE: 75

```
gtgggtaaaa gtatccttct ttgtgcattt ggtattttta agcatgtaat aagaaaaacc       60
aaaatagacg gctggtattt aataaaagga gactaatgta tgtatagtat atgatttgtg      120
tggaatataa taaagttgta aaatatagat gtgaagcgag tatctatctt ttgactttca      180
aaggtgatcg atcgtgttct ttgtgatagt tttggtcgtc ggtctacaag tcaacaacca      240
ccttgaagtt ttcgcgtctc ggtttcctct tcgcatctgg tatccaatag catacatata      300
ccagtgcgga aaatggcgaa gactagtggg cttgaaccat aaggtttggc cccaatacgg      360
attccaaaca acaagcctag cgcagtcttt tgggatgcat aagactaaac tgtcgcagtg      420
atagacgtaa gatatatcga cttgattgga atcgtctaag ctaataagtt taccttgacc      480
gtttatagtt gcgtcaacgt ccttatggag attgatgccc atcaaataaa cctgaaaatc      540
catcaccatg accaccataa actcccttgc tgccgctgct ttggcttgag caaggtgttt      600
ccttgtaaag ctccgatctt tggataaagt gttccacttt ttgcaagtag ctctgacccc      660
tctcagagat gtcaccggaa tcttagacag aacctcctct gccaaatcac ttggaagatc      720
ggacaatgtc atcattttg caggtaattt ctccttcgtt gctgctttgg cttgagcacg      780
gtgcttcttt gtaaagctcc gatctttgga taagagcgga tcggaatcct ctaggaggtg      840
ccagtccctt gacctattaa tttatagaag gttttagtgt attttgttcc aatttcttct      900
ctaacttaac aaataacaac tgcctcatag tcatgggctt caaatttat cgcttggtgt      960
atttcgttat ttgcaaggcc ttggcccatt ttgagcccaa taactaaatc tagccttttc     1020
agaccggaca tgaacttcgc atattggcgt aactgtgcag ttttaccttt ttcggatcag     1080
acaagatcag atttagacca cccaacaata gtcagtcata tttgacaacc taagctagcc     1140
gacactacta aaaagcaaac aaaagaagaa ttctatgttg tcatttttacc ggtggcaagt     1200
ggacccttct ataaaagagt aaagagacag cctgtgtgtg tataatctct aattatgttc     1260
accgacacaa tcacacaaac ccttctctaa tcacacaact tcttcatgat ttcgacatt      1320
aattatcatt aactctttaa attcacttta catgctcaaa aatatctaat ttgcagcatt     1380
```

```
aatttgagta ccgataacta ttattataat cgtcgtgatt cgcaatcttc ttcattagat    1440
gctgtcaagt tgtactcgca cgcggtggtc cagtgaagca aatccaacgg tttaaaacct    1500
tcttacattt ctagatctaa tctgaaccgt cagatatcta gatctcattg tctgaacaca    1560
gttagatgaa actgggaatg aatctggacg aaattacgat cttacaccaa cccctcgac    1620 gagctcgtat atataaagct tatacgctcc tccttcacct tcgtactact actaccacca    1680
catttcttta gctcaacctt cattactaat ctccttttaa ggtatgttca cttttcttcg    1740
attcatactt tctcaagatt cctgcatttc tgtagaattt gaaccaagtg tcgattttg     1800 tttgagagaa gtgttgattt atagatctgg ttattgaatc tagattccaa tttttaattg    1860
attcgagttt gttatgtgtg tttatactac ttctcattga tcttgtttga tttctctgct    1920
ctgtattagg tttcttccgt gaatcagatc ggaa                                1954

<210> SEQ ID NO 76
<211> LENGTH: 2016
<212> TYPE: DNA
<213> ORGANISM: Arabidopsis thaliana
<220> FEATURE:
<221> NAME/KEY: misc_feature
<223> OTHER INFORMATION: Ceres Promoter p32449

<400> SEQUENCE: 76
gatcggcctt cttcaggtct tctctgtagc tctgttactt ctatcacagt tatcgggtat      60
ttgagaaaaa agagttagct aaaatgaatt tctccatata atcatggttt actacaggtt     120
tacttgattc gcgttagctt tatctgcatc caaagttttt tccatgatgt tatgtcatat     180
gtgataccgt tactatgttt ataactttat acagtctggt tcactggagt ttctgtgatt     240
atgttgagta catactcatt catcctttgg taactctcaa gtttaggttg tttgaattgc     300
ctctgttgtg atacttattg tctattgcat caatcttcta atgcaccacc ctagactatt     360
tgaacaaaga gctgtttcat tcttaaacct ctgtgtctcc ttgctaaatg gtcatgcttt     420
aatgtcttca cctgtctttc tcttctatag atatgtagtc ttgctagata gttagttcta     480
cagctctctt ttgtagtctt gttagagagt tagttgagat attacctctt aaaagtatcc     540
ttgaacgctt tccggttatg accaatttgt tgtagctcct tgtaagtaga acttactggg     600
accagcgaga cagtttatgt gaatgttcat gcttaagtgt cgaacgtatc tatctctact     660
atagctctgt agtcttgtta gacagttagt tttatatctc catttttttg tagtcttgct     720
agttgagata ttacctcttc tcttcaaagt atccttgaac gctcaccggt tatgaaatct     780
ctacactata gctctgtagt cttgctagat agttagttct ttagctctct ttttgtagcc     840
tagttcttta gctctccttt tgtagccttg ctacagagta agatgggata ttacctcctt     900
gaacgctctc cggttatgac caatttgttg tagctccttg taagtagaac ttaggataga     960
gtgagtcaac tttaagaaag aacctagtat gtggcataac cagattgcag gctctgtctc    1020
ggctacagta acgtaactct atagctcttt gttttgttca gaaagaacca gtgattggat    1080
gattcgtcct tagaaactgg acctaacaac agtcattggc tttgaaatca agccacaaca    1140
atgcctatat gaaccgtcca tttcatttat ccgtttcaaa ccagcccatt acatttcgtc    1200
ccattgataa ccaaaagcgg ttcaatcaga ttatgtttta attttaccaa attctttatg    1260
aagtttaaat tatactcaca ttaaaaggat tattggataa tgtaaaaatt ctgaacaatt    1320
actgattttg gaaaattaac aaatattctt tgaaatagaa gaaaaagcct ttttcctttt    1380
gacaacaaca tataaaatca tactcccatt aaaaagattt taatgtaaaa ttctgaatat    1440
```

-continued

| | |
|---|---|
| aagatatttt ttacaacaac aaccaaaaat atttattttt ttccttttt acagcaacaa | 1500 |
| gaaggaaaaa cttttttttt tgtcaagaaa aggggagatt atgtaaacag ataaaacagg | 1560 |
| gaaaataact aaccgaactc tcttaattaa catcttcaaa taaggaaaat tatgatccgc | 1620 |
| atatttagga agatcaatgc attaaaacaa cttgcacgtg gaaagagaga ctatacgctc | 1680 |
| cacacaagtt gcactaatgg tacctctcac aaaccaatca aaatactgaa taatgccaac | 1740 |
| gtgtacaaat tagggtttta cctcacaacc atcgaacatt ctcgaaacat tttaaacagc | 1800 |
| ctggcgccat agatctaaac tctcatcgac caattttga ccgtccgatg gaaactctag | 1860 |
| cctcaaccca aaactctata taagaaatc tttccttcg ttattgctta ccaaatacaa | 1920 |
| accctagccg ccttattcgt cttcttcgtt ctctagtttt ttcctcagtc tctgttctta | 1980 |
| gatcccttgt agtttccaaa tcttccgata aggcct | 2016 |

```
<210> SEQ ID NO 77
<211> LENGTH: 667
<212> TYPE: DNA
<213> ORGANISM: Arabidopsis thaliana
<220> FEATURE:
<221> NAME/KEY: misc_feature
<223> OTHER INFORMATION: Ceres Promoter PD1367

<400> SEQUENCE: 77
```

| | |
|---|---|
| acagttttct tttctcatct tacaacaagt ttccaggagg atagagacat aaacgaagct | 60 |
| cggattgtat cgttcttttt agcttttatt cacatccgaa agtcctgtag tttagattct | 120 |
| gttatcttgc ggttttgagt taatcagaaa cagagtaatc aatgtaatgt tgcaggctag | 180 |
| atctttcatc tttggaaatt tgttttttc tcatgcaatt tctttagctt gaccatgagt | 240 |
| gactaaaaga tcaatcagta gcaatgattt gatttggcta agagacattt gtccacttgg | 300 |
| catcttgatt tggatggtta caacttgcaa gacccaattg gatacttgct atgacaactc | 360 |
| caactcaaga gtgtcgtgta actaagaacc ttgactaatt tgtaatttca atcccaagtc | 420 |
| atgttactat atgttttttt gtttgtatta ttttctctcc tacaattaag ctctttgacg | 480 |
| tacgtaatct ccggaaccaa ctcctatatc caccatttac tccacgttgt ctccaattat | 540 |
| tggacgttga aacttgacac aacgtaaacg tatctacgtg gttgattgta tgtacatatg | 600 |
| tacaaacgta cacctttctc ctctttcact tcatcacttg gcttgtgaat tcattaattc | 660 |
| ctgcgaa | 667 |

```
<210> SEQ ID NO 78
<211> LENGTH: 252
<212> TYPE: DNA
<213> ORGANISM: Arabidopsis thaliana
<220> FEATURE:
<221> NAME/KEY: misc_feature
<223> OTHER INFORMATION: Ceres Promoter PD0898

<400> SEQUENCE: 78
```

| | |
|---|---|
| cgcaggcccg atcggcctaa ataattatag tcataagagg acccaaataa ataaataatg | 60 |
| ggattctctg aggtgtattt ttttatgcac acgtaaaagc gtgaaagatt tgtaaaccta | 120 |
| ctttatatat atacttccat ctctttgtct ttgttacaat ttgaatcaga gagaaattaa | 180 |
| gaagcgaaaa acaaagaacg agaggaggcg agaggtatag aagaatattc cttgtggccg | 240 |
| gcaaggccaa tc | 252 |

```
<210> SEQ ID NO 79
<211> LENGTH: 283
<212> TYPE: DNA
```

```
<213> ORGANISM: Arabidopsis thaliana
<220> FEATURE:
<221> NAME/KEY: misc_feature
<223> OTHER INFORMATION: Ceres Promoter PD0901

<400> SEQUENCE: 79 caaagtatttt gacaagccat atggttttgg atcaaaaagt cggtccaaaa ttaatgtttt      60
atgtgcaaga accgacccat tgtacacacg tgttaacatc ttcaagactt tcatctctat     120
ttttcttttg gtcattaaga tacccattga tccgaatctg ttacattccc acctactttt     180
ttaattttta ctatccactc caaattaaac acaaccgatg attttaataa ttggaagctt     240
tttaaaatat ttctccacgt gcctctttgt gtttgtctat ata                       283

<210> SEQ ID NO 80
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0022

<400> SEQUENCE: 80
tagttccatt acaatttcca atgatttgt tacaaagcta caagattatt cgaaatagga       60
tttcatccat aagagagaat ggtgtggtcg acgctacaat gttgatttat tggttgtggt     120
ttgcatcttg gggatgtcaa atcctaagtt tcaagttctt gtaaaaacgt tttcaggttt     180 cttaatata ttttaatatt aatgtaaaaa gaaaagatat agcttttgta caaaaaaatt      240
tgtttaatca ctatgtagga ggatgcgatc aaattcatgg aatgatgtat tattagctttt    300 tctatcctca ctctaaaaac aatactatag tgagttaaat aatttgatca tttcaatgta     360
gattaaaatt ttattaaaag aagaaaaatt taaaagccta taacaaaata aaaaaggagg     420
ctcgaggtat gatgggtgta gcagaagagc tggcaacagc tatcgactga gtgattacga     480
actcagtact cagtgttctc agctcacaca ctctttttt gttctctttc ttttggacag      540 cttttcatttt ctcttttctt ttttctattt tgtttcaaaa ttccatccat attaaaatag    600
gcctgatcat gagaataaag gaaatactaa tgatgagttt ctcaataatg caataagatg     660
caattattat gagctatttta ctattgaaaa tgagcaaata aatgtcaaaa cacaatctgg    720
ttaagttaga gcaactccat tgtataggat tcatgtagtt tctaagaaaa caaaatgtat     780 taatattta cttttacatc caaaaacca acttatatga gtaatagaaa cgatcctaat       840
attaggaatt ttagagattt tctctcatct gtttcttaac ttttcaatat ttttattttt    900
taaaattgta tgagtttcta ctaagaaact actgctggag ttggtcttag cttcccaatg     960
cttctccacc tatatatgtg catatctcct tcttaaaac                            999

<210> SEQ ID NO 81
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0080

<400> SEQUENCE: 81
aagcggcaat ttagtaagaa gtactcaaag tatcatttac caaaagtata tggttttggg      60
aagagttgtt agggatgtat tcttttctaaa cagatgatat gacgatgttc ttgaaaacta   120
atgttaaaga cggaatctct ggcatcttca ctcgggagat atattaaacc gttgattgta    180
gttagccatg tacttagctt agtgcacaaa taatctgctg caagaaatct ttttctatta    240
```

-continued

```
taatatctct catttaaaca ttagaacata ttgtttaact tgttcttcta gaaataaaac    300
tgctaatttc ttatggtaaa ctattttcct ttagattgca caatcgaact cgaaaatcta    360
gtggagacta tgtgactatg tttatatata tgaaacctaa atcaaattat cccaataatt    420
gggagacaca aaagaaaaat tacgaaagaa aacaggaaat caaatcaaaa gataaagaga    480
aggtaaaaaa aggcaagaag cactaatgtt taatatttat agttttctcc attaaagaaa    540
aagcgatgat gtgtgttctc atcttttgtg aaagtatata tattgctttt gcttttctca    600
aaagcaaaag actcatccaa caagaacaaa aaaaaaaact aaagctcaat ccaaagacg     660 aagaatgcat tggatactac aacttctttt tcacttttct ttcaaattta caattatgat    720
tttcacaata cagtttattc aaaaataaat aaaaaaacga ggcatgaaaa taatgattat    780
cctcttcact tattaagcca ctcactataa gcagagcaac tccagaacat agtgagcccc    840
caaaacatta aagcatgatg atgtctaatg atgatgatct tcttcgttcc atttctctaa    900 attttggga tttctgcgaa gacccttctt ctctttctct tctctgaact tcaagattcg     960
tgtcggacaa attttgtttt ttatttttct gatgttaca                           999
```

<210> SEQ ID NO 82
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0087

<400> SEQUENCE: 82

```
tgaattgagt aaaatgtgtt ttcaaacagt taggtggtag aaggtaaagg taataacatc     60
atgatcttac taaagaatt gttgcatact aactatcaat attctcaaca acataatata    120 atgtttttt aggtaatttt ccatttaat tttttgtgat taaacaatta aacaactcga     180
atgatgatga taaaaaaaaa aaattaacaa ctcgaataag ttaaagtagc aatacacatg    240
tcgttcaatt caaccaataa agtaagactt atattttaa gaagttgact aatagcttaa    300
taagttggaa aacttgtgta gtttcttaat tcccacgtgc agtaagaaat aaaaatgaaa    360
aaaattatta tatccttccc actctgcgac ttttcttta ttttatcaaa tattaaaaag     420
attcatatca cagtttacac attgaaatca taaacgataa ttatgtattt tgtaataaaa    480
agttagttct gaagctcata ctttggatag tcgctagtcg ctaatatgct ccttgtaata    540
attaaagtca ctacgacgca cgtcaaagcc gatatttagg gcttaattga tgcgtgtttt    600
tcttttcata taatagtaat ataaattagt actaataaag tatgatggat ggttgagaca    660
gaaaagaaaa aagatgactg tatggtcatc attacaaaga agaatgtatt cttcatgttc    720
ttaagaataa taaaatgtca cttgtaaatc aagttggtaa gcattttgag aactttgttc    780
gatgcaacgt atgatgattt atgtagacaa aagataaaac cgtatcttca actattgcca    840
agaaaagata aaacctaatc tagtcagtct ctcaacataa atacaaccca atagccaaac    900
tgtgtccaat tcggagagaa actaaactaa aacaaacac aaaagcccaa cataagccca    960
ataaaaccca ttttataaac agaacattac taacactca                           999
```

<210> SEQ ID NO 83
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0093

<400> SEQUENCE: 83

```
atgatgaaca ttctacatat ataattatta tgtttaagca cttagacagc ataaattctt      60
tctaattata taaatctaac cttgttacat tgtacatcta taaattactt gaagaaataa     120
cgagttctat ttcttttttaa aaattaaaaa tactatacca tatctcagtg attaagttga    180
accaaaaggt acggaggaga aacaagcatt tgattcttcc ttattttatt ttattcatct     240
ctcactaatg atggtggaga aaaaagaaa atacctaaca aacaaatata tattgtcata      300
caaaaatatt tctatatttt tagttaatta gtttatattc ctcactttc agggcttata     360
taagaaagtg agcaaacaca aatcaaaatg cagcagcaaa tactatcatc acccatctcc     420
ttagttctat tttataattc ctcttctttt tgttcatagc tttgtaatta tagtcttatt     480
tctctttaag gctcaataag aggaggtact attactacac ttctctctac ttttacttgt    540
attttagcat taaatccta aaatccgttt taaattcaaa aataaactta gagatgttta     600
atctcgattc ggttttcgg ctttaggaga ataattat gaaattagta tggatatctt       660
tactagtttc cattcaaatg attctgattt caatctaata ctctcactct ttaattaaac   720
tatatgtagt gtaatttcac actgttaaat ttctaccatg tcatgtatat tagagttgca   780
tagaaaattg taaacatcc atttgaattc gaatgaaaca aatgttttta aaataaaatt    840
ttggttttta aaagaaaaat ctaaaactga attatatcgt ttaaccaagt tgtaaaagtc   900
ataaaacgta gtatcttgta aatcgctctt ccacggtcca aatagacttc tagtaataaa   960
caagtaaaac taattttggt ttcttactaa ttttcacaga                         1000
```

<210> SEQ ID NO 84
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0108

<400> SEQUENCE: 84

```
ttagctgaac caggaaattg atctcttata ccagtttccg ggtttagatt ggtttgatgg     60
cgatttgatt aaaccccga aatttttatgt cgtagttgtg catagtatta ttattctttg   120
cggacaatag acgtatcggg accaagttct gtagcaaaat tgtataagct taagtttgat   180
gaaatttaaa ggtaatcact aaaacccaaa tgggacaata aaccggtgaa gatttagagt   240
ttttaatttt gactcatgaa tctggagaaa gagccctcgt taaaggagt gaatcaatcc    300
ataggggaaa aagttttgtc ttttttaaaaa ctaagaaacc aaaccttaat agaagcagct   360
caatgtgtga caacttttcca ctggcactaa gataaagtga ctagcgatga gtgcaattat   420
tgaaatagta gatggtaaat attacataca agagtaaaaa tatctttatg tcaatgctta   480
attcagtgtt tctggttaac aagagaaact tctctaactt tcgtaattgg gtcttataaa    540
attttatgca attatgattt taccctttta ctactttca ttagctttca cgaatctatt    600
ttgacaagag aaatcattag aggtaaacat gcttttggt caagggcctt aacagttcca     660
ccaatcaagc tcaaaagttg tacttaaccg acatcttctg tgaaaacata taattacatg    720
tacaaatcaa aactacctta tgaaataaat agaaatattg cagttcattt ctaatttaac   780
ctcttcaact tttaaaacta tttacatttc tttatgtcat ttcagtcat tttgatgcaa    840
attgtaccat ttatggatta tcttcacaaa tttttaagtt ggtgaaaact ttttggtggg   900
tagttaaaac ttgaaataga aatttacttt accaaaataa actaatgaaa agtaatcact   960
```

```
ccactcccta taataagatt tccaacgttc ccactaagc                          999
```

<210> SEQ ID NO 85
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0388

<400> SEQUENCE: 85

```
agaagtattc acgcaccaag gttatatttg tagtgacata ttctacaatt atcacatttt    60
tctcttatgt ttcgtagtcg cagatggtca atttttttcta taataatttg tccttgaaca  120
caccaaactt tagaaacgat gatatatacc gtattgtcac gctcacaatg aaacaaacgc   180
gatgaatcgt catcaccagc taaaagccta aacaccatc ttagttttca ctcagataaa    240
aagattattt gtttccaacc tttctattga attgattagc agtgatgacg taattagtga   300
tagtttatag taaaacaaat ggaagtggta ataaatttac acaacaaaat atggtaagaa   360
tctataaaat aagaggttaa gagatctcat gttatattaa atgattgaaa gaaaaacaaa   420
ctattggttg atttccatat gtaatagtaa gttgtgatga aagtgatgac gtaattagtt   480
gtatttatag taaaacaaat taaaatggta aggtaaattt ccacaacaaa acttggtaaa   540
aatcttaaaa aaaaaaaaag aggtttagag atcgcatgcg tgtcatcaaa ggttcttttt   600
cactttaggt ctgagtagtg ttagactttg attggtgcac gtaagtgttt cgtatcgcga   660
tttaggagaa gtacgttta cacgtggaca caatcaacgg tcaagatttc gtcgtccaga    720
tagaggagcg atacgtcacg ccattcaaca atctcctctt cttcattcct tcattttgat   780
tttgagtttt gatctgcccg ttcaaaagtc tcggtcatct gcccgtaaat ataaagatga   840
ttatatttat ttatatcttc tggtgaaaga agctaatata aagcttccat ggctaatctt   900
gtttaagctt ctcttcttct tctctctcct gtgtctcgtt cactagtttt ttttcggggg   960
agagtgatgg agtgtgtttg ttgaatagtt ttgacgatca                        1000
```

<210> SEQ ID NO 86
<211> LENGTH: 3000
<212> TYPE: DNA
<213> ORGANISM: Arabidopsis thaliana
<220> FEATURE:
<221> NAME/KEY: misc_feature
<223> OTHER INFORMATION: Ceres Promoter PR0924

<400> SEQUENCE: 86

```
atctataacg agttaacatg ttgccagttt gaatcaagaa gcttggatga tgaatgaatg    60
gatcggtttg tggtacaatt cttaaaattg tagtagagga gacagagaaa aaacatgata   120
agactttggt atttacaact tgacggagac aagacagtaa gccaaatctg tcacaaaaac   180
actcaaactc ttttctcagt gttttgagtt taaagagaga cttattcact tcccctttcg   240
taacacttat ttgtctccca accaaacagt ttctgtcctt tcccttgtcc tcccacgtgc   300
atctttatat ctcatgactt ttcgtttcta gatcttgaat aatgtcttag tggattaggt   360
ttgttgtcgg taaattaggt gaccgttttt ttcttatatt tggaagatcg cgggatgaag   420
cagatactga gtttcagggc atacacacct aatttgaaaa tcattgttag tccaatttca   480
ctttaatctt gtttacaaaa aaattgatct gaaaatgttg atgggataag taaaaatgta   540
agttttgcta gtagtcatga tataataata gcaaaaccag atcaatttg agcaaaagga   600
agaaacaaaa aacagatcga tcccacgagc aagactaagt gtaaagtggt tcccacaaga   660
```

```
gccatatgga tatggtcctt caacttttaa agcccattac ttcagtggtc gacccgacat    720
tacgccacga gtagtcacgc acgcacgact ccgttcacgt gacattcacg ttgatatttc    780
cccctctact ctcttctgct tggttgatct aaaaaacatg aagagaccaa cctaatttca    840
tattaatata tgatatagac ttcatactca acagtcactt tcgtaatcca aatccatatc    900
ttacgaaatt agttcttaat aaaggttgtg gattaagtta taatattgtg ttaagagtta    960
agacacagca tataaccttg taccaacagt gctttattct taaatggaaa caaaacatat   1020
gtcaatgtca agcatacagc taaaatatca ttatctaata ttaagagtaa aacaagataa   1080
ttaaaaattg aaacaacacc atattttat agctttactt atcgtatttt tctagtcttc    1140
atggtaattg tgttgcttta ttttgtttat aaatgaattt ggttcgacca gatagtctaa   1200
tatcagtttt taaacactgg ttttaataaa atcatatgtc ggcaattcaa cctgttacgt   1260
tgtatgattg tatcctagtc aaataggga ggaggtacta gtcgtttcaa ttagtttacg    1320
taatcaatcc aaagaaacta taagctataa agatcctcaa tttgttggtt acaataaaaa   1380
caacagttgt caaaatttat gtttataaaa agtaataact atgttccttc ccatatagag   1440
caaagtacct caggataggc aaaccgtact taatagccct tattcataat ttgatccaac   1500
tcttccccac aaaattgcaa ctgatgaagt caatacttgt atagtgagtc aagctataaa   1560
tgtctagtga tagttttgtc tcttaaaagg ttaacaaaag ttatgacaag ctgaaaaatc   1620
agagtttgct aggagtatta cttacagtta tcagtttaag tatcacattt atagtattgt   1680
atacaatgat tcttaaattc cacctttcc gtgcgaaacc aaattttcta ttggaaacat    1740
agaatgtaaa caaaaatatg ggacgttgtc cgttccaaca ttaaccaaac ttgtctatta   1800
ctaatattcg tgttggtttg atgttggatg tctaaattcg ttgaatcatg tgtctcttga   1860
cgaaatatgc atcttcttat ttcttagtat agatgcactt tatcattctt ttagtacatg   1920
cttaattttt tttttaaaa tatgttgatt gtcatattgc caaaagtatg aattaaagac    1980
gcacatctaa cacaagttag cagccgtaaa tccttccata aatttatttt gcaagttttg   2040
ctcattatat aatgagcgga atttatgata taatcgtttg taataatgtt atgttttgat   2100
caaaatttga aattaaaagt aggtgagaac ttgttataca gtgtagataa ggtggatctt   2160
gaatataaaa ataaaattta taagatgtat ttaaagcaga aaagcataaa actttagata   2220
aaataatgta aaaatgtgtt agcatcaatg ttgggatatt ggccgacccg aacttaatca   2280
atgtcggaag ccattacttc tctcccaaaa gaccttttc cttcggagaa ctaggaactt    2340
cctcactacc tttcgcttaa cgtgaaagcc ataaatttca tatattcata aaaatcagaa   2400
aatctaaaac tgtttagtat cacctgtttt tggtatagac tattggtttt gtgttacttc   2460
ctaaactata tgatttcgta cttcattgga tcttatagag atgaatattc gtaaaaagat   2520
aagttatctg gtgaaacgtt acttcagtca tgttgggtct agatttacat actactatga   2580 aacatttaa gataataatt atcctagcca actatatgtt ctatattatg ggccaagaag    2640
atatagaact aaaagttcag aatttaacga tataaattac tagtatattc taatacttga   2700
atgattactg tttagttgt ttagaataaa tagtagcgtg ttggttaaga taccatctat    2760
ccacatctat atttgtgtgg gttacataaa atgtacataa tattatatac atatatatgt   2820 atattttga taaagccata tattactcct tgacctctgc ccccatttcc ttttactata    2880
aataggaata ctcatgatcc tctaattcag caatcaacac caacgaacac aacctttccc   2940
aaagccaata ataaaagaac aaaagctttt agtttcatca aagacgaagc tgccttagaa   3000

<210> SEQ ID NO 87
```

```
<211> LENGTH: 815
<212> TYPE: DNA
<213> ORGANISM: Arabidopsis thaliana
<220> FEATURE:
<221> NAME/KEY: misc_feature
<223> OTHER INFORMATION: Ceres CLONE ID no. 28780
<220> FEATURE:
<221> NAME/KEY: misc_feature
<223> OTHER INFORMATION: Encodes the peptide sequence at SEQ ID NO. 88

<400> SEQUENCE: 87
aactactaaa cactaaatta tcaatccgct ctcttctcaa aaaaaaaaaa tcgactctaa      60
aatcaaactc tctcaaagct ccccaaaaaa accctagttc tgaatggaat cggcggattc     120
cggacgatcc gatccggtaa aaggagacga cccgggtcca tctttcgtct cttcaccacc     180
agctacacct agcaggtatg agtcacagaa gcgacgcgac tggaacacgt tcttgcagta     240
cctcaagaac cacaagccgc ctctcgcgtt gtcacggtgt agcggagcgc atgtgatcga     300
gtttctcaag tacctcgacc agttcggtaa gaccaaagtc cacgtggcgg cttgtcctta     360
cttcggccat cagcaacctc cgtctccttg ctcatgccct ctcaagcaag cttggggatc     420
tctcgatgct ttgatcggac ggttgagagc tgcctacgag gagaacggtg gacgccggaa     480
ttctaacccg ttcgccgcac gtgcggttcg gatttacttg agggaagtca gagagagtca     540
ggcaaaggct cgtgggattc cttacgagaa aaagaaacgg aaacggccgc caactgtcac     600
caccgttaga gttgacgtcg cttcttcgag acaaagtgac ggagacccct gtaacgtcgg     660
tgctccatct gttgccgagg ccgtaccgcc ttagatcgaa ttatatataa tattatagtt     720
ttcttgatta atgatatata tatacttatc tctatgtatg tatggaactc acttcatctt     780
ttgttcctta gtacctaatt attaaatttt gttcc                                815

<210> SEQ ID NO 88
<211> LENGTH: 196
<212> TYPE: PRT
<213> ORGANISM: Arabidopsis thaliana
<220> FEATURE:
<221> NAME/KEY: MISC_FEATURE
<223> OTHER INFORMATION: Ceres CLONE ID no. 28780
<220> FEATURE:
<221> NAME/KEY: misc_feature
<222> LOCATION: (13)..(145)
<223> OTHER INFORMATION: Pfam Name: DUF640
      Pfam Description: Protein of unknown function (DUF640)

<400> SEQUENCE: 88

Met Glu Ser Ala Asp Ser Gly Arg Ser Asp Pro Val Lys Gly Asp Asp
 1               5                  10                  15

Pro Gly Pro Ser Phe Val Ser Pro Pro Ala Thr Pro Ser Arg Tyr
            20                  25                  30

Glu Ser Gln Lys Arg Arg Asp Trp Asn Thr Phe Leu Gln Tyr Leu Lys
         35                  40                  45

Asn His Lys Pro Pro Leu Ala Leu Ser Arg Cys Ser Gly Ala His Val
     50                  55                  60

Ile Glu Phe Leu Lys Tyr Leu Asp Gln Phe Gly Lys Thr Lys Val His
 65                  70                  75                  80

Val Ala Ala Cys Pro Tyr Phe Gly His Gln Gln Pro Pro Ser Pro Cys
                 85                  90                  95

Ser Cys Pro Leu Lys Gln Ala Trp Gly Ser Leu Asp Ala Leu Ile Gly
            100                 105                 110

Arg Leu Arg Ala Ala Tyr Glu Glu Asn Gly Gly Arg Pro Asp Ser Asn
        115                 120                 125
```

```
Pro Phe Ala Arg Ala Val Arg Ile Tyr Leu Arg Glu Val Arg Glu
    130                 135                 140

Ser Gln Ala Lys Ala Arg Gly Ile Pro Tyr Glu Lys Lys Arg Lys
145                 150                 155                 160

Arg Pro Pro Thr Val Thr Val Arg Val Asp Val Ala Ser Ser Arg
                165                 170                 175

Gln Ser Asp Gly Asp Pro Cys Asn Val Gly Ala Pro Ser Val Ala Glu
                180                 185                 190

Ala Val Pro Pro
        195

<210> SEQ ID NO 89
<211> LENGTH: 198
<212> TYPE: PRT
<213> ORGANISM: Glycine max
<220> FEATURE:
<221> NAME/KEY: MISC_FEATURE
<223> OTHER INFORMATION: Ceres CLONE 1073674
<220> FEATURE:
<221> NAME/KEY: misc_feature
<222> LOCATION: (14)..(146)
<223> OTHER INFORMATION: Pfam Name: DUF640
      Pfam Description: Protein of unknown function (DUF640)
<220> FEATURE:
<221> NAME/KEY: MISC_FEATURE
<223> OTHER INFORMATION: Functional Homolog of Ceres Clone ID no. 28780
      at SEQ ID NO. 88

<400> SEQUENCE: 89

Met Asp Ser Gly Ser Gln Arg Pro Gly Val Ser Glu Gly Asp Pro
1               5                   10                  15

Gly Pro Ser Ile Val Thr Pro Ser Ser Pro Ala Thr Pro Ser Arg
            20                  25                  30

Tyr Glu Ser Gln Lys Arg Arg Asp Trp Thr Thr Phe Leu Gln Tyr Leu
                35                  40                  45

Lys Asn His Lys Pro Pro Leu Ser Leu Ser Arg Cys Ser Gly Ala His
50                  55                          60

Ala Ile Glu Phe Leu Lys Tyr Leu Asp Gln Phe Gly Lys Thr Lys Val
65                  70                  75                  80

His Val Ala Ala Cys Pro Tyr Phe Gly His Gln Gln Pro Pro Ser Pro
                85                  90                  95

Cys Ala Cys Pro Leu Lys Gln Ala Trp Gly Ser Leu Asp Ala Leu Ile
                100                 105                 110

Gly Arg Leu Arg Ala Ala Tyr Glu Glu Asn Gly Gly Arg Pro Glu Ser
            115                 120                 125

Asn Pro Phe Ala Ala Arg Ala Val Arg Ile Tyr Leu Arg Glu Val Arg
        130                 135                 140

Glu Ser Gln Ala Lys Ala Arg Gly Arg Pro Tyr Glu Lys Lys Lys Arg
145                 150                 155                 160

Lys Arg Pro Thr Thr Val Thr Val Arg Val Asp Val Ala Ser Ser
                165                 170                 175

Arg Gln Ser Glu Gly Asp Gly Cys Asn Ile Gly Asp Pro Ser Tyr Val
                180                 185                 190

Ala Glu Ala Val Pro Pro
        195

<210> SEQ ID NO 90
<211> LENGTH: 198
<212> TYPE: PRT
<213> ORGANISM: Brassica napus
<220> FEATURE:
```

```
<221> NAME/KEY: MISC_FEATURE
<223> OTHER INFORMATION: Ceres CLONE 1118987
<220> FEATURE:
<221> NAME/KEY: misc_feature
<222> LOCATION: (13)..(146)
<223> OTHER INFORMATION: Pfam Name: DUF640
      Pfam Description: Protein of unknown function (DUF640)
<220> FEATURE:
<221> NAME/KEY: MISC_FEATURE
<223> OTHER INFORMATION: Functional Homolog of Ceres Clone ID no. 28780
      at SEQ ID NO. 88

<400> SEQUENCE: 90

Met Glu Ser Thr Asp Ser Gly Ser Gln Gln His Gly Gly Asp Pro Gly
1               5                   10                  15

Pro Ser Ser Val Thr Pro Ser Ser Pro Pro Ala Thr Pro Pro Ser Arg
                20                  25                  30

Tyr Glu Ser Gln Lys Arg Arg Asp Trp Asn Thr Phe Leu Gln Tyr Leu
            35                  40                  45

Lys Asn His Lys Pro Pro Leu Ala Leu Ser Arg Cys Ser Gly Ala His
50                  55                  60

Val Ile Glu Phe Leu Lys Tyr Leu Asp Gln Phe Gly Lys Thr Lys Val
65                  70                  75                  80

His Val Ala Thr Cys Pro Tyr Phe Gly His Gln Pro Pro Ser Pro
                85                  90                  95

Cys Ala Cys Pro Leu Lys Gln Ala Trp Gly Ser Leu Asp Ala Leu Ile
            100                 105                 110

Gly Arg Leu Arg Ala Ala Tyr Glu Glu His Gly Gly Arg Pro Asp Ser
        115                 120                 125

Asn Pro Phe Ala Ala Arg Ala Val Arg Ile Tyr Leu Arg Glu Val Arg
130                 135                 140

Glu Ser Gln Ala Lys Ala Arg Gly Ile Pro Tyr Glu Lys Lys Lys Arg
145                 150                 155                 160

Lys Arg Ala Pro Thr Val Thr Thr Ala Arg Ile Asp Val Ala Pro Ser
                165                 170                 175

Arg Gln Ser Glu Gly Gly Gly Gly Cys Asn Asp Ser Asp Pro Ser Val
            180                 185                 190

Ala Glu Ala Val Pro Pro
        195

<210> SEQ ID NO 91
<211> LENGTH: 672
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT 1461298
<220> FEATURE:
<221> NAME/KEY: misc_feature
<223> OTHER INFORMATION: Encodes the peptide sequence at SEQ ID NO. 92

<400> SEQUENCE: 91
atggactcaa catctggagt agcttctgcg cccgacccga atagtggaga accgggtcca      60
tcagcgggat catcttcagc atcagcatca ctgccacaac aacagcaacc agagggatca     120
tcaccgccag caccaccaag tagatacgag tcgcagaaga ggagagactg gaacactttc     180
ttacagtact aaagaaccaa caagccacca ttaactctag ctcgttgcag tggtgcacat     240
gtgatcgagt tcttgaaata cttggatcaa tttggtaaga ccaaagtcca cataacgggc     300
tgtccttatt ttgggcaccc gaaccgcca gcacccttgct cttgtccact taagcaggcc     360
tggggtagtc ttgatgcgct aatcggacgg cttagagctg cttatgaaga aaacggtgga     420
```

-continued

```
cggccagaat cgaacccttt tggggctaga gctgtcagga tttacttgag ggaagttcga    480
gaaggtcaag ctaaagctag agggattccc tacgagaaga agaagcgaaa aaggtctaat    540
gttgctgttg ctacggtgaa tgtgtcggtg gaggcagctg gtggtggctc tactagtggt    600
ggcggagggg ggagtggtga tgctgatagt agtgctgctg cagcagctgc tgctgctaca    660
acaaccgtat ag                                                        672
```

```
<210> SEQ ID NO 92
<211> LENGTH: 223
<212> TYPE: PRT
<213> ORGANISM: Populus balsamifera subsp. trichocarpa
<220> FEATURE:
<221> NAME/KEY: MISC_FEATURE
<223> OTHER INFORMATION: Ceres ANNOT 1461298
<220> FEATURE:
<221> NAME/KEY: misc_feature
<222> LOCATION: (30)..(162)
<223> OTHER INFORMATION: Pfam Name: DUF640
      Pfam Description: Protein of unknown function (DUF640)
<220> FEATURE:
<221> NAME/KEY: MISC_FEATURE
<223> OTHER INFORMATION: Functional Homolog of Ceres Clone ID no. 28780
      at SEQ ID NO. 88

<400> SEQUENCE: 92
```

Met Asp Ser Thr Ser Gly Val Ala Ser Ala Pro Asp Pro Asn Ser Gly
1               5                   10                  15

Glu Pro Gly Pro Ser Ala Gly Ser Ser Ser Ala Ser Ala Ser Leu Pro
            20                  25                  30

Gln Gln Gln Gln Pro Glu Gly Ser Ser Pro Pro Ala Pro Pro Ser Arg
        35                  40                  45

Tyr Glu Ser Gln Lys Arg Arg Asp Trp Asn Thr Phe Leu Gln Tyr Leu
    50                  55                  60

Lys Asn His Lys Pro Pro Leu Thr Leu Ala Arg Cys Ser Gly Ala His
65                  70                  75                  80

Val Ile Glu Phe Leu Lys Tyr Leu Asp Gln Phe Gly Lys Thr Lys Val
                85                  90                  95

His Ile Thr Gly Cys Pro Tyr Phe Gly His Pro Asn Pro Pro Ala Pro
            100                 105                 110

Cys Ser Cys Pro Leu Lys Gln Ala Trp Gly Ser Leu Asp Ala Leu Ile
        115                 120                 125

Gly Arg Leu Arg Ala Ala Tyr Glu Glu Asn Gly Gly Arg Pro Glu Ser
    130                 135                 140

Asn Pro Phe Gly Ala Arg Ala Val Arg Ile Tyr Leu Arg Glu Val Arg
145                 150                 155                 160

Glu Gly Gln Ala Lys Ala Arg Gly Ile Pro Tyr Glu Lys Lys Lys Arg
                165                 170                 175

Lys Arg Ser Asn Val Ala Val Ala Thr Val Asn Val Ser Val Glu Ala
            180                 185                 190

Ala Gly Gly Gly Ser Thr Ser Gly Gly Gly Gly Ser Gly Asp Ala
        195                 200                 205

Asp Ser Ser Ala Ala Ala Ala Ala Ala Ala Thr Thr Thr Val
    210                 215                 220

```
<210> SEQ ID NO 93
<211> LENGTH: 212
<212> TYPE: PRT
<213> ORGANISM: Oryza sativa subsp. japonica
<220> FEATURE:
<221> NAME/KEY: MISC_FEATURE
```

<223> OTHER INFORMATION: Public GI 34907938
<220> FEATURE:
<221> NAME/KEY: misc_feature
<222> LOCATION: (13)..(145)
<223> OTHER INFORMATION: Pfam Name: DUF640
      Pfam Description: Protein of unknown function (DUF640)
<220> FEATURE:
<221> NAME/KEY: MISC_FEATURE
<223> OTHER INFORMATION: Functional Homolog of Ceres Clone ID no. 28780
      at SEQ ID NO. 88

<400> SEQUENCE: 93

Met Asp Pro Ser Gly Pro Gly Pro Ser Ala Ala Ala Gly Gly Ala
1               5                   10                  15

Pro Ala Val Ala Ala Ala Pro Gln Pro Pro Ala Gln Leu Ser Arg Tyr
                20                  25                  30

Glu Ser Gln Lys Arg Arg Asp Trp Asn Thr Phe Leu Gln Tyr Leu Arg
            35                  40                  45

Asn His Arg Pro Pro Leu Thr Leu Ala Arg Cys Ser Gly Ala His Val
        50                  55                  60

Ile Glu Phe Leu Arg Tyr Leu Asp Gln Phe Gly Lys Thr Lys Val His
65                  70                  75                  80

Ala Ser Gly Cys Ala Phe Tyr Gly Gln Pro Ser Pro Gly Pro Cys
                85                  90                  95

Pro Cys Pro Leu Arg Gln Ala Trp Gly Ser Leu Asp Ala Leu Ile Gly
                100                 105                 110

Arg Leu Arg Ala Ala Tyr Glu Glu Ser Gly Gly Thr Pro Glu Ser Asn
            115                 120                 125

Pro Phe Ala Ala Arg Ala Val Arg Ile Tyr Leu Arg Glu Val Arg Asp
        130                 135                 140

Ser Gln Ala Lys Ala Arg Gly Ile Pro Tyr Glu Lys Lys Lys Arg Lys
145                 150                 155                 160

Arg Ser Gln Ala Ala Gln Pro Ala Gly Val Glu Pro Ser Gly Ser Ser
                165                 170                 175

Ser Ala Ala Ala Ala Ala Gly Gly Gly Asp Ala Gly Ser Gly Gly
            180                 185                 190

Gly Ala Ala Ala Thr Thr Thr Ala Gln Pro Gly Gly Ser Gly Thr Ala
            195                 200                 205

Pro Ser Ala Ser
        210

<210> SEQ ID NO 94
<211> LENGTH: 167
<212> TYPE: PRT
<213> ORGANISM: Parthenium argentatum
<220> FEATURE:
<221> NAME/KEY: MISC_FEATURE
<223> OTHER INFORMATION: Ceres CLONE 1603237
<220> FEATURE:
<221> NAME/KEY: misc_feature
<222> LOCATION: (6)..(148)
<223> OTHER INFORMATION: Pfam Name: DUF640
      Pfam Description: Protein of unknown function (DUF640)
<220> FEATURE:
<221> NAME/KEY: MISC_FEATURE
<223> OTHER INFORMATION: Functional Homolog of Ceres Clone ID no. 28780
      at SEQ ID NO. 88

<400> SEQUENCE: 94

Met Leu Ser Pro Thr Ser Ser Ser Ser Ile Ala Ser Thr Ala Ser
1               5                   10                  15

Thr Ala Thr Ser Arg Leu Asn Arg Tyr Glu Ser Gln Lys Arg Arg Asp
                20                  25                  30

```
Trp Asn Thr Phe Gly Gln Phe Leu Arg Asn His Asp Pro Pro Leu Thr
             35                  40                  45

Leu Ser Asn Cys Thr Ser Thr His Val Ile Glu Phe Leu Arg Tyr Leu
 50                  55                  60

Asp Pro Phe Gly Lys Thr Lys Val His Thr His Leu Cys Pro Ser Phe
 65                  70                  75                  80

Gly Gln Pro Asn Pro Pro Thr Leu Cys Pro Cys Pro Leu Arg Gln Ala
                 85                  90                  95

Trp Gly Ser Leu Asp Ala Leu Ile Gly Arg Leu Arg Ala Ala Phe Glu
                100                 105                 110

Glu Asn Gly Gly Gln Pro Glu Ser Asn Pro Phe Gly Ala Arg Ala Val
                115                 120                 125

Arg Phe Tyr Leu Arg Glu Val Lys Asp Ala Gln Ala Lys Ala Arg Gly
            130                 135                 140

Ile Ser Cys Glu Lys Lys Arg Thr Lys Lys Arg Pro Pro Pro Pro Thr
145                 150                 155                 160

Pro Asp Ile Cys Leu Asp Arg
                165
```

<210> SEQ ID NO 95
<211> LENGTH: 20
<212> TYPE: DNA
<213> ORGANISM: Arabidopsis thaliana
<220> FEATURE:
<221> NAME/KEY: misc_feature
<223> OTHER INFORMATION: TUB-F1: Foward primer for tubulin gene
      amplification

<400> SEQUENCE: 95
gttgagccgt acaatgcaac                                              20

<210> SEQ ID NO 96
<211> LENGTH: 19
<212> TYPE: DNA
<213> ORGANISM: Arabidopsis thaliana
<220> FEATURE:
<221> NAME/KEY: misc_feature
<223> OTHER INFORMATION: TUB-R1: Reverse primer for tubulin gene
      amplification

<400> SEQUENCE: 96
ctgttcgtcc acttccttg                                               19

<210> SEQ ID NO 97
<211> LENGTH: 24
<212> TYPE: DNA
<213> ORGANISM: Arabidopsis thaliana
<220> FEATURE:
<221> NAME/KEY: misc_feature
<223> OTHER INFORMATION: 05917-F: Forward primer used to detect
      At1g07090

<400> SEQUENCE: 97
agcaggtatg agtcacagaa gcga                                         24

<210> SEQ ID NO 98
<211> LENGTH: 24
<212> TYPE: DNA
<213> ORGANISM: Arabidopsis thaliana
<220> FEATURE:
<221> NAME/KEY: misc_feature
<223> OTHER INFORMATION: 05917-R: Reverse primer used to detect
      At1g07090

```
<400> SEQUENCE: 98
acagatggag caccgacgtt acaa                                          24

<210> SEQ ID NO 99
<211> LENGTH: 576
<212> TYPE: DNA
<213> ORGANISM: Arabidopsis thaliana
<220> FEATURE:
<221> NAME/KEY: misc_feature
<223> OTHER INFORMATION: Ceres SEED LINE ME16572
<220> FEATURE:
<221> NAME/KEY: misc_feature
<223> OTHER INFORMATION: Ceres ANNOT ID no. 1285138
<220> FEATURE:
<221> NAME/KEY: misc_feature
<223> OTHER INFORMATION: Encodes the peptide sequence at SEQ ID NO. 100

<400> SEQUENCE: 99
atgtcttcgg atcgtcacac accgacgaaa gatccaccgg atcatccgtc ttcttcctcc   60
aaccaccaca agcaaccact tcctcctcaa ccgcagcaac cactcagccg ctatgaatcg  120
cagaaacgcc gcgactggaa cacgttcgtc caatacctaa aatcacaaaa tccaccgttg  180
atgatgtctc aattcgacta cacgcacgtg ctaagtttcc taaggtactt agatcagttt  240
ggtaagacca agtacatca tcaagcttgt gtcttcttcg acaaccgga tccaccaggt  300 ccgtgcacgt gtcctctcaa acaagcttgg ggaagcctag atgctttgat cggacggcta  360
agagctgctt acgaggaaca cggtggcggg tcacctgata ctaacccgtt tgcaaacggg  420
tcgatccggg ttcacttgag ggaagtgaga gaatctcaag ccaaggctcg tgggattccg  480
tacaggaaga agaaaaggag gaagactaaa aacgaggtcg ttgttgtcaa gaaggatgtt  540
gcaaactctt cgactcctaa tcagtagttc acttga                            576

<210> SEQ ID NO 100
<211> LENGTH: 188
<212> TYPE: PRT
<213> ORGANISM: Arabidopsis thaliana
<220> FEATURE:
<221> NAME/KEY: misc_feature
<223> OTHER INFORMATION: Ceres SEED LINE ME16572
<220> FEATURE:
<221> NAME/KEY: misc_feature
<223> OTHER INFORMATION: Ceres ANNOT ID no. 1285138
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (19)..(152)
<223> OTHER INFORMATION: Pfam Name: DUF640
      Pfam Description: Protein of unknown function (DUF640)

<400> SEQUENCE: 100

Met Ser Ser Asp Arg His Thr Pro Thr Lys Asp Pro Pro Asp His Pro
1               5                   10                  15

Ser Ser Ser Ser Asn His His Lys Gln Pro Leu Pro Pro Gln Pro Gln
            20                  25                  30

Gln Pro Leu Ser Arg Tyr Glu Ser Gln Lys Arg Arg Asp Trp Asn Thr
        35                  40                  45

Phe Val Gln Tyr Leu Lys Ser Gln Asn Pro Pro Leu Met Met Ser Gln
    50                  55                  60

Phe Asp Tyr Thr His Val Leu Ser Phe Leu Arg Tyr Leu Asp Gln Phe
65                  70                  75                  80

Gly Lys Thr Lys Val His His Gln Ala Cys Val Phe Phe Gly Gln Pro
```

```
                    85                  90                  95
Asp Pro Pro Gly Pro Cys Thr Cys Pro Leu Lys Gln Ala Trp Gly Ser
                100                 105                 110

Leu Asp Ala Leu Ile Gly Arg Leu Arg Ala Ala Tyr Glu Glu His Gly
            115                 120                 125

Gly Gly Ser Pro Asp Thr Asn Pro Phe Ala Asn Gly Ser Ile Arg Val
        130                 135                 140

His Leu Arg Glu Val Arg Glu Ser Gln Ala Lys Ala Arg Gly Ile Pro
145                 150                 155                 160

Tyr Arg Lys Lys Lys Arg Arg Lys Thr Lys Asn Glu Val Val Val
                165                 170                 175

Lys Lys Asp Val Ala Asn Ser Ser Thr Pro Asn Gln
            180                 185

<210> SEQ ID NO 101
<211> LENGTH: 573
<212> TYPE: DNA
<213> ORGANISM: Arabidopsis thaliana
<220> FEATURE:
<221> NAME/KEY: misc_feature
<223> OTHER INFORMATION: Ceres SEED LINE ME16623
<220> FEATURE:
<221> NAME/KEY: misc_feature
<223> OTHER INFORMATION: Ceres ANNOT ID no.1290753
<220> FEATURE:
<221> NAME/KEY: misc_feature
<223> OTHER INFORMATION: Ceres SEED LINE ME23453
<220> FEATURE:
<221> NAME/KEY: misc_feature
<223> OTHER INFORMATION: Ceres ANNOT ID no. 853637
<220> FEATURE:
<221> NAME/KEY: misc_feature
<223> OTHER INFORMATION: Encodes the peptide sequence at SEQ ID NO. 102

<400> SEQUENCE: 101
atggatttga tctctcacca accaaacaag aaccctaatt cctcaacaca actaacacca      60
ccttcctcaa gccggtacga gaaccaaaaa cgccgtgact ggaacacttt ctgtcaatac     120
ctccggaacc accgtcctcc gctctctctc ccctcgtgta gcggcgcaca cgtgctcgag     180
ttcctccgct accttgacca gttcgggaaa acaaaagttc accaccagaa ctgtgccttc     240
tttggcctcc ctaaccctcc tgctccttgt ccttgtcctc tccggcaagc ttggggctca     300
ctcgacgctc ttatcggccg cctccgcgcc gcctacgagg agaacggtgg cccacctgaa     360
gctaacccat ttggctcacg cgccgtcagg ttattcctcc gtgaagtcag agactttcaa     420
gccaaagctc gaggtgttag ctatgagaag aagaggaaga gagtcaacag gcagaaaccg     480
caaacgcagc cgcctctaca gcttcagcaa cagcaacagc agccacaaca aggtcagtct     540
atgatggcta attactcggg tgcaacagta tga                                  573

<210> SEQ ID NO 102
<211> LENGTH: 190
<212> TYPE: PRT
<213> ORGANISM: Arabidopsis thaliana
<220> FEATURE:
<221> NAME/KEY: misc_feature
<223> OTHER INFORMATION: Ceres SEED LINE ME16623
<220> FEATURE:
<221> NAME/KEY: misc_feature
<223> OTHER INFORMATION: Ceres ANNOT ID no. 1290753
<220> FEATURE:
<221> NAME/KEY: misc_feature
<223> OTHER INFORMATION: Ceres SEED LINE ME23453
<220> FEATURE:
<221> NAME/KEY: misc_feature
<223> OTHER INFORMATION: Ceres ANNOT ID no. 853637
```

```
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (7)..(139)
<223> OTHER INFORMATION: Pfam Name: DUF640
      Pfam Description: Protein of unknown function (DUF640)

<400> SEQUENCE: 102
```

Met Asp Leu Ile Ser His Gln Pro Asn Lys Asn Pro Asn Ser Ser Thr
1               5                   10                  15

Gln Leu Thr Pro Pro Ser Ser Arg Tyr Glu Asn Gln Lys Arg Arg
            20                  25                  30

Asp Trp Asn Thr Phe Cys Gln Tyr Leu Arg Asn His Arg Pro Pro Leu
            35                  40                  45

Ser Leu Pro Ser Cys Ser Gly Ala His Val Leu Glu Phe Leu Arg Tyr
        50                  55                  60

Leu Asp Gln Phe Gly Lys Thr Lys Val His His Gln Asn Cys Ala Phe
65                  70                  75                  80

Phe Gly Leu Pro Asn Pro Pro Ala Pro Cys Pro Cys Pro Leu Arg Gln
                85                  90                  95

Ala Trp Gly Ser Leu Asp Ala Leu Ile Gly Arg Leu Arg Ala Ala Tyr
            100                 105                 110

Glu Glu Asn Gly Gly Pro Pro Glu Ala Asn Pro Phe Gly Ser Arg Ala
        115                 120                 125

Val Arg Leu Phe Leu Arg Glu Val Arg Asp Phe Gln Ala Lys Ala Arg
    130                 135                 140

Gly Val Ser Tyr Glu Lys Lys Arg Lys Arg Val Asn Arg Gln Lys Pro
145                 150                 155                 160

Gln Thr Gln Pro Pro Leu Gln Leu Gln Gln Gln Gln Gln Pro Gln
                165                 170                 175

Gln Gly Gln Ser Met Met Ala Asn Tyr Ser Gly Ala Thr Val
            180                 185                 190

```
<210> SEQ ID NO 103
<211> LENGTH: 639
<212> TYPE: DNA
<213> ORGANISM: Oryza sativa
<220> FEATURE:
<221> NAME/KEY: misc_feature
<223> OTHER INFORMATION: Ceres SEED LINE ME25698
<220> FEATURE:
<221> NAME/KEY: misc_feature
<223> OTHER INFORMATION: Ceres ANNOT ID no. 1373087
<220> FEATURE:
<221> NAME/KEY: misc_feature
<223> OTHER INFORMATION: Encodes the peptide sequence at SEQ ID NO. 104

<400> SEQUENCE: 103
atggatccgt ctggccccgg tccgtcctct gcggcggctg gcggcgcgcc ggccgtggcg    60
gcggcgccgc agccgccggc gcagctgagc aggtacgagt cgcagaagcg gagggactgg   120
aacacgttcc tgcagtacct gcggaaccac cggccgccgc tgacgctggc gcggtgcagc   180
ggcgcgcacg tgatcgagtt cctgaggtac ctggaccagt tcgggaagac caaggtgcac   240
gcgtcggggt gcgccttcta cggccagccc agccgccggg gccgtgccc gtgcccgctg   300 cgtcaggcgt ggggatccct cgacgcgctc atcggccgcc tccgcgccgc gtacgaggag   360
agcggcggca cgcccgagtc caacccgttc gccgcgcgcg ccgtccggat ctacctccgc   420
gaggtgcggg actcgcaggc caaggcgcgc ggcatcccgt acgagaagaa gaagcgcaag   480
```

```
cgctcgcagg cggcgcagcc cgccggcgtc gagccgtccg gctcgtcttc tgctgcagct      540
gcagctgccg gtggtggaga cgcgggcagc ggtggcggtg cagctgctac taccacagct      600
caacctggag ggagtggcac tgcaccaagc gcctcctga                             639
```

<210> SEQ ID NO 104
<211> LENGTH: 212
<212> TYPE: PRT
<213> ORGANISM: Oryza sativa
<220> FEATURE:
<221> NAME/KEY: misc_feature
<223> OTHER INFORMATION: Ceres SEED LINE ME25698
<220> FEATURE:
<221> NAME/KEY: misc_feature
<223> OTHER INFORMATION: Ceres ANNOT ID no. 1373087
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (13)..(145)
<223> OTHER INFORMATION: Pfam Name: DUF640
      Pfam Description: Protein of unknown function (DUF640)

<400> SEQUENCE: 104

```
Met Asp Pro Ser Gly Pro Gly Pro Ser Ala Ala Gly Gly Ala
1               5                   10                  15

Pro Ala Val Ala Ala Pro Gln Pro Ala Gln Leu Ser Arg Tyr
                20                  25                  30

Glu Ser Gln Lys Arg Arg Asp Trp Asn Thr Phe Leu Gln Tyr Leu Arg
                35                  40                  45

Asn His Arg Pro Pro Leu Thr Leu Ala Arg Cys Ser Gly Ala His Val
50                  55                  60

Ile Glu Phe Leu Arg Tyr Leu Asp Gln Phe Gly Lys Thr Lys Val His
65                  70                  75                  80

Ala Ser Gly Cys Ala Phe Tyr Gly Gln Pro Ser Pro Gly Pro Cys
                85                  90                  95

Pro Cys Pro Leu Arg Gln Ala Trp Gly Ser Leu Asp Ala Leu Ile Gly
                100                 105                 110

Arg Leu Arg Ala Ala Tyr Glu Glu Ser Gly Gly Thr Pro Glu Ser Asn
                115                 120                 125

Pro Phe Ala Ala Arg Ala Val Arg Ile Tyr Leu Arg Glu Val Arg Asp
                130                 135                 140

Ser Gln Ala Lys Ala Arg Gly Ile Pro Tyr Glu Lys Lys Arg Lys
145                 150                 155                 160

Arg Ser Gln Ala Ala Gln Pro Ala Gly Val Glu Pro Ser Gly Ser Ser
                165                 170                 175

Ser Ala Ala Ala Ala Ala Gly Gly Asp Ala Gly Ser Gly Gly
                180                 185                 190

Gly Ala Ala Thr Thr Thr Ala Gln Pro Gly Gly Ser Gly Thr Ala
                195                 200                 205

Pro Ser Ala Ser
    210
```

<210> SEQ ID NO 105
<211> LENGTH: 687
<212> TYPE: DNA
<213> ORGANISM: Populus balsamifera subsp. trichocarpa
<220> FEATURE:
<221> NAME/KEY: misc_feature
<223> OTHER INFORMATION: Ceres SEED LINE ME25953

```
<220> FEATURE:
<221> NAME/KEY: misc_feature
<223> OTHER INFORMATION: Ceres ANNOT ID no. 1440417
<220> FEATURE:
<221> NAME/KEY: misc_feature
<223> OTHER INFORMATION: Encodes the peptide sequence at SEQ ID NO. 106

<400> SEQUENCE: 105
atggactcga catctggagg agccactgca cccggcccga atagtggaga accttgtcca      60
tcagcagcaa cagcaggatc gtcttcagca tcgcagccac aacagcaacc ggagggatca     120
tcaccgccag caccaccaag tagatacgag tcacagaaga ggagagactg gaacactttc     180
ttacagtaca taaagaacca caagccacct ttaaccctag ctcgttgcag tggtgcacat     240
gtgattgagt tcttgaaata cttggatcaa tttggtaaga ctaaagtcca cataacgggt     300
tgtccttatt ttgggcaccc gaacccgcca gcaccttgtt cttgtccact aaagcaggct     360
tggggtagtc ttgatgcgct aatcggacgg cttagagctg cttatgaaga aaacggtgga     420
ctgccagaat caaacccttt tggggctaga gctgttagga tttatttgag ggaagttcga     480
gaaggtcaag ctaaagccag agggattcct tatgagaaga agaagaagcg aaaaaggcct     540
aatgttgctg tttccgtagc gagtgtgtcg gtgaaggcag ctgctggtgg ctctaatagt     600
ggcggtggag aagaaagtgg tggtggtggt gatagtagtg ccgccgctac aagtgctgct     660
gcggctgctg ctacaactac cgtatag                                        687

<210> SEQ ID NO 106
<211> LENGTH: 228
<212> TYPE: PRT
<213> ORGANISM: Populus balsamifera subsp. trichocarpa
<220> FEATURE:
<221> NAME/KEY: misc_feature
<223> OTHER INFORMATION: Ceres SEED LINE ME25953
<220> FEATURE:
<221> NAME/KEY: misc_feature
<223> OTHER INFORMATION: Ceres ANNOT ID no. 1440417
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (30)..(162)
<223> OTHER INFORMATION: Pfam Name: DUF640
      Pfam Description: Protein of unknown function (DUF640)

<400> SEQUENCE: 106

Met Asp Ser Thr Ser Gly Gly Ala Thr Ala Pro Gly Pro Asn Ser Gly
1               5                   10                  15

Glu Pro Cys Pro Ser Ala Ala Thr Ala Gly Ser Ser Ser Ala Ser Gln
            20                  25                  30

Pro Gln Gln Gln Pro Glu Gly Ser Ser Pro Ala Pro Pro Ser Arg
        35                  40                  45

Tyr Glu Ser Gln Lys Arg Arg Asp Trp Asn Thr Phe Leu Gln Tyr Ile
    50                  55                  60

Lys Asn His Lys Pro Pro Leu Thr Leu Ala Arg Cys Ser Gly Ala His
65                  70                  75                  80

Val Ile Glu Phe Leu Lys Tyr Leu Asp Gln Phe Gly Lys Thr Lys Val
                85                  90                  95

His Ile Thr Gly Cys Pro Tyr Phe Gly His Pro Asn Pro Ala Pro
            100                 105                 110

Cys Ser Cys Pro Leu Lys Gln Ala Trp Gly Ser Leu Asp Ala Leu Ile
        115                 120                 125
```

```
Gly Arg Leu Arg Ala Ala Tyr Glu Glu Asn Gly Gly Leu Pro Glu Ser
        130                 135                 140

Asn Pro Phe Gly Ala Arg Ala Val Arg Ile Tyr Leu Arg Glu Val Arg
145                 150                 155                 160

Glu Gly Gln Ala Lys Ala Arg Gly Ile Pro Tyr Glu Lys Lys Lys
                165                 170                 175

Arg Lys Arg Pro Asn Val Ala Val Ser Val Ala Ser Val Ser Val Lys
                180                 185                 190

Ala Ala Ala Gly Gly Ser Asn Ser Gly Gly Glu Glu Ser Gly
                195                 200                 205

Gly Gly Asp Ser Ser Ala Ala Ala Thr Ser Ala Ala Ala Ala Ala
        210                 215                 220

Thr Thr Thr Val
225

<210> SEQ ID NO 107
<211> LENGTH: 723
<212> TYPE: DNA
<213> ORGANISM: Populus balsamifera subsp. trichocarpa
<220> FEATURE:
<221> NAME/KEY: misc_feature
<223> OTHER INFORMATION: Ceres SEED LINE ME25957
<220> FEATURE:
<221> NAME/KEY: misc_feature
<223> OTHER INFORMATION: Ceres ANNOT ID no. 1505805
<220> FEATURE:
<221> NAME/KEY: misc_feature
<223> OTHER INFORMATION: Encodes the peptide sequence at SEQ ID NO. 108

<400> SEQUENCE: 107
atgaattcaa tccaagaaat ggagagctcc aactctgaaa acacaagttt caacagcata      60
ggcaacagca acaccaccaa cacagccatg tcagtctcaa acttgccacc accatcctcc     120
accactccga gtcgctatga gaatcaaaag cgccgagact ggaacacctt tggccagtac     180
ctcaagaacc acaggcctcc tctttctctg tccaggtgca gtggtgctca tgtccttgaa     240
ttccttcgct accttgacca atttggcaag accaaagtgc acactccaat ctgccccttt     300
tatggccacc caaacccacc cgcccctgc ccatgccctc tccgccaggc ctggggtagc     360
cttgacgcgc tcattggacg cctccgagca gcctttgagg aaaatggagg gaaacctgaa     420
gcaaaccctt ttggagctcg tgctgttagg ctgtatcttc gtgaggttcg tgatttgcag     480
tctaaagcaa gagggattag ctatgagaaa aagaagcgta agcgtccacc acagcaacaa     540
atccaagccc tgccactgcc acttccactg ccaatgccac caccaccagc tagatctgcg     600
gataccatga atctgctttt gatgcaaaca gtggtagtaa tattactagt aatgggacta     660
gcggtagtgt tatggtctgt gttgggactg agagcatcta taattgctct tacatttgtg     720
taa                                                                   723

<210> SEQ ID NO 108
<211> LENGTH: 240
<212> TYPE: PRT
<213> ORGANISM: Populus balsamifera subsp. trichocarpa
<220> FEATURE:
<221> NAME/KEY: misc_feature
<223> OTHER INFORMATION: Ceres SEED LINE ME25957
<220> FEATURE:
<221> NAME/KEY: misc_feature
<223> OTHER INFORMATION: Ceres ANNOT ID no. 1505805
<220> FEATURE:
<221> NAME/KEY: misc_feature
<223> OTHER INFORMATION: Functional Homolog of Ceres Clone ID no. 28780
      at SEQ ID NO. 88
<220> FEATURE:
```

```
<221> NAME/KEY: misc_feature
<222> LOCATION: (27)..(159)
<223> OTHER INFORMATION: Pfam Name: DUF640
      Pfam Description: Protein of unknown function (DUF640)

<400> SEQUENCE: 108

Met Asn Ser Ile Gln Glu Met Glu Ser Ser Asn Ser Glu Asn Thr Ser
1               5                   10                  15

Phe Asn Ser Ile Gly Asn Ser Asn Thr Thr Asn Thr Ala Met Ser Val
                20                  25                  30

Ser Asn Leu Pro Pro Pro Ser Ser Thr Thr Pro Ser Arg Tyr Glu Asn
            35                  40                  45

Gln Lys Arg Arg Asp Trp Asn Thr Phe Gly Gln Tyr Leu Lys Asn His
        50                  55                  60

Arg Pro Pro Leu Ser Leu Ser Arg Cys Ser Gly Ala His Val Leu Glu
65                  70                  75                  80

Phe Leu Arg Tyr Leu Asp Gln Phe Gly Lys Thr Lys Val His Thr Pro
                85                  90                  95

Ile Cys Pro Phe Tyr Gly His Pro Asn Pro Ala Pro Cys Pro Cys
                100                 105                 110

Pro Leu Arg Gln Ala Trp Gly Ser Leu Asp Ala Leu Ile Gly Arg Leu
            115                 120                 125

Arg Ala Ala Phe Glu Glu Asn Gly Gly Lys Pro Glu Ala Asn Pro Phe
        130                 135                 140

Gly Ala Arg Ala Val Arg Leu Tyr Leu Arg Glu Val Arg Asp Leu Gln
145                 150                 155                 160

Ser Lys Ala Arg Gly Ile Ser Tyr Glu Lys Lys Arg Lys Arg Pro
                165                 170                 175

Pro Gln Gln Gln Ile Gln Ala Leu Pro Leu Pro Leu Pro Leu Pro Met
            180                 185                 190

Pro Pro Pro Pro Ala Arg Ser Ala Asp Thr Met Asn Leu Leu Leu Met
                195                 200                 205

Gln Thr Val Val Val Ile Leu Leu Val Met Gly Leu Ala Val Val Leu
        210                 215                 220

Trp Ser Val Leu Gly Leu Arg Ala Ser Ile Ile Ala Leu Thr Phe Val
225                 230                 235                 240

<210> SEQ ID NO 109
<211> LENGTH: 660
<212> TYPE: DNA
<213> ORGANISM: Arabidopsis thaliana
<220> FEATURE:
<221> NAME/KEY: misc_feature
<223> OTHER INFORMATION: Ceres SEED LINE ME25288
<220> FEATURE:
<221> NAME/KEY: misc_feature
<223> OTHER INFORMATION: Ceres ANNOT ID no. 828846
<220> FEATURE:
<221> NAME/KEY: misc_feature
<223> OTHER INFORMATION: Encodes the peptide sequence at SEQ ID NO. 110

<400> SEQUENCE: 109
atggatatga ttccccaatt gatggaaggc tcttcagctt acggaggtgt cacaaacctc      60
aacatcatct caaacaactc ctcctccgtc accggagcca ccggaggtga agcaacgcaa     120
ccactgtctt cctcctcctc accatcggcg aactcaagcc gttacgagaa ccagaagagg     180
agagactgga cacgttcgg acagtactta aggaaccatc ggccaccgct ttcgctttcc      240
cgatgcagtg gagctcacgt gctcgagttc ctccgttact tggaccagtt cggtaagaca     300
aaagtccaca cgaacatttg tcacttctat ggccatccta atcctccggc accgtgtccg     360
```

-continued

```
tgtcctctcc gacaagcttg gggaagtctt gacgctctta tcggtcgtct tcgagctgcc    420
tttgaggaaa acggaggcaa gcctgagacg aatccttttg gagctcgtgc cgttaggctt    480
tatctaaggg aagttagaga tatgcagagt aaagctagag gtgttagcta cgagaagaag    540
aagcgaaagc gtcctcttcc ttcgtcgtcg acttcttctt cctccgccgt agctagccac    600
cagcaatttc aaatgctacc gggtactagt tctactactc aattaaagtt tgagaagtaa    660
```

<210> SEQ ID NO 110
<211> LENGTH: 219
<212> TYPE: PRT
<213> ORGANISM: Arabidopsis thaliana
<220> FEATURE:
<221> NAME/KEY: misc_feature
<223> OTHER INFORMATION: Ceres SEED LINE ME25288
<220> FEATURE:
<221> NAME/KEY: misc_feature
<223> OTHER INFORMATION: Ceres ANNOT ID no. 828846
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (36)..(168)
<223> OTHER INFORMATION: Pfam Name: DUF640
      Pfam Description: Protein of unknown function (DUF640)

<400> SEQUENCE: 110

```
Met Asp Met Ile Pro Gln Leu Met Glu Gly Ser Ser Ala Tyr Gly Gly
1               5                   10                  15

Val Thr Asn Leu Asn Ile Ile Ser Asn Asn Ser Ser Val Thr Gly
            20                  25                  30

Ala Thr Gly Gly Glu Ala Thr Gln Pro Leu Ser Ser Ser Ser Pro
        35                  40                  45

Ser Ala Asn Ser Ser Arg Tyr Glu Asn Gln Lys Arg Arg Asp Trp Asn
    50                  55                  60

Thr Phe Gly Gln Tyr Leu Arg Asn His Arg Pro Pro Leu Ser Leu Ser
65                  70                  75                  80

Arg Cys Ser Gly Ala His Val Leu Glu Phe Leu Arg Tyr Leu Asp Gln
                85                  90                  95

Phe Gly Lys Thr Lys Val His Thr Asn Ile Cys His Phe Tyr Gly His
            100                 105                 110

Pro Asn Pro Pro Ala Pro Cys Pro Cys Pro Leu Arg Gln Ala Trp Gly
        115                 120                 125

Ser Leu Asp Ala Leu Ile Gly Arg Leu Arg Ala Ala Phe Glu Glu Asn
    130                 135                 140

Gly Gly Lys Pro Glu Thr Asn Pro Phe Gly Ala Arg Ala Val Arg Leu
145                 150                 155                 160

Tyr Leu Arg Glu Val Arg Asp Met Gln Ser Lys Ala Arg Gly Val Ser
                165                 170                 175

Tyr Glu Lys Lys Lys Arg Lys Arg Pro Leu Pro Ser Ser Thr Ser
            180                 185                 190

Ser Ser Ser Ala Val Ala Ser His Gln Gln Phe Gln Met Leu Pro Gly
        195                 200                 205

Thr Ser Thr Thr Gln Leu Lys Phe Glu Lys
    210                 215
```

<210> SEQ ID NO 111
<211> LENGTH: 495
<212> TYPE: DNA

<213> ORGANISM: Arabidopsis thaliana
<220> FEATURE:
<221> NAME/KEY: misc_feature
<223> OTHER INFORMATION: Ceres SEED LINE ME23423
<220> FEATURE:
<221> NAME/KEY: misc_feature
<223> OTHER INFORMATION: Ceres ANNOT ID no. 832857
<220> FEATURE:
<221> NAME/KEY: misc_feature
<223> OTHER INFORMATION: Encodes the peptide sequence at SEQ ID NO. 112

<400> SEQUENCE: 111

```
atgacgagta caaacacgag aaacaaaggc aaatgcatag tagaaggacc accaccgact      60
ctaagccgtt atgagtcaca aaaaagccgc gactggaaca cgttttgcca gtatctcatg     120
accaagatgc caccagttca cgtatgggag tgtgaatcaa accacatcct cgatttcctc     180
caaagtcgtg accagtttgg taaaacaaaa gttcatatcc aaggatgcgt tttcttcgga     240
cagaaagagc caccaggaga gtgtaactgc ccgttgaaac aggcgtgggg aagcttagat     300
gctttgatcg gacggctgag agcagcttac gaggagaacg gtggcttaac ggagaaaaac     360
ccgtttgccc ggggagggat taggattttt ctgagggaag tgagaggttc acaggcgaag     420
gcgagaggag ttttgtacaa aaaaaagaag cgtcttgtag ttgttggtac gggaactagt     480
actacttgga cttaa                                                     495
```

<210> SEQ ID NO 112
<211> LENGTH: 164
<212> TYPE: PRT
<213> ORGANISM: Arabidopsis thaliana
<220> FEATURE:
<221> NAME/KEY: misc_feature
<223> OTHER INFORMATION: Ceres SEED LINE ME23423
<220> FEATURE:
<221> NAME/KEY: misc_feature
<223> OTHER INFORMATION: Ceres ANNOT ID no. 832857
<220> FEATURE:
<221> NAME/KEY: misc_feature
<223> OTHER INFORMATION: Functional Homolog of Ceres Clone ID no. 28780
    at SEQ ID NO. 88
<220> FEATURE:
<221> NAME/KEY: misc_feature
<222> LOCATION: (5)..(137)
<223> OTHER INFORMATION: Pfam Name: DUF640
    Pfam Description: Protein of unknown function (DUF640)

<400> SEQUENCE: 112

```
Met Thr Ser Thr Asn Thr Arg Asn Lys Gly Lys Cys Ile Val Glu Gly
1               5                   10                  15

Pro Pro Pro Thr Leu Ser Arg Tyr Glu Ser Gln Lys Ser Arg Asp Trp
            20                  25                  30

Asn Thr Phe Cys Gln Tyr Leu Met Thr Lys Met Pro Pro Val His Val
        35                  40                  45

Trp Glu Cys Glu Ser Asn His Ile Leu Asp Phe Leu Gln Ser Arg Asp
    50                  55                  60

Gln Phe Gly Lys Thr Lys Val His Ile Gln Gly Cys Val Phe Phe Gly
65                  70                  75                  80

Gln Lys Glu Pro Pro Gly Glu Cys Asn Cys Pro Leu Lys Gln Ala Trp
                85                  90                  95

Gly Ser Leu Asp Ala Leu Ile Gly Arg Leu Arg Ala Ala Tyr Glu Glu
            100                 105                 110

Asn Gly Gly Leu Thr Glu Lys Asn Pro Phe Ala Arg Gly Gly Ile Arg
        115                 120                 125

Ile Phe Leu Arg Glu Val Arg Gly Ser Gln Ala Lys Ala Arg Gly Val
    130                 135                 140
```

Leu Tyr Lys Lys Lys Lys Arg Leu Val Val Val Gly Thr Gly Thr Ser
145                 150                 155                 160

Thr Thr Trp Thr

<210> SEQ ID NO 113
<211> LENGTH: 576
<212> TYPE: DNA
<213> ORGANISM: Arabidopsis thaliana
<220> FEATURE:
<221> NAME/KEY: misc_feature
<223> OTHER INFORMATION: Ceres SEED LINE ME23459
<220> FEATURE:
<221> NAME/KEY: misc_feature
<223> OTHER INFORMATION: Ceres ANNOT ID no. 847799
<220> FEATURE:
<221> NAME/KEY: misc_feature
<223> OTHER INFORMATION: Encodes the peptide sequence at SEQ ID NO. 114

<400> SEQUENCE: 113
atgtcttcgg atcgtcacac accgacgaaa gatccaccgg atcatccgtc ttcttcctcc    60
aaccaccaca agcaaccact tcctcctcaa ccgcagcaac cactcagccg ctatgaatcg   120
cagaaacgcc gcgactggaa cacgttcgtc caatacctaa aatcacaaaa tccaccgttg   180
atgatgtctc aattcgacta cacgcacgtg ctaagtttcc taaggtactt agatcagttt   240
ggtaagacca aagtacatca tcaagcttgt gtcttcttcg acaaccgga tccaccaggt   300 ccgtgcacgt gtcctctcaa acaagcttgg ggaagcctag atgctttgat cggacggcta   360
agagctgctt acgaggaaca cggtggcggg tcacctgata ctaacccgtt tgcaaacggg   420
tcgatccggg ttcacttgag ggaagtgaga gaatctcaag ccaaggctcg tgggattccg   480
tacaggaaga agaaaaggag gaagactaaa aacgaggtcg ttgttgtcaa gaaggatgtt   540
gcaaactctt cgactcctaa tcagtcgttc acttga                             576

<210> SEQ ID NO 114
<211> LENGTH: 191
<212> TYPE: PRT
<213> ORGANISM: Arabidopsis thaliana
<220> FEATURE:
<221> NAME/KEY: misc_feature
<223> OTHER INFORMATION: Ceres SEED LINE ME23459
<220> FEATURE:
<221> NAME/KEY: misc_feature
<223> OTHER INFORMATION: Ceres ANNOT ID no. 847799
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (19)..(152)
<223> OTHER INFORMATION: Pfam Name: DUF640
      Pfam Description: Protein of unknown function (DUF640)

<400> SEQUENCE: 114

Met Ser Ser Asp Arg His Thr Pro Thr Lys Asp Pro Pro Asp His Pro
1               5                   10                  15

Ser Ser Ser Asn His His Lys Gln Pro Leu Pro Pro Gln Pro Gln
            20                  25                  30

Gln Pro Leu Ser Arg Tyr Glu Ser Gln Lys Arg Arg Asp Trp Asn Thr
        35                  40                  45

Phe Val Gln Tyr Leu Lys Ser Gln Asn Pro Pro Leu Met Met Ser Gln
    50                  55                  60

Phe Asp Tyr Thr His Val Leu Ser Phe Leu Arg Tyr Leu Asp Gln Phe
65                  70                  75                  80

```
Gly Lys Thr Lys Val His His Gln Ala Cys Val Phe Gly Gln Pro
                85                  90                  95

Asp Pro Pro Gly Pro Cys Thr Cys Pro Leu Lys Gln Ala Trp Gly Ser
            100                 105                 110

Leu Asp Ala Leu Ile Gly Arg Leu Arg Ala Ala Tyr Glu Glu His Gly
        115                 120                 125

Gly Gly Ser Pro Asp Thr Asn Pro Phe Ala Asn Gly Ser Ile Arg Val
    130                 135                 140

His Leu Arg Glu Val Arg Glu Ser Gln Ala Lys Ala Arg Gly Ile Pro
145                 150                 155                 160

Tyr Arg Lys Lys Lys Arg Arg Lys Thr Lys Asn Glu Val Val Val
                165                 170                 175

Lys Lys Asp Val Ala Asn Ser Ser Thr Pro Asn Gln Ser Phe Thr
            180                 185                 190

<210> SEQ ID NO 115
<211> LENGTH: 549
<212> TYPE: DNA
<213> ORGANISM: Arabidopsis thaliana
<220> FEATURE:
<221> NAME/KEY: misc_feature
<223> OTHER INFORMATION: Ceres SEED LINE ME23517
<220> FEATURE:
<221> NAME/KEY: misc_feature
<223> OTHER INFORMATION: Ceres ANNOT ID no. 856813
<220> FEATURE:
<221> NAME/KEY: misc_feature
<223> OTHER INFORMATION: Encodes the peptide sequence at SEQ ID NO. 116

<400> SEQUENCE: 115
atggagggag aaaccgcagc caaagcagcg gcaagttcct cctcatcccc gagccggtac      60
gagtctcaaa agaggcgaga ctggaacact tccttcagt atctaaggaa ccacaagcca     120
cctctgaatc tgtctcgttg tagtggcgca cacgtccttg agttccttaa gtacctcgac     180
cagtttggta agaccaaagt ccatgccacg gcttgtccct tcttcggaca acctaaccca     240
ccgtctcagt gcacttgccc ctcaagcaa gcttggggaa gtctcgatgc tctcatcggc     300
cgtctaaggg ctgctttcga ggaaatcggc ggtggtcttc ctgagtcaaa ccctttcgct     360
gccaaggctg ttaggatcta tcttaaagaa gtccgtcaaa cacaggctaa ggctcgaggg     420
attccttacg acaagaagaa aagaaaacgt ccgcatacag acacggcaac tccaatcgcc     480
ggtgacggag acgatgccga aggaagtggt ggtgctgctt tggtcgttac ggctgcaact     540
acggtatag                                                             549

<210> SEQ ID NO 116
<211> LENGTH: 182
<212> TYPE: PRT
<213> ORGANISM: Arabidopsis thaliana
<220> FEATURE:
<221> NAME/KEY: misc_feature
<223> OTHER INFORMATION: Ceres SEED LINE ME23517
<220> FEATURE:
<221> NAME/KEY: misc_feature
<223> OTHER INFORMATION: Ceres ANNOT ID no. 856813
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (1)..(134)
<223> OTHER INFORMATION: Pfam Name: DUF640
      Pfam Description: Protein of unknown function (DUF640)
```

<400> SEQUENCE: 116

```
Met Glu Gly Glu Thr Ala Ala Lys Ala Ala Ser Ser Ser Ser
1               5                   10                  15

Pro Ser Arg Tyr Glu Ser Gln Lys Arg Arg Asp Trp Asn Thr Phe Leu
            20                  25                  30

Gln Tyr Leu Arg Asn His Lys Pro Pro Leu Asn Leu Ser Arg Cys Ser
        35                  40                  45

Gly Ala His Val Leu Glu Phe Leu Lys Tyr Leu Asp Gln Phe Gly Lys
    50                  55                  60

Thr Lys Val His Ala Thr Ala Cys Pro Phe Phe Gly Gln Pro Asn Pro
65              70                  75                  80

Pro Ser Gln Cys Thr Cys Pro Leu Lys Gln Ala Trp Gly Ser Leu Asp
            85                  90                  95

Ala Leu Ile Gly Arg Leu Arg Ala Ala Phe Glu Glu Ile Gly Gly
        100                 105                 110

Leu Pro Glu Ser Asn Pro Phe Ala Ala Lys Ala Val Arg Ile Tyr Leu
        115                 120                 125

Lys Glu Val Arg Gln Thr Gln Ala Lys Ala Arg Gly Ile Pro Tyr Asp
    130                 135                 140

Lys Lys Lys Arg Lys Arg Pro His Thr Asp Thr Ala Thr Pro Ile Ala
145                 150                 155                 160

Gly Asp Gly Asp Asp Ala Glu Gly Ser Gly Ala Ala Leu Val Val
            165                 170                 175

Thr Ala Ala Thr Thr Val
            180
```

<210> SEQ ID NO 117
<211> LENGTH: 588
<212> TYPE: DNA
<213> ORGANISM: Arabidopsis thaliana
<220> FEATURE:
<221> NAME/KEY: misc_feature
<223> OTHER INFORMATION: Ceres SEED LINE ME16579
<220> FEATURE:
<221> NAME/KEY: misc_feature
<223> OTHER INFORMATION: Ceres ANNOT ID no. 870022
<220> FEATURE:
<221> NAME/KEY: misc_feature
<223> OTHER INFORMATION: Encodes the peptide sequence at SEQ ID NO. 118

<400> SEQUENCE: 117

```
atggctagtc atagcaacaa aggcaaaggc atagcagaag gatcgtctca accgcaatcg    60
caaccgcaac cacaaccaca ccaaccgcaa tcacctccta acccgccagc gttaagccgg   120
tacgagtcac agaaacgacg agactggaac acgttttgtc aatacctgcg taaccaacag   180
ccaccggttc acatctcgca gtgtggatca aaccacatcc tcgatttcct ccaatatctc   240
gaccagtttg ggaagacaaa ggttcatatc catggatgcg ttttcttcgg acaggttgag   300
ccagcgggac agtgtaactg tccttttaaaa caagcgtggg ggagtttaga tgctttgatc   360
ggacggctaa gagcggcttt cgaggagaac ggaggattgc cggagagaaa ccctttttgcc   420
ggcggcggaa ttagggtttt tctgagggaa gtgagagatt cacaggcgaa ggcaaggaga   480
gttccgtaca gaaaagaaa aagaggaag aagaggaatc ctatgaagag tcatgatggt   540
gaagatggta ctacgggaac tagtagtagc tccaacttgg cttcttag              588
```

<210> SEQ ID NO 118
<211> LENGTH: 195
<212> TYPE: PRT
<213> ORGANISM: Arabidopsis thaliana

```
<220> FEATURE:
<221> NAME/KEY: misc_feature
<223> OTHER INFORMATION: Ceres SEED LINE ME16579
<220> FEATURE:
<221> NAME/KEY: misc_feature
<223> OTHER INFORMATION: Ceres ANNOT ID no. 870022
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (22)..(154)
<223> OTHER INFORMATION: Pfam Name: DUF640
      Pfam Description: Protein of unknown function (DUF640)

<400> SEQUENCE: 118

Met Ala Ser His Ser Asn Lys Gly Lys Gly Ile Ala Glu Gly Ser Ser
1               5                   10                  15

Gln Pro Gln Ser Gln Pro Gln Pro Gln Pro His Gln Pro Gln Ser Pro
            20                  25                  30

Pro Asn Pro Pro Ala Leu Ser Arg Tyr Glu Ser Gln Lys Arg Arg Asp
        35                  40                  45

Trp Asn Thr Phe Cys Gln Tyr Leu Arg Asn Gln Pro Pro Val His
50                  55                  60

Ile Ser Gln Cys Gly Ser Asn His Ile Leu Asp Phe Leu Gln Tyr Leu
65                  70                  75                  80

Asp Gln Phe Gly Lys Thr Lys Val His Ile His Gly Cys Val Phe Phe
                85                  90                  95

Gly Gln Val Glu Pro Ala Gly Gln Cys Asn Cys Pro Leu Lys Gln Ala
            100                 105                 110

Trp Gly Ser Leu Asp Ala Leu Ile Gly Arg Leu Arg Ala Ala Phe Glu
        115                 120                 125

Glu Asn Gly Gly Leu Pro Glu Arg Asn Pro Phe Ala Gly Gly Gly Ile
130                 135                 140

Arg Val Phe Leu Arg Glu Val Arg Asp Ser Gln Ala Lys Ala Arg Gly
145                 150                 155                 160

Val Pro Tyr Lys Lys Arg Lys Lys Arg Lys Arg Asn Pro Met Lys
                165                 170                 175

Ser His Asp Gly Glu Asp Gly Thr Thr Gly Thr Ser Ser Ser Ser Asn
                180                 185                 190

Leu Ala Ser
        195

<210> SEQ ID NO 119
<211> LENGTH: 838
<212> TYPE: DNA
<213> ORGANISM: Arabidopsis thaliana
<220> FEATURE:
<221> NAME/KEY: misc_feature
<223> OTHER INFORMATION: Ceres SEED LINE ME24513
<220> FEATURE:
<221> NAME/KEY: misc_feature
<223> OTHER INFORMATION: Ceres SEED LINE ME24480
<220> FEATURE:
<221> NAME/KEY: misc_feature
<223> OTHER INFORMATION: Ceres SEED LINE ME24762
<220> FEATURE:
<221> NAME/KEY: misc_feature
<223> OTHER INFORMATION: Ceres CLONE ID no. 1025179
<220> FEATURE:
<221> NAME/KEY: misc_feature
<223> OTHER INFORMATION: Encodes the peptide sequence at SEQ ID NO. 120

<400> SEQUENCE: 119
```

-continued

```
acgatagcct ctcatcttct ttttcctct ccatcatctt ctcttatcaa ctttagactc      60
acaagcctcc tctcatcttc accataaccg aaaaaccaaa caaaaaatcc ttagataatc     120
agatcttgat attatggatc atatcatcgg ctttatgggc acaacaaaca tgtcacataa     180
cacaaacctt atgatcgctg ccgcagccac taccactacg acctcttcgt cttcctcttc     240
ttcctccgga ggctcgggga ctaaccagct aagcaggtac gagaatcaga agagaagaga     300
ttggaacact ttcggacagt atctacgcaa tcaccgtcca ccactttctc tctcccgttg     360
cagtggtgct catgttcttg aattcctcag gtacctcgac caattcggca agactaaggt     420
tcacacacac ctatgtccgt tcttcggaca cccaaaccca ccagcaccat gtgcctgtcc     480
actccgacaa gcgtggggta gtctggacgc actcattggc cgtcttagag ctgcttttga     540
agagaacggt ggttcaccag agacgaaccc ttttggtgca cgagccgttc gactctacct     600
aagggaagta cgtgactcgc aggctaaagc acgtgggatc agctatgaaa aaagaagcg      660 caagcgacct cctccgccac taccaccggc tcagccggcg atttcaagta gccctaatta     720
acattaagtc atgagtaaga tgtttcaatg aactacgttt gtttacaaat ttttatcaat     780
gacgaacatg cacgagttct tttaaagtca catgcccttt cctaaacttt tatttgac      838
```

<210> SEQ ID NO 120
<211> LENGTH: 195
<212> TYPE: PRT
<213> ORGANISM: Arabidopsis thaliana
<220> FEATURE:
<221> NAME/KEY: misc_feature
<223> OTHER INFORMATION: Ceres SEED LINE ME24513
<220> FEATURE:
<221> NAME/KEY: misc_feature
<223> OTHER INFORMATION: Ceres SEED LINE ME24480
<220> FEATURE:
<221> NAME/KEY: misc_feature
<223> OTHER INFORMATION: Ceres SEED LINE ME24762
<220> FEATURE:
<221> NAME/KEY: misc_feature
<223> OTHER INFORMATION: Ceres CLONE ID no. 1025179
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (30)..(162)
<223> OTHER INFORMATION: Pfam Name: DUF640
      Pfam Description: Protein of unknown function (DUF640)

<400> SEQUENCE: 120

```
Met Asp His Ile Ile Gly Phe Met Gly Thr Thr Asn Met Ser His Asn
1               5                   10                  15

Thr Asn Leu Met Ile Ala Ala Ala Ala Thr Thr Thr Thr Thr Ser Ser
            20                  25                  30

Ser Ser Ser Ser Ser Ser Gly Gly Ser Gly Thr Asn Gln Leu Ser Arg
        35                  40                  45

Tyr Glu Asn Gln Lys Arg Arg Asp Trp Asn Thr Phe Gly Gln Tyr Leu
    50                  55                  60

Arg Asn His Arg Pro Pro Leu Ser Leu Ser Arg Cys Ser Gly Ala His
65                  70                  75                  80

Val Leu Glu Phe Leu Arg Tyr Leu Asp Gln Phe Gly Lys Thr Lys Val
                85                  90                  95

His Thr His Leu Cys Pro Phe Phe Gly His Pro Asn Pro Ala Pro
            100                 105                 110

Cys Ala Cys Pro Leu Arg Gln Ala Trp Gly Ser Leu Asp Ala Leu Ile
        115                 120                 125
```

Gly Arg Leu Arg Ala Ala Phe Glu Glu Asn Gly Gly Ser Pro Glu Thr
        130                 135                 140

Asn Pro Phe Gly Ala Arg Ala Val Arg Leu Tyr Leu Arg Glu Val Arg
145                 150                 155                 160

Asp Ser Gln Ala Lys Ala Arg Gly Ile Ser Tyr Glu Lys Lys Lys Arg
                165                 170                 175

Lys Arg Pro Pro Pro Pro Leu Pro Pro Ala Gln Pro Ala Ile Ser Ser
            180                 185                 190

Ser Pro Asn
        195

<210> SEQ ID NO 121
<211> LENGTH: 939
<212> TYPE: DNA
<213> ORGANISM: Brassica napus
<220> FEATURE:
<221> NAME/KEY: misc_feature
<223> OTHER INFORMATION: Ceres SEED LINE ME25665
<220> FEATURE:
<221> NAME/KEY: misc_feature
<223> OTHER INFORMATION: Ceres CLONE ID no. 1084747
<220> FEATURE:
<221> NAME/KEY: misc_feature
<223> OTHER INFORMATION: Encodes the peptide sequence at SEQ ID NO. 122

<400> SEQUENCE: 121
acactctttc tctcattttc tctctctttt aaaacactaa tcactaaaat cttgattcac      60
tgtatcctca aaccaactc taaatcaaac tctctcaaag aaaacaagcc aaagccctac     120
tttggatgga ttcagggtca caacgaccgg ggcctgtcag cgaaggcgat ccgggtccgt     180
ccatcgtaac cccctcttca ccgcctgcgg cgcctagcag gtacgagtca cagaaacgac     240
gtgactggac cacgttctta cagtacctca agaaccacaa gccgcctctt tccttgtcac     300
ggtgtagcgg ggcacatgcc atcgagttcc tcaagtactt agatcagttc ggtaagacca     360
aagtccacgt ggcggcgtgt ccttacttcg gccatcagca acctccgtct ccttgcgctt     420
gtcctctcaa gcaagcctgg gggtctctcg atgccctgat cggacggctg agagcagcct     480
atgaggagaa cggtggacgg cccgagtcga acccgttcgc ggcacgtgcg gtcaggattt     540
acttgaggga agtcagagaa agtcaagcca aggcccgtgg agaccctac gagaaaaaga     600 aacggaaacg gccaacaact gttaccaccg tgagagttga cgttgctccg tcgagacaaa     660
gtgaaggaga tggttgtaac atcggtgatc cgtcgtctct ggccgaggct gtacctcctt     720
aattacgtta ttattattgt catgatatat taaatacatt atacatgtct ggaactcaca     780
tcaccaaaaa aaaactcaca tcaccttctt gagttaacta tcgaaaatat atttttgttc     840
tagttcagtt gatctttgat gaattacgtt cttgaatttt tcttttaatt cttatgaatt     900
ccacacattt ttaaggacta attaacgagg ttttcattc                            939

<210> SEQ ID NO 122
<211> LENGTH: 198
<212> TYPE: PRT
<213> ORGANISM: Brassica napus
<220> FEATURE:
<221> NAME/KEY: misc_feature
<223> OTHER INFORMATION: Ceres SEED LINE ME25665
<220> FEATURE:
<221> NAME/KEY: misc_feature
<223> OTHER INFORMATION: Ceres CLONE ID no. 1084747
<220> FEATURE:
<221> NAME/KEY: misc_feature
<223> OTHER INFORMATION: Functional Homolog of Ceres Clone ID no. 28780
        at SEQ ID NO. 88

```
<220> FEATURE:
<221> NAME/KEY: misc_feature
<222> LOCATION: (14)..(146)
<223> OTHER INFORMATION: Pfam Name: DUF640
      Pfam Description: Protein of unknown function (DUF640)

<400> SEQUENCE: 122

Met Asp Ser Gly Ser Gln Arg Pro Gly Pro Val Ser Glu Gly Asp Pro
1               5                   10                  15

Gly Pro Ser Ile Val Thr Pro Ser Ser Pro Pro Ala Ala Pro Ser Arg
            20                  25                  30

Tyr Glu Ser Gln Lys Arg Arg Asp Trp Thr Thr Phe Leu Gln Tyr Leu
        35                  40                  45

Lys Asn His Lys Pro Pro Leu Ser Leu Ser Arg Cys Ser Gly Ala His
    50                  55                  60

Ala Ile Glu Phe Leu Lys Tyr Leu Asp Gln Phe Gly Lys Thr Lys Val
65              70                  75                  80

His Val Ala Ala Cys Pro Tyr Phe Gly His Gln Gln Pro Pro Ser Pro
                85                  90                  95

Cys Ala Cys Pro Leu Lys Gln Ala Trp Gly Ser Leu Asp Ala Leu Ile
            100                 105                 110

Gly Arg Leu Arg Ala Ala Tyr Glu Glu Asn Gly Gly Arg Pro Glu Ser
        115                 120                 125

Asn Pro Phe Ala Ala Arg Ala Val Arg Ile Tyr Leu Arg Glu Val Arg
    130                 135                 140

Glu Ser Gln Ala Lys Ala Arg Gly Arg Pro Tyr Glu Lys Lys Lys Arg
145                 150                 155                 160

Lys Arg Pro Thr Thr Val Thr Thr Val Arg Val Asp Val Ala Pro Ser
                165                 170                 175

Arg Gln Ser Glu Gly Asp Gly Cys Asn Ile Gly Asp Pro Ser Ser Leu
            180                 185                 190

Ala Glu Ala Val Pro Pro
        195

<210> SEQ ID NO 123
<211> LENGTH: 802
<212> TYPE: DNA
<213> ORGANISM: Zea mays
<220> FEATURE:
<221> NAME/KEY: misc_feature
<223> OTHER INFORMATION: Ceres SEED LINE ME25661
<220> FEATURE:
<221> NAME/KEY: misc_feature
<223> OTHER INFORMATION: Ceres CLONE ID no. 1464359
<220> FEATURE:
<221> NAME/KEY: misc_feature
<223> OTHER INFORMATION: Encodes the peptide sequence at SEQ ID NO. 124

<400> SEQUENCE: 123
agacacacga cccacacaca cacacacaga gattcacaag caaaatcaag aaccctaaaa      60
tctaaagaac gtcctgacat aatcacacga tcaaaaatgg agggagaaac cgcagtgaag     120
gcagcggcaa gttcctcatc atcaccaagc cgctatgagt cgcaaaagag acgagactgg     180
aacactttcc tacagtatct aaaaaaccac aagccacctt taaccctgtc tcgttgcagt     240
ggcgcacacg tcatcgagtt ccttaagtac ctcgaccagt ttggtaagac caaagtccac     300
gtcgcggctt gtcccttctt cggagtaccg tacccaccgg ttcagtgcac ttgccctctc     360
aggcaggctt ggggaagcct cgactctctc atcggccgtc taagggctgc gttcgaggaa     420
atcggcggtg gtcttccaga gtcaaaccct ttagctgcca aagcgattag gatctatctt     480
```

```
aaagaagtac gtgaaactca ggctaaggct cgagggattc catacgacaa gaagaaacgg      540
aaacgacctc gtacagctaa ggaaactcag aagcccgatg atggagaagg tgccggtgga      600
agtggaagtg gtgattctgc tttggttatt tctgcaactg tggtatagtc caaatataag      660
atgctaaaac taaatataag aaaactttgg catagtaatt ctctccgtgt tctttactt      720 ataaatttta tatgttgtgt agtcgtttat ttgagttgta gaatgcaatt ataaatggaa      780
aagacggatc atagattatt at                                              802
```

```
<210> SEQ ID NO 124
<211> LENGTH: 183
<212> TYPE: PRT
<213> ORGANISM: Zea mays
<220> FEATURE:
<221> NAME/KEY: misc_feature
<223> OTHER INFORMATION: Ceres SEED LINE ME25661
<220> FEATURE:
<221> NAME/KEY: misc_feature
<223> OTHER INFORMATION: Ceres CLONE ID no. 1464359
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (1)..(134)
<223> OTHER INFORMATION: Pfam Name: DUF640
      Pfam Description: Protein of unknown function (DUF640)

<400> SEQUENCE: 124
```

```
Met Glu Gly Glu Thr Ala Val Lys Ala Ala Ser Ser Ser Ser
1               5                   10                  15

Pro Ser Arg Tyr Glu Ser Gln Lys Arg Arg Asp Trp Asn Thr Phe Leu
                20                  25                  30

Gln Tyr Leu Lys Asn His Lys Pro Pro Leu Thr Leu Ser Arg Cys Ser
            35                  40                  45

Gly Ala His Val Ile Glu Phe Leu Lys Tyr Leu Asp Gln Phe Gly Lys
        50                  55                  60

Thr Lys Val His Val Ala Ala Cys Pro Phe Phe Gly Val Pro Tyr Pro
65                  70                  75                  80

Pro Ala Gln Cys Thr Cys Pro Leu Arg Gln Ala Trp Gly Ser Leu Asp
                85                  90                  95

Ser Leu Ile Gly Arg Leu Arg Ala Ala Phe Glu Glu Ile Gly Gly Gly
            100                 105                 110

Leu Pro Glu Ser Asn Pro Leu Ala Ala Lys Ala Ile Arg Ile Tyr Leu
        115                 120                 125

Lys Glu Val Arg Glu Thr Gln Ala Lys Ala Arg Gly Ile Pro Tyr Asp
    130                 135                 140

Lys Lys Lys Arg Lys Arg Pro Arg Thr Ala Lys Glu Thr Gln Lys Pro
145                 150                 155                 160

Asp Asp Gly Glu Gly Ala Gly Gly Ser Gly Ser Gly Asp Ser Ala Leu
                165                 170                 175

Val Ile Ser Ala Thr Val Val
            180
```

```
<210> SEQ ID NO 125
<211> LENGTH: 858
<212> TYPE: DNA
<213> ORGANISM: Glycine max
<220> FEATURE:
<221> NAME/KEY: misc_feature
<223> OTHER INFORMATION: Ceres SEED LINE ME24758
<220> FEATURE:
```

```
<221> NAME/KEY: misc_feature
<223> OTHER INFORMATION: Ceres SEED LINE ME25680
<220> FEATURE:
<221> NAME/KEY: misc_feature
<223> OTHER INFORMATION: Ceres SEED LINE ME24978
<220> FEATURE:
<221> NAME/KEY: misc_feature
<223> OTHER INFORMATION: Ceres CLONE ID no. 604111
<220> FEATURE:
<221> NAME/KEY: misc_feature
<223> OTHER INFORMATION: Encodes the peptide sequence at SEQ ID NO. 126

<400> SEQUENCE: 125
agtcccataa acctcacttc ctcaacctca atccaacaga aacaaaaaaa aacctcactt     60
agatcacata gatcaaacaa caaaacacag agttacctaa attgaaccta ccccagtagg    120
ttctacaagc tcttgatcat ggcctcagca tcagggagg caccaccacc ccaacccact    180
tcaacagaag ctgctccagc atcaggctct tcagctccag ccatatcagc agcaccacca    240
caacccggag gatcatcgcc ggcgcctccg agccgctacg aatcgcaaaa gcgtcgagac    300
tggaacacgt ttctgcagta cctgcagaac cacaagcccc cattaacgct ggcgcggtgc    360
agtggcgcac acgtcattga gttcttgaag tacttggacc aattcgggaa accaaggtt    420 cacatcacgg ggtgcccgta ctacgggtac cccaaccctc ctgcgccctg cgcttgccca    480
ctgaaacaag cgtggggaag ccttgacgcc ctgatcgggc gactcagggc ggcttacgag    540
gaaaacggag gccgccctga gtctaacccg ttcggcgcca gggccgtcag aatttacctc    600
agggaggtaa gagaaggtca ggctaaagca gagggatcc cttatgagaa gaagaagcgg    660
aagaggacca ccgtggtgac ggtgagtagt ggtggtggtg gtagtagcgg tgcagttgcc    720
tctccgagtg gcggtggtga taccgctatt ggtggtggag ctggttctag tgctagttta    780
acttcttcag caactgccac agctaatgat actacaacca cagtataatt ttaatagtta    840
tttaattatt tattttttc                                                 858

<210> SEQ ID NO 126
<211> LENGTH: 229
<212> TYPE: PRT
<213> ORGANISM: Glycine max
<220> FEATURE:
<221> NAME/KEY: misc_feature
<223> OTHER INFORMATION: Ceres SEED LINE ME24758
<220> FEATURE:
<221> NAME/KEY: misc_feature
<223> OTHER INFORMATION: Ceres SEED LINE ME25680
<220> FEATURE:
<221> NAME/KEY: misc_feature
<223> OTHER INFORMATION: Ceres SEED LINE ME24978
<220> FEATURE:
<221> NAME/KEY: misc_feature
<223> OTHER INFORMATION: Ceres CLONE ID no. 604111
<220> FEATURE:
<221> NAME/KEY: misc_feature
<223> OTHER INFORMATION: Functional Homolog of Ceres Clone ID no. 28780
    at SEQ ID NO. 88
<220> FEATURE:
<221> NAME/KEY: misc_feature
<222> LOCATION: (28)..(107)
<223> OTHER INFORMATION: Pfam Name: DUF640
    Pfam Description: Protein of unknown function (DUF640)

<400> SEQUENCE: 126

Met Ala Ser Ala Ser Gly Glu Ala Pro Pro Gln Pro Thr Ser Thr
1               5                   10                  15

Glu Ala Ala Pro Ala Ser Gly Ser Ser Ala Pro Ala Ile Ser Ala Ala
            20                  25                  30

Pro Pro Gln Pro Gly Gly Ser Ser Pro Ala Pro Pro Ser Arg Tyr Glu
```

```
                35                   40                   45
Ser Gln Lys Arg Arg Asp Trp Asn Thr Phe Leu Gln Tyr Leu Gln Asn
 50                   55                   60

His Lys Pro Pro Leu Thr Leu Ala Arg Cys Ser Gly Ala His Val Ile
 65                   70                   75                   80

Glu Phe Leu Lys Tyr Leu Asp Gln Phe Gly Lys Thr Lys Val His Ile
                 85                   90                   95

Thr Gly Cys Pro Tyr Tyr Gly Tyr Pro Asn Pro Pro Ala Pro Cys Ala
                100                  105                  110

Cys Pro Leu Lys Gln Ala Trp Gly Ser Leu Asp Ala Leu Ile Gly Arg
                115                  120                  125

Leu Arg Ala Ala Tyr Glu Glu Asn Gly Gly Arg Pro Glu Ser Asn Pro
            130                  135                  140

Phe Gly Ala Arg Ala Val Arg Ile Tyr Leu Arg Glu Val Arg Glu Gly
145                  150                  155                  160

Gln Ala Lys Ala Arg Gly Ile Pro Tyr Glu Lys Lys Arg Lys Arg
                165                  170                  175

Thr Thr Val Val Thr Val Ser Ser Gly Gly Gly Ser Gly Ala
                180                  185                  190

Val Ala Ser Pro Ser Gly Gly Gly Asp Thr Ala Ile Gly Gly Gly Ala
                195                  200                  205

Gly Ser Ser Ala Ser Leu Thr Ser Ser Ala Thr Ala Thr Ala Asn Asp
    210                  215                  220

Thr Thr Thr Thr Val
225

<210> SEQ ID NO 127
<211> LENGTH: 897
<212> TYPE: DNA
<213> ORGANISM: Brassica napus
<220> FEATURE:
<221> NAME/KEY: misc_feature
<223> OTHER INFORMATION: Ceres SEED LINE ME25647
<220> FEATURE:
<221> NAME/KEY: misc_feature
<223> OTHER INFORMATION: Ceres CLONE ID no. 964932
<220> FEATURE:
<221> NAME/KEY: misc_feature
<223> OTHER INFORMATION: Encodes the peptide sequence at SEQ ID NO. 128

<400> SEQUENCE: 127 acgataccccc ctcctctcct ccttttcct ctccaccatc ttcccttatc aactcaagac     60
ccataaagtt caagactcaa gactcataaa gctcctctca tattcatcat aacctaaaac    120
caaaacctca aagagttaat aaaacctaaa ttatacatca gatcttgata tcatggatcc    180
tatccacggc tttatgagca catcaaacat ctcacacaac acaaaccttt atgatcgccgc    240 cgcagcagcc accactacca ctacctcctc ctcctcgtct tcctctggcg gctccgcgac    300
aaaccaactg agtaggtacg agaatcagaa gagaagagac tggaacactt tcggacaata    360
tctacgcaac caccgtccac cactttctct ctcccgttgc agtggtgctc atgttcttga    420
gttcctcagg tacctcgacc aattcggcaa gaccaaggtt cacatgcaaa tatgtccttt    480
ctttggacac ccaaacccac cagcaccatg tacctgccca ctcagacaag cgtgggggcag    540 cctcgacgca ctcattggcc ggcttcgagc tgcttttgaa gagaacggtg ttcaccaga    600 gacgaaccct tttggtgcac gagctgttcg actctaccta agggaagttc gtgattcgca    660
ggctaaagcg cgtgggatca gctatgaaaa gaagaagcgg aagcgacctc tcaggcgcc    720 actaccaccg cctcatcagc cggtgatttc gaatagtcct aatttgcaat aagtcatatc    780
```

```
agtaagatat gtttcagtca actacgtttc cttacaactt tatatagtat ttgtcaatga    840
cgaacatgca ggagttgtct aaaaagctgc atgcccttct tctttatttg gccagct      897

<210> SEQ ID NO 128
<211> LENGTH: 199
<212> TYPE: PRT
<213> ORGANISM: Brassica napus
<220> FEATURE:
<221> NAME/KEY: misc_feature
<223> OTHER INFORMATION: Ceres SEED LINE ME25647
<220> FEATURE:
<221> NAME/KEY: misc_feature
<223> OTHER INFORMATION: Ceres CLONE ID no. 964932
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (30)..(162)
<223> OTHER INFORMATION: Pfam Name: DUF640
      Pfam Description: Protein of unknown function (DUF640)

<400> SEQUENCE: 128

Met Asp Pro Ile His Gly Phe Met Ser Thr Ser Asn Ile Ser His Asn
1               5                   10                  15

Thr Asn Leu Met Ile Ala Ala Ala Ala Thr Thr Thr Thr Thr Thr Ser
            20                  25                  30

Ser Ser Ser Ser Ser Ser Gly Gly Ser Ala Thr Asn Gln Leu Ser Arg
        35                  40                  45

Tyr Glu Asn Gln Lys Arg Arg Asp Trp Asn Thr Phe Gly Gln Tyr Leu
    50                  55                  60

Arg Asn His Arg Pro Pro Leu Ser Leu Ser Arg Cys Ser Gly Ala His
65                  70                  75                  80

Val Leu Glu Phe Leu Arg Tyr Leu Asp Gln Phe Gly Lys Thr Lys Val
                85                  90                  95

His Met Gln Ile Cys Pro Phe Phe Gly His Pro Asn Pro Pro Ala Pro
            100                 105                 110

Cys Thr Cys Pro Leu Arg Gln Ala Trp Gly Ser Leu Asp Ala Leu Ile
        115                 120                 125

Gly Arg Leu Arg Ala Ala Phe Glu Glu Asn Gly Gly Ser Pro Glu Thr
    130                 135                 140

Asn Pro Phe Gly Ala Arg Ala Val Arg Leu Tyr Leu Arg Glu Val Arg
145                 150                 155                 160

Asp Ser Gln Ala Lys Ala Arg Gly Ile Ser Tyr Glu Lys Lys Lys Arg
                165                 170                 175

Lys Arg Pro Pro Gln Ala Pro Leu Pro Pro His Gln Pro Val Ile
            180                 185                 190

Ser Asn Ser Pro Asn Leu Gln
        195

<210> SEQ ID NO 129
<211> LENGTH: 874
<212> TYPE: DNA
<213> ORGANISM: Glycine max
<220> FEATURE:
<221> NAME/KEY: misc_feature
<223> OTHER INFORMATION: Ceres SEED LINE ME24507
<220> FEATURE:
<221> NAME/KEY: misc_feature
<223> OTHER INFORMATION: Ceres CLONE ID no. 604111
<220> FEATURE:
<221> NAME/KEY: misc_feature
```

-continued

<223> OTHER INFORMATION: Encodes the peptide sequence at SEQ ID NO. 146

<400> SEQUENCE: 129

```
agtcccataa acctcacttc ctcaacctca atccaacaga aacaaaaaaa aacctcactt    60
agatcacata gatcaaacaa caaaacacag agttacctaa attgaaccta ccccagtagg   120
ttctacaagc tcttgatcat ggcctcagca tcagggggg caccaccacc ccaacccact    180
tcaacagaag ctgctccagc atcaggctct tcagctccag ccatatcagc agcaccacca   240
caacccggag gatcatcgcc ggcgcctccg agccgctacg aatcgcaaaa gcgtcgagac   300
tggaacacgt ttctgcagta cctgcagaac cacaagcccc cattaacgct ggcgcggtgc   360
agtggcgcac acgtcattga gttcttgaag tacttggacc aattcgggaa aaccaaggtt   420
cacatcacgg ggtgcccgta ctacgggtac cccaaccctc ctgcgccctg cgcttgccca   480
ctgaaacaag cgtggggaag ccttgacgcc ctgatcgggc gactcagggc ggcttacgag   540
gaaaacggag gccgccctga gtctaacccg ttcggcgcca gggccgtcag aatttacctc   600
agggaggtaa gagaaggtca ggctaaagca agagggatcc cttatgagaa gaagaagcgg   660
aagaggacca ccgtggtgac ggtgagtagt ggtggtggtg gtagtagcgg tgcagttgcc   720
tctccgagtg gcggtggtga taccgctatt ggtggtggag ctggttctag tgctagttta   780
acttcttcag caactgccac agctaatgat actacaacca cagtataatt ttaatagtta   840
tttaattatt tattttcaa aaaaaaaaaa aaaa                                874
```

<210> SEQ ID NO 130
<211> LENGTH: 1278
<212> TYPE: DNA
<213> ORGANISM: Gossypium hirsutum
<220> FEATURE:
<221> NAME/KEY: misc_feature
<223> OTHER INFORMATION: Ceres CLONE ID no. 1855399
<220> FEATURE:
<221> NAME/KEY: misc_feature
<223> OTHER INFORMATION: Encodes the peptide sequence at SEQ ID NO. 131

<400> SEQUENCE: 130

```
aaatctttcc cgtgaaagga tcccatggag cactacttct ttcaatgaac cctaaacacc    60
ctcaattatc atactcttat ttgactgacc taatcaaaca gaagcagcta ataagggttt   120
gtcaattgtg agtgactgat aaatagcttg gattttggaa tctctcccta cacttggatt   180
tcagataaaa acaaaatccc aggtgggaaa aattcatcac tgcccatcaa cagttcatca   240
ccaaaacccc aacagtttcc tcttcttttt ttccaagtca atggattctg cctccggagg   300
gagtgacaat agcatcaaag aggctatacc agcaacagct tcagccctgc tgtccgcggc   360
ttcacaacaa ggaggaggag gtggtagtga gtcgtctcct tccccagctc caccgagtag   420
gtacgagtca caaaagcgtc gagactggaa cactttcttg cagtacttga ccaaccataa   480
acccccatta acactagctc gttgcagtgg cgcacacgta attgagttct tgaaatacct   540
tgaccagttc ggcaagacta aggttcacat aacggattgt ccctatttcg acatgtaaa    600
cccacctgct ccctgcgctt gcccactgaa gcaagcgtgg ggtagcctcg acgcgctgat   660
cggacggctc agagctgctt atgaagaaaa cggtggacgt ccagaatcca accctttgg    720
cgcaagggct gtgaggattt atttgaggga agtgagagaa gggcaggcta aagctagagg   780
gattccttat gagaagaaga agcgaaaaag gcccactgtc acaactacgg ctgtcggggt   840
caatgtgtcc aggacttcca ctcaaccagt tgatggcggt ggggtcgcg gcggcattgg   900
tggtggagat gatagtgttg gtgctaaaac tggggcaaat gttggtagtg ccaccgcagt   960
```

```
tgctgctgct accactaata gcgtatagtt cttttccct attaacaaat tcttttcctc        1020
tttttttgcc tttaacagct gttttaaatg tgattacgag ttatatatat ctggtggttc        1080
tgtcgggaaa ttggattgac atcccatgaa ccaaatttag aatttaggta gaattctagt        1140
tttaatctct ttcaatcaat ctctcctatt ttcccctttc tctactttct tcatcatttc        1200
ttgctatgca tgtacttgaa aaaggaatat aagaagtttt aatctttttt ccctttctaa        1260
aaaaaaaaaa aaaaaaaa                                                     1278

<210> SEQ ID NO 131
<211> LENGTH: 235
<212> TYPE: PRT
<213> ORGANISM: Gossypium hirsutum
<220> FEATURE:
<221> NAME/KEY: misc_feature
<223> OTHER INFORMATION: Ceres CLONE ID no. 1855399
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (29)..(161)
<223> OTHER INFORMATION: Pfam Name: DUF640
      Pfam Description: Protein of unknown function (DUF640)

<400> SEQUENCE: 131

Met Asp Ser Ala Ser Gly Gly Ser Asp Asn Ser Ile Lys Glu Ala Ile
1               5                   10                  15

Pro Ala Thr Ala Ser Ala Leu Leu Ser Ala Ala Ser Gln Gln Gly Gly
            20                  25                  30

Gly Gly Gly Ser Glu Ser Ser Pro Ser Pro Ala Pro Pro Ser Arg Tyr
        35                  40                  45

Glu Ser Gln Lys Arg Arg Asp Trp Asn Thr Phe Leu Gln Tyr Leu Thr
    50                  55                  60

Asn His Lys Pro Pro Leu Thr Leu Ala Arg Cys Ser Gly Ala His Val
65                  70                  75                  80

Ile Glu Phe Leu Lys Tyr Leu Asp Gln Phe Gly Lys Thr Lys Val His
                85                  90                  95

Ile Thr Asp Cys Pro Tyr Phe Gly His Val Asn Pro Pro Ala Pro Cys
            100                 105                 110

Ala Cys Pro Leu Lys Gln Ala Trp Gly Ser Leu Asp Ala Leu Ile Gly
        115                 120                 125

Arg Leu Arg Ala Ala Tyr Glu Glu Asn Gly Gly Arg Pro Glu Ser Asn
    130                 135                 140

Pro Phe Gly Ala Arg Ala Val Arg Ile Tyr Leu Arg Glu Val Arg Glu
145                 150                 155                 160

Gly Gln Ala Lys Ala Arg Gly Ile Pro Tyr Glu Lys Lys Arg Lys
                165                 170                 175

Arg Pro Thr Val Thr Thr Thr Ala Val Gly Val Asn Val Ser Arg Thr
            180                 185                 190

Ser Thr Gln Pro Val Asp Gly Gly Gly Arg Gly Gly Ile Gly Gly
        195                 200                 205

Gly Asp Asp Ser Val Gly Ala Lys Thr Gly Ala Asn Val Gly Ser Ala
    210                 215                 220

Thr Ala Val Ala Ala Ala Thr Thr Asn Ser Val
225                 230                 235

<210> SEQ ID NO 132
<211> LENGTH: 2276
```

<212> TYPE: DNA
<213> ORGANISM: Panicum virgatum
<220> FEATURE:
<221> NAME/KEY: misc_feature
<223> OTHER INFORMATION: Ceres CLONE ID no. 1858527
<220> FEATURE:
<221> NAME/KEY: misc_feature
<223> OTHER INFORMATION: Encodes the peptide sequence at SEQ ID NO. 133

<400> SEQUENCE: 132

```
gtccccgcat atctgaccac atcttcttcc cccacctctc cccaagctcg ctcacctcag      60
ctgctggcct cctcctctcc cgtccctttc caccgatcga gcttcttcta actgctggta     120
tgctgccttc gtgttcaact cgagccgtcg ctttgcaatt ctttgcatac tttcttgcaa     180
aaaaaaatct ttgtatgcat gtttcatgtt tctgaagctg tacgattgat cttgctgctc     240
ttattcggct catcatccgc acatctgtcc atgcatgtcg tcagcttgtg ttgtgtagct     300
tctgttcccc tggtgtctgg tcgatcgatc gtgcgcgcac ggattgtcta gtggtaggct     360
cttggccctg cgcctacagt acgcccacac atggatcaag ggccctgtaa accctgttct     420
gcagcgaccc accgtgtcga tcattaaccg ggcggcgaca ctctggctgt tctggatcaa     480
ttcgccttcg ccttcttgga gtaggtaggt agacgcatgt tcgacagttc tctcccctct     540
tttctgatgc acctcgcact catctctggc attcaggcag agccgaccag ccagctcctg     600
aataaactga atgtttgctg acctctagtc ctgcctctgt tcgtcctgct ttgctcaccg     660
atcgccggcg tggcgcaggc gaagccgaaa ttttctgtt atttgctttg cagttttgtt     720
ttactcctcc gttccgtttt gtgcttttcg ccctttcccc tgtgctttgc ttcagacttt     780
ccgtgtaggc gtcagttctt gcatgtctgc taaggatcag cggcctcagt cctcaggtgc     840
tctagacttg aaatcccact accggttgat aggtactact aggtggccgc tagctccgac     900
ctgaaaccct agttcattca gaatatctga tccgtcctag ctctgctggc cggccaagaa     960
cagacgaagc gactgtttct tgtccgatcg gcccttttgc atacgatcag tattattgtt    1020
tcttgtccga ccattggtcg aagcgttgga ctaacaggca tggcacatgg tgccggtgca    1080
ggtgcagatc tgggttggcc ttcgtggaca ggctgcggcg aaggagctat ggagatggcc    1140
ggcgcggcga acagcccggg cccggcagcg gcgcggccga gccggtacga gtcgcagaag    1200
cgccgggact ggcagacgtt cgggcagtac ctgcgcaacc accggccgcc gctgagctg    1260
gcccggtgca gcggcgcgca cgtgctcgag ttcctccgct acctggacca gttcggcaag    1320
accaaggtgc acgcgccggg gtgccccttc ttcggccacc cgtcgccgcc ggcgccgtgc    1380
ccgtgcccgc tcaagcaggc gtggggcagc ctcgacgcgc tcgttggccg cctccgcgcc    1440
gccttcgagg agcacggcgg ccgccccgag gccaatccct tcggggtgcg cgccgtccgg    1500
ctctacctcc gcgaggtccg cgacacccag gccaaggcgc gcggcatcgc ctacgagaag    1560
aagcgccgca agcgccaccc gccggcacac aggcaggcca agcagcagca ggacgccggc    1620
cagcagcagc agcagcagca ctaccacccc caccaccacc accaggcgtc gcccgccgcg    1680
gctgcggtga ccgagagtag gcgcgtgctg gcggacatgg ccgagccgct ggcgccgcac    1740
ttcctgatcc cgcacgcgca gttcctccac ggccacttcc tggtgccggt caccgagccg    1800
accgaccccg ccgcgggcat gggcggcggc ggcaccggcg aggacttggt gctggcaatg    1860
gcggccgccg ccgaggcgca cgccgccgcg ccgggttct tgatgccgct gtccgtgttt    1920
cactagctag cttgctgggt ccactctccg ctgcctctat agctccaggg gcagggatgc    1980
aaggctaggt aattaggcgt aatcaagcat gcaggttttg ctaatggcga tcggcctgat    2040
ctctgcgcgc cgtttggtcg tccatccggc ttttggtgtt tatgcgcttg catcaaccgc    2100
```

```
tgctgccttt tggttgtatt ttgggtgcgt ggttttgtgt acgcagtgat agaatggctg   2160
gattagaccg ctgtgtgtgt ttttctccat gacttggatc ttgtgggaat tcatgtact   2220 acagctgatc tcaatcgact taacattgtt cctggtaaaa aaaaaaaaaa aaaaaa       2276
```

<210> SEQ ID NO 133
<211> LENGTH: 288
<212> TYPE: PRT
<213> ORGANISM: Panicum virgatum
<220> FEATURE:
<221> NAME/KEY: misc_feature
<223> OTHER INFORMATION: Ceres CLONE ID no. 1858527
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (24)..(156)
<223> OTHER INFORMATION: Pfam Name: DUF640
      Pfam Description: Protein of unknown function (DUF640)

<400> SEQUENCE: 133

```
Met Ala His Gly Ala Gly Ala Gly Ala Asp Leu Gly Trp Pro Ser Trp
1               5                   10                  15

Thr Gly Cys Gly Glu Gly Ala Met Glu Met Ala Gly Ala Ala Asn Ser
            20                  25                  30

Pro Gly Pro Ala Ala Ala Arg Pro Ser Arg Tyr Glu Ser Gln Lys Arg
        35                  40                  45

Arg Asp Trp Gln Thr Phe Gly Gln Tyr Leu Arg Asn His Arg Pro Pro
    50                  55                  60

Leu Glu Leu Ala Arg Cys Ser Gly Ala His Val Leu Glu Phe Leu Arg
65                  70                  75                  80

Tyr Leu Asp Gln Phe Gly Lys Thr Lys Val His Ala Pro Gly Cys Pro
                85                  90                  95

Phe Phe Gly His Pro Ser Pro Pro Ala Pro Cys Pro Cys Pro Leu Lys
            100                 105                 110

Gln Ala Trp Gly Ser Leu Asp Ala Leu Val Gly Arg Leu Arg Ala Ala
        115                 120                 125

Phe Glu Glu His Gly Gly Arg Pro Glu Ala Asn Pro Phe Gly Val Arg
    130                 135                 140

Ala Val Arg Leu Tyr Leu Arg Glu Val Arg Asp Thr Gln Ala Lys Ala
145                 150                 155                 160

Arg Gly Ile Ala Tyr Glu Lys Lys Arg Lys Arg His Pro Pro Ala
                165                 170                 175

His Arg Gln Ala Lys Gln Gln Asp Ala Gly Gln Gln Gln Gln
            180                 185                 190

Gln His Tyr His Pro His His His Gln Ala Ser Pro Ala Ala Ala
        195                 200                 205

Ala Val Thr Glu Ser Arg Arg Val Leu Ala Asp Met Ala Glu Pro Leu
210                 215                 220

Ala Pro His Phe Leu Ile Pro His Ala Gln Phe Leu His Gly His Phe
225                 230                 235                 240

Leu Val Pro Val Thr Glu Pro Thr Asp Pro Ala Ala Gly Met Gly Gly
                245                 250                 255

Gly Gly Thr Gly Glu Asp Leu Val Leu Ala Met Ala Ala Ala Glu
            260                 265                 270

Ala His Ala Ala Ala Ala Gly Phe Leu Met Pro Leu Ser Val Phe His
        275                 280                 285
```

<210> SEQ ID NO 134
<211> LENGTH: 797
<212> TYPE: DNA
<213> ORGANISM: Unknown
<220> FEATURE:
<221> NAME/KEY: misc_feature
<223> OTHER INFORMATION: Ceres CLONE ID no. 1896482
<220> FEATURE:
<221> NAME/KEY: misc_feature
<223> OTHER INFORMATION: Encodes the peptide sequence at SEQ ID NO. 135

<400> SEQUENCE: 134

```
atggattctg caacggaccc gaataccatc aaggaggatc cagtatcagt tacagtttca      60
gcaccaccgt ccaagggtat ccagcaagga gttggtgagt cgccgtcgtc ttctacttcc     120
ccagcagcac cgagtcgtta cgagtcacaa agcgtcgag actggaacac gttcttgcag      180
tacttgaaga accataagcc gccattgact ctggctcgtt gcagcggagc acacgtgatc     240
gagttcttga agtacctcga ccagttcggg aaaaccaagg ttcacatgac gggttgtcct     300
tatttcggac acccgaaccc gcctggtcct tgctcttgtc cactcaagca agcgtggggt     360
agcctcgacg cgctgatcgg acggctgaga gctgcttacg aagagagcgg gggacgaccg     420
gaatcaaacc cgtttgcggc aagggctgtg aggatttatt tgagggaagt gagggaagga     480
caggctagag ctagagggat acctaatgag aaaaagaagc gaaaaaggac ttctgttaca     540
actagcgctg tagggatcaa tgtgtcggcg gtggctgcca ctcaagcggt tgattatggt     600
ggggttagcg gaggaactgc gagtaatctt ggtactgcta ctaccactac tagcttatag     660
attcttcaat gattatttta tatatatatt ttgctttcaa tatttgatat aaatgtgata     720
tgtggcggtt ctttcttaaa actggatcaa tatccccatg aaccaaattt agatggaaat     780
ataattttaa tctttct                                                    797
```

<210> SEQ ID NO 135
<211> LENGTH: 219
<212> TYPE: PRT
<213> ORGANISM: Unknown
<220> FEATURE:
<221> NAME/KEY: misc_feature
<223> OTHER INFORMATION: Ceres CLONE ID no. 1896482
<220> FEATURE:
<221> NAME/KEY: misc_feature
<223> OTHER INFORMATION: Functional Homolog of Ceres Clone ID no. 28780
    at SEQ ID NO. 88
<220> FEATURE:
<221> NAME/KEY: misc_feature
<222> LOCATION: (28)..(160)
<223> OTHER INFORMATION: Pfam Name: DUF640
    Pfam Description: Protein of unknown function (DUF640)

<400> SEQUENCE: 135

```
Met Asp Ser Ala Thr Asp Pro Asn Thr Ile Lys Glu Asp Pro Val Ser
1               5                   10                  15

Val Thr Val Ser Ala Pro Pro Ser Lys Gly Ile Gln Gln Gly Val Gly
                20                  25                  30

Glu Ser Pro Ser Ser Ser Thr Ser Pro Ala Ala Pro Ser Arg Tyr Glu
            35                  40                  45

Ser Gln Lys Arg Arg Asp Trp Asn Thr Phe Leu Gln Tyr Leu Lys Asn
        50                  55                  60

His Lys Pro Pro Leu Thr Leu Ala Arg Cys Ser Gly Ala His Val Ile
65                  70                  75                  80

Glu Phe Leu Lys Tyr Leu Asp Gln Phe Gly Lys Thr Lys Val His Met
                85                  90                  95
```

Thr Gly Cys Pro Tyr Phe Gly His Pro Asn Pro Pro Gly Pro Cys Ser
            100                 105                 110

Cys Pro Leu Lys Gln Ala Trp Gly Ser Leu Asp Ala Leu Ile Gly Arg
        115                 120                 125

Leu Arg Ala Ala Tyr Glu Glu Ser Gly Gly Arg Pro Glu Ser Asn Pro
    130                 135                 140

Phe Ala Ala Arg Ala Val Arg Ile Tyr Leu Arg Glu Val Arg Glu Gly
145                 150                 155                 160

Gln Ala Arg Ala Arg Gly Ile Pro Asn Glu Lys Lys Arg Lys Arg
                165                 170                 175

Thr Ser Val Thr Thr Ser Ala Val Gly Ile Asn Val Ser Ala Val Ala
            180                 185                 190

Ala Thr Gln Ala Val Asp Tyr Gly Gly Val Ser Gly Thr Ala Ser
        195                 200                 205

Asn Leu Gly Thr Ala Thr Thr Thr Ser Leu
    210                 215

<210> SEQ ID NO 136
<211> LENGTH: 1125
<212> TYPE: DNA
<213> ORGANISM: Gossypium hirsutum
<220> FEATURE:
<221> NAME/KEY: misc_feature
<223> OTHER INFORMATION: Ceres CLONE ID no. 1934537
<220> FEATURE:
<221> NAME/KEY: misc_feature
<223> OTHER INFORMATION: Encodes the peptide sequence at SEQ ID NO. 137

<400> SEQUENCE: 136
aagaattatt ttttggacgt ctcatcattt agttttttt tcctctcttt cacactttat      60
cacttcaaat ttcttcttcg ttttgatttt cattcaaaac catctctgaa ttgtttttta     120
aaagccaatc ttcggatccc agcagttttt tcagtgaacc ctagtcaaaa agagaagcag     180
ctagagcaaa gagtttatga attgttagtg attgattgat tgatagtata tgttagagtt     240
tatatagaaa agaaaacgac gatttgatgg aaatttagtg acagccaatt atcatcaaaa     300
gtgcgaagcc ctaatagttt tttttaagtc aatggattct gcaacgaacc cgaatatcat     360
caagaaggat ccagtaccag ttacagtttc agcaccatcg tccacgggta tccagcaagg     420
agttggtgag tcgccgtcgt cttctacttc cccagcagca ccgagtcggt acgagtcaca     480
aaagcgtcga gactggaaca cgttcttgca gtacttgaag aaccataagc cgccattgac     540
tctggctcgt tgcagcggcg cacacgtgat cgagttcttg aagtacctcg accagttcgg     600
gaaaaccaag gttcacatga cgggttgtcc ttatttcgga cacccgaacc cgcctggtcc     660
ttgctcttgt ccactcaagc aagcgtgggg tagcctcgac gcgctgatcg gacggctgag     720
agctgcttac gaagagagcg ggggacgacc ggaatcgaac ccgtttgcgg caagggctgt     780
gaggatttat ttgagggaag tgagggaagg acaggctaga gctagaggga taccttatga     840 gaaaagaag cgaaaaggc cttctgtcac aactagcgct gtaggggtca atgtgtcggc      900
ggtggctgcc actcaagcgg ttgattatgg tggggtagc ggaggaactg cgggtaatct      960
tggtactgct actaccacta ctagcttata aattcttcaa tgattattat atatatatat    1020
attgctttca atatttgata taaatgtgat atgtggcggt tctttcttaa aattggatcc    1080
atatccccat gaaccaaatt tagacaaaaa aaaaaaaaaa aaaaa                    1125

<210> SEQ ID NO 137
<211> LENGTH: 219

```
<212> TYPE: PRT
<213> ORGANISM: Gossypium hirsutum
<220> FEATURE:
<221> NAME/KEY: misc_feature
<223> OTHER INFORMATION: Ceres CLONE ID no. 1934537
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (28)..(160)
<223> OTHER INFORMATION: Pfam Name: DUF640
      Pfam Description: Protein of unknown function (DUF640)

<400> SEQUENCE: 137

Met Asp Ser Ala Thr Asn Pro Asn Ile Ile Lys Lys Asp Pro Val Pro
1               5                   10                  15

Val Thr Val Ser Ala Pro Ser Ser Thr Gly Ile Gln Gln Gly Val Gly
            20                  25                  30

Glu Ser Pro Ser Ser Ser Thr Ser Pro Ala Ala Pro Ser Arg Tyr Glu
        35                  40                  45

Ser Gln Lys Arg Arg Asp Trp Asn Thr Phe Leu Gln Tyr Leu Lys Asn
50                  55                  60

His Lys Pro Pro Leu Thr Leu Ala Arg Cys Ser Gly Ala His Val Ile
65                  70                  75                  80

Glu Phe Leu Lys Tyr Leu Asp Gln Phe Gly Lys Thr Lys Val His Met
                85                  90                  95

Thr Gly Cys Pro Tyr Phe Gly His Pro Asn Pro Pro Gly Pro Cys Ser
            100                 105                 110

Cys Pro Leu Lys Gln Ala Trp Gly Ser Leu Asp Ala Leu Ile Gly Arg
        115                 120                 125

Leu Arg Ala Ala Tyr Glu Glu Ser Gly Gly Arg Pro Glu Ser Asn Pro
130                 135                 140

Phe Ala Ala Arg Ala Val Arg Ile Tyr Leu Arg Glu Val Arg Glu Gly
145                 150                 155                 160

Gln Ala Arg Ala Arg Gly Ile Pro Tyr Glu Lys Lys Lys Arg Lys Arg
                165                 170                 175

Pro Ser Val Thr Thr Ser Ala Val Gly Val Asn Val Ser Ala Val Ala
            180                 185                 190

Ala Thr Gln Ala Val Asp Tyr Gly Gly Gly Ser Gly Gly Thr Ala Gly
        195                 200                 205

Asn Leu Gly Thr Ala Thr Thr Thr Ser Leu
210                 215

<210> SEQ ID NO 138
<211> LENGTH: 1159
<212> TYPE: DNA
<213> ORGANISM: Gossypium hirsutum
<220> FEATURE:
<221> NAME/KEY: misc_feature
<223> OTHER INFORMATION: Ceres CLONE ID no. 1942084
<220> FEATURE:
<221> NAME/KEY: misc_feature
<223> OTHER INFORMATION: Encodes the peptide sequence at SEQ ID NO. 139

<400> SEQUENCE: 138
acgtcccaca tcatcgatat tcctgttctt gctacttggt ttttttttct aacatcaatt      60
cattttcttt ccttctttaa ctcagaatca tatcttcttc tctatcacca ataaagagaa     120
tacaagcaaa tctttcctgt caccgggggg ggggggagcc tatcacttct tcaatatga     180 accctaatac tactatttta cctaacctaa gagcttagga ttttgatagg tttagtgttc     240
```

```
tttttttgttt taaatcgatg gattctggtt ccggagccaa cccgaatagc atcaacgagg    300
gttcatcatc agctacagca ccggtgctga tggattcaca acaaggtgga gctggtgaat    360
tgtcttcttc tccagctcat ccaccgagtc gctacgagtc acaaaagcgt cgcgactgga    420
acactttctt gcagtacttg aagaaccaca agcccccact gacgctatct cgttgcagcg    480
gcgcacacgt aatcgagttc ttgaaatatc ttgaccagtt cggcaaaact aaggttcacg    540
taacggcttg tccttatttc ggacatgcaa acccgcccga tccttgttct tgtccactca    600
agcaagcgtg gggtagcctc gacgcgttga tcggacggct gagagctgct tatgaagaaa    660
acggtggacg tcgggaatca aacccttttg gacaagggc tgtgaggatt tatttgaggg     720
aagtgagagg agggcaggct aaagctagag ggattcctta tgagaaaaag aagcgaaaaa    780
ggcctactac tacggctgtg tcggcggctt ctggtactca accacctggt ggtgctgccg    840
gtgatgatag ttctggtgga actacggcta acgtgggtac tgtcaccgct gctgctacca    900
ctaatagctt atagttgttc tcttaattac tattttattt ttttattttg tcttctaata    960
gctgttttat atgtgattat gatgagttat cacatgaact aagtttagtt agcaatcttg    1020
tttaatcact ttcgacattt ttccacttct acagtttctt catttcttgt catgcatgaa    1080
catgattact atatatataa acacatacat atatatgtat aagttgaaat aaaaacaata    1140
agacgagagt tattaatct                                                 1159
```

<210> SEQ ID NO 139
<211> LENGTH: 218
<212> TYPE: PRT
<213> ORGANISM: Gossypium hirsutum
<220> FEATURE:
<221> NAME/KEY: misc_feature
<223> OTHER INFORMATION: Ceres CLONE ID no. 1942084
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (27)..(159)
<223> OTHER INFORMATION: Pfam Name: DUF640
      Pfam Description: Protein of unknown function (DUF640)

<400> SEQUENCE: 139

```
Met Asp Ser Gly Ser Gly Ala Asn Pro Asn Ser Ile Asn Glu Gly Ser
1               5                   10                  15

Ser Ser Ala Thr Ala Pro Val Leu Met Asp Ser Gln Gln Gly Gly Ala
            20                  25                  30

Gly Glu Leu Ser Ser Ser Pro Ala His Pro Pro Ser Arg Tyr Glu Ser
        35                  40                  45

Gln Lys Arg Arg Asp Trp Asn Thr Phe Leu Gln Tyr Leu Lys Asn His
    50                  55                  60

Lys Pro Pro Leu Thr Leu Ser Arg Cys Ser Gly Ala His Val Ile Glu
65                  70                  75                  80

Phe Leu Lys Tyr Leu Asp Gln Phe Gly Lys Thr Lys Val His Val Thr
                85                  90                  95

Ala Cys Pro Tyr Phe Gly His Ala Asn Pro Pro Asp Pro Cys Ser Cys
            100                 105                 110

Pro Leu Lys Gln Ala Trp Gly Ser Leu Asp Ala Leu Ile Gly Arg Leu
        115                 120                 125

Arg Ala Ala Tyr Glu Glu Asn Gly Gly Arg Arg Glu Ser Asn Pro Phe
    130                 135                 140
```

```
Gly Thr Arg Ala Val Arg Ile Tyr Leu Arg Glu Val Arg Gly Gly Gln
145                 150                 155                 160

Ala Lys Ala Arg Gly Ile Pro Tyr Glu Lys Lys Arg Lys Arg Pro
                165                 170                 175

Thr Thr Thr Ala Val Ser Ala Ala Ser Gly Thr Gln Pro Pro Gly Gly
            180                 185                 190

Ala Gly Asp Asp Ser Ser Gly Gly Thr Thr Ala Asn Val Gly Thr
        195                 200                 205

Val Thr Ala Ala Ala Thr Thr Asn Ser Leu
    210                 215
```

```
<210> SEQ ID NO 140
<211> LENGTH: 1533
<212> TYPE: DNA
<213> ORGANISM: Panicum virgatum
<220> FEATURE:
<221> NAME/KEY: misc_feature
<223> OTHER INFORMATION: Ceres CLONE ID no. 1988960
<220> FEATURE:
<221> NAME/KEY: misc_feature
<223> OTHER INFORMATION: Encodes the peptide sequence at SEQ ID NO. 141

<400> SEQUENCE: 140
```

| | | | | | |
|---|---|---|---|---|---|
| acctctcccc | aagctcgctc | aactcagctg | ctggcctcct | ctcccgtccc | tttccaccga | 60 |
| tcgagcttct | tctaactgcc | tgtccatgca | tgtcgtcagc | ttgtgttgtg | tagcttctgt | 120 |
| ttccctggtg | tctggtcgat | cgatcgtgcg | cgcacggatt | gtctagtggt | aggctcttgg | 180 |
| ccctgcgcct | acagtacgcc | cacacatgga | tcaagggccc | tgtaaaccct | gttctgcagc | 240 |
| gacccaccgt | gtcgatcatt | aaccgggcgg | cgacactctg | gctgttctgg | aatctggatc | 300 |
| aattcgcctt | cgccttcttg | gagtaggtgc | agatctgggt | tggccttcgt | ggacaggcgg | 360 |
| cggcgaagga | gctatggaga | tggccggcgc | ggcggacagc | ccgggcctgg | cggcggcgcg | 420 |
| gccgaaccgg | tacgagtcgc | agaagcgccg | ggactggcag | acgttcgggc | agtacctgcg | 480 |
| caaccaccgg | ccgccgctgg | agctggcccg | gtgcagcggc | gcgcacgtgc | tcgagttcct | 540 |
| ccgctacctg | gaccagttcg | gcaagaccaa | ggtgcacgcg | ccggggtgcc | ccttcttcgg | 600 |
| ccacccgtcg | ccgccggcgc | cgtgcccgtg | ccgctcaag | caggcgtggg | gcagcctcga | 660 |
| cgcgctcgtc | ggccgcctcc | gcgccgccta | tgaggagcac | ggcggccgcc | cgaggccaa | 720 |
| cccccttcggg | gcgcgcgccg | tccggctcta | cctccgcgag | gtccgcgaca | cccaggccaa | 780 |
| ggcgcgcggc | atcgcctacg | agaagaagcg | ccgcaagcgc | cacccgccgg | cacacaggca | 840 |
| ggccaagcag | cagcaggacg | ccggccagca | gcagcagcag | cactaccacc | ccaccacca | 900 |
| ccaccaggcg | tcgcccgccg | cggccgcggt | gaccgagagt | aggcgcgtgc | tggctgacat | 960 |
| ggccgaaccg | ccggcgccgc | acttcctgat | cccgcacgcg | cagttcctcc | acggccactt | 1020 |
| cctggtgccg | gtcaccgagc | cgaccgaccc | caccgcgggc | atgggcggcg | gcggcaccgg | 1080 |
| cgaggacttg | gtgctggcaa | tggcggccgc | cgccgaggcg | cacgccgccg | cggccgggtt | 1140 |
| cttgatgccg | ctgtccttct | ttcactagct | agcttgctgg | gtccactctc | cgctgcctct | 1200 |
| atagctccat | gggcagggat | gcaaggctag | gtaattaggc | gtaatcaagc | atgcaggttt | 1260 |
| tgctaatggc | gatcggcctg | atctctgcgc | gccgtttggt | cgtccatccg | gcttttggtg | 1320 |
| tttatgcgca | gtcgtctcct | ccgcgcgaca | ttgccggcgg | cgcttgcatc | aaccgctgct | 1380 |
| gccttctggt | tgtatttttgg | gtgcgtggtt | ttgtggacgc | agtgatagaa | tggctggatt | 1440 |
| agacggctct | gtgtgttttt | ctccatgact | cggatcttgt | gggaatttca | tgtactacag | 1500 |
| ctgatctcaa | tcgacttaac | atttttcctg | gtt | | | 1533 |

```
<210> SEQ ID NO 141
<211> LENGTH: 264
<212> TYPE: PRT
<213> ORGANISM: Panicum virgatum
<220> FEATURE:
<221> NAME/KEY: misc_feature
<223> OTHER INFORMATION: Ceres CLONE ID no. 1988960
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (1)..(133)
<223> OTHER INFORMATION: Pfam Name: DUF640
      Pfam Description: Protein of unknown function (DUF640)

<400> SEQUENCE: 141

Met Glu Met Ala Gly Ala Ala Asp Ser Pro Gly Leu Ala Ala Arg
1               5                   10                  15

Pro Asn Arg Tyr Glu Ser Gln Lys Arg Arg Asp Trp Gln Thr Phe Gly
                20                  25                  30

Gln Tyr Leu Arg Asn His Arg Pro Leu Glu Leu Ala Arg Cys Ser
        35                  40                  45

Gly Ala His Val Leu Glu Phe Leu Arg Tyr Leu Asp Gln Phe Gly Lys
    50                  55                  60

Thr Lys Val His Ala Pro Gly Cys Pro Phe Phe Gly His Pro Ser Pro
65                  70                  75                  80

Pro Ala Pro Cys Pro Cys Pro Leu Lys Gln Ala Trp Gly Ser Leu Asp
                85                  90                  95

Ala Leu Val Gly Arg Leu Arg Ala Ala Tyr Glu Glu His Gly Gly Arg
            100                 105                 110

Pro Glu Ala Asn Pro Phe Gly Ala Arg Ala Val Arg Leu Tyr Leu Arg
        115                 120                 125

Glu Val Arg Asp Thr Gln Ala Lys Ala Arg Gly Ile Ala Tyr Glu Lys
    130                 135                 140

Lys Arg Arg Lys Arg His Pro Ala His Arg Gln Ala Lys Gln Gln
145                 150                 155                 160

Gln Asp Ala Gly Gln Gln Gln Gln His Tyr His Pro His His His
                165                 170                 175

His Gln Ala Ser Pro Ala Ala Ala Ala Val Thr Glu Ser Arg Arg Val
            180                 185                 190

Leu Ala Asp Met Ala Glu Pro Pro Ala Pro His Phe Leu Ile Pro His
        195                 200                 205

Ala Gln Phe Leu His Gly His Phe Leu Val Pro Val Thr Glu Pro Thr
    210                 215                 220

Asp Pro Thr Ala Gly Met Gly Gly Gly Thr Gly Glu Asp Leu Val
225                 230                 235                 240

Leu Ala Met Ala Ala Ala Glu Ala His Ala Ala Ala Gly Phe
                245                 250                 255

Leu Met Pro Leu Ser Phe Phe His
            260

<210> SEQ ID NO 142
<211> LENGTH: 214
<212> TYPE: PRT
<213> ORGANISM: Medicago truncatula
<220> FEATURE:
<221> NAME/KEY: misc_feature
<223> OTHER INFORMATION: Public GI ID no. 92891522
```

```
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (47)..(179)
<223> OTHER INFORMATION: Pfam Name: DUF640
      Pfam Description: Protein of unknown function (DUF640)

<400> SEQUENCE: 142
```

Met Asn Ser Leu Gln Glu Phe Glu Ser Ser Thr Asn Asn Lys Asp Met
1               5                   10                  15

Met Asn Thr Asn Pro Met Ile Asn Ile Thr Asn Pro Ser Ser Ser Met
            20                  25                  30

Thr Met Thr Ile Pro Ser Ser Ser Thr Thr Ser Ala Ser Ser Ser Ser
        35                  40                  45

Thr Ala Thr Thr Ser Pro Pro Ser Thr Thr Ser Thr Thr Thr Pro Ser
    50                  55                  60

Arg Tyr Glu Asn Gln Lys Arg Arg Asp Trp Asn Thr Phe Gly Gln Tyr
65                  70                  75                  80

Leu Arg Asn His Arg Pro Pro Leu Ser Leu Ser Arg Cys Ser Gly Ala
                85                  90                  95

His Val Leu Glu Phe Leu Arg Tyr Leu Asp Gln Phe Gly Lys Thr Lys
            100                 105                 110

Val His Thr Leu Ile Cys Pro Phe Tyr Gly His Pro Asn Pro Pro Ala
        115                 120                 125

Ser Cys Pro Cys Pro Leu Arg Gln Ala Trp Gly Ser Leu Asp Ala Leu
    130                 135                 140

Ile Gly Arg Leu Arg Ala Ala Phe Glu Glu Asn Gly Gly Lys Pro Glu
145                 150                 155                 160

Ala Asn Pro Phe Gly Ala Arg Ala Val Arg Leu Tyr Leu Arg Glu Val
                165                 170                 175

Arg Asp Ser Gln Ala Lys Ala Arg Gly Ile Ser Tyr Glu Lys Lys Lys
            180                 185                 190

Arg Lys Arg Pro Pro Gln Pro Pro Pro Pro Pro Ser Asn Asn Ala
        195                 200                 205

Thr Ile Thr Asp Leu His
    210

```
<210> SEQ ID NO 143
<211> LENGTH: 828
<212> TYPE: DNA
<213> ORGANISM: Glycine max
<220> FEATURE:
<221> NAME/KEY: misc_feature
<223> OTHER INFORMATION: Ceres CLONE ID no. 1073674
<220> FEATURE:
<221> NAME/KEY: misc_feature
<223> OTHER INFORMATION: Encodes the peptide sequence at SEQ ID NO. 89

<400> SEQUENCE: 143
acactctttc tctcaatttc tctctctttt aaaacactaa tcactaaaat cttgattcac    60
tatatcgtca aaaccaacgc taaatcaatt aaactctctc aaagaaaaca agacaaagcc   120 ctactttga tggattcagg gtcacaacga ccggggcctg ttagcgaagg cgatccgggt   180
ccgtccatcg taaccccctc ttcaccgcct gcgacgccta gcaggtacga gtcgcagaaa   240
cgacgtgact ggaccacgtt cttgcagtac ctcaagaacc acaagccgcc tctttccttg   300
tcacggtgta gcggagcaca tgccatcgag ttcctcaagt acttagatca gttcggtaag   360
```

```
accaaagtcc acgtggcggc atgtccttac tttggccatc agcaacctcc gtctccttgc    420
gcttgtcctc tcaagcaagc ctgggggtct ctcgatgccc tgatcggacg gttgagagca    480
gcctacgaag agaacggtgg acggcccgag tcgaacccgt tcgcggcacg tgcggttagg    540
atttacttga gggaagtcag agaaagtcaa gccaaggccc gtgggagacc ctacgagaaa    600
aagaaacgga aacggccaac aactgttacc accgtgagag ttgacgttgc ttcgtcgaga    660
caaagtgaag gagatggttg taacatcggt gatccgtcgt atgtggccga ggctgtacct    720
ccttaattaa gttattatta ttgtcatgat atattaaata cattatatat gtctggaact    780
cacatcacct tcttgagtta actattgaaa atattttgt tctagttc                   828
```

<210> SEQ ID NO 144
<211> LENGTH: 799
<212> TYPE: DNA
<213> ORGANISM: Brassica napus
<220> FEATURE:
<221> NAME/KEY: misc_feature
<223> OTHER INFORMATION: Ceres CLONE ID no. 1118987
<220> FEATURE:
<221> NAME/KEY: misc_feature
<223> OTHER INFORMATION: Encodes the peptide sequence at SEQ ID NO. 90

<400> SEQUENCE: 144

```
aaattctcga ttcgcttata ttctcaaaac caacgctaaa taaaaacact ctcaaagaaa     60
aacaaaaaaa aaaccctagt tttgatggaa tcgactgatt cggggtcaca acaacatgga    120
ggtgacccag gtccgtcctc cgtaacgccc tcttcacctc cggcgacgcc gcctagcagg    180
tacgagtcgc aaaaacgacg tgactggaac acgttcttgc agtacctcaa gaaccacaag    240
ccgcctctcg cgttatcacg atgtagcgga gcgcacgtga tcgagttcct caagtaccta    300
gatcagttcg gtaagaccaa agtccacgtg gcgacctgcc cttacttcgg acatcagcag    360
cctccctctc cttgcgcttg tcctctcaag caagcctggg gatctctcga tgctctgatc    420
ggacggttga gagctgcgta cgaggagcac ggtgggaggc ctgattccaa cccttttcgcc   480 gcacgtgcgg tcaggattta cttgagagaa gtcagagaaa gtcaagccaa ggcacgtggg    540
attccatacg agaagaagaa acggaaacgg caccaactg tcactaccgc tagaattgac     600
gttgctccgt cgagacaaag tgaaggaggt ggtggttgta acgacagtga tccgtctgtc    660
gccgaagctg taccgcctta aattaaatta ttatatcata ttaattagtt ttcttgttat    720
attaagcatg gaactcacac ctttcgtact ataatgtatt ttattttctct atatgaacta   780 ttaagagttt tcttttgcc                                                 799
```

<210> SEQ ID NO 145
<211> LENGTH: 797
<212> TYPE: DNA
<213> ORGANISM: Parthenium argenta
<220> FEATURE:
<221> NAME/KEY: misc_feature
<223> OTHER INFORMATION: Ceres CLONE ID no. 1603237
<220> FEATURE:
<221> NAME/KEY: misc_feature
<223> OTHER INFORMATION: Encodes the peptide sequence at SEQ ID NO. 94

<400> SEQUENCE: 145

```
aacgaaataa accctaatca aacacccacc cactcaccca caaacatgtt aagcccaaca     60
tcctcttcat cttcaatagc ctcaaccgcc tcaaccgcca ccagtcgcct caaccgctac    120
gagagccaaa aacgccgtga ctggaacaca ttcggtcagt tcctccgtaa ccacgaccca    180
cccttaaccc tttccaactg caccagcaca cacgttatcg agttcctccg ttaccttgac    240
```

-continued

```
ccgtttggca aaactaaagt ccacacacat ctctgtccat ccttcggtca acccaaccct    300
cccacactct gcccgtgccc cctccgtcag gcctggggca gcctcgatgc cctcattggt    360
cgtctccggg cagcttttga agaaaacggt gggcagcccg agagtaaccc gtttggagct    420
agggctgtta ggtttttattt acgtgaagtt aaggatgctc aagctaaagc tagagggatt    480
agttgtgaga agaagaggac gaagaaacgg ccaccgccac ccactccgga tatttgtttg    540
gatcgctgat cgcgggcgtg ggtgaccttt tgctatcgct gatcgcgggc gtgggtgacc    600
ttttgctaat gggtgtacct gggtggttgg gccgggttgt ttgacttaaa aaaaaaaag    660 ttacccgagt taatggttaa tatcattgtc tggttaatta atgggtataa agctatgtaa    720
tttgaatatt gaactcgata ttctgtttct tggaaatggt tagccataat tttgaagatc    780
attattgtta ttatctt                                                    797
```

<210> SEQ ID NO 146
<211> LENGTH: 229
<212> TYPE: PRT
<213> ORGANISM: Glycine max
<220> FEATURE:
<221> NAME/KEY: misc_feature
<223> OTHER INFORMATION: Ceres SEED LINE ME24507
<220> FEATURE:
<221> NAME/KEY: misc_feature
<223> OTHER INFORMATION: Ceres CLONE ID no. 604111
<220> FEATURE:
<221> NAME/KEY: misc_feature
<223> OTHER INFORMATION: Functional Homolog of Ceres Clone ID no. 28780
      at SEQ ID NO. 88
<220> FEATURE:
<221> NAME/KEY: misc_feature
<222> LOCATION: (28)..(160)
<223> OTHER INFORMATION: Pfam Name: DUF640
      Pfam Description: Protein of unknown function (DUF640)

<400> SEQUENCE: 146

```
Met Ala Ser Ala Ser Gly Gly Ala Pro Pro Pro Gln Pro Thr Ser Thr
 1               5                  10                  15

Glu Ala Ala Pro Ala Ser Gly Ser Ser Ala Pro Ala Ile Ser Ala Ala
                20                  25                  30

Pro Pro Gln Pro Gly Gly Ser Ser Pro Ala Pro Pro Ser Arg Tyr Glu
            35                  40                  45

Ser Gln Lys Arg Arg Asp Trp Asn Thr Phe Leu Gln Tyr Leu Gln Asn
        50                  55                  60

His Lys Pro Pro Leu Thr Leu Ala Arg Cys Ser Gly Ala His Val Ile
    65                  70                  75                  80

Glu Phe Leu Lys Tyr Leu Asp Gln Phe Gly Lys Thr Lys Val His Ile
                85                  90                  95

Thr Gly Cys Pro Tyr Tyr Gly Tyr Pro Asn Pro Pro Ala Pro Cys Ala
            100                 105                 110

Cys Pro Leu Lys Gln Ala Trp Gly Ser Leu Asp Ala Leu Ile Gly Arg
        115                 120                 125

Leu Arg Ala Ala Tyr Glu Glu Asn Gly Gly Arg Pro Glu Ser Asn Pro
    130                 135                 140

Phe Gly Ala Arg Ala Val Arg Ile Tyr Leu Arg Glu Val Arg Glu Gly
145                 150                 155                 160

Gln Ala Lys Ala Arg Gly Ile Pro Tyr Glu Lys Lys Arg Lys Arg
                165                 170                 175

Thr Thr Val Val Thr Val Ser Ser Gly Gly Gly Ser Ser Gly Ala
            180                 185                 190

Val Ala Ser Pro Ser Gly Gly Gly Asp Thr Ala Ile Gly Gly Gly Ala
```

```
                195                 200                 205
Gly Ser Ser Ala Ser Leu Thr Ser Ser Ala Thr Ala Thr Ala Asn Asp
    210                 215                 220
Thr Thr Thr Thr Val
225
```